US007179448B2

(12) United States Patent
Dattwyler et al.

(10) Patent No.: US 7,179,448 B2

(45) Date of Patent: Feb. 20, 2007

(54) RECOMBINANT CONSTRUCTS OF *BORRELIA BURGDORFERI*

(75) Inventors: Raymond J. Dattwyler, Setauket, NY (US); Maria J. C. Gomes-Solecki, New York, NY (US); Benjamin J. Luft, East Setauket, NY (US); John J. Dunn, Bellport, NY (US)

(73) Assignees: Research Foundation of the State of New York, Stony Brook, NY (US); Brookhaven Sciences Associates, LLC, Upton, NY (US)

( * ) Notice: Subject to any disclaimer, the term of this patent is extended or adjusted under 35 U.S.C. 154(b) by 17 days.

(21) Appl. No.: 11/196,475

(22) Filed: Aug. 3, 2005 (Under 37 CFR 1.47)

(65) Prior Publication Data

US 2005/0271682 A1 Dec. 8, 2005

Related U.S. Application Data

(60) Division of application No. 10/369,100, filed on Feb. 18, 2003, which is a continuation of application No. PCT/US01/24736, filed on Aug. 7, 2001, and a continuation-in-part of application No. 09/666,017, filed on Sep. 19, 2000, now abandoned, which is a continuation-in-part of application No. 08/235,836, filed on Apr. 29, 1994, now Pat. No. 6,248,562, which is a continuation-in-part of application No. 08/148,191, filed on Nov. 1, 1993, now abandoned.

(60) Provisional application No. 60/226,484, filed on Aug. 18, 2000.

(51) Int. Cl.

*A61K 39/00* (2006.01)
*A61K 39/02* (2006.01)
*A61K 39/38* (2006.01)
*A61K 49/00* (2006.01)

(52) U.S. Cl. .................... 424/9.1; 424/9.2; 424/184.1; 424/185.1; 424/190.1; 424/192.1; 424/234.1; 530/300; 530/350

(58) Field of Classification Search ................ 424/9.1, 424/9.2, 184.1, 185.1, 190.1, 192.1, 234.1; 530/300, 350

See application file for complete search history.

(56) References Cited

U.S. PATENT DOCUMENTS

| | | | |
|---|---|---|---|
| 5,217,872 | A | 6/1993 | Dorward et al. |
| 5,470,712 | A | 11/1995 | Simpson et al. |
| 5,523,089 | A | 6/1996 | Bergstrom et al. |
| 5,571,718 | A | 11/1996 | Dunn et al. |
| 5,620,862 | A | 4/1997 | Padula |
| 5,688,512 | A | 11/1997 | Bergstrom et al. |
| 5,747,294 | A | 5/1998 | Flavell et al. |
| 5,777,095 | A | 7/1998 | Barbour et al. |
| 5,780,041 | A | 7/1998 | Simpson et al. |
| 6,113,914 | A | 9/2000 | Lobet et al. |
| 6,197,301 | B1 | 3/2001 | Flavell et al. |
| 6,210,676 | B1 | 4/2001 | Callister et al. |
| 6,248,562 | B1 | 6/2001 | Dunn et al. |
| 2004/0023325 | A1 | 2/2004 | Luft et al. |
| 2004/0033236 | A1 | 2/2004 | Luft et al. |

FOREIGN PATENT DOCUMENTS

| | | | |
|---|---|---|---|
| EP | 0 418 827 | A1 | 3/1991 |
| EP | 0 465 204 | A2 | 1/1992 |
| EP | 0 492 964 | A2 | 7/1992 |
| EP | 0 522 560 | A2 | 1/1993 |
| EP | 0 540 457 | A1 | 5/1993 |
| EP | 0 711 563 | A1 | 5/1996 |
| EP | 0 643 974 | B1 | 1/1999 |
| EP | 0 598 816 | B1 | 6/1999 |
| EP | 1 016 416 | A2 | 5/2000 |
| EP | 0 726 955 | | 4/2004 |
| WO | WO 90/04411 | | 5/1990 |
| WO | WO 91/09870 | | 7/1991 |
| WO | WO 91/13630 | | 9/1991 |
| WO | WO 92/00055 | | 1/1992 |
| WO | WO 93/04175 | | 3/1993 |
| WO | WO 93/08286 | | 4/1993 |
| WO | WO 93/08299 | | 4/1993 |
| WO | WO 93/08306 | | 4/1993 |
| WO | WO 93/10237 | | 5/1993 |

(Continued)

OTHER PUBLICATIONS

Wallich, R. et al., "DNA Vaccines Expressing a Fusion Product of Outer Surface Proteins A and C from *Borrelia burgdorferi* Induce Protective Antibodies Suitable for Prophylaxis but Not for Resolution of Lyme Disease," *Infect. Immun.*, 69(4):2130-2136 (2001).

(Continued)

*Primary Examiner*—Rodney P Swartz

(74) *Attorney, Agent, or Firm*—Hamilton, Brook, Smith & Reynolds, P.C.

(57) ABSTRACT

Novel chimeric nucleic acids, encoding chimeric *Borrelia* proteins comprising OspC or an antigenic fragment thereof and OspA or an antigenic fragment thereof, are disclosed. Chimeric proteins encoded by the nucleic acid sequences are also disclosed. The chimeric proteins are useful as vaccine immunogens against Lyme borreliosis, as well as for immunodiagnostic reagents.

6 Claims, 188 Drawing Sheets

FOREIGN PATENT DOCUMENTS

| | | |
|---|---|---|
| WO | WO 94/19697 | 9/1994 |
| WO | WO 94/20536 | 9/1994 |
| WO | WO 94/25596 | 11/1994 |
| WO | WO 95/12676 | 5/1995 |
| WO | WO 96/40290 | 12/1996 |
| WO | WO 96/40718 | 12/1996 |
| WO | WO 97/42221 | 11/1997 |
| WO | WO 99/14345 | 3/1999 |
| WO | WO 00/06745 | 2/2000 |
| WO | WO 02/16422 | 2/2002 |

OTHER PUBLICATIONS

Kalish, R.S., et al., "Lyme Disease: Human T-cell Response to OspA and OspC Borrelia Lipoproteins Includes Both CD8+ and CD4+ T-Cells," *J. Invest. Dermatol.*, 114(4):836 Abstract 523 (2000).

Luft, B.J., et al., "A New Multi-Target OspA-OspC Vaccine for Lyme Disease," *Abstracts of the Interscience Conference on Antimicrobial Agents and Chemotherapy*, 40:248 Abstract 1932 (2000).

Gomes-Solecki, M.J.C., et al., "Recombinant Chimeric Borrelia Proteins for Diagnosis of Lyme Disease," *J. Clin. Microbiol.*, 38(7):2530-2535 (2000).

Bakken, L.L., et al., "Interlaboratory Comparison of Test Results for Detection of Lyme Disease by 516 Participants in the Wisconsin State Laboratory of Hygiene/College of American Pathologists Proficiency Testing Program," *J. Clin. Microbiol.*, 35(3):537-543 (1997).

Chang, Y-F., et al., "Expression and Secretion of Outer Surface Protein (OSP-A) of *Borrelia burgdorferi* From *Escherichia coli," FEMS Microbiol. Lett.* 109:297-301 (1993).

De, B.K., et al., "Purification and Characterization of *Streptococcus pneumoniae* Palmitoylated pneumococcal surface adhesin A expressed in *Escherichia coli," Vaccine*, 18:1811-1821 (2000).

de Silva, A.M., et al., "*Borrelia burgdorferi* OspA Is an Arthropod-Specific Transmission-Blocking Lyme Disease Vaccine," *J. Exp. Med.* 183(1):271-275 (1996).

de Silva, A.M. and E. Fikrig, "Arthopod- and Host-Specific Gene Expression by *Borrelia burgdorferi," J. Clin. Invest.* 99(3):377-379 (1997).

Fingerle, V., et al., "Expression of Outer Surface Proteins A and C of *Borrelia burgdorferi* in *Ixodes ricinus* Ticks Remove from Humans," *Med. Microbiol. Immunol.* 187(2):121-126 (1998).

Dykhuizen, D.E., et al., "*Borrelia burgdorferi* is Clonal: Implications for Taxonomy and Vaccine Development," *Proc. Natl. Acad. Sci. USA* 90:10163-10167 (1993).

Gilmore, R.D., Jr., et al., "Outer Surface Protein C (OspC), but Not P39, Is a Protective Immunogen Against a Tick-Transmitted *Borrelia burgdorferi* Challenge: Evidence for a Conformational Protective Epitope in OspC," *Infect. Immun.* (64)6:2234-2239 (1996).

Montgomery, R.R., et al., "Direct Demonstration of Antigenic Substitution of *Borrelia burgdorferi* Ex Vivo: Exploration of the Paradox of the Early Immune Response to Outer Surface Proteins A and C in Lyme Disease," *J. Exp. Med.* 183 (1):261-269 (1996).

Probert, W.S. and R.B. LeFebvre, "Protection of C3H/HeN Mice from Challenge with *Borrelia burgdorferi* through Active Immunization with OspA, OspB, or OspC, but Not OspD or the 83-Kilodalton Antigen," *Infect. Immun.* 62(5):1920-1926 (1994).

Probert, W.S., et al., "Immunization with Outer Surface Protein (Osp) A, but Not OspC, Provides Cross-Protection of Mice Challenged with North American Isolates of *Borrelia burgdorferi," J. Infect. Dis.* 175(2):400-405 (1997).

Schwan, T.G., et al., "Induction of an Outer Surface Protein on *Borrelia burgdorferi* During Tick Feeding," *Proc. Natl. Acad. Sci. USA* 92:2909-2913 (1995).

Simon, M.M., et al., "Protective Immunization with Plasmid DNA Containing the Outer Surface Lipoprotein A Gene of *Borrelia burgdorferi* is Independent of an Eukaryotic Promoter," *Eur. J. Immunol.* 26(12):2831-2840 (1996).

Simon, M.M., et al., "Lyme Disease: Pathogenesis and Vaccine Development," *Zent.bl. Bakteriol.* 289:690-695 (1999).

Solé, M., et al., "*Borrelia burgdorferi* Escape Mutants That Survive in the Presence of Antiserum to the OspA Vaccine Are Killed When Complement Is Also Present," *Infect. Immun.* 66(6):2540-2546 (1998).

Steigbigel, R.T. and J.L. Benach, "Immunization Against Lyme Disease-An Important First Step," *N. Engl. J. Med.* 339(4):263-264 (1998).

Stover, C.K., et al., "Protective Immunity Elicited by rBCG Vaccines," *Dev. Biol. Stand.* 82:163-170 (1994).

Thanassi, W.T. and R.T. Schoen, "The Lyme Disease Vaccine: Conception, Development, and Implementation," *Ann. Intern. Med.* 132:661-668 (2000).

Wahlberg, P., "Vaccination Against Lyme borreliosis," *Ann. Med.* 31:233-235 (1999).

Wang, I-N., et al., "Genetic Diversity of *ospC* in a Local Population of *Borrelia burgdorferi sensu stricto," Genetics* 151:15-30 (1999).

Wienke, C.A., et al., "Evaluation of Whole-Cell and OspC Enzyme-Linked Immunosorbent Assays for Discrimination of Early Lyme Borreliosis from OspA Vaccination," *J. Clin. Microbiol.*, 38(1):313-317 (2000).

Wilske, B., et al., "Diversity of OspA and OspC among Cerebrospinal Fluid Isolates of *Borrelia burgdorferi* sensu lato from Patients with Neuroborreliosis in Germany," *Med. Microbiol. Immunol.* 184:195-201 (1996).

Wilske, B., et al., "Immunological and Molecular Variability of OspA and OspC. Implications for *Borrelia* Vaccine Development," *Infection* 24(2):208-212 (1996).

Wilske, B., et al., "Immunological and Molecular Polymorphisms of OspC, an Immunodominant Major Outer Surface Protein of *Borrelia burgdorferi," Infect. Immun.* 61(5):2182-2191 (1993).

Zhong, W. et al., "Therapeutic Passive Vaccination Against Chronic Lyme Disease in Mice," *Proc. Natl. Acad. Sci. USA* 94:12533-12538 (1997).

Zhong, W. et al., "Resolution of Experimental and Tick-borne *Borrelia burgdorferi* Infection in Mice by Passive, But Not Active Immunization Using Recombinant OspC," *Eur. J. Immunol.* 29:946-957 (1999).

Fikrig, E., et al., "Selection of Variant *Borrelia burgdorferi* Isolates From Mice Immunized With Outer Surface Protein A or B," *Infect. Immun.*, 63(5):1658-1662 (1995).

Sellati, T.J., et al., "Outer Surface Lipoproteins of *Borrelia burgdorferi* Activate Vascular Endothelium in Vitro," *Infect. Immun.* 64(8):3180-3187 (1996).

Zhang, Y-Q., et al., "*Borrelia burgdorferi* Enzyme-Linked Immunosorbent Assay for Discrimination of OspA Vaccination from Spirochete Infection," *J. Clin. Microbiol.*, 35(1):233-238 (1997).

Bunikis, J., et al., "Access of Antibody or Trypsin to an Integral Outer Membrane Protein (P66) of *Borrelia burgdorferi* Is Hindered by Osp Lipoproteins," *Infect. Immun.*, 67(6):2874-2883 (1999).

Hughes, C.A.N., et al., "Protective Immunity Is Induced by a *Borrelia burgdorferi* Mutant That Lacks OspA and OspB," *Infect. Immun.* 61(12):5115-5122 (1993).

Wallich, R., et al., "A Recombinant Vaccine for Lyme Disease," *Behring Inst. Mitt.*, 95:106-108 (1994).

Rosa, P.A., et al., "Recombination Between Genes Encoding Major Outer Surface Proteins A and B of *Borrelia burgdorferi," Mol. Microbiol.*, 6(20):3031-3040 (1992).

Stover, C.K., et al., "Protective Immunity Elicited by Recombinant Bacille Calmette-Guerin (BCG) Expressing Outer Surface Protein A (OspA) Lipoprotein: A Candidate Lyme Disease Vaccine," *J. Exp. Med.*, 178:197-209 (1993).

Schwan, T.G., et al., "Distribution and Molecular Analysis of Lyme Disease Spirochetes, *Borrelia burgdorferi*, Isolated From Ticks Throughout California," *J. Clin. Microbiol.*, 31(12):3096-3108 (1993).

Hu, C.M., et al., "Comparison in the Immunological Properties of *Borrelia burgdorferi* Isolates from *Ixodes ricinus* Derived From Three Endemic Areas in Switzerland," *Epidemiol. Infect.*, 112:533-542 (1994).

Schubach, W.H., et al., "Mapping Antibody-Binding Domains of the Major Outer Surface Membrane Protein (OspA) of *Borrelia burgdorferi," Infect. Immun.* 59(6):1911-1915 (1991).

Kitten, T., et al., "Intragenic Recombination and a Chimeric Outer Membrane Protein in the Relapsing Fever Agent *Borrelia hermsii", J. Bacteriol.*, 175(9):2516-2522 (1993).
McGrath, B.C., et al., "Biochemical and Biophysical Characterization of the Major Outer Surface Protein from North American and European Isolates of *Borrelia burgdorferi", Vaccines* 93:365-370 (1993).
France, L.L., et al., "Evidence for an α-Helical Epitope on Outer Surface Protein A From the Lyme Disease Spirochete, *Borrelia burgdorferi*: An Application of Steady-State and Time-Resolved Fluorescence Quenching Techniques," *Biochim. Biophys. Acta.*, 1202:287-296 (1993).
Kantor, F.S., "Disarming Lyme Disease," *Scientific American*, pp. 34-39 (1994).
McGrath, B.C., et al., "Identification of an Immunologically Important Hypervariable Domain of Major Outer Surface Protein A of *Borrelia burgdorferi," Infect. Immun.*, 63(4):1356-1361 (1995).
Wilske, B., et al., "An OspA Serotyping System for *Borrelia burgdorferi* Based on Reactivity With Monoclonal Antibodies and OspA Sequence Analysis," *J. Clin. Microbiol.*, 31(2):340-350 (1993).
Marconi, R.T., et al., "Variability of *osp* Genes and Gene Products Among Species of Lyme Disease Spirochetes," *Infect. Immun.*, 61(6):2611-2617 (1993).
Fikrig, E., et al., "*Borrelia burgdorferi* Strain 25015: Characterization of Outer Surface Protein A and Vaccination Against Infection," *J. Immunol.* 148(7):2256-2260 (1992).
Schaible, U., et al., "Immune Sera to Individual *Borrelia burgdorferi* Isolates or Recombinant OspA Thereof Protect SCID Mice Against Infection With Homologous Strains but Only Partially or Not at All Against Those of Difference OspA/OspB Genotype," *Vaccine* 11(10):1049-1054 (1993).
Masuzawa, T., et al., "Protective Activity of Antisera Against Isolates of *Borrelia burgdorferi* From Various Geographical Origins," *Microbiol. Immunol.*, 37(1):79-83 (1993).
Wallich, R., et al., "Evaluation of Genetic Divergence Among *Borrelia burgdorferi* Isolates by Use of OspA, *fla*, HSP60, and HSP70 Gene Probes," *Infect. Immun.*, 60(11):4856-4866 (1992).
Simon, M.M., et al., "A Mouse Model for *Borrelia burgdorferi* Infection: Approach to a Vaccine Against Lyme Disease," *Immunol. Today*, 12(1):11-16 (1991).
Schaible, U.E., et al., "Monoclonal Antibodies Specific for the Outer Surface Protein A (OspA) of *Borrelia burgdorferi* Prevent Lyme Borreliosis in Severe Combined Immunodeficiency (*scid*) Mice," *Proc. Natl. Acad. Sci. USA*, 87:3768-3772 (1990).
Preac-Mursic, V., et al., "Active Immunization With pC Protein of *Borrelia burgdorferi* Protects Gerbils Against *B. burgdorferi* Infection," *Infection*, 20(6):342-349 (1992).
Simon, M., et al., "Spirochetes: Vaccines, Animal Models and Diagnostics," *Res. Microbiol.*, 143:641-647 (1992).
Simon, M.M., et al., "Recombinant Outer Surface Protein A from *Borrelia burgdorferi* Induces Antibodies Protective against Spirochetal Infection in Mice," *J. Infect. Dis.*, 164:123-132 (1991).
Howe, T.R., et al., "A Single Recombinant Plasmid Expressing Two Major Outer Surface Proteins of the Lyme Disease Spirochete," *Science*, 227:645-46 (1985).
Johnson, R.C., et al., "Experimental Infection of the Hamster with *Borrelia burgdorferi," Ann. N.Y. Acad. Sci.*, 539:258-263 (1988).
France, L.L., et al., "Structural Analysis of an Outer Surface Protein From the Lyme Disease Spirochete, *Borrelia burgdorferi*, Using Circular Dichroism and Fluorescence Spectroscopy," *Biochim. Biophys. Acta*, 1120:59-68 (1992).
Howe, T.R., et al., "Organization of Genes Encoding Two Outer Membrane Proteins of the Lyme Disease Agent *Borrelia burgdorferi* within a Single Transcriptional Unit," *Infect. Immun.*, 54(1):207-212 (1986).
Johnson, R.C., et al., "Vaccination of Hamsters Against Experimental Infection with *Borrelia burgdorferi," Zbl. Bakt. Hyg. A*, 263:45-48 (1986).
Johnson, R.C., et al., "Passive Immunization of Hamsters Against Experimental Infection with the Lyme Disease Spirochete," *Infect. and Immun.*, 53(3):713-714 (1986).
Johnson, R.C., et al., "Active Immunization of Hamsters Against Experimental Infection with *Borrelia burgdorferi," Infect. Immun.*, 54(3):897-898 (1986).
Fikrig, E., et al., "Elimination of *Borrelia burgdorferi* from Vector Ticks Feeding on OspA-Immunized Mice," *Proc. Natl. Acad. Sci. USA*, 89:5418-5421 (1992).
Fikrig, E., et al., "Long-Term Protection of Mice From Lyme Disease by Vaccination with OspA," *Infect. Immun.*, 60(3):773-777 (1992).
Fikrig, E., et al., "Protection of Mice Against the Lyme Disease Agent by Immunizing with Recombinant OspA," *Science*, 250:553-556 (1990).
Erdile, L. F. et al., "Role of Attached Lipid in Immunogenicity of *Borrelia burgdorferi* OspA," *Infect. Immun.*, 61(1):81-90 (1993).
Bockenstedt, L.K., et al., "Inability of Truncated Recombinant Osp A Proteins To Elicit Protective Immunity to *Borrelia burgdorferi* in Mice," *J. Immun.*, 151(2):900-906 (1993).
Lovrich, S.D., et al., "Seroprotective Groups Among Isolates of *Borrelia burgdorferi," Infect. Immun.*, 61(10):4367-4374 (1993).
Wilske, B., et al., "Molecular Analysis of the Outer Surface Protein A (OspA) of *Borrelia burgdorferi* For Conserved and Variable Antibody Binding Domains," *Med. Microbiol. Immunol.*, 181:191-207 (1992).
Sears, J.E., et al., "Molecular Mapping of Osp-A Mediated Immunity Against *Borrelia burgdorferi*, The Agent of Lyme Disease," *J. Immunol.*, 147(6):1995-2000 (1991).
Lovrich, S.D., et al., "Seroprotective Groups of Lyme Borreliosis Spirochetes from North America and Europe," *J. Inf. Dis* 170:115-121 (1994).
Gern, L., et al., "Immunization With a Polyvalent OspA Vaccine Protects Mice Against *Ixodes ricinus* Tick Bites Infected by *Borrelia burgdorferi ss, Borrelia garinii* and *Borrelia afzelli," Vaccine* 15(14):1551-1557 (1997).
Golde, W.T., et al., "The Lyme Disease Vaccine Candidate Outer Surface Protein A (OspA) in a Formulation Compatible With Human Use Protects Mice Against Natural Tick Transmission of *B. burgdorferi," Vaccine* 13(5):435-441 (1995).
Masuzawa, T., et al., "Negative Finding in Cross-Protective Activity of Japanese *Borrelia* Isolates Against Infection with Three Species of Lyme Disease *Borrelia* in Outbred Mice," *Microbiol. Immunol.*, 41(9):733-736 (1997).
Kumaran D., et al. "Crystal Structure of Outer Surface Protein C (OspC) From The Lyme Disease Spirochete, *Borrelia burgdorferi," EMBO J.* 20(5):971-978 (2001).
Li, H., et al., "Crystal Structure of Lyme Disease Antigen Outer Surface Protein A Complexed With An Fab," *Proc. Natl. Acad. Sci. USA*, 94:3584-3589 (1997).
Barbour, A.G., et al., "Lyme Disease Spirochetes and Ixodid Tick Spirochetes Share a Common Surface Antigenic Determinant Defined by a Monoclonal Antibody," *Infect. Immun. 41(2)*:795-804 (1983).

Domain 1

| | 34 | 35 | 36 | 37 | 38 | 39 | 40 | 41 |
|---|---|---|---|---|---|---|---|---|
| A-B31 | L | P | G | E | M | K | V | L |
| A-TRo | L | P | G | E | M | K | V | L |
| A-K48 | L | P | G | G | M | T | V | L |
| A-DK29 | L | P | G | G | M | T | V | L |
| A-P/Gau | L | P | G | E | M | K | V | L |
| A-PKo | L | P | G | E | M | K | V | L |
| A-IP3 | L | P | G | E | I | K | V | L |
| A-IP90 | L | P | G | G | M | G | V | L |
| A-25015 | L | P | G | E | M | K | V | L |

Domain 2

| | 65 | 66 | 67 | 68 | 69 | 70 | 71 | 72 | 73 | 74 | 75 |
|---|---|---|---|---|---|---|---|---|---|---|---|
| A-B31 | G | T | S | D | K | N | N | G | S | G | V |
| A-TRo | G | T | S | D | K | S | N | G | S | G | T |
| A-K48 | G | T | S | D | K | N | N | G | S | G | T |
| A-DK29 | G | T | S | D | K | N | N | G | S | G | T |
| A-P/Gau | G | T | S | D | K | D | N | G | S | G | T |
| A-PKo | G | T | S | D | K | D | N | G | S | G | T |
| A-IP3 | G | T | S | D | K | D | N | G | S | G | V |
| A-IP90 | G | T | S | D | K | N | N | G | S | G | T |
| A-25015 | G | T | S | D | K | N | N | G | S | G | V |

Domain 3

| | 190 200 210 220 |
|---|---|
| A-B31 | NISKSGEVSVELNDTDSSAATKKTAAWNSGT |
| A-TRo | HIPNSGEITVELNDSNSTQATKKTGKWDSNT |
| A-K48 | NILKSGEITVALDDSDTTQATKKTGKWDSKT |
| A-DK29 | NILKSGEITAALDDSDTTRATKKTGKWDSKT |
| A-P/Gau | EIAKSGEVTVALNDTNTTQATKKTGAWDSKT |
| A-PKo | EIAKSGEVTVALNDTNTTQATKKTGAWDSKT |
| A-IP3 | EIAKSGEVTVALNDTNTTQATKKTGAWDSKT |
| A-IP90 | HISNSGEITVELNDSDTTQATKKTGTWDSKT |
| A-25015 | HISKSGEVTAELNDTDSTQATKKTGKWDAGT |

Domain 4

| | 250 260 270 |
|---|---|
| A-B31 | SNGTKLEGSAVEITKLDEIKN |
| A-TRo | SAGTNLEGNAVEIKTLDELKN |
| A-K48 | SAGTNLEGKAVEITTLKELKN |
| A-DK29 | SAGTNLEGKAVEITTLKELKN |
| A-P/Gau | SAGTNLEGTAVEIKTLDELKN |
| A-PKo | SAGTNLEGTAVEIKTLDELKN |
| A-IP3 | SAGTNLEGTAVEIKTLDELKN |
| A-IP90 | SAGTNLEGKAVEITTLKELKN |
| A-25015 | SAGTNLEGTAVEIKTLDEIKN |

FIG. 2

Protein sequence of OspAs from B31, K48 and the site-directed mutants from amino acids 200-220.

↓

B31: ELNDTDSSAATKKTAAWNSGT

K48: ALDDSDTTQATKKTGKWDSKT

613: ELNDSDTSAATKKTAAWNSGT

625: ELNDTDSSAATKKTGKWNSGT

640: ELNDTDSSAATKKTAAWDSKT

613/625: ELNDSDTSAATKKTGKWNSGT

613/640: ELNDSDTSAATKKTAAWDSKT

FIG. 4

```
        10          20          30          40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

 100         110         120         130         140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

   150         160         170         180         190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

      200         210         220         230         240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

        250         260         270         280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290         300         310         320         330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

  340         350         360         370         380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 7A

```
      390         400         410         420         430
 *     *     *     *     *     *     *     *     *     *
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

        440         450         460         470         480
 *     *     *     *     *     *     *     *     *     *
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

          490         500         510         520
     *     *     *     *     *     *     *     *     *
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530         540         550         560         570
 *     *     *     *     *     *     *     *     *     *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

   580         590         600         610         620
     *     *     *     *     *     *     *     *     *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

     630         640         650         660         670
 *     *     *     *     *     *     *     *     *     *
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

       680         690         700         710         720
 *     *     *     *     *     *     *     *     *     *
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

         730         740         750         760
     *     *     *     *     *     *     *     *     *
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770         780         790         800         810
 *     *     *     *     *     *     *     *     *     *
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

   820
     *
AAA TAA
TTT ATT
Lys ***>
```

FIG. 7B

```
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

 50          60          70          80          90
TGT AAG CAA AAT GTT AGC AGC CTT GAT GAA AAA AAT AGC GTT TCA GTA
ACA TTC GTT TTA CAA TCG TCG GAA CTA CTT TTT TTA TCG CAA AGT CAT
Cys Lys Gln Asn Val Ser Ser Leu Asp Glu Lys Asn Ser Val Ser Val>

 100         110         120         130         140
GAT TTA CCT GGT GGA ATG ACA GTT CTT GTA AGT AAA GAA AAA GAC AAA
CTA AAT GGA CCA CCT TAC TGT CAA GAA CAT TCA TTT CTT TTT CTG TTT
Asp Leu Pro Gly Gly Met Thr Val Leu Val Ser Lys Glu Lys Asp Lys>

 150         160         170         180         190
GAC GGT AAA TAC AGT CTA GAG GCA ACA GTA GAC AAG CTT GAG CTT AAA
CTG CCA TTT ATG TCA GAT CTC CGT TGT CAT CTG TTC GAA CTC GAA TTT
Asp Gly Lys Tyr Ser Leu Glu Ala Thr Val Asp Lys Leu Glu Leu Lys>

 200         210         220         230         240
GGA ACT TCT GAT AAA AAC AAC GGT TCT GGA ACA CTT GAA GGT GAA AAA
CCT TGA AGA CTA TTT TTG TTG CCA AGA CCT TGT GAA CTT CCA CTT TTT
Gly Thr Ser Asp Lys Asn Asn Gly Ser Gly Thr Leu Glu Gly Glu Lys>

 250         260         270         280
ACT GAC AAA AGT AAA GTA AAA TTA ACA ATT GCT GAT GAC CTA AGT CAA
TGA CTG TTT TCA TTT CAT TTT AAT TGT TAA CGA CTA CTG GAT TCA GTT
Thr Asp Lys Ser Lys Val Lys Leu Thr Ile Ala Asp Asp Leu Ser Gln>

 290         300         310         320         330
ACT AAA TTT GAA ATT TTC AAA GAA GAT GCC AAA ACA TTA GTA TCA AAA
TGA TTT AAA CTT TAA AAG TTT CTT CTA CGG TTT TGT AAT CAT AGT TTT
Thr Lys Phe Glu Ile Phe Lys Glu Asp Ala Lys Thr Leu Val Ser Lys>

 340         350         360         370         380
AAA GTA ACC CTT AAA GAC AAG TCA TCA ACA GAA GAA AAA TTC AAC GAA
TTT CAT TGG GAA TTT CTG TTC AGT AGT TGT CTT CTT TTT AAG TTG CTT
Lys Val Thr Leu Lys Asp Lys Ser Ser Thr Glu Glu Lys Phe Asn Glu>
```

FIG. 8A

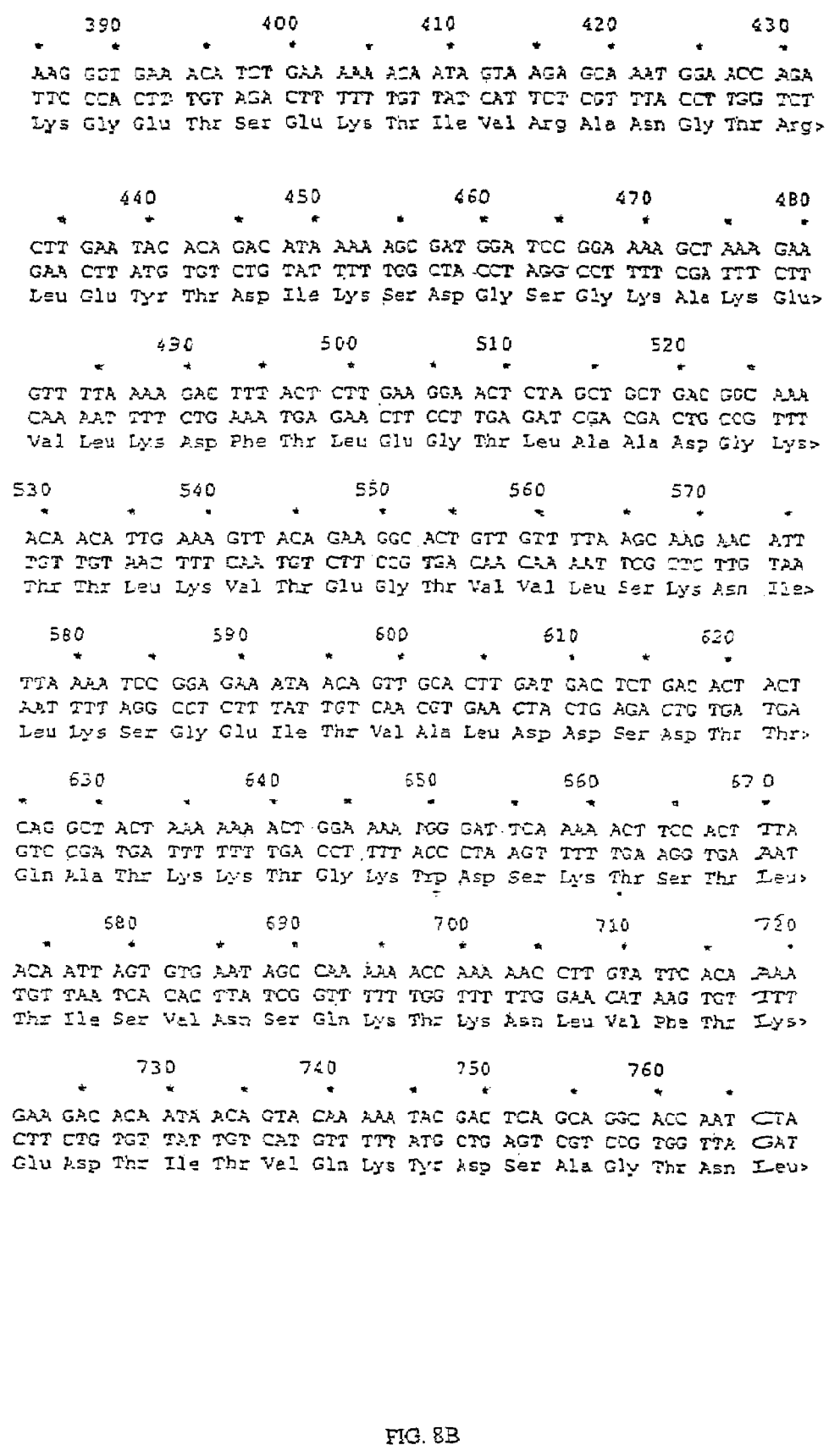

```
    390         400         410         420         430
AAG GGT GAA ACA TCT GAA AAA ACA ATA GTA AGA GCA AAT GGA ACC AGA
TTC CCA CTT TGT AGA CTT TTT TGT TAT CAT TCT CGT TTA CCT TGG TCT
Lys Gly Glu Thr Ser Glu Lys Thr Ile Val Arg Ala Asn Gly Thr Arg>

        440         450         460         470         480
CTT GAA TAC ACA GAC ATA AAA AGC GAT GGA TCC GGA AAA GCT AAA GAA
GAA CTT ATG TGT CTG TAT TTT TCG CTA CCT AGG CCT TTT CGA TTT CTT
Leu Glu Tyr Thr Asp Ile Lys Ser Asp Gly Ser Gly Lys Ala Lys Glu>

           490         500         510         520
GTT TTA AAA GAC TTT ACT CTT GAA GGA ACT CTA GCT GCT GAC GGC AAA
CAA AAT TTT CTG AAA TGA GAA CTT CCT TGA GAT CGA CGA CTG CCG TTT
Val Leu Lys Asp Phe Thr Leu Glu Gly Thr Leu Ala Ala Asp Gly Lys>

530         540         550         560         570
ACA ACA TTG AAA GTT ACA GAA GGC ACT GTT GTT TTA AGC AAG AAC ATT
TGT TGT AAC TTT CAA TGT CTT CCG TGA CAA CAA AAT TCG TTC TTG TAA
Thr Thr Leu Lys Val Thr Glu Gly Thr Val Val Leu Ser Lys Asn Ile>

  580         590         600         610         620
TTA AAA TCC GGA GAA ATA ACA GTT GCA CTT GAT GAC TCT GAC ACT ACT
AAT TTT AGG CCT CTT TAT TGT CAA CGT GAA CTA CTG AGA CTG TGA TGA
Leu Lys Ser Gly Glu Ile Thr Val Ala Leu Asp Asp Ser Asp Thr Thr>

    630         640         650         660         670
CAG GCT ACT AAA AAA ACT GGA AAA TGG GAT TCA AAA ACT TCC ACT TTA
GTC CGA TGA TTT TTT TGA CCT TTT ACC CTA AGT TTT TGA AGG TGA AAT
Gln Ala Thr Lys Lys Thr Gly Lys Trp Asp Ser Lys Thr Ser Thr Leu>

        680         690         700         710         720
ACA ATT AGT GTG AAT AGC CAA AAA ACC AAA AAC CTT GTA TTC ACA AAA
TGT TAA TCA CAC TTA TCG GTT TTT TGG TTT TTG GAA CAT AAG TGT TTT
Thr Ile Ser Val Asn Ser Gln Lys Thr Lys Asn Leu Val Phe Thr Lys>

           730         740         750         760
GAA GAC ACA ATA ACA GTA CAA AAA TAC GAC TCA GCA GGC ACC AAT CTA
CTT CTG TGT TAT TGT CAT GTT TTT ATG CTG AGT CGT CCG TGG TTA GAT
Glu Asp Thr Ile Thr Val Gln Lys Tyr Asp Ser Ala Gly Thr Asn Leu>
```

FIG. 8B

```
770         780         790         800         810
 *     *     *     *     *     *     *     *     *     *
GAA GGC AAA GCA GTC GAA ATT ACA ACA CTT AAA GAA CTT AAA AAC GCT
CTT CCG TTT CGT CAG CTT TAA TGT TGT GAA TTT CTT GAA TTT TTG CGA
Glu Gly Lys Ala Val Glu Ile Thr Thr Leu Lys Glu Leu Lys Asn Ala>
```

```
  820
   *     *
TTA AAA TAA
AAT TTT ATT
Leu Lys ***>
```

FIG. 8C

```
        10              20              30              40
         •               •               •               •
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

        50              60              70              80              90
         •               •               •               •               •
TGC AAG CAA AAT GTT AGC AGC CTT GAT GAA AAA AAC AGC GCT TCA GTA
ACG TTC GTT TTA CAA TCG TCG GAA CTA CTT TTT TTG TCG CGA AGT CAT
Cys Lys Gln Asn Val Ser Ser Leu Asp Glu Lys Asn Ser Ala Ser Val>

        100             110             120             130             140
         •               •               •               •               •
GAT TTG CCT GGT GAG ATG AAA GTT CTT GTA AGT AAA GAA AAA GAC AAA
CTA AAC GGA CCA CTC TAC TTT CAA GAA CAT TCA TTT CTT TTT CTG TTT
Asp Leu Pro Gly Glu Met Lys Val Leu Val Ser Lys Glu Lys Asp Lys>

        150             160             170             180             190
         •               •               •               •               •
GAC GGT AAG TAC AGT CTA AAG GCA ACA GTA GAC AAG ATT GAG CTA AAA
CTG CCA TTC ATG TCA GAT TTC CGT TGT CAT CTG TTC TAA CTC GAT TTT
Asp Gly Lys Tyr Ser Leu Lys Ala Thr Val Asp Lys Ile Glu Leu Lys>

        200             210             220             230             240
         •               •               •               •               •
GGA ACT TCT GAT AAA GAC AAT GGT TCT GGA GTG CTT GAA GGT ACA AAA
CCT TGA AGA CTA TTT CTG TTA CCA AGA CCT CAC GAA CTT CCA TGT TTT
Gly Thr Ser Asp Lys Asp Asn Gly Ser Gly Val Leu Glu Gly Thr Lys>

        250             260             270             280
         •               •               •               •
GAT GAC AAA AGT AAA GCA AAA TTA ACA ATT GCT GAC GAT CTA AGT AAA
CTA CTG TTT TCA TTT CGT TTT AAT TGT TAA CGA CTG CTA GAT TCA TTT
Asp Asp Lys Ser Lys Ala Lys Leu Thr Ile Ala Asp Asp Leu Ser Lys>

        290             300             310             320             330
         •               •               •               •               •
ACC ACA TTC GAA CTT TTA AAA GAA GAT GGC AAA ACA TTA GTG TCA AGA
TGG TGT AAG CTT GAA AAT TTT CTT CTA CCG TTT TGT AAT CAC AGT TCT
Thr Thr Phe Glu Leu Leu Lys Glu Asp Gly Lys Thr Leu Val Ser Arg>

        340             350             360             370             380
         •               •               •               •               •
AAA GTA AGT TCT AGA GAC AAA ACA TCA ACA GAT GAA ATG TTC AAT GAA
TTT CAT TCA AGA TCT CTG TTT TGT AGT TGT CTA CTT TAC AAG TTA CTT
Lys Val Ser Ser Arg Asp Lys Thr Ser Thr Asp Glu Met Phe Asn Glu>
```

FIG. 9A

```
     390             400            410           420            430
 *    *       *       *      *      *      *      *      *      *
AAA GGT GAA TTG TCT GCA AAA ACC ATG ACA AGA GAA AAT GGA ACC AAA
TTT CCA CTT AAC AGA CGT TTT TGG TAC TGT TCT CTT TTA CCT TGG TTT
Lys Gly Glu Leu Ser Ala Lys Thr Met Thr Arg Glu Asn Gly Thr Lys>

        440            450            460           470           480
 *       *      *       *      *      *      *      *      *      *
CTT GAA TAT ACA GAA ATG AAA AGC GAT GGA ACC GGA AAA GCT AAA GAA
GAA CTT ATA TGT CTT TAC TTT TCG CTA CCT TGG CCT TTT CGA TTT CTT
Leu Glu Tyr Thr Glu Met Lys Ser Asp Gly Thr Gly Lys Ala Lys Glu>

           490            500           510           520
      *      *      *      *      *      *      *      *      *
GTT TTA AAA AAG TTT ACT CTT GAA GGA AAA GTA GCT AAT GAT AAA GTA
CAA AAT TTT TTC AAA TGA GAA CTT CCT TTT CAT CGA TTA CTA TTT CAT
Val Leu Lys Lys Phe Thr Leu Glu Gly Lys Val Ala Asn Asp Lys Val>

530            540             550          560           570
 *      *      *       *      *      *      *      *      *      *
ACA TTG GAA GTA AAA GAA GGA ACC GTT ACT TTA AGT AAG GAA ATT GCA
TGT AAC CTT CAT TTT CTT CCT TGG CAA TGA AAT TCA TTC CTT TAA CGT
Thr Leu Glu Val Lys Glu Gly Thr Val Thr Leu Ser Lys Glu Ile Ala>

  580            590            600          610           620
     *      *      *       *      *      *      *      *      *
AAA TCT GGA GAA GTA ACA GTT GCT CTT AAT GAC ACT AAC ACT ACT CAG
TTT AGA CCT CTT CAT TGT CAA CGA GAA TTA CTG TGA TTG TGA TGA GTC
Lys Ser Gly Glu Val Thr Val Ala Leu Asn Asp Thr Asn Thr Thr Gln>

     630            640            650          660            670
 *     *      *       *      *      *      *      *      *      *
GCT ACT AAA AAA ACT GGC GCA TGG GAT TCA AAA ACT TCT ACT TTA ACA
CGA TGA TTT TTT TGA CCG CGT ACC CTA AGT TTT TGA AGA TGA AAT TGT
Ala Thr Lys Lys Thr Gly Ala Trp Asp Ser Lys Thr Ser Thr Leu Thr>

        680            690            700          710           720
   *      *      *      *      *      *      *      *      *      *
ATT AGT GTT AAC AGC AAA AAA ACT ACA CAA CTT GTG TTT ACT AAA CAA
TAA TCA CAA TTG TCG TTT TTT TGA TGT GTT GAA CAC AAA TGA TTT GTT
Ile Ser Val Asn Ser Lys Lys Thr Thr Gln Leu Val Phe Thr Lys Gln>

           730            740           750           760
      *      *      *      *      *      *      *      *      *
TAC ACA ATA ACT GTA AAA CAA TAC GAC TCC GCA GGT ACC AAT TTA GAA
ATG TGT TAT TGA CAT TTT GTT ATG CTG AGG CGT CCA TGG TTA AAT CTT
Tyr Thr Ile Thr Val Lys Gln Tyr Asp Ser Ala Gly Thr Asn Leu Glu>
```

FIG. 9B

```
770            780            790           800           810
 *       *      *       *       *       *      *       *      *       *
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
Gly Thr Ala Val Glu Ile Lys Thr Leu Asp Glu Leu Lys Asn Ala Leu>

  820
   *
AAA TAA
TTT ATT
Lys ***>
```

FIG. 9C

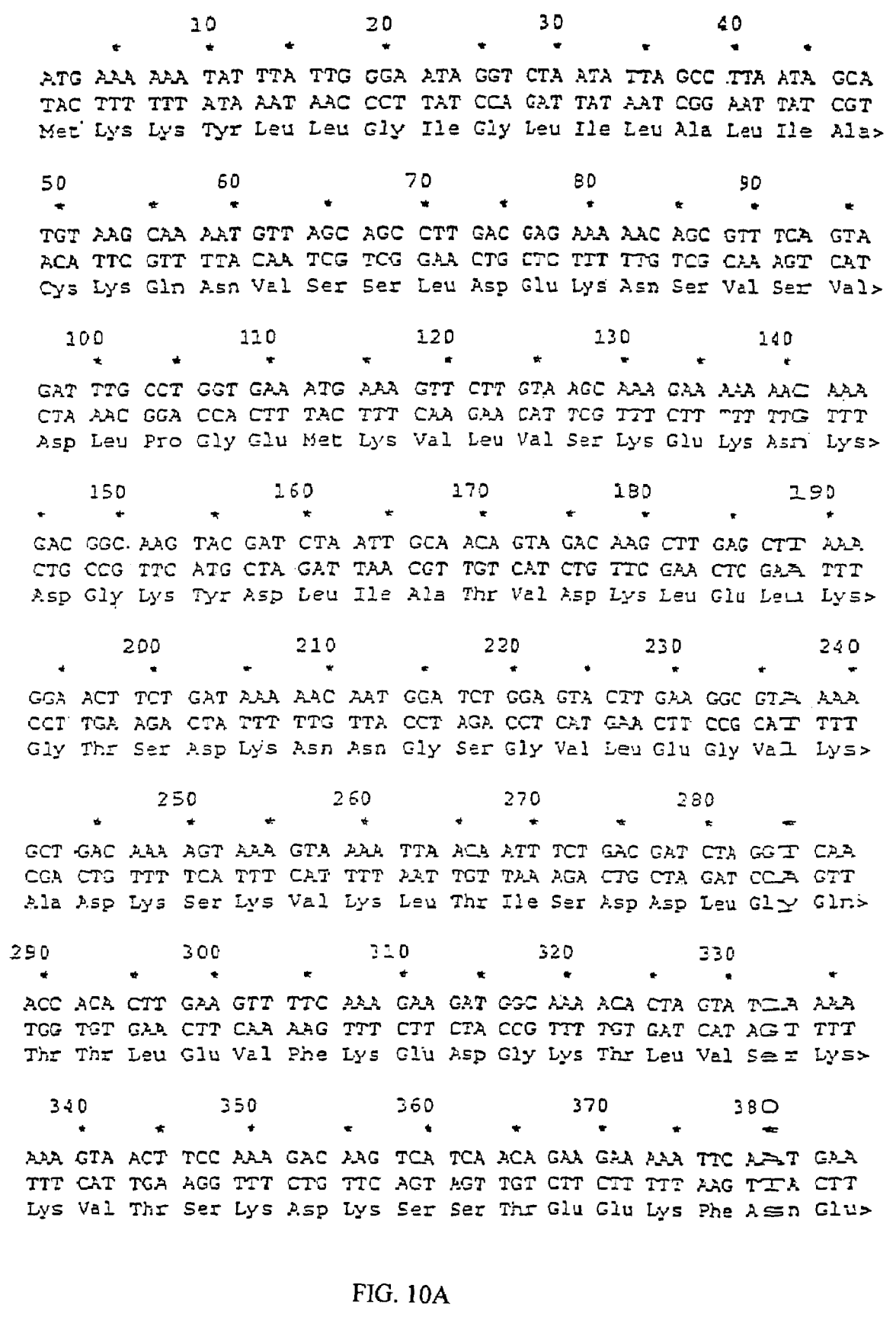

```
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 10A

```
     390         400         410         420         430
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

        440         450         460         470         480
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

           490         500         510         520
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530         540         550         560         570
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

  580         590         600         610         620
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

     630         640         650         660         670
GCT ACT AAA AAA ACT GCA GCT TGG AAT GCA GGC ACT TCA ACT TTA ACA
CGA TGA TTT TTT TGA CGT CGA ACC TTA CGT CCG TGA AGT TGA AAT TGT
Ala Thr Lys Lys Thr Ala Ala Trp Asn Ala Gly Thr Ser Thr Leu Thr>

        680         690         700         710         720
ATT ACT GTA AAC AAC AAA AAA ACT AAA GCC CTT GTA TTT ACA AAA CAA
TAA TGA CAT TTG TTG TTT TTT TGA TTT CGG GAA CAT AAA TGT TTT GTT
Ile Thr Val Asn Asn Lys Lys Thr Lys Ala Leu Val Phe Thr Lys Gln>

           730         740         750         760
GAC ACA ATT ACA TCA CAA AAA TAC GAC TCA GCA GGA ACC AAC TTG GAA
CTG TGT TAA TGT AGT GTT TTT ATG CTG AGT CGT CCT TGG TTG AAC CTT
Asp Thr Ile Thr Ser Gln Lys Tyr Asp Ser Ala Gly Thr Asn Leu Glu>

     OSPA 25015
770         780         790         800         810
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
Gly Thr Ala Val Glu Ile Lys Thr Leu Asp Glu Leu Lys Asn Ala Leu>

AGA
TCT
Arg>
```

FIG. 10B

```
        10          20          30          40
ATG AGA TTA TTA ATA GGA TTT GCT TTA GCG TTA GCT TTA ATA GGA TGT
TAC TCT AAT AAT TAT CCT AAA CGA AAT CGC AAT CGA AAT TAT CCT ACA
Met Arg Leu Leu Ile Gly Phe Ala Leu Ala Leu Ala Leu Ile Gly Cys>

50          60          70          80          90
GCA CAA AAA GGT GCT GAG TCA ATT GGT TCT CAA AAA GAA AAT GAT CTA
CGT GTT TTT CCA CGA CTC AGT TAA CCA AGA GTT TTT CTT TTA CTA GAT
Ala Gln Lys Gly Ala Glu Ser Ile Gly Ser Gln Lys Glu Asn Asp Leu>

 100         110         120         130         140
AAC CTT GAA GAC TCT AGT AAA AAA TCA CAT CAA AAC GCT AAA CAA GAC
TTG GAA CTT CTG AGA TCA TTT TTT AGT GTA GTT TTG CGA TTT GTT CTG
Asn Leu Glu Asp Ser Ser Lys Lys Ser His Gln Asn Ala Lys Gln Asp>

  150         160         170         180         190
CTT CCT GCG GTG ACA GAA GAC TCA GTG TCT TTG TTT AAT GGT AAT AAA
GAA GGA CGC CAC TGT CTT CTG AGT CAC AGA AAC AAA TTA CCA TTA TTT
Leu Pro Ala Val Thr Glu Asp Ser Val Ser Leu Phe Asn Gly Asn Lys>

    200         210         220         230         240
ATT TTT GTA AGC AAA GAA AAA AAT AGC TCC GGC AAA TAT GAT TTA AGA
TAA AAA CAT TCG TTT CTT TTT TTA TCG AGG CCG TTT ATA CTA AAT TCT
Ile Phe Val Ser Lys Glu Lys Asn Ser Ser Gly Lys Tyr Asp Leu Arg>

       250         260         270         280
GCA ACA ATT GAT CAG GTT GAA CTT AAA GGA ACT TCC GAT AAA AAC AAT
CGT TGT TAA CTA GTC CAA CTT GAA TTT CCT TGA AGG CTA TTT TTG TTA
Ala Thr Ile Asp Gln Val Glu Leu Lys Gly Thr Ser Asp Lys Asn Asn>

290         300         310         320         330
GGT TCT GGA ACC CTT GAA GGT TCA AAG CCT GAC AAG AGT AAA GTA AAA
CCA AGA CCT TGG GAA CTT CCA AGT TTC GGA CTG TTC TCA TTT CAT TTT
Gly Ser Gly Thr Leu Glu Gly Ser Lys Pro Asp Lys Ser Lys Val Lys>

  340         350         360         370         380
TTA ACA GTT TCT GCT GAT TTA AAC ACA GTA ACC TTA GAA GCA TTT GAT
AAT TGT CAA AGA CGA CTA AAT TTG TGT CAT TGG AAT CTT CGT AAA CTA
Leu Thr Val Ser Ala Asp Leu Asn Thr Val Thr Leu Glu Ala Phe Asp>
   390         400         410         420         430
```

FIG. 11A

```
 *     *     *     *     *     *     *     *     *     *
GCC AGC AAC CAA AAA ATT TCA AGT AAA GTT ACT AAA AAA CAG GGG TCA
CGG TCG TTG GTT TTT TAA AGT TCA TTT CAA TGA TTT TTT GTC CCC AGT
Ala Ser Asn Gln Lys Ile Ser Ser Lys Val Thr Lys Lys Gln Gly Ser>

        440         450         460         470         480
 *     *     *     *     *     *     *     *     *     *
ATA ACA GAG GAA ACT CTC AAA GCT AAT AAA TTA GAC TCA AAG AAA TTA
TAT TGT CTC CTT TGA GAG TTT CGA TTA TTT AAT CTG AGT TTC TTT AAT
Ile Thr Glu Glu Thr Leu Lys Ala Asn Lys Leu Asp Ser Lys Lys Leu>

          490         500         510         520
     *     *     *     *     *     *     *     *     *
ACA AGA TCA AAC GGA ACT ACA CTT GAA TAC TCA CAA ATA ACA GAT GCT
TGT TCT AGT TTG CCT TGA TGT GAA CTT ATG AGT GTT TAT TGT CTA CGA
Thr Arg Ser Asn Gly Thr Thr Leu Glu Tyr Ser Gln Ile Thr Asp Ala>

530         540         550         560         570
 *     *     *     *     *     *     *     *     *     *
GAC AAT GCT ACA AAA GCA GTA GAA ACT CTA AAA AAT AGC ATT AAG CTT
CTG TTA CGA TGT TTT CGT CAT CTT TGA GAT TTT TTA TCG TAA TTC GAA
Asp Asn Ala Thr Lys Ala Val Glu Thr Leu Lys Asn Ser Ile Lys Leu>

  580         590         600         610         620
     *     *     *     *     *     *     *     *     *
GAA GGA AGT CTT GTA GTC GGA AAA ACA ACA GTG GAA ATT AAA GAA GGT
CTT CCT TCA GAA CAT CAG CCT TTT TGT TGT CAC CTT TAA TTT CTT CCA
Glu Gly Ser Leu Val Val Gly Lys Thr Thr Val Glu Ile Lys Glu Gly>

    630         640         650         660         670
 *     *     *     *     *     *     *     *     *     *
ACT GTT ACT CTA AAA AGA GAA ATT GAA AAA GAT GGA AAA GTA AAA GTC
TGA CAA TGA GAT TTT TCT CTT TAA CTT TTT CTA CCT TTT CAT TTT CAG
Thr Val Thr Leu Lys Arg Glu Ile Glu Lys Asp Gly Lys Val Lys Val>

      680         690         700         710         720
 *     *     *     *     *     *     *     *     *     *
TTT TTG AAT GAC ACT GCA GGT TCT AAC AAA AAA ACA GGT AAA TGG GAA
AAA AAC TTA CTG TGA CGT CCA AGA TTG TTT TTT TGT CCA TTT ACC CTT
Phe Leu Asn Asp Thr Ala Gly Ser Asn Lys Lys Thr Gly Lys Trp Glu>

        730         740         750         760
     *     *     *     *     *     *     *     *     *
GAC AGT ACT AGC ACT TTA ACA ATT AGT GCT GAC AGC AAA AAA ACT AAA
CTG TCA TGA TCG TGA AAT TGT TAA TCA CGA CTG TCG TTT TTT TGA TTT
Asp Ser Thr Ser Thr Leu Thr Ile Ser Ala Asp Ser Lys Lys Thr Lys>

770         780         790         800         810
 *     *     *     *     *     *     *     *     *     *
GAT TTG GTG TTC TTA ACA GAT GGT ACA ATT ACA GTA CAA CAA TAC AAC
CTA AAC CAC AAG AAT TGT CTA CCA TGT TAA TGT CAT GTT GTT ATG TTG
Asp Leu Val Phe Leu Thr Asp Gly Thr Ile Thr Val Gln Gln Tyr Asn>
```

FIG. 11B

```
   820         830         840          850         860
    *     *     *     *     *     *      * *    *     *
ACA GCT GGA ACC AGC CTA GAA GGA TCA GCA AGT GAA ATT AAA AAT CTT
TGT CGA CCT TGG TCG GAT CTT CCT AGT CGT TCA CTT TAA TTT TTA GAA
Thr Ala Gly Thr Ser Leu Glu Gly Ser Ala Ser Glu Ile Lys Asn Leu>

    870         880         890
*     *     *     *     *     *
TCA GAG CTT AAA AAC GCT TTA AAA TAA
AGT CTC GAA TTT TTG CGA AAT TTT ATT
Ser Glu Leu Lys Asn Ala Leu Lys ***>
```

FIG. 11C 10 20 30 40
* * * * * * * * *
ATG AAA AAG AAT ACA TTA AGT GCG ATA TTA ATG ACT TTA TTT TTA TTT
TAC TTT TTC TTA TGT AAT TCA CGC TAT AAT TAC TGA AAT AAA AAT AAA
Met Lys Lys Asn Thr Leu Ser Ala Ile Leu Met Thr Leu Phe Leu Phe>

50 60 70 80 90
* * * * * * * * * *
ATA TCT TGT AAT AAT TCA GGG AAA GAT GGG AAT ACA TCT GCA AAT TCT
TAT AGA ACA TTA TTA AGT CCC TTT CTA CCC TTA TGT AGA CGT TTA AGA
Ile Ser Cys Asn Asn Ser Gly Lys Asp Gly Asn Thr Ser Ala Asn Ser>

100 110 120 130 140
* * * * * * * * *
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
Ala Asp Glu Ser Val Lys Gly Pro Asn Leu Thr Glu Ile Ser Lys Lys>

150 160 170 180 190
* * * * * * * * * *
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
Ile Thr Asp Ser Asn Ala Val Leu Leu Ala Val Lys Glu Val Glu Ala>

200 210 220 230 240
* * * * * * * * * *
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
Leu Leu Ser Ser Ile Asp Glu Ile Ala Ala Lys Ala Ile Gly Lys Lys>

250 260 270 280
* * * * * * * *
ATA CAC CAA AAT AAT GGT TTG GAT ACC GAA TAT AAT CAC AAT GGA TCA
TAT GTG GTT TTA TTA CCA AAC CTA TGG CTT ATA TTA GTG TTA CCT AGT
Ile His Gln Asn Asn Gly Leu Asp Thr Glu Tyr Asn His Asn Gly Ser>

290 300 310 320 330
* * * * * * * * * *
TTG TTA GCG GGA CGT TAT GCA ATA TCA ACC CTA ATA AAA CAA AAA TTA
AAC AAT CGC CCT GCA ATA CGT TAT AGT TGG GAT TAT TTT GTT TTT AAT
Leu Leu Ala Gly Arg Tyr Ala Ile Ser Thr Leu Ile Lys Gln Lys Leu>

340 350 360 370 380
* * * * * * * * *
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
Asp Gly Leu Lys Asn Glu Gly Leu Lys Glu Lys Ile Asp Ala Ala Lys>

FIG. 12A

```
    390         400         410         420         430
 *     *     *     *     *     *     *     *     *     *
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
Lys Cys Ser Glu Thr Phe Thr Asn Lys Leu Lys Glu Lys His Thr Asp>

       440         450         460         470         480
 *     *     *     *     *     *     *     *     *     *
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
Leu Gly Lys Glu Gly Val Thr Asp Ala Asp Ala Lys Glu Ala Ile Leu>

          490         500         510         520
    *     *     *     *     *     *     *     *     *
AAA ACA AAT GGT ACT AAA ACT AAA GGT GCT GAA GAA CTT GGA AAA TTA
TTT TGT TTA CCA TGA TTT TGA TTT CCA CGA CTT CTT GAA CCT TTT AAT
Lys Thr Asn Gly Thr Lys Thr Lys Gly Ala Glu Glu Leu Gly Lys Leu>

530         540         550         560         570
 *     *     *     *     *     *     *     *     *     *
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
Phe Glu Ser Val Glu Val Leu Ser Lys Ala Ala Lys Glu Met Leu Ala>

  580         590         600         610         620
    *     *     *     *     *     *     *     *     *
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
Asn Ser Val Lys Glu Leu Thr Ser Pro Val Val Ala Glu Ser Pro Lys>

     630
 *     *
AAA CCT TAA
TTT GGA ATT
Lys Pro ***>
```

FIG. 12B

```
              10          20          30          40
     *         *     *     *     *     *     *     *     *
ATG AAA AAG AAT ACA TTA AGT GCG ATA TTA ATG ACT TTA TTT TTA TTT
TAC TTT TTC TTA TGT AAT TCA CGC TAT AAT TAC TGA AAT AAA AAT AAA
Met Lys Lys Asn Thr Leu Ser Ala Ile Leu Met Thr Leu Phe Leu Phe>

50          60          70          80          90
 *     *     *     *     *     *     *     *     *     *
ATA TCT TGT AAT AAT TCA GGT GGG GAT ACC GCA TCT ACT AAT CCT GAT
TAT AGA ACA TTA TTA AGT CCA CCC CTA TGG CGT AGA TGA TTA GGA CTA
Ile Ser Cys Asn Asn Ser Gly Gly Asp Thr Ala Ser Thr Asn Pro Asp>

  100         110         120         130         140
    *     *     *     *     *     *     *     *     *
GAG TCT GCA AAA GGA CCT AAT CTT ACA GTA ATA AGC AAA AAA ATT ACA
CTC AGA CGT TTT CCT GGA TTA GAA TGT CAT TAT TCG TTT TTT TAA TGT
Glu Ser Ala Lys Gly Pro Asn Leu Thr Val Ile Ser Lys Lys Ile Thr>

    150         160         170         180         190
*     *     *     *     *     *     *     *     *     *
GAT TCT AAT GCA TTT GTA CTG GCT GTG AAA GAA GTT GAG GCT TTG ATC
CTA AGA TTA CGT AAA CAT GAC CGA CAC TTT CTT CAA CTC CGA AAC TAG
Asp Ser Asn Ala Phe Val Leu Ala Val Lys Glu Val Glu Ala Leu Ile>

       200         210         220         230         240
  *     *     *     *     *     *     *     *     *     *
TCA TCT ATA GAT GAA CTT GCT AAT AAA GCT ATT GGT AAA GTA ATA CAT
AGT AGA TAT CTA CTT GAA CGA TTA TTT CGA TAA CCA TTT CAT TAT GTA
Ser Ser Ile Asp Glu Leu Ala Asn Lys Ala Ile Gly Lys Val Ile His>

          250         260         270         280
    *     *     *     *     *     *     *     *     *
CAA AAT AAT GGT TTA AAT GCT AAT GCG GGT CAA AAC GGA TCA TTG TTA
GTT TTA TTA CCA AAT TTA CGA TTA CGC CCA GTT TTG CCT AGT AAC AAT
Gln Asn Asn Gly Leu Asn Ala Asn Ala Gly Gln Asn Gly Ser Leu Leu>

290         300         310         320         330
  *     *     *     *     *     *     *     *     *     *
GCA GGA GCC TAT GCA ATA TCA ACC CTA ATA ACA GAA AAA TTA AGT AAA
CGT CCT CGG ATA CGT TAT AGT TGG GAT TAT TGT CTT TTT AAT TCA TTT
Ala Gly Ala Tyr Ala Ile Ser Thr Leu Ile Thr Glu Lys Leu Ser Lys>

  340         350         360         370         380
    *     *     *     *     *     *     *     *     *
TTG AAA AAT TCA GAA GAG TTA AAT AAA AAA ATT GAA GAG GCT AAG AAC
AAC TTT TTA AGT CTT CTC AAT TTA TTT TTT TAA CTT CTC CGA TTC TTG
Leu Lys Asn Ser Glu Glu Leu Asn Lys Lys Ile Glu Glu Ala Lys Asn>
```

FIG. 13A

```
    390         400         410         420         430
 *   *     *     *    *     *     *    *     *     *
CAT TCT GAA GCA TTT ACT AAT AGA CTA AAA GGT TCT CAT GCA CAA CTT
GTA AGA CTT CGT AAA TGA TTA TCT GAT TTT CCA AGA GTA CGT GTT GAA
His Ser Glu Ala Phe Thr Asn Arg Leu Lys Gly Ser His Ala Gln Leu>

      440         450         460         470         480
 *     *     *     *     *     *     *     *     *     *
GGA GTT GCT GCT GCT ACT GAT GAT CAT GCA AAA GAA GCT ATT TTA AAG
CCT CAA CGA CGA CGA TGA CTA CTA GTA CGT TTT CTT CGA TAA AAT TTC
Gly Val Ala Ala Ala Thr Asp Asp His Ala Lys Glu Ala Ile Leu Lys>

          490         500         510         520
     *     *     *     *     *     *     *     *     *
TCA AAT CCT ACT AAA GAT AAG GGT GCT AAA GCA CTT AAA GAC TTA TCT
AGT TTA GGA TGA TTT CTA TTC CCA CGA TTT CGT GAA TTT CTG AAT AGA
Ser Asn Pro Thr Lys Asp Lys Gly Ala Lys Ala Leu Lys Asp Leu Ser>

530         540         550         560         570
 *     *     *     *     *     *     *     *     *     *
GAA TCA GTA GAA AGC TTG GCA AAA GCA GCG CAA GAA GCA TTA GCT AAT
CTT AGT CAT CTT TCG AAC CGT TTT CGT CGC GTT CTT CGT AAT CGA TTA
Glu Ser Val Glu Ser Leu Ala Lys Ala Ala Gln Glu Ala Leu Ala Asn>

  580         590         600         610         620
     *     *     *     *     *     *     *     *     *
TCA GTT AAA GAA CTT ACA AAT CCT GTT GTG GCA GAA AGT CCA AAA AAA
AGT CAA TTT CTT GAA TGT TTA GGA CAA CAC CGT CTT TCA GGT TTT TTT
Ser Val Lys Glu Leu Thr Asn Pro Val Val Ala Glu Ser Pro Lys Lys>

    630
 *   *
CCT TAA
GGA ATT
Pro ***>
```

FIG. 13B

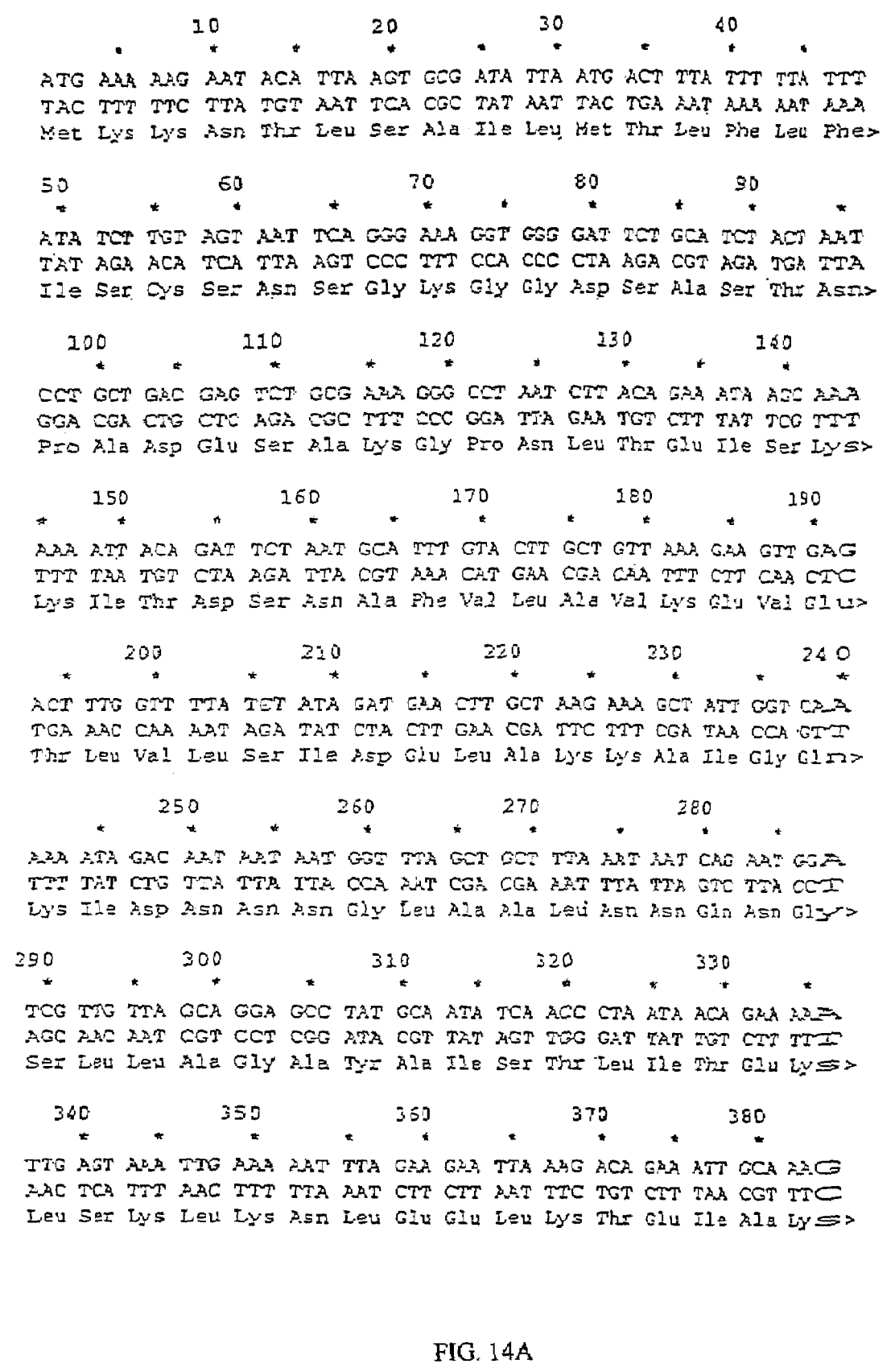

```
         10          20          30          40
ATG AAA AAG AAT ACA TTA AGT GCG ATA TTA ATG ACT TTA TTT TTA TTT
TAC TTT TTC TTA TGT AAT TCA CGC TAT AAT TAC TGA AAT AAA AAT AAA
Met Lys Lys Asn Thr Leu Ser Ala Ile Leu Met Thr Leu Phe Leu Phe>

 50          60          70          80          90
ATA TCT TGT AGT AAT TCA GGG AAA GGT GGG GAT TCT GCA TCT ACT AAT
TAT AGA ACA TCA TTA AGT CCC TTT CCA CCC CTA AGA CGT AGA TGA TTA
Ile Ser Cys Ser Asn Ser Gly Lys Gly Gly Asp Ser Ala Ser Thr Asn>

  100         110         120         130         140
CCT GCT GAC GAG TCT GCG AAA GGG CCT AAT CTT ACA GAA ATA AGC AAA
GGA CGA CTG CTC AGA CGC TTT CCC GGA TTA GAA TGT CTT TAT TCG TTT
Pro Ala Asp Glu Ser Ala Lys Gly Pro Asn Leu Thr Glu Ile Ser Lys>

     150         160         170         180         190
AAA ATT ACA GAT TCT AAT GCA TTT GTA CTT GCT GTT AAA GAA GTT GAG
TTT TAA TGT CTA AGA TTA CGT AAA CAT GAA CGA CAA TTT CTT CAA CTC
Lys Ile Thr Asp Ser Asn Ala Phe Val Leu Ala Val Lys Glu Val Glu>

        200         210         220         230         240
ACT TTG GTT TTA TCT ATA GAT GAA CTT GCT AAG AAA GCT ATT GGT CAA
TGA AAC CAA AAT AGA TAT CTA CTT GAA CGA TTC TTT CGA TAA CCA GTT
Thr Leu Val Leu Ser Ile Asp Glu Leu Ala Lys Lys Ala Ile Gly Gln>

           250         260         270         280
AAA ATA GAC AAT AAT AAT GGT TTA GCT GCT TTA AAT AAT CAG AAT GGA
TTT TAT CTG TTA TTA TTA CCA AAT CGA CGA AAT TTA TTA GTC TTA CCT
Lys Ile Asp Asn Asn Asn Gly Leu Ala Ala Leu Asn Asn Gln Asn Gly>

290         300         310         320         330
TCG TTG TTA GCA GGA GCC TAT GCA ATA TCA ACC CTA ATA ACA GAA AAA
AGC AAC AAT CGT CCT CGG ATA CGT TAT AGT TGG GAT TAT TGT CTT TTT
Ser Leu Leu Ala Gly Ala Tyr Ala Ile Ser Thr Leu Ile Thr Glu Lys>

  340         350         360         370         380
TTG AGT AAA TTG AAA AAT TTA GAA GAA TTA AAG ACA GAA ATT GCA AAG
AAC TCA TTT AAC TTT TTA AAT CTT CTT AAT TTC TGT CTT TAA CGT TTC
Leu Ser Lys Leu Lys Asn Leu Glu Glu Leu Lys Thr Glu Ile Ala Lys>
```

FIG. 14A

```
      390           400           410           420           430
*     *     *     *     *     *     *     *     *     *
GCT AAG AAA TGT TCC GAA GAA TTT ACT AAT AAA CTA AAA AGT GGT CAT
CGA TTC TTT ACA AGG CTT CTT AAA TGA TTA TTT GAT TTT TCA CCA GTA
Ala Lys Lys Cys Ser Glu Glu Phe Thr Asn Lys Leu Lys Ser Gly His>

        440           450           460           470           480
*     *     *     *     *     *     *     *     *     *
GCA GAT CTT GGC AAA CAG GAT GCT ACC GAT GAT CAT GCA AAA GCA GCT
CGT CTA GAA CCG TTT GTC CTA CGA TGG CTA CTA GTA CGT TTT CGT CGA
Ala Asp Leu Gly Lys Gln Asp Ala Thr Asp Asp His Ala Lys Ala Ala>

           490           500           510           520
*     *     *     *     *     *     *     *     *
ATT TTA AAA ACA CAT GCA ACT ACC GAT AAA GGT GCT AAA GAA TTT AAA
TAA AAT TTT TGT GTA CGT TGA TGG CTA TTT CCA CGA TTT CTT AAA TTT
Ile Leu Lys Thr His Ala Thr Thr Asp Lys Gly Ala Lys Glu Phe Lys>

530           540           550           560           570
*     *     *     *     *     *     *     *     *     *
GAT TTA TTT GAA TCA GTA GAA GGT TTG TTA AAA GCA GCT CAA GTA GCA
CTA AAT AAA CTT AGT CAT CTT CCA AAC AAT TTT CGT CGA GTT CAT CGT
Asp Leu Phe Glu Ser Val Glu Gly Leu Leu Lys Ala Ala Gln Val Ala>

   580           590           600           610           620
*     *     *     *     *     *     *     *     *
CTA ACT AAT TCA GTT AAA GAA CTT ACA AGT CCT GTT GTA GCA GAA AGT
GAT TGA TTA AGT CAA TTT CTT GAA TGT TCA GGA CAA CAT CGT CTT TCA
Leu Thr Asn Ser Val Lys Glu Leu Thr Ser Pro Val Val Ala Glu Ser>

     630
*     *     *
CCA AAA AAA CCT TAA
GGT TTT TTT GGA ATT
Pro Lys Lys Pro ***>
```

FIG. 14B

```
            10          20          30          40
ATG AAA AAG AAT ACA TTA AGT GCG ATA TTA ATG ACT TTA TTT TTA TTT
TAC TTT TTC TTA TGT AAT TCA CGC TAT AAT TAC TGA AAT AAA AAT AAA
Met Lys Lys Asn Thr Leu Ser Ala Ile Leu Met Thr Leu Phe Leu Phe>

50          60          70          80          90
ATA TCT TGT AAT AAT TCA GGT GGG GAT TCT GCA TCT ACT AAT CCT GAT
TAT AGA ACA TTA TTA AGT CCA CCC CTA AGA CGT AGA TGA TTA GGA CTA
Ile Ser Cys Asn Asn Ser Gly Gly Asp Ser Ala Ser Thr Asn Pro Asp>

  100         110         120         130         140
GAG TCT GCA AAA GGA CCT AAT CTT ACC GTA ATA AGC AAA AAA ATT ACA
CTC AGA CGT TTT CCT GGA TTA GAA TGG CAT TAT TCG TTT TTT TAA TGT
Glu Ser Ala Lys Gly Pro Asn Leu Thr Val Ile Ser Lys Lys Ile Thr>

    150         160         170         180         190
GAT TCT AAT GCA TTT TTA CTG GCT GTG AAA GAA GTT GAG GCT TTG CTT
CTA AGA TTA CGT AAA AAT GAC CGA CAC TTT CTT CAA CTC CGA AAC GAA
Asp Ser Asn Ala Phe Leu Leu Ala Val Lys Glu Val Glu Ala Leu Leu>

      200         210         220         230         240
TCA TCT ATA GAT GAA CTT TCT AAA GCT ATT GGT AAA AAA ATA AAA AAT
AGT AGA TAT CTA CTT GAA AGA TTT CGA TAA CCA TTT TTT TAT TTT TTA
Ser Ser Ile Asp Glu Leu Ser Lys Ala Ile Gly Lys Lys Ile Lys Asn>

        250         260         270         280
GAT GGT ACT TTA GAT AAC GAA GCA AAT CGA AAC GAA TCA TTG ATA GCA
CTA CCA TGA AAT CTA TTG CTT CGT TTA GCT TTG CTT AGT AAC TAT CGT
Asp Gly Thr Leu Asp Asn Glu Ala Asn Arg Asn Glu Ser Leu Ile Ala>

290         300         310         320         330
GGA GCT TAT GAA ATA TCA AAA CTA ATA ACA CAA AAA TTA AGT GTA TTG
CCT CGA ATA CTT TAT AGT TTT GAT TAT TGT GTT TTT AAT TCA CAT AAC
Gly Ala Tyr Glu Ile Ser Lys Leu Ile Thr Gln Lys Leu Ser Val Leu>

  340         350         360         370         380
AAT TCA GAA GAA TTA AAG AAA AAA ATT AAA GAG GCT AAG GAT TGT TCC
TTA AGT CTT CTT AAT TTC TTT TTT TAA TTT CTC CGA TTC CTA ACA AGG
Asn Ser Glu Glu Leu Lys Lys Lys Ile Lys Glu Ala Lys Asp Cys Ser>
```

FIG. 15A

OspC-TRO

```
    390              400             410             420              430
 *     *      *        *      *       *       *        *       *       *
GAA AAA TTT ACT ACT AAG CTA AAA GAT AGT CAT GCA GAG CTT GGT ATA
CTT TTT AAA TGA TGA TTC GAT TTT CTA TCA GTA CGT CTC GAA CCA TAT
Glu Lys Phe Thr Thr Lys Leu Lys Asp Ser His Ala Glu Leu Gly Ile>

        440              450             460             470              480
   *      *        *       *       *       *       *       *       *       *
CAA AGC GTT CAG GAT GAT AAT GCA AAA AAA GCT ATT TTA AAA ACA CAT
GTT TCG CAA GTC CTA CTA TTA CGT TTT TTT CGA TAA AAT TTT TGT GTA
Gln Ser Val Gln Asp Asp Asn Ala Lys Lys Ala Ile Leu Lys Thr His>

           490              500             510             520
      *      *       *        *       *       *       *       *       *
GGA ACT AAA GAC AAG GGT GCT AAA GAA CTT GAA GAG TTA TTT AAA TCA
CCT TGA TTT CTG TTC CCA CGA TTT CTT GAA CTT CTC AAT AAA TTT AGT
Gly Thr Lys Asp Lys Gly Ala Lys Glu Leu Glu Glu Leu Phe Lys Ser>

530            540              550             560             570
  *      *       *       *       *       *       *       *       *       *
CTA GAA AGC TTG TCA AAA GCA GCG CAA GCA GCA TTA ACT AAT TCA GTT
GAT CTT TCG AAC AGT TTT CGT CGC GTT CGT CGT AAT TGA TTA AGT CAA
Leu Glu Ser Leu Ser Lys Ala Ala Gln Ala Ala Leu Thr Asn Ser Val>

   580            590              600             610             620
     *      *       *       *       *       *       *       *       *
AAA GAG CTT ACA AAT CCT GTT GTG GCA GAA AGT CCA AAA AAA CCT TAA
TTT CTC GAA TGT TTA GGA CAA CAC CGT CTT TCA GGT TTT TTT GGA ATT
Lys Glu Leu Thr Asn Pro Val Val Ala Glu Ser Pro Lys Lys Pro ***>
```

FIG. 15B

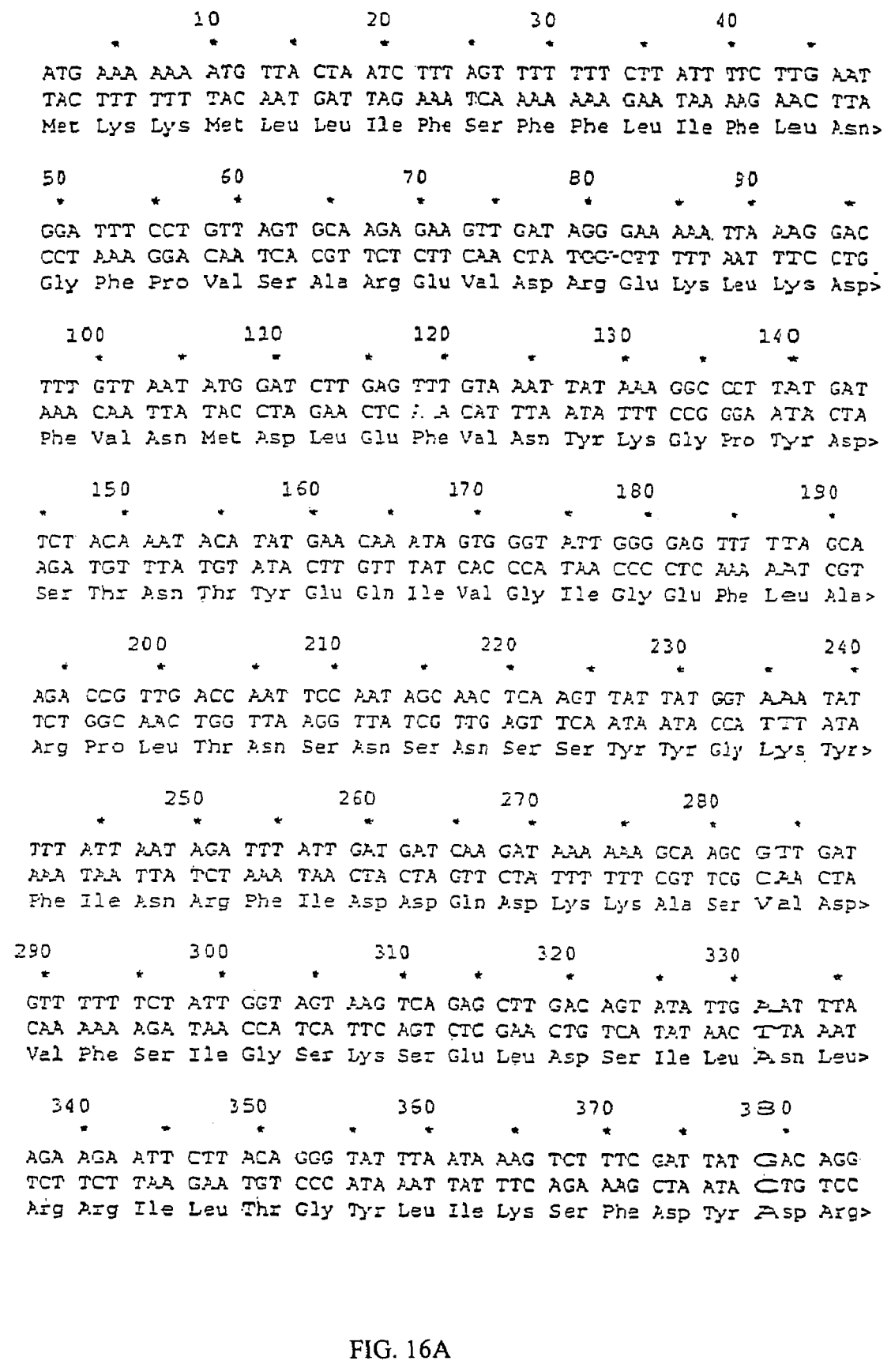

```
         10         20         30          40
ATG AAA AAA ATG TTA CTA ATC TTT AGT TTT TTT CTT ATT TTC TTG AAT
TAC TTT TTT TAC AAT GAT TAG AAA TCA AAA AAA GAA TAA AAG AAC TTA
Met Lys Lys Met Leu Leu Ile Phe Ser Phe Phe Leu Ile Phe Leu Asn>

50         60          70         80         90
GGA TTT CCT GTT AGT GCA AGA GAA GTT GAT AGG GAA AAA TTA AAG GAC
CCT AAA GGA CAA TCA CGT TCT CTT CAA CTA TCC CTT TTT AAT TTC CTG
Gly Phe Pro Val Ser Ala Arg Glu Val Asp Arg Glu Lys Leu Lys Asp>

 100        110        120         130        140
TTT GTT AAT ATG GAT CTT GAG TTT GTA AAT TAT AAA GGC CCT TAT GAT
AAA CAA TTA TAC CTA GAA CTC AAA CAT TTA ATA TTT CCG GGA ATA CTA
Phe Val Asn Met Asp Leu Glu Phe Val Asn Tyr Lys Gly Pro Tyr Asp>

   150        160         170         180         190
TCT ACA AAT ACA TAT GAA CAA ATA GTG GGT ATT GGG GAG TTT TTA GCA
AGA TGT TTA TGT ATA CTT GTT TAT CAC CCA TAA CCC CTC AAA AAT CGT
Ser Thr Asn Thr Tyr Glu Gln Ile Val Gly Ile Gly Glu Phe Leu Ala>

       200        210         220        230        240
AGA CCG TTG ACC AAT TCC AAT AGC AAC TCA AGT TAT TAT GGT AAA TAT
TCT GGC AAC TGG TTA AGG TTA TCG TTG AGT TCA ATA ATA CCA TTT ATA
Arg Pro Leu Thr Asn Ser Asn Ser Asn Ser Ser Tyr Tyr Gly Lys Tyr>

         250        260         270         280
TTT ATT AAT AGA TTT ATT GAT GAT CAA GAT AAA AAA GCA AGC GTT GAT
AAA TAA TTA TCT AAA TAA CTA CTA GTT CTA TTT TTT CGT TCG CAA CTA
Phe Ile Asn Arg Phe Ile Asp Asp Gln Asp Lys Lys Ala Ser Val Asp>

290         300        310        320        330
GTT TTT TCT ATT GGT AGT AAG TCA GAG CTT GAC AGT ATA TTG AAT TTA
CAA AAA AGA TAA CCA TCA TTC AGT CTC GAA CTG TCA TAT AAC TTA AAT
Val Phe Ser Ile Gly Ser Lys Ser Glu Leu Asp Ser Ile Leu Asn Leu>

 340        350        360        370        380
AGA AGA ATT CTT ACA GGG TAT TTA ATA AAG TCT TTC GAT TAT GAC AGG
TCT TCT TAA GAA TGT CCC ATA AAT TAT TTC AGA AAG CTA ATA CTG TCC
Arg Arg Ile Leu Thr Gly Tyr Leu Ile Lys Ser Phe Asp Tyr Asp Arg>
```

FIG. 16A

```
    390         400         410         420         430
TCT AGT GCA GAA TTA ATT GCT AAG GTT ATT ACA ATA TAT AAT GCT GTT
AGA TCA CGT CTT AAT TAA CGA TTC CAA TAA TGT TAT ATA TTA CGA CAA
Ser Ser Ala Glu Leu Ile Ala Lys Val Ile Thr Ile Tyr Asn Ala Val>

       440         450         460         470         480
TAT AGA GGA GAT TTG GAT TAT TAT AAA GGG TTT TAT ATT GAG GCT GCT
ATA TCT CCT CTA AAC CTA ATA ATA TTT CCC AAA ATA TAA CTC CGA CGA
Tyr Arg Gly Asp Leu Asp Tyr Tyr Lys Gly Phe Tyr Ile Glu Ala Ala>

          490         500         510         520
TTA AAG TCT TTA AGT AAA GAA AAT GCA GGT CTT TCT AGG GTT TAT AGT
AAT TTC AGA AAT TCA TTT CTT TTA CGT CCA GAA AGA TCC CAA ATA TCA
Leu Lys Ser Leu Ser Lys Glu Asn Ala Gly Leu Ser Arg Val Tyr Ser>

530         540         550         560         570
CAG TGG GCT GGA AAG ACA CAA ATA TTT ATT CCT CTT AAA AAG GAT ATT
GTC ACC CGA CCT TTC TGT GTT TAT AAA TAA GGA GAA TTT TTC CTA TAA
Gln Trp Ala Gly Lys Thr Gln Ile Phe Ile Pro Leu Lys Lys Asp Ile>

  580         590         600         610         620
TTG TCT GGA AAT ATT GAG TCT GAC ATT GAT ATT GAC AGT TTA GTT ACA
AAC AGA CCT TTA TAA CTC AGA CTG TAA CTA TAA CTG TCA AAT CAA TGT
Leu Ser Gly Asn Ile Glu Ser Asp Ile Asp Ile Asp Ser Leu Val Thr>

     630         640         650         660         670
GAT AAG GTG GTG GCA GCT CTT TTA AGT GAA AAT GAA GCA GGT GTT AAC
CTA TTC CAC CAC CGT CGA GAA AAT TCA CTT TTA CTT CGT CCA CAA TTG
Asp Lys Val Val Ala Ala Leu Leu Ser Glu Asn Glu Ala Gly Val Asn>

        680         690         700         710         720
TTT GCA AGA GAT ATT ACA GAT ATT CAA GGC GAA ACT CAT AAG GCA GAT
AAA CGT TCT CTA TAA TGT CTA TAA GTT CCG CTT TGA GTA TTC CGT CTA
Phe Ala Arg Asp Ile Thr Asp Ile Gln Gly Glu Thr His Lys Ala Asp>

           730         740         750         760
CAA GAT AAA ATT GAT ATT GAA TTA GAC AAT ATT CAT GAA AGT GAT TCC
GTT CTA TTT TAA CTA TAA CTT AAT CTG TTA TAA GTA CTT TCA CTA AGG
Gln Asp Lys Ile Asp Ile Glu Leu Asp Asn Ile His Glu Ser Asp Ser>

770         780         790         800         810
AAT ATA ACA GAA ACT ATT GAA AAT TTA AGG GAT CAG CTT GAA AAA GCT
TTA TAT TGT CTT TGA TAA CTT TTA AAT TCC CTA GTC GAA CTT TTT CGA
Asn Ile Thr Glu Thr Ile Glu Asn Leu Arg Asp Gln Leu Glu Lys Ala>
```

FIG. 16B

```
        820                 830                 840                 850                 860
ACA GAT GAA GAG CAT AAA AAA GAG ATT GAA AGT CAG GTT GAT GCT AAA
TGT CTA CTT CTC GTA TTT TTT CTC TAA CTT TCA GTC CAA CTA CGA TTT
Thr Asp Glu Glu His Lys Lys Glu Ile Glu Ser Gln Val Asp Ala Lys>

        870                 880                 890                 900                 910
AAG AAA CAA AAG GAA GAG CTA GAT AAA AAG GCA ATA AAT CTT GAT AAA
TTC TTT GTT TTC CTT CTC GAT CTA TTT TTC CGT TAT TTA GAA CTA TTT
Lys Lys Gln Lys Glu Glu Leu Asp Lys Lys Ala Ile Asn Leu Asp Lys>

        920                 930                 940                 950                 960
GCT CAG CAA AAA TTA GAT TCT GCT GAA GAT AAT TTA GAT GTT CAA AGA
CGA GTC GTT TTT AAT CTA AGA CGA CTT CTA TTA AAT CTA CAA GTT TCT
Ala Gln Gln Lys Leu Asp Ser Ala Glu Asp Asn Leu Asp Val Gln Arg>

        970                 980                 990                 1000
AAT ACT GTT AGA GAG AAA ATT CAA GAG GAT ATT AAC GAA ATT AAC AAG
TTA TGA CAA TCT CTC TTT TAA GTT CTC CTA TAA TTG CTT TAA TTG TTC
Asn Thr Val Arg Glu Lys Ile Gln Glu Asp Ile Asn Glu Ile Asn Lys>

1010                1020                1030                1040                1050
GAA AAG AAT TTA CCA AAG CCT GGT GAT GTA AGT TCT CCT AAA GTT GAT
CTT TTC TTA AAT GGT TTC GGA CCA CTA CAT TCA AGA GGA TTT CAA CTA
Glu Lys Asn Leu Pro Lys Pro Gly Asp Val Ser Ser Pro Lys Val Asp>

1060                1070                1080                1090                1100
AAG CAA CTA CAA ATA AAA GAG AGC CTG GAA GAT TTG CAG GAG CAG CTT
TTC GTT GAT GTT TAT TTT CTC TCG GAC CTT CTA AAC GTC CTC GTC GAA
Lys Gln Leu Gln Ile Lys Glu Ser Leu Glu Asp Leu Gln Glu Gln Leu>

    1110                1120                1130                1140                1150
AAA GAA ACT GGT GAT GAA AAT CAG AAA AGA GAA ATT GAA AAG CAA ATT
TTT CTT TGA CCA CTA CTT TTA GTC TTT TCT CTT TAA CTT TTC GTT TAA
Lys Glu Thr Gly Asp Glu Asn Gln Lys Arg Glu Ile Glu Lys Gln Ile>

        1160                1170                1180                1190                1200
GAA ATC AAA AAA AGT GAT GAA AAG CTT TTA AAA AGT AAA GAT GAT AAA
CTT TAG TTT TTT TCA CTA CTT TTC GAA AAT TTT TCA TTT CTA CTA TTT
Glu Ile Lys Lys Ser Asp Glu Lys Leu Leu Lys Ser Lys Asp Asp Lys>

        1210                1220                1230                1240
GCA AGT AAA GAT GGT AAA GCC TTG GAT CTT GAT CGA GAA TTA AAT TCT
CGT TCA TTT CTA CCA TTT CGG AAC CTA GAA CTA GCT CTT AAT TTA AGA
Ala Ser Lys Asp Gly Lys Ala Leu Asp Leu Asp Arg Glu Leu Asn Ser>
```

FIG. 16C

```
1250       1260       1270       1280       1290
AAA GCT TCT AGC AAA GAA AAA AGT AAA GCC AAG GAA GAA GAA ATA ACC
TTT CGA AGA TCG TTT CTT TTT TCA TTT CGG TTC CTT CTT CTT TAT TGG
Lys Ala Ser Ser Lys Glu Lys Ser Lys Ala Lys Glu Glu Glu Ile Thr>

1300       1310       1320       1330       1340
AAG GGT AAG TCA CAG AAA AGC TTA GGC GAT TTG AAT AAT GAT GAA AAT
TTC CCA TTC AGT GTC TTT TCG AAT CCG CTA AAC TTA TTA CTA CTT TTA
Lys Gly Lys Ser Gln Lys Ser Leu Gly Asp Leu Asn Asn Asp Glu Asn>

1350       1360       1370       1380       1390
CTT ATG ATG CCA GAA GAT CAA AAA TTA CCT GAG GTT AAA AAA TTA GAT
GAA TAC TAC GGT CTT CTA GTT TTT AAT GGA CTC CAA TTT TTT AAT CTA
Leu Met Met Pro Glu Asp Gln Lys Leu Pro Glu Val Lys Lys Leu Asp>

1400       1410       1420       1430       1440
AGC AAA AAA GAA TTT AAA CCT GTT TCT GAG GTT GAG AAA TTA GAT AAG
TCG TTT TTT CTT AAA TTT GGA CAA AGA CTC CAA CTC TTT AAT CTA TTC
Ser Lys Lys Glu Phe Lys Pro Val Ser Glu Val Glu Lys Leu Asp Lys>

1450       1460       1470       1480
ATT TTC AAG TCT AAT AAC AAT GTT GGA GAA TTA TCA CCG TTA GAT AAA
TAA AAG TTC AGA TTA TTG TTA CAA CCT CTT AAT AGT GGC AAT CTA TTT
Ile Phe Lys Ser Asn Asn Asn Val Gly Glu Leu Ser Pro Leu Asp Lys>

1490       1500       1510       1520       1530
TCT TCT TAT AAA GAC ATT GAT TCA AAA GAG GAG ACA GTT AAT AAA GAT
AGA AGA ATA TTT CTG TAA CTA AGT TTT CTC CTC TGT CAA TTA TTT CTA
Ser Ser Tyr Lys Asp Ile Asp Ser Lys Glu Glu Thr Val Asn Lys Asp>

1540       1550       1560       1570       1580
GTT AAT TTG CAA AAG ACT AAG CCT CAG GTT AAA GAC CAA GTT ACT TCT
CAA TTA AAC GTT TTC TGA TTC GGA GTC CAA TTT CTG GTT CAA TGA AGA
Val Asn Leu Gln Lys Thr Lys Pro Gln Val Lys Asp Gln Val Thr Ser>

1590       1600       1610       1620       1630
TTG AAT GAA GAT TTG ACT ACT ATG TCT ATA GAT TCC AGT AGT CCT GTA
AAC TTA CTT CTA AAC TGA TGA TAC AGA TAT CTA AGG TCA TCA GGA CAT
Leu Asn Glu Asp Leu Thr Thr Met Ser Ile Asp Ser Ser Ser Pro Val>

1640       1650       1660       1670       1680
TTT TTA GAG GTT ATT GAT CCA ATT ACA AAT TTA GGA ACT CTT CAA CTT
AAA AAT CTC CAA TAA CTA GGT TAA TGT TTA AAT CCT TGA GAA GTT GAA
Phe Leu Glu Val Ile Asp Pro Ile Thr Asn Leu Gly Thr Leu Gln Leu>
```

FIG. 16D

```
        1690        1700        1710        1720
ATT GAT TTA AAT ACT GGT GTT AGG CTT AAA GAA AGC ACT CAG CAA GGC
TAA CTA AAT TTA TGA CCA CAA TCC GAA TTT CTT TCG TGA GTC GTT CCG
Ile Asp Leu Asn Thr Gly Val Arg Leu Lys Glu Ser Thr Gln Gln Gly>

1730        1740        1750        1760        1770
ATT CAG CGG TAT GGA ATT TAT GAA CGT GAA AAA GAT TTG GTT GTT ATT
TAA GTC GCC ATA CCT TAA ATA CTT GCA CTT TTT CTA AAC CAA CAA TAA
Ile Gln Arg Tyr Gly Ile Tyr Glu Arg Glu Lys Asp Leu Val Val Ile>

 1780        1790        1800        1810        1820
AAA ATG GAT TCA GGA AAA GCT AAG CTT CAG ATA CTT GAT AAA CTT GAA
TTT TAC CTA AGT CCT TTT CGA TTC GAA GTC TAT GAA CTA TTT GAA CTT
Lys Met Asp Ser Gly Lys Ala Lys Leu Gln Ile Leu Asp Lys Leu Glu>

   1830        1840        1850        1860        1870
AAT TTA AAA GTG GTA TCA GAG TCT AAT TTT GAG ATT AAT AAA AAT TCA
TTA AAT TTT CAC CAT AGT CTC AGA TTA AAA CTC TAA TTA TTT TTA AGT
Asn Leu Lys Val Val Ser Glu Ser Asn Phe Glu Ile Asn Lys Asn Ser>

      1880        1890        1900        1910        1920
TCT CTT TAT GTT GAT TCT AAA ATG ATT TTA GTA GCT GTT AGG GAT AAA
AGA GAA ATA CAA CTA AGA TTT TAC TAA AAT CAT CGA CAA TCC CTA TTT
Ser Leu Tyr Val Asp Ser Lys Met Ile Leu Val Ala Val Arg Asp Lys>

         1930        1940        1950        1960
GAT AGT AGT AAT GAT TGG AGA TTG GCC AAA TTT TCT CCT AAA AAT TTA
CTA TCA TCA TTA CTA ACC TCT AAC CGG TTT AAA AGA GGA TTT TTA AAT
Asp Ser Ser Asn Asp Trp Arg Leu Ala Lys Phe Ser Pro Lys Asn Leu>

1970        1980        1990        2000        2010
GAT GAG TTT ATT CTT TCA GAG AAT AAA ATT ATG CCT TTT ACT AGC TTT
CTA CTC AAA TAA GAA AGT CTC TTA TTT TAA TAC GGA AAA TGA TCG AAA
Asp Glu Phe Ile Leu Ser Glu Asn Lys Ile Met Pro Phe Thr Ser Phe>

 2020        2030        2040        2050        2060
TCT GTG AGA AAA AAT TTT ATT TAT TTG CAA GAT GAG TTT AAA AGT CTA
AGA CAC TCT TTT TTA AAA TAA ATA AAC GTT CTA CTC AAA TTT TCA GAT
Ser Val Arg Lys Asn Phe Ile Tyr Leu Gln Asp Glu Phe Lys Ser Leu>

   2070        2080        2090        2100
GTT ATT TTA GAT GTA AAT ACT TTA AAA AAA GTT AAG TA
CAA TAA AAT CTA CAT TTA TGA AAT TTT TTT CAA TTC AT
Val Ile Leu Asp Val Asn Thr Leu Lys Lys Val Lys Xxx>
```

FIG. 16E

```
   1 ATGAAAAAAT TGTTACTAAT CTTTAGTTTT TTTCTTATTT CTTTGAATGG ATTTCCTCTT
  61 AATTCAAGGG AAGTTGATAA GGAAAAATTA AAGGATTTTG TTAATATGGA TCTTGAGTTT
 121 GTAAACTATA AAGGTCCTTA TGATTCTACA AATACATATG AACAAATAGT AGGTATTGGT
 181 GAGTTTTTAG CAAGACCATT GATTAATTCC AATAGCAACT CAATTTATTA TGGTAAATAT
 241 TTTATTAATA GATTTATTGA TGATCAAGAT AAAAAAGCAA GCGTTGATGT TTTTTCTATT
 301 GGTAGTAGGT CACAGCTTGA CAGTATATTG AATCTAAGAA GAATTCTTAC AGGGTATTTG
 361 ATAAAGTCTT TTGATTATGA AAGATCTAGT GCTGAATTAA TTGCTAAGGT TATTACAATA
 421 CATAATGCTG TTTATAGAGG GGATTTAAAT TATTATAAAG AGGTTTATAT TGAGGCTGCT
 481 TTAAAGTCTT TAACTAAAGA AAATGCAGGT CTTTCTAGAG TGTACAGTCA ATGGGCTGGA
 541 AAGACACAAA TATTTATTCC TCTTAAAAAG AATATTTTAT CTGGAAAAGT TGAGTCTGAC
 601 ATTGATATTG ACAGTTTGGT TACAGATAAG GTTGTGGCAG GTGTTTTAAG CGAGAATGAA
 661 GCAGGTGTTA ACTTTGCAAG AGATATTACA GATATTCAAG GCGAAACTCA TAAAGCAGAT
 721 CAAGATAAAA TTGATATTGA ATTAGATAAT GTTCATAAAA GTGATTCCAA TATAACAGAG
 781 ACTATTGAGA ATTTAAGAGA TCAGCTTGAA AAGGCTACAG ATGAAGAGCA TAGAAAAGAG
 841 ATTGAAAGTC AGGTTGATGC TAAAAAGAAA CAAAAAGAAG AACTAGATAA AAAGGCAATC
 901 GATCTTGATA AAGCCCAACA AAAATTAGAT TCTTCTGAAG ATAATTTAGA TATTCAAAGC
 961 GATACTGTTA GAGAGAAGAT TCAAGAGGAT ATTGACGAGA TTAATAAAGA AAAGAATTTG
1021 CCAAAACCTG GTGATGTAAG TTCTCCTAAA GTTGATAAGC AGCTACAAAT AAAAGAGAGT
1081 CTAGAAGACT TGCAGGAACA GCTTAAAGAA ACTAGCGATG AAAATCAAAA AAGAGAAATT
1141 GAAAAGCAAA TTGAAATCAA AAAAAGTGAT GAAGAACTTT TAAAAAGTAA AGATCCTAAA
1201 GCATTAGATC TTAATGGAGA TTTAAATTCT AAAGTTTCTA GTAAAGAAAA AATTAAAGGC
1261 AAAGAAGGAG AAATAGTCAA AGAGGAATCA AAGGCAAGTT TAGCTGATTT GAATAATGAC
1321 GAAAATCTTA TGAGGCCGGA AGATCAAAAA TTATCTGAGG ATAAAAAATT AGATAGTAAA
1381 AAAAATTTAA AACCTGTTTC TGAGATTGAG AGAGTAAATG AAATTTCGAA GTCTAACAAC
1441 AATGAGATTA GTGAATCATC ACCATTATAT AAGCCTTCTT ATAGCGATAT GGATTCAAAA
1501 GAGGGTATAG ATAATAAAGA TGTTAACTTG CAAGAAACCA AGTCTCAAAC TAAAAGTCAA
1561 CCTACTTCTT TAAATCAAGA TTTGACTACT ATGTCTATAG ATTCTAGTAA TCCTGTATTT
1621 TTAGAGGTTA TTGATCCTAT TACAAATTTA GGAACGCTTC AACTTATTGA TTTGAATACC
1681 GGTGTTAGAC TTAAAGAAAG TACTCAGCAA GGCATTCAGC GGTATGGAAT TTATGAACGT
1741 GAAAAAGATT TAGTTGTTAT TAAAATGGAT TCAGGAAAAG CCAAGCTTCA AATACTTAAT
1801 AAACTTGAGA ATTTAAAAGT GATATCGGAG TCTAATTTTG AGATTAATAA AAATTCATCT
1861 CTTTATGTTG ACTCTAAAAT GATTTTAGTA GTTGTGAGAG ATAGTGGTAA TGTTTGGAGA
1921 TTGGCTAAAT TTTCTCCTAA AAATTTAAAT GAGTTTATTC TTTCAGAGAA TAAAATTTTG
1981 CCTTTTACTA GCTTTTCTGT GAGAAAGAAT TTTATTTATT TGCAGGATGA GTTTAAAAGT
2041 CTTATTACTT TAGATGTAAA TACTTTAAAA AAAGTTAAGT A
```

FIG. 17

1 ATGAAAAAAA TGTTACTAAT CTTTAGTTTT TTTCTTGTTT TTTTAAATGG ATTTCCTCTT
61 AATGCAAGGG AAGTTGATAA GGAAAAATTA AAGGACTTTG TTAATATGGA TCTTGAATTT
121 GTTAATTACA AGGGTCCTTA TGATTCTACA GATACATATG AACAAATAGT AGGTATTGGG
181 GAGTTTTTAG CAAGGCCGTT GAACAATTCC AATAGTAATT CAAGTTATTA TGGTAAAATAT
241 TTTGTTAATA GATTTATTGA CGATCAAGAT AAAAAAGCAA GTGTTGATAT TTTTTCTATT
301 GGTAGTAAGT CAGAGCTTGA TAGTATATTA AATCTAAGAA GAATTCTTAC AGGGTATTTA
361 ATGAAGTCTT TTGATTATGA GAGGTCTAGT GCGGAATTAA TTGCTAAAGC TATTACAATA
421 TATAATGCTG TTTATAGAGG AGATTTAGAT TATTACAAAG AGTTTTATAT TGAGGCTTCT
481 TTGAAGTCTT TGACTAAAGA AAATGCAGGT CTTTCTAGGG TGTACAGTCA ATGGGCTGGG
541 AAGACACAAA TATTTATTCC TCTTAAAAAG AATATTTTAT CTGGAAATGT TGAGTCTGAC
601 ATTGATATTG ATAGTTTGGT TACAGATAAG GTGGTGGCAG CTCTTTTAAG TGAGAATGAA
661 TCAGGTGTTA ACTTTGCAAG AGATATTACA GACATTCAAG GCGAAACTCA TAAAGCAGAT
721 CAAGATAAAA TTGATATTGA ATTAGATAAT TTTCATGAAA GTGATTCCAA TATAACAGAA
781 ACTATTGAGA ATTTAAGGGA TCAGCTTGAA AAAGCTACAG ATGAAGAGCA TAAAAAAGAG
841 ATTGAAAGTC AGGTTGATGC TAAAAAGAAA CAAAAGGAAG AATTAGATAA AAAGGCAATT
901 GATCTTGATA AAGCTCAACA AAAATTAGAT TTTGCTGAAG ATAATCTAGA TATTCAAAGG
961 GATACTGTTA GAGAGAAGCT TCAAGAAAAT ATTAACGAGA CTAATAAGGA AAAGAATTTA
1021 CCAAAGCCTG GTGATGTAAG TTCTCCTAAG GTTGATAAGC AGTTGCAGAT AAAAGAGAGT
1081 CTAGAAGATT TGCAAGAGCA GCTTAAAGAA GCTAGTGATG AAAATCAAAA AAGAGAAATA
1141 GAAAAGCAAA TTGAAATCAA AAAAAATGAT GAAGAACTTT TTAAAAATAA AGATCATAAA
1201 GCATTAGATC TTAAGCAAGA ATTAAATTCT AAAGCTTCTA GTAAAGAAAA AATTGAAGGC
1261 GAAGAAGAGG ATAAAGAATT AGATAGTAAA AAAAATTTAG AGCCTGTTTC TGAGGCTGAT
1321 AAAGTAGATA AAATTTCCAA GTCTAACAAC AATGAGGTTA GTAAATTATC CCCGTTAGAT
1381 GAGCCTTCTT ATAGCGACAT TGATTCGAAA GAGGGTGTAG ATAACAAAGA TGTTGATTTG
1441 CAAAAAACTA AACCCCAAGT TGAAAGTCAA CCTACTTCGT TAAATGAAGA TTTGATTGAT
1501 GTGTCTATAG ATTCCAGTAA TCCTGTCTTT TTAGAGGTTA TCGATCCGAT TACAAATTTA
1561 GGAACGCTTC AACTTATTGA TTTGAATACC GGTGTTAGAC TTAAAGAAAG TGCTCAACAA
1621 GGTATTCAGC GATATGGAAT TTATGAACGT GAAAAAGATT TGGTTGTTAT TAAAATAGAT
1681 TCAGGAAAAG CTAAGCTTCA GATACTTGAT AAACTCGAGA ATTTAAAAGT GATATCAGAG
1741 TCTAATTTTG AGATTAATAA AAATTCATCT CTTTATGTTG ACTCTAGAAT GATTTTAGTA
1801 GTTGTTAAGG ACGATAGTAA TGCTTGGAGA TTGGCTAAAT TTTCTCCTAA AAATTTAGAT
1861 GAATTTATTC TGTCAGAAAA TAAAATTTTG CCTTTTACTA GCTTTGCTGT GAGAAAGAAT
1921 TTTATTTATT TGCAAGATGA ACTTAAAAGC TTAGTTACTT TAGATGTAAA TACTTTAAAA
1981 AAAGTTAAGT A

FIG. 18

```
   1 ATGAAAAAAA TGTTACTAAT CTTTAGTTTT TTTCTTATTT CTTTGAATGG ATTTCCCCTT
  61 AATGCAAGGG AAGTTGATAA GGAAAAATTA AAGGACTTTG TTAATATGGA TCTTGAGTTT
 121 GTAAACTATA AAGGTCCTTA TGATTCTACA AATACATATG AACAAATAGT AGGTATTGGT
 181 GAGTTTTTAG CAAGACCATT GATTAATTTC AATAGCAACT CAAGTTATTA TGGTAAATAT
 241 TTTATTAATA GATTTATTGA CGATCAAGAT AAAAAAGCAA GCGTTGATGT TTTTTCTATT
 301 AGTAGTAAGT CACAGCTTGA CAGTATATTG AATTTAAGAA GAATTCTTAC AGGGTATTTG
 361 ATAAAGTCTT TTGATTATGA AAGATCTAGT GCTGAATTAA TTGCCAAGGT TATTACAATA
 421 CATAATGCTG TTTATAGAGG TGATTTAAAT TATTATAAAG AGTTTTATAT TGAGTCTGCT
 481 TTAAAGTCTT TAACTAAAGA AAATGCAGGT CTTTCTAGAG TGTACAGTCA ATGGGCTGGA
 541 AAGACACAAA TATTTATTCC TCTTAAAAAG AATATTTTAT CTGGAAAAAT TGAGTCTGAC
 601 ATTGATATTG ATAGTTTGGT TACAGATAAG GTTGTGGCAG CTGTTTTAAG CGAAAATGAA
 661 GCAGGTGTTA ACTTTGCAAG GGATATTACA GATATTCAAG GAGAAACTCA TAAAGCAGAT
 721 CAAGATAAAA TTGATATTGA ATTAGATAAT GTTCATGAAA GTGATTCCAA TATAACAGAA
 781 ACTATTGAGA ATTTAAGAGA TCAGCTTGAA AAGGCTACAG ATGAAGAGCA TAGAAAAGAG
 841 ATTGAAAGTC AAGTTGATGC TAAAAAGAAA CAAAAAGAAG AACTAGATAA AAAGGCAATC
 901 GATCTTGATA AAGCCCAACA AAAATTAGAT TTTTCTGAAG ATAATTTAGA TATTCAAAGG
 961 GATACTGTTA GAGAGAAGAT TCAAGAGGAT ATTAACGAGA TTAATAAGGA AAAGAATTTA
1021 CCAAAACCTG GTGATGTAAG TTCTCCTTAA GTTGATAAGC AGCTACAAAT AAAAGAGAGT
1081 CTAGAAGACT TGCAGGAGCA GCTTAAAGAA ACTAGCGATG AAAATCAAAA AAGAGAAATT
1141 GAAAAGCAAA TTGAAATCAA AAAAAGTGAT GAAGAACTTT TAAAAAGCAA AGATCCTAAA
1201 GCATTAGATC TTAATCGAGA TTTAAATTCT AAAGCTTCTA GTAAAGAAAA AATTAAAGGC
1261 AAAGAAAAAG AAATAGTCAA AGAGAAATCA AAGGTAAGTT TAGGTGATTT GGATAAATGAC
1321 GAAACCCTTA TGACGCCGGA AGATCAAAAA TTATCTGAGG ATAAAAAATT AGATAGTAAA
1381 AAAAATTTAA AACCTGTTTC TGAGATTGAG AGAGTAAATG AAATTTCAAA GTCTAACAAC
1441 AATGAGGTTA GCAAATCATC ACCATTAGAT AAGCCTTCTT ATAGTGATAT CGATTTCAAAA
1501 GAGGTTGTAG ATAATAAAGA TGTTAATTTG CAAGAAACCA AGCCTCAAGC TAAAAGTCAA
1561 TCTACTTCTT TAAATCAAGA TTTGATTACT ATGTCTATAG ATTCTAGTAA TCCTGTATTT
1621 TTAGAGGTTA TTGATCCTAT TACAAATTTA GGAATGCTTC AACTTATTGA TTTAAATACT
1681 GGTGTTAGAC TTAAAGAAAG CACTCAGCAA GGCATTCAGC GTTATGGAAT TTATGAACGT
1741 GAAAAAGATT TAGTTGTTAT TAAAATGGAT TCAGGAAAAG CTAAGCTTCA AATACTTAAT
1801 AAACTTGAGA ATTTAAAAGT GATATCAGAG TCTAATTTTG AGATTAATAA AAATTTCATCT
1861 CTTTATGTTG ACTCTAAAAT GATTTTAGTA GCTGTGAAAG ATAGTGGTTA TGTTTTGGAGA
1921 TTGGCTAAAT TTTCTCCTAA AAATTTAGAT GAGTTTATTC TTTCAGAGAA TAAAATTTTG
1981 CCTTTTACTA GCTTTTCTGT GAGAAAGAAT TTTATTTATT TGCAAGATGA GTTTAAAAGT
2041 CTTATTACTT TAGATGTAAA TACTTTAAAA AAAGTTAAGT A
```

FIG. 19

```
   1 ATGAAAAAAA TGTTACTAAT CTTTAGTTTT TTTCTTGTTT TTTTAAATGG ATTTCCTCTT
  61 AATGCAAGGG AAGTTGATAA GGAAAAATTA AAGGACTTTG TTAATATGGA TCTTGAATTT
 121 GTTAATTACA AGGGTCCTTA TGATTCTACA AATACATATG AACAAATAGT AGGTATTGGG
 181 GAGTTTTTAG CAAGGCCGTT GATCAATTCC AATAGTAATT CAAGTTATTA TGGTAAATAT
 241 TTTGTTAATA GATTTATTGA CGATCAAGAT AAAAAAGCAA GTGTTGATAT TTTTTCTATT
 301 GGTAGTAAGT CAGAGCTTGA TAGTATATTA AATCTAAGAA GAATTCTTAC AGGGTATTTA
 361 ATGAAGTCTT TTGATTATGA GAGGTCTAGT GCGGAATTAA TTGCTAAAGC TATTACAATA
 421 TATAATGCTG TTTATAGAGG AGATTTAGAT TATTACAAAG AGTTTTATAT TGAGGCTTCT
 481 TTGAAGTCTT TGACTAAAGA AAATGCAGGT CTTTCTAGGG TGTACAGTCA ATGGGCTGGG
 541 AAGACACAAA TATTTATTCC TCTTAAAAAG AATATTTTAT CTGGAAATGT TGAGTCTGAC
 601 ATTGATATTG ATAGTTTGGT TACAGATAAG GTGGTGGCAG CTCTTTTAAG TGAGAATGAA
 661 TCAGGTGTTA ACTTTGCAAG AGATATTACA GACATTCAAG GCGAAACTCA TAAAGCAGAT
 721 CAAGATAAAA TTGATATTGA ATTAGATAAT ATTCATGAAA GTGATTCCAA TATAACAGAA
 781 ACTATTGAGA ATTTAAGGGA TCAGCTTGAA AAAGCTACAG ATGAAGAGCA TAAAAAAGAG
 841 ATTGAAAGTC AGGTTGATGC TAAAAAGAAA CAAAAGGAAG AATTAGATAA AAAGGCAATT
 901 GATCTTGATA AAGCTCAACA AAAATTAGAT TTTGCTGAAG ATAATCTAGA TATTCAAAGG
 961 GATACTGTTA GAGAGAAGCT TCAAGAGAAT ATTAACGAGA CTAATAAGGA AAAGAATTTA
1021 CCAAAGCCTG GTGATGTAAG TTCTCCTAAA GTTGATAAGC AACTACAAAT AAAAGAGAGC
1081 CTGGAAGATT TGCAGGAGCA GCTTAAAGAA ACTGGTGATG AAAATCAGAA AAGAGAAATT
1141 GAAAAGCAAA TTGAAATCAA AAAAAGTGAT GAAAAGCTTT TAAAAAGTAA AGATGATAAA
1201 GCAAGTAAAG ATGGTAAAGC CTTGGATCTT GATCGAGAAT TAAATTCTAA AGCTTCTAGC
1261 AAAGAAAAAA GTAAAGCCAA GGAAGAAGAA ATAACCAAGG GTAAGTCACA GAAAAGCTTA
1321 GGCGATTTGA ATAATGATGA AAATCTTATG ATGCCAGAAG ATCAAAAATT ACCTGAGGTT
1381 AAAAAATTAG ATAGCAAAAA AGAATTTAAA CCTGTTTCTG AGGTTGAGAA ATTAGATAAG
1441 ATTTTCAAGT CTAATAACAA TGTTGGAGAA TTATCACCGT TAGATAAATC TTCTTATAAA
1501 GACATTGATT CAAAAGAGGA GACAGTTAAT AAAGATGTTA ATTTGCAAAA GACTAAGCCT
1561 CAGGTTAAAG ACCAAGTTAC TTCTTTGAAT GAAGATTTGA CTACTATGTC TATAGATTCC
1621 AGTAGTCCTG TATTTTTAGA GGTTATTGAT CCAATTACAA ATTTAGGAAC TCTTCAACTT
1681 ATTGATTTAA ATACTGGTGT TAGGCTTAAA GAAAGCACTC AGCAAGGCAT TCAGCGGTAT
1741 GGAATTTATG AACGTGAAAA AGATTTGGTT GTTATTAAAA TGGATTCAGG AAAAGCTAAG
1801 CTTCAGATAC TTGATAAACT TGAAAATTTA AAAGTGGTAT CAGAGTCTAA TTTTGAGATT
1861 AATAAAAATT CATCTCTTTA TGTTGATTCT AAAATGATTT TAGTAGCTGT TAGGGATAAA
1921 GATAGTAGTA ATGATTGGAG ATTGGCCAAA TTTTCTCCTA AAAATTTAGA TGAGTTTATT
1981 CTTTCAGAGA ATAAAATTAT GCCTTTTACT AGCTTTTCTG TGAGAAAAAA TTTTATTTAT
2041 TTGCAAGATG AGTTTAAAAG TCTAGTTATT TTAGATGTAA ATACTTTAAA AAAAGTTAAG
2101 TAAAGCC
```

FIG. 20

```
   1 ATGAAAAAAA TGTTACTAAT CTTTAGTTTT TTTCTTGTTT TTTTAAATGG ATTTCCTCTT
  61 AATGCAAGGG AAGTTGATAA GGAAAAATTA AAGGACTTTG TTAATATGGA TCTTGAATTT
 121 GTTAATTACA AGGGTCCTTA TGATTCTACA AATACATATG AACAAATAGT AGGTATTGGG
 181 GAGTTTTTAG CAAGGCCGTT GATCAATTCC AATAGTAATT CAAGTTATTA TGGTAAATAT
 241 TTTGTTAATA GATTTATTGA CGATCAAGAT AAAAAAGCAA GTGTTGATAT TTTTTCTATT
 301 GGTAGTAAGT CAGAGCTTGA TAGTATATTA AATCTAAGAA GAATTCTTAC AGGGTATTTA
 361 ATGAAGTCTT TTGATTATGA GAGGTCTAGT GCGGAATTAA TTGCTAAAGC TATTACAATA
 421 TATAATGCTG TTTATAGAGG AGATTTAGAT TATTACAAAG AGTTTTATAT TGAGGCTTCT
 481 TTGAAGTCTT TGACTAAAGA AAATGCAGGT CTTTCTAGGG TGTACAGTCA ATGGGCTGGG
 541 AAGACACAAA TATTTATTCC TCTTAAAAAG AATATTTTAT CTGGAAATGT TGAGTCTGAC
 601 ATTGATATTG ATAGTTTGGT TACAGATAAG GTGGTGGCAG CTCTTTTAAG TGAGAATGAA
 661 TCAGGTGTTA ACTTTGCAAG AGATATTACA GACATTCAAG GCGAAACTCA TAAAGCAGAT
 721 CAAGATAAAA TTGATATTGA ATTAGATAAT TTTCATGAAA GTGATTCCAA TATAACAGAA
 781 ACTATTGAGA ATTTAAGGGA TCAGCTTGAA AAAGCTACAG ATGAAGAGCA TAAAAAAGAG
 841 ATTGAAAGTC AGGTTGATGC TAAAAAGAAA CAAAAGGAAG AATTAGATAA AAAGGCAATT
 901 GATCTTGATA AAGCTCAACA AAAATTAGAT TTTGCTGAAG ATAATCTAGA TATTCAAAGG
 961 GATACTGTTA GAGAGAAGCT TCAAGAAAAT ATTAACGAGA CTAATAAGGA AAAGAATTTA
1021 CCAAAGCCTG GTGATGTAAG TTCTCCTAAG GTTGATAAGC AGTTGCAGAT AAAAGAGAGT
1081 CTAGAAGATT TGCAAGAGCA GCTTAAAGAA GCTAGTGATG AAAATCAAAA AACAGAAATA
1141 GAAAAGCAAA TTGAAATCAA AAAAAATGAT GAAGAACTTT TTAAAAATAA AGATCATAAA
1201 GCATTAGATC TTAAGCAAGA ATTAAATTCT AAAGCTTCTA GTAAAGAAAA AATTGAAGGC
1261 GAAGAAGAGG ATAAAGAATT AGATAGTAAA AAAAATTTAG AGCCTGTTTC TGAGGCTGAT
1321 AAAGTAGATA AAATTTCCAA GTCTAACAAC AATGAGGTTA GTAAATTATC CCCGTTAGAT
1381 GAGCCTTCTT ATAGCGACAT TGATTCGAAA GAGGGTGTAG ATAACAAAGA TGTTGATTTG
1441 CAAAAAACTA AACCCCAAGT TGAAAGTCAA CCTACTTCGT TAAATGAAGA CTTGATTGAT
1501 GTGTCTATAG ATTCCAGTAA TCCTGTCTTT TTAGAGGTTA TCGATCCGAT TACAAATTTA
1561 GGAACGCTTC AACTTATTGA TTTGAATACC GGTGTTAGAC TTAAAGAAAG TGCTCAACAA
1621 GGTATTCAGC GATATGGAAT TTATGAACGT GAAAAAGATT TGGTTGTTAT TAAAATAGAT
1681 TCAGGAAAAG CTAAGCTTCA GATACTTGAT AAACTCGAGA ATTTAAAAGT GATATCAGAG
1741 TCTAATTTTG AGATTAATAA AAATTCATCT CTTTATGTTG ACTCTAGAAT GATTTTAGTA
1801 GTTGTTAAGG ACGATAGTAA TGCTTGGAGA TTGGCTAAAT TTTCTCCTAA AAATTTAGAT
1861 GAATTTATTC TGTCAGAAAA TAAAATTTTG CCTTTTACTA GCTTTGCTGT GAGAAAGAAT
1921 TTTATTTATT TGCAAGATGA ACTTAAAAGC TTAGTTACTT TAGATGTAAA TACTTTAAAA
1981 AAAGTTAAGT A
```

FIG. 21

1 ATGAAAAAAA TGTTACTAAT CTTTAGTTTT TTTCTTATTT TTTTGAATGG ATTTCCTCTT
61 AATGCAAGGA AAGTTGATAA GGAAAAATTA AAGGATTTTG TTAATATGGA TCTTGAGTTT
121 GTAAATTATA AAGGTCCTTA TGATTCTACA AATACGTATG AACAAATAGT GGGTATTGGG
181 GAGTTTTTAG CAAGACCGCT GACCAATTCC AATAGCAACT CAAGTTATTA TGGCAAATAT
241 TTTATTAATA GATTTATTGA TGATCAAGAT AAAAAAGCAA GTGTTGATGT TTTTTCTATA
301 AGCAGCAAAT CAGAGCTTGA CAGTATATTG AATTTAAGAA GAATTCTTAC AGGGTATATA
361 ATAAAGTCTT TCGATTATGA CAGGTCTAGT GCAGAATTAA TTGCTAAGGT TATTACAATA
421 TATAATGCTG TTTATAGAGG AGATTTGGAT TATTATAAAG GGTTTTATAT TGAGCCTGCT
481 TTGAAGTCTT TAACTAAAGA AAACGCAGGT CTTTCTAGGG TTTACAGTCA GTGGGCTGGA
541 AAGACTCAAA TATTTATTCC TCTTAAAAAG GATATTTTGT CTGGAAATAT TGAATCTGAC
601 ATTGATATTG ACAGTTTGGT TACAGATAAG GTGATAGCAG CTCTTTTAAG CGAAAATGAA
661 GCAGGCGTTA ACTTTGCAAG AGATATTACA GATATTCAAG GCGAAACTCA TAAGGCAGAT
721 CAAGATAAGA TTGATACTGA ATTAGACAAT ATCCATGAAA GCGATTCTAA TATAACAGAA
781 ACTATTGAAA ATTTAAGGGA TCAGCTTGAA AAAGCTACAG ATGAAGAGCA TAAAAAAGAG
841 ATTGAAAGTC AGGTTGATGC TAAAAAGAAA GAAAAGGAAG AGCTAGATAA AAAGGCAATC
901 AATCTTGATA AAGCTCAGCA AAAATTAGAC TCTGCTGAAG ATAATTTAGA TGTTCAAAGA
961 GATACTGTTA GAGAGAAAAT TCAAGAGGAT ATTAATGAGA TTAATAAGGA AAAGAATTTG
1021 CCAAAACCTG GTGATGTAAG TTCTCCTAAA GTTGATAAGC AACTGCAAAT AAAAGAGAGT
1081 CTAGAAGATT TGCAGGAGCA GCTTAAAGAA GCTGGTGATG AAAATCAGAA AAGAGAAATT
1141 GAGAAGCAAA TTGAAATCAA AAAAAGGGAC GAAGAACTTT TAAAAAGTAA AGATGGCAAA
1201 GTAAGTAAAG ATTATGAAGC ATTAGATCTT GATCGAGAAT TATCCAAAGC TTCTAGTAAA
1261 GAAAAAAGTA AGGTCAAGGA AGAAGAAATA ACTAAAGGTA AATCACGGGC AAGCTTAGGC
1321 GATTTGAATA ATGATAAAAA CCTTATGTTG CCAGAAGATC AAAAATTACC TGAAGATAAA
1381 AAATTGGATA GTAAATTAGA TGGTAAAAAA GAATTTAAAC CAGTTTCTGA GGTTGAAAAA
1441 TTAGATAAGA TTTCCAAGTC TAATAACAAT GAGGTTGGCA AGTTATCACC ATTAGATAAG
1501 CCTTCTTATG ATGATATTGA TTCAAAAGAG GAGGTAGATA ATAAAGCTAT TAATTTGCAA
1561 AAGATCGACC CTAAAGTTAA AGACCAAACT ACTTCTTTGA ATGAAGATTT GGATAAAGAT
1621 TTGACTACTA TGTCTATAGA TTCCAGCAGT CCTGTATTTC TAGAGGTTAT TGATCCTATT
1681 ACAAATTTAG GAACCCTGCA GCTTATTGAT TTAAATACTG GGGTTAGGCT TAAGGAAAGC
1741 ACTCAGCAAG GCATTCAGCG GTATGGAATT TATGAACGTG AAAAAGATTT GGTTGTTATT
1801 AAAATGGATT CAGGAAAGGC TAAGCTTCAA ATACTTAATA AGCTTGAAAA TTTCAAAGTG
1861 GTATCAGAGT CTAATTTTGA GATCAATAAA AATTCATCTC TTTATGTTGA CTCTAAAATG
1921 ATTTTGGCAG CTGTTAGAGA TAAGGATGAT AGCAATGCTT GGAGATTGGC TAAATTTTCT
1981 CCTAAAAATT TGGATGAGTT TATTCTTTCA GAGAATAAAA TTTTGCCTTT TACTAGCTTT
2041 TCTGTGAGAA AAAATTTTAT TTATTTGCAA GATGAGCTTA AAAATCTAGT TATTTTAGAT
2101 GTAAATACTT TAAAAAAAGT TAAGTA

FIG. 22

```
              10          20          30          40
               *     *     *     *     *     *     *     *     *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
 *     *     *     *     *     *     *     *     *     *
TGT AAG CAA AAT GTT AGC AGC CTT GAT GAA AAA-AAT AGC GTT TCA GTA
ACA TTC GTT TTA CAA TCG TCG GAA CTA CTT TTT TTA TCG CAA AGT CAT
Cys Lys Gln Asn Val Ser Ser Leu Asp Glu Lys Asn Ser Val Ser Val>

  100         110         120         130         140
   *     *     *     *     *     *     *     *     *
GAT TTA CCT GGT GGA ATG ACA GTT CTT GTA AGT AAA GAA AAA GAC AAA
CTA AAT GGA CCA CCT TAC TGT CAA GAA CAT TCA TTT CTT TTT CTG TTT
Asp Leu Pro Gly Gly Met Thr Val Leu Val Ser Lys Glu Lys Asp Lys>

    150         160         170         180         190
*    *     *     *     *     *     *     *     *     *
GAC GGT AAA TAC AGT CTA GAG GCA ACA GTA GAC AAG CTT GAG CTT AAA
CTG CCA TTT ATG TCA GAT CTC CGT TGT CAT CTG TTC GAA CTC GAA TTT
Asp Gly Lys Tyr Ser Leu Glu Ala Thr Val Asp Lys Leu Glu Leu Lys>

      200         210         220         230         240
*     *     *     *     *     *     *     *     *     *
GGA ACT TCT GAT AAA AAC AAC GGT TCT GGA ACA CTT GAA GGT GAA AAA
CCT TGA AGA CTA TTT TTG TTG CCA AGA CCT TGT GAA CTT CCA CTT TTT
Gly Thr Ser Asp Lys Asn Asn Gly Ser Gly Thr Leu Glu Gly Glu Lys>

        250         260         270         280
     *     *     *     *     *     *     *     *     *
ACT GAC AAA AGT AAA GTA AAA TTA ACA ATT GCT GAT GAC CTA AGT CAA
TGA CTG TTT TCA TTT CAT TTT AAT TGT TAA CGA CTA CTG GAT TCA GTT
Thr Asp Lys Ser Lys Val Lys Leu Thr Ile Ala Asp Asp Leu Ser Gln>

290         300         310         320         330
 *     *     *     *     *     *     *     *     *     *
ACT AAA TTT GAA ATT TTC AAA GAA GAT GCC AAA ACA TTA GTA TCA AAA
TGA TTT AAA CTT TAA AAG TTT CTT CTA CGG TTT TGT AAT CAT AGT TTT
Thr Lys Phe Glu Ile Phe Lys Glu Asp Ala Lys Thr Leu Val Ser Lys>

  340         350         360         370         380
   *     *     *     *     *     *     *     *     *
AAA GTA ACC CTT AAA GAC AAG TCA TCA ACA GAA GAA AAA TTC AAC GAA
TTT CAT TGG GAA TTT CTG TTC AGT AGT TGT CTT CTT TTT AAG TTG CTT
Lys Val Thr Leu Lys Asp Lys Ser Ser Thr Glu Glu Lys Phe Asn Glu>
```

FIG. 23A

```
     390          400          410          420          430
AAG GGT GAA ACA TCT GAA AAA ACA ATA GTA AGA GCA AAT GGA ACC AGA
TTC CCA CTT TGT AGA CTT TTT TGT TAT CAT TCT CGT TTA CCT TGG TCT
Lys Gly Glu Thr Ser Glu Lys Thr Ile Val Arg Ala Asn Gly Thr Arg>

        440          450          460          470          480
CTT GAA TAC ACA GAC ATA AAA AGC GAT GGA TCC GGA AAA GCT AAA GAA
GAA CTT ATG TGT CTG TAT TTT TCG CTA CCT AGG CCT TTT CGA TTT CTT
Leu Glu Tyr Thr Asp Ile Lys Ser Asp Gly Ser Gly Lys Ala Lys Glu>

           490          500          510          520
GTT TTA AAA GAC TTT ACT CTT GAA GGA ACT CTA GCT GCT GAC GGC AAA
CAA AAT TTT CTG AAA TGA GAA CTT CCT TGA GAT CGA CGA CTG CCG TTT
Val Leu Lys Asp Phe Thr Leu Glu Gly Thr Leu Ala Ala Asp Gly Lys>

530          540          550          560          570
ACA ACA TTG AAA GTT ACA GAA GGC ACT GTT GTT TTA AGC AAG AAC ATT
TGT TGT AAC TTT CAA TGT CTT CCG TGA CAA CAA AAT TCG TTC TTG TAA
Thr Thr Leu Lys Val Thr Glu Gly Thr Val Val Leu Ser Lys Asn Ile>

  580          590          600          610          620
TTA AAA TCC GGA GAA ATA ACA GTT GCA CTT GAT GAC TCT GAC ACT ACT
AAT TTT AGG CCT CTT TAT TGT CAA CGT GAA CTA CTG AGA CTG TGA TGA
Leu Lys Ser Gly Glu Ile Thr Val Ala Leu Asp Asp Ser Asp Thr Thr>

     630          640          650          660          670
CAG GCT ACT AAA AAA ACT GGA AAA TGG GAT TCA AAA ACT TCT ACT TTA
GTC CGA TGA TTT TTT TGA CCT TTT ACC CTA AGT TTT TGA AGA TGA AAT
Gln Ala Thr Lys Lys Thr Gly Lys Trp Asp Ser Lys Thr Ser Thr Leu>

        680          690          700          710          720
ACA ATT AGT GTT AAC AGC AAA AAA ACT ACA CAA CTT GTG TTT ACT AAA
TGT TAA TCA CAA TTG TCG TTT TTT TGA TGT GTT GAA CAC AAA TGA TTT
Thr Ile Ser Val Asn Ser Lys Lys Thr Thr Gln Leu Val Phe Thr Lys>

           730          740          750          760
CAA TAC ACA ATA ACT GTA AAA CAA TAC GAC TCC GCA GGT ACC AAT TTA
GTT ATG TGT TAT TGA CAT TTT GTT ATG CTG AGG CGT CCA TGG TTA AAT
Gln Tyr Thr Ile Thr Val Lys Gln Tyr Asp Ser Ala Gly Thr Asn Leu>
```

FIG. 23B

```
770          780          790          800          810
 *     *      *     *      *     *      *     *      *     *
GAA GGC ACA GCA GTC GAA ATT AAA ACA CTT GAT GAA CTT AAA AAC GCT
CTT CCG TGT CGT CAG CTT TAA TTT TGT GAA CTA CTT GAA TTT TTG CGA
Glu Gly Thr Ala Val Glu Ile Lys Thr Leu Asp Glu Leu Lys Asn Ala>
```

```
  820
   *     *
TTA AAA TAA
AAT TTT ATT
Leu Lys ***>
```

FIG. 23C

```
          10         20         30         40
 *        *     *    *     *    *     *    *     *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50         60         70         80         90
 *     *    *     *    *     *    *     *    *     *
TGC AAG CAA AAT GTT AGC AGC CTT GAT GAA AAA AAC AGC GCT TCA GTA
ACG TTC GTT TTA CAA TCG TCG GAA CTA CTT TTT TTG TCG CGA AGT CAT
Cys Lys Gln Asn Val Ser Ser Leu Asp Glu Lys Asn Ser Ala Ser Val>

 100        110        120        130        140
 *     *    *     *    *     *    *     *    *
GAT TTG CCT GGT GAG ATG AAA GTT CTT GTA AGT AAA GAA AAA GAC AAA
CTA AAC GGA CCA CTC TAC TTT CAA GAA CAT TCA TTT CTT TTT CTG TTT
Asp Leu Pro Gly Glu Met Lys Val Leu Val Ser Lys Glu Lys Asp Lys>

   150        160        170        180        190
 *     *    *     *    *     *    *     *    *     *
GAC GGT AAG TAC AGT CTA AAG GCA ACA GTA GAC AAG ATT GAG CTA AAA
CTG CCA TTC ATG TCA GAT TTC CGT TGT CAT CTG TTC TAA CTC GAT TTT
Asp Gly Lys Tyr Ser Leu Lys Ala Thr Val Asp Lys Ile Glu Leu Lys>

      200        210        220        230        240
 *     *    *     *    *     *    *     *    *     *
GGA ACT TCT GAT AAA GAC AAT GGT TCT GGA GTG CTT GAA GGT ACA AAA
CCT TGA AGA CTA TTT CTG TTA CCA AGA CCT CAC GAA CTT CCA TGT TTT
Gly Thr Ser Asp Lys Asp Asn Gly Ser Gly Val Leu Glu Gly Thr Lys>

         250        260        270        280
     *     *    *     *    *     *    *     *    *
GAT GAC AAA AGT AAA GCA AAA TTA ACA ATT GCT GAC GAT CTA AGT AAA
CTA CTG TTT TCA TTT CGT TTT AAT TGT TAA CGA CTG CTA GAT TCA TTT
Asp Asp Lys Ser Lys Ala Lys Leu Thr Ile Ala Asp Asp Leu Ser Lys>

290        300        310        320        330
 *     *    *     *    *     *    *     *    *     *
ACC ACA TTC GAA CTT TTA AAA GAA GAT GGC AAA ACA TTA GTG TCA AGA
TGG TGT AAG CTT GAA AAT TTT CTT CTA CCG TTT TGT AAT CAC AGT TCT
Thr Thr Phe Glu Leu Leu Lys Glu Asp Gly Lys Thr Leu Val Ser Arg>

 340        350        360        370        380
 *     *    *     *    *     *    *     *    *
AAA GTA AGT TCT AGA GAC AAA ACA TCA ACA GAT GAA ATG TTC AAT GAA
TTT CAT TCA AGA TCT CTG TTT TGT AGT TGT CTA CTT TAC AAG TTA CTT
Lys Val Ser Ser Arg Asp Lys Thr Ser Thr Asp Glu Met Phe Asn Glu>
```

FIG. 24A

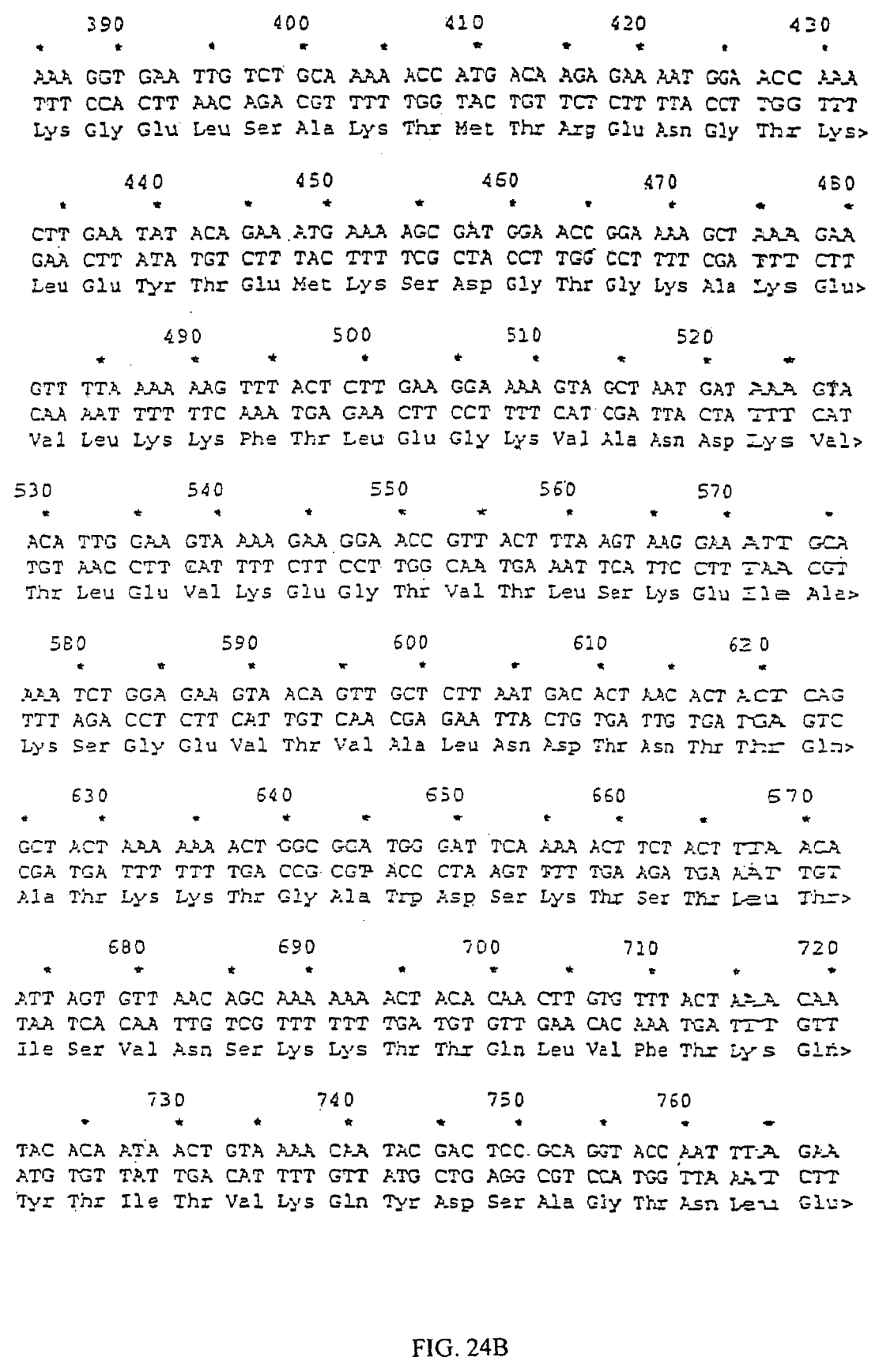

```
     390         400         410         420         430
AAA GGT GAA TTG TCT GCA AAA ACC ATG ACA AGA GAA AAT GGA ACC AAA
TTT CCA CTT AAC AGA CGT TTT TGG TAC TGT TCT CTT TTA CCT TGG TTT
Lys Gly Glu Leu Ser Ala Lys Thr Met Thr Arg Glu Asn Gly Thr Lys>

        440         450         460         470         480
CTT GAA TAT ACA GAA ATG AAA AGC GAT GGA ACC GGA AAA GCT AAA GAA
GAA CTT ATA TGT CTT TAC TTT TCG CTA CCT TGG CCT TTT CGA TTT CTT
Leu Glu Tyr Thr Glu Met Lys Ser Asp Gly Thr Gly Lys Ala Lys Glu>

           490         500         510         520
GTT TTA AAA AAG TTT ACT CTT GAA GGA AAA GTA GCT AAT GAT AAA GTA
CAA AAT TTT TTC AAA TGA GAA CTT CCT TTT CAT CGA TTA CTA TTT CAT
Val Leu Lys Lys Phe Thr Leu Glu Gly Lys Val Ala Asn Asp Lys Val>

530         540         550         560         570
ACA TTG GAA GTA AAA GAA GGA ACC GTT ACT TTA AGT AAG GAA ATT GCA
TGT AAC CTT CAT TTT CTT CCT TGG CAA TGA AAT TCA TTC CTT TAA CGT
Thr Leu Glu Val Lys Glu Gly Thr Val Thr Leu Ser Lys Glu Ile Ala>

  580         590         600         610         620
AAA TCT GGA GAA GTA ACA GTT GCT CTT AAT GAC ACT AAC ACT ACT CAG
TTT AGA CCT CTT CAT TGT CAA CGA GAA TTA CTG TGA TTG TGA TGA GTC
Lys Ser Gly Glu Val Thr Val Ala Leu Asn Asp Thr Asn Thr Thr Gln>

    630         640         650         660         670
GCT ACT AAA AAA ACT GGC GCA TGG GAT TCA AAA ACT TCT ACT TTA ACA
CGA TGA TTT TTT TGA CCG CGT ACC CTA AGT TTT TGA AGA TGA AAT TGT
Ala Thr Lys Lys Thr Gly Ala Trp Asp Ser Lys Thr Ser Thr Leu Thr>

       680         690         700         710         720
ATT AGT GTT AAC AGC AAA AAA ACT ACA CAA CTT GTG TTT ACT AAA CAA
TAA TCA CAA TTG TCG TTT TTT TGA TGT GTT GAA CAC AAA TGA TTT GTT
Ile Ser Val Asn Ser Lys Lys Thr Thr Gln Leu Val Phe Thr Lys Gln>

          730         740         750         760
TAC ACA ATA ACT GTA AAA CAA TAC GAC TCC GCA GGT ACC AAT TTA GAA
ATG TGT TAT TGA CAT TTT GTT ATG CTG AGG CGT CCA TGG TTA AAT CTT
Tyr Thr Ile Thr Val Lys Gln Tyr Asp Ser Ala Gly Thr Asn Leu Glu>
```

FIG. 24B

```
770         780         790        800        810
 *     *     *     *     *     *     *     *     *     *
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
Gly Thr Ala Val Glu Ile Lys Thr Leu Asp Glu Leu Lys Asn Ala Leu>

 820
  *
AAA TAA
TTT ATT
Lys ***>
```

FIG. 24C 10 20 30 40

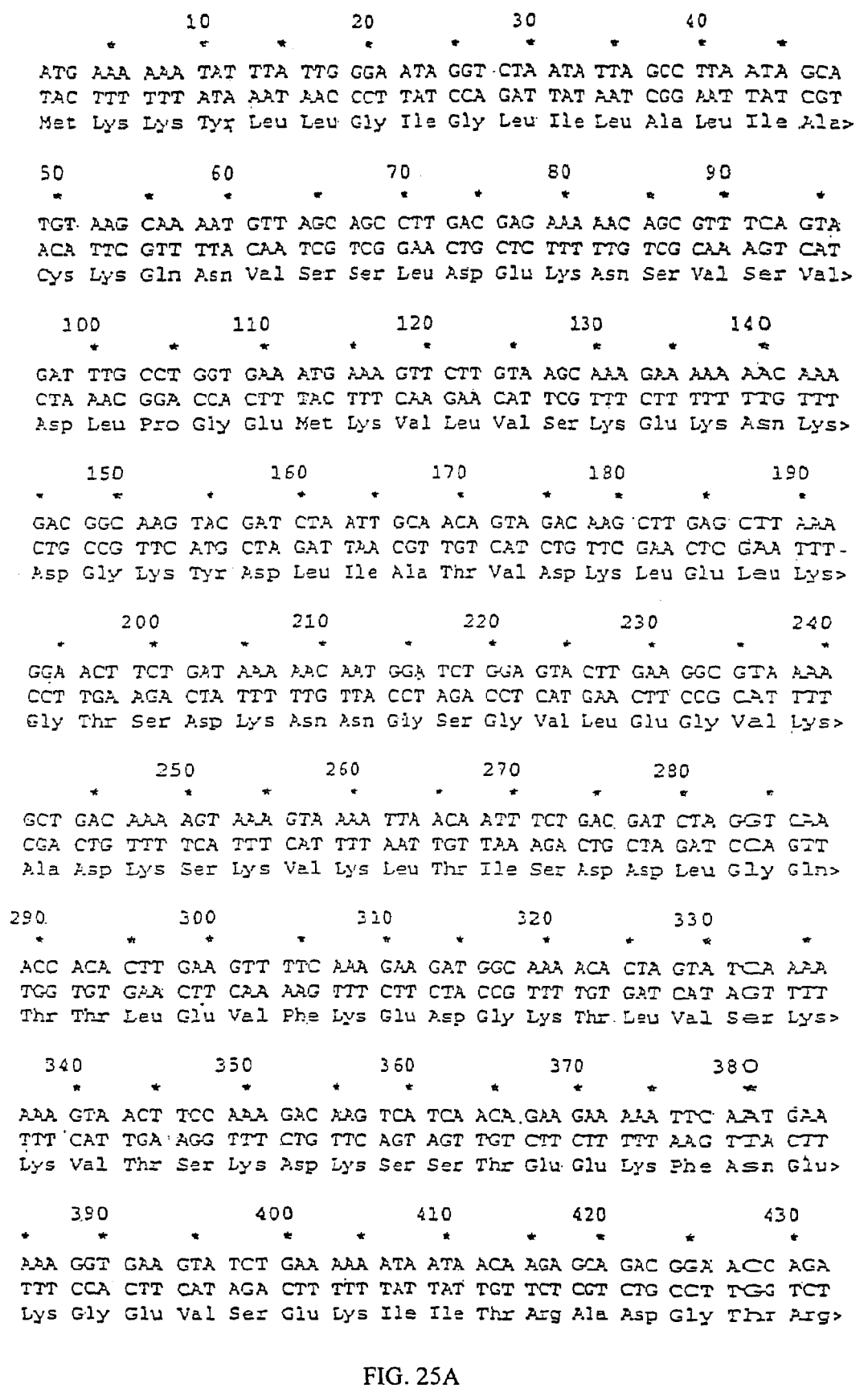

ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50 60 70 80 90

TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100 110 120 130 140

GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150 160 170 180 190

GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200 210 220 230 240

GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250 260 270 280

GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290 300 310 320 330

ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

340 350 360 370 380

AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>

390 400 410 420 430

AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

FIG. 25A

```
        440       450       460       470       480
    *    *    *    *    *    *    *    *    *    *
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

         490       500       510       520
    *    *    *    *    *    *    *    *    *
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530       540       550       560       570
  *    *    *    *    *    *    *    *    *    *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

  580       590       600       610       620
    *    *    *    *    *    *    *    *    *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

     630       640       650       660       670
  *    *    *    *    *    *    *    *    *    *
GCT ACT AAA AAA ACT GCA GCT TGG AAT TCA AAA ACT TCC ACT TTA ACA
CGA TGA TTT TTT TGA CGT CGA ACC TTA AGT TTT TGA AGG TGA AAT TGT
Ala Thr Lys Lys Thr Ala Ala Trp Asn Ser Lys Thr Ser Thr Leu Thr>

       680       690       700       710       720
  *    *    *    *    *    *    *    *    *    *
ATT AGT GTG AAT AGC CAA AAA ACC AAA AAC CTT GTA TTC ACA AAA GAA
TAA TCA CAC TTA TCG GTT TTT TGG TTT TTG GAA CAT AAG TGT TTT CTT
Ile Ser Val Asn Ser Gln Lys Thr Lys Asn Leu Val Phe Thr Lys Glu>

         730       740       750       760
    *    *    *    *    *    *    *    *    *
GAC ACA ATA ACA GTA CAA AAA TAC GAC TCA GCA GGC ACC AAT CTA GAA
CTG TGT TAT TGT CAT GTT TTT ATG CTG AGT CGT CCG TGG TTA GAT CTT
Asp Thr Ile Thr Val Gln Lys Tyr Asp Ser Ala Gly Thr Asn Leu Glu>

770       780       790       800       810
  *    *    *    *    *    *    *    *    *    *
GGC AAA GCA GTC GAA ATT ACA ACA CTT AAA GAA CTT AAA AAC GCT TTA
CCG TTT CGT CAG CTT TAA TGT TGT GAA TTT CTT GAA TTT TTG CGA AAT
Gly Lys Ala Val Glu Ile Thr Thr Leu Lys Glu Leu Lys Asn Ala Leu>

  820
    *
AAA TAA
TTT ATT
Lys ***>
```

FIG. 25B

```
                10          20          30          40
       *        *       *       *       *       *       *       *       *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
 *       *       *       *       *       *       *       *       *       *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

 100         110         120         130         140
    *       *       *       *       *       *       *       *       *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

   150         160         170         180         190
 *       *       *       *       *       *       *       *       *       *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

       200         210         220         230         240
    *       *       *       *       *       *       *       *       *       *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

          250         260         270         280
       *       *       *       *       *       *       *       *       *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290         300         310         320         330
 *       *       *       *       *       *       *       *       *       *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

 340         350         360         370         380
    *       *       *       *       *       *       *       *       *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 26A

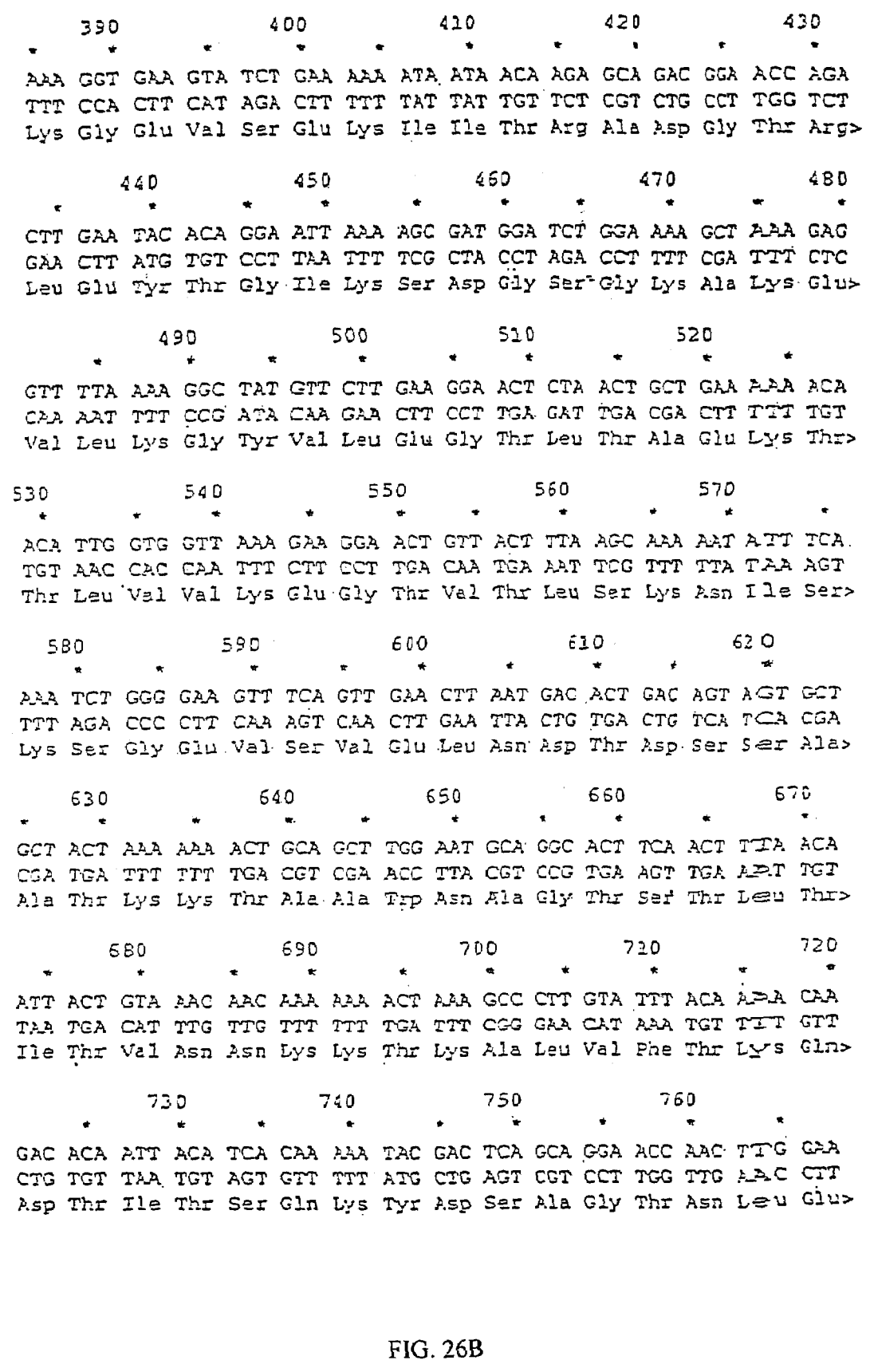

```
      390         400         410         420         430
   *    *     *     *     *     *     *     *     *     *
 AAA GGT GAA GTA TCT GAA AAA ATA ATA ACA AGA GCA GAC GGA ACC AGA
 TTT CCA CTT CAT AGA CTT TTT TAT TAT TGT TCT CGT CTG CCT TGG TCT
 Lys Gly Glu Val Ser Glu Lys Ile Ile Thr Arg Ala Asp Gly Thr Arg>

         440         450         460         470         480
   *    *     *     *     *     *     *     *     *     *
 CTT GAA TAC ACA GGA ATT AAA AGC GAT GGA TCT GGA AAA GCT AAA GAG
 GAA CTT ATG TGT CCT TAA TTT TCG CTA CCT AGA CCT TTT CGA TTT CTC
 Leu Glu Tyr Thr Gly Ile Lys Ser Asp Gly Ser Gly Lys Ala Lys Glu>

         490         500         510         520
   *    *     *     *     *     *     *     *     *
 GTT TTA AAA GGC TAT GTT CTT GAA GGA ACT CTA ACT GCT GAA AAA ACA
 CAA AAT TTT CCG ATA CAA GAA CTT CCT TGA GAT TGA CGA CTT TTT TGT
 Val Leu Lys Gly Tyr Val Leu Glu Gly Thr Leu Thr Ala Glu Lys Thr>

 530         540         550         560         570
   *    *     *     *     *     *     *     *     *     *
 ACA TTG GTG GTT AAA GAA GGA ACT GTT ACT TTA AGC AAA AAT ATT TCA
 TGT AAC CAC CAA TTT CTT CCT TGA CAA TGA AAT TCG TTT TTA TAA AGT
 Thr Leu Val Val Lys Glu Gly Thr Val Thr Leu Ser Lys Asn Ile Ser>

         580         590         600         610         620
   *    *     *     *     *     *     *     *     *     *
 AAA TCT GGG GAA GTT TCA GTT GAA CTT AAT GAC ACT GAC AGT AGT GCT
 TTT AGA CCC CTT CAA AGT CAA CTT GAA TTA CTG TGA CTG TCA TCA CGA
 Lys Ser Gly Glu Val Ser Val Glu Leu Asn Asp Thr Asp Ser Ser Ala>

         630         640         650         660         670
   *    *     *     *     *     *     *     *     *     *
 GCT ACT AAA AAA ACT GCA GCT TGG AAT GCA GGC ACT TCA ACT TTA ACA
 CGA TGA TTT TTT TGA CGT CGA ACC TTA CGT CCG TGA AGT TGA AAT TGT
 Ala Thr Lys Lys Thr Ala Ala Trp Asn Ala Gly Thr Ser Thr Leu Thr>

         680         690         700         710         720
   *    *     *     *     *     *     *     *     *     *
 ATT ACT GTA AAC AAC AAA AAA ACT AAA GCC CTT GTA TTT ACA AAA CAA
 TAA TGA CAT TTG TTG TTT TTT TGA TTT CGG GAA CAT AAA TGT TTT GTT
 Ile Thr Val Asn Asn Lys Lys Thr Lys Ala Leu Val Phe Thr Lys Gln>

         730         740         750         760
   *    *     *     *     *     *     *     *     *
 GAC ACA ATT ACA TCA CAA AAA TAC GAC TCA GCA GGA ACC AAC TTG GAA
 CTG TGT TAA TGT AGT GTT TTT ATG CTG AGT CGT CCT TGG TTG AAC CTT
 Asp Thr Ile Thr Ser Gln Lys Tyr Asp Ser Ala Gly Thr Asn Leu Glu>
```

FIG. 26B

```
770         780         790         800         810
 *     *     *     *     *     *     *     *     *     *
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
Gly Thr Ala Val Glu Ile Lys Thr Leu Asp Glu Leu Lys Asn Ala Leu>

AGA
TCT
Arg>
```

FIG. 26C 10 20 30 40

ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50 60 70 80 90

TGT AAG CAA AAT GTT AGC AGC CTT GAT GAA AAA AAT AGC GTT TCA GTA
ACA TTC GTT TTA CAA TCG TCG GAA CTA CTT TTT TTA TCG CAA AGT CAT
Cys Lys Gln Asn Val Ser Ser Leu Asp Glu Lys Asn Ser Val Ser Val>

100 110 120 130 140

GAT TTA CCT GGT GGA ATG ACA GTT CTT GTA AGT AAA GAA AAA GAC AAA
CTA AAT GGA CCA CCT TAC TGT CAA GAA CAT TCA TTT CTT TTT CTG TTT
Asp Leu Pro Gly Gly Met Thr Val Leu Val Ser Lys Glu Lys Asp Lys>

150 160 170 180 190

GAC GGT AAA TAC AGT CTA GAG GCA ACA GTA GAC AAG CTT GAG CTT AAA
CTG CCA TTT ATG TCA GAT CTC CGT TGT CAT CTG TTC GAA CTC GAA TTT
Asp Gly Lys Tyr Ser Leu Glu Ala Thr Val Asp Lys Leu Glu Leu Lys>

200 210 220 230 240

GGA ACT TCT GAT AAA AAC AAC GGT TCT GGA ACA CTT GAA GGT GAA AAA
CCT TGA AGA CTA TTT TTG TTG CCA AGA CCT TGT GAA CTT CCA CTT TTT
Gly Thr Ser Asp Lys Asn Asn Gly Ser Gly Thr Leu Glu Gly Glu Lys>

250 260 270 280

ACT GAC AAA AGT AAA GTA AAA TTA ACA ATT GCT GAT GAC CTA AGT CAA
TGA CTG TTT TCA TTT CAT TTT AAT TGT TAA CGA CTA CTG GAT TCA GTT
Thr Asp Lys Ser Lys Val Lys Leu Thr Ile Ala Asp Asp Leu Ser Gln>

290 300 310 320 330

ACT AAA TTT GAA ATT TTC AAA GAA GAT GCC AAA ACA TTA GTA TCA AAA
TGA TTT AAA CTT TAA AAG TTT CTT CTA CGG TTT TGT AAT CAT AGT TTT
Thr Lys Phe Glu Ile Phe Lys Glu Asp Ala Lys Thr Leu Val Ser Lys>

340 350 360 370 380

AAA GTA ACC CTT AAA GAC AAG TCA TCA ACA GAA GAA AAA TTC AAC GAA
TTT CAT TGG GAA TTT CTG TTC AGT AGT TGT CTT CTT TTT AAG TTG CTT
Lys Val Thr Leu Lys Asp Lys Ser Ser Thr Glu Glu Lys Phe Asn Glu>

FIG. 27A 390 400 410 420 430

AAG GGT GAA ACA TCT GAA AAA ACA ATA GTA AGA GCA AAT GGA ACC AGA
TTC CCA CTT TGT AGA CTT TTT TGT TAT CAT TCT CGT TTA CCT TGG TCT
Lys Gly Glu Thr Ser Glu Lys Thr Ile Val Arg Ala Asn Gly Thr Arg>

440 450 460 470 480

CTT GAA TAC ACA GAC ATA AAA AGC GAT GGA TCC GGA AAA GCT AAA GAA
GAA CTT ATG TGT CTG TAT TTT TCG CTA CCT AGG CCT TTT CGA TTT CTT
Leu Glu Tyr Thr Asp Ile Lys Ser Asp Gly Ser Gly Lys Ala Lys Glu>

490 500 510 520

GTT TTA AAA GAC TTT ACT CTT GAA GGA ACT CTA GCT GCT GAC GGC AAA
CAA AAT TTT CTG AAA TGA GAA CTT CCT TGA GAT CGA CGA CTG CCG TTT
Val Leu Lys Asp Phe Thr Leu Glu Gly Thr Leu Ala Ala Asp Gly Lys>

530 540 550 560 570

ACA ACA TTG AAA GTT ACA GAA GGC ACT GTT GTT TTA AGC AAG ATT TCA
TGT TGT AAC TTT CAA TGT CTT CCG TGA CAA CAA AAT TCG TTC TAA AGT
Thr Thr Leu Lys Val Thr Glu Gly Thr Val Val Leu Ser Lys Ile Ser>

580 590 600 610 620

AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630 640 650 660 670

GCT ACT AAA AAA ACT GCA GCT TGG AAT TCA AAA ACT TCC ACT TTA ACA
CGA TGA TTT TTT TGA CGT CGA ACC TTA AGT TTT TGA AGG TGA AAT TGT
Ala Thr Lys Lys Thr Ala Ala Trp Asn Ser Lys Thr Ser Thr Leu Thr>

680 690 700 710 720

ATT AGT GTG AAT AGC CAA AAA ACC AAA AAC CTT GTA TTC ACA AAA GAA
TAA TCA CAC TTA TCG GTT TTT TGG TTT TTG GAA CAT AAG TGT TTT CTT
Ile Ser Val Asn Ser Gln Lys Thr Lys Asn Leu Val Phe Thr Lys Glu>

730 740 750 760

GAC ACA ATA ACA GTA CAA AAA TAC GAC TCA GCA GGC ACC AAT CTA GAA
CTG TGT TAT TGT CAT GTT TTT ATG CTG AGT CGT CCG TGG TTA GAT CTT
Asp Thr Ile Thr Val Gln Lys Tyr Asp Ser Ala Gly Thr Asn Leu Glu>

FIG. 27B

```
770       780       790       800       810
 *    *    *    *    *    *    *    *    *    *
GGC AAA GCA GTC GAA ATT ACA ACA CTT AAA GAA CTT AAA AAC GCT TTA
CCG TTT CGT CAG CTT TAA TGT TGT GAA TTT CTT GAA TTT TTG CGA AAT
Gly Lys Ala Val Glu Ile Thr Thr Leu Lys Glu Leu Lys Asn Ala Leu>

 820
   *
AAA TAA
TTT ATT
Lys ***>
```

FIG. 27C 10 20 30 40

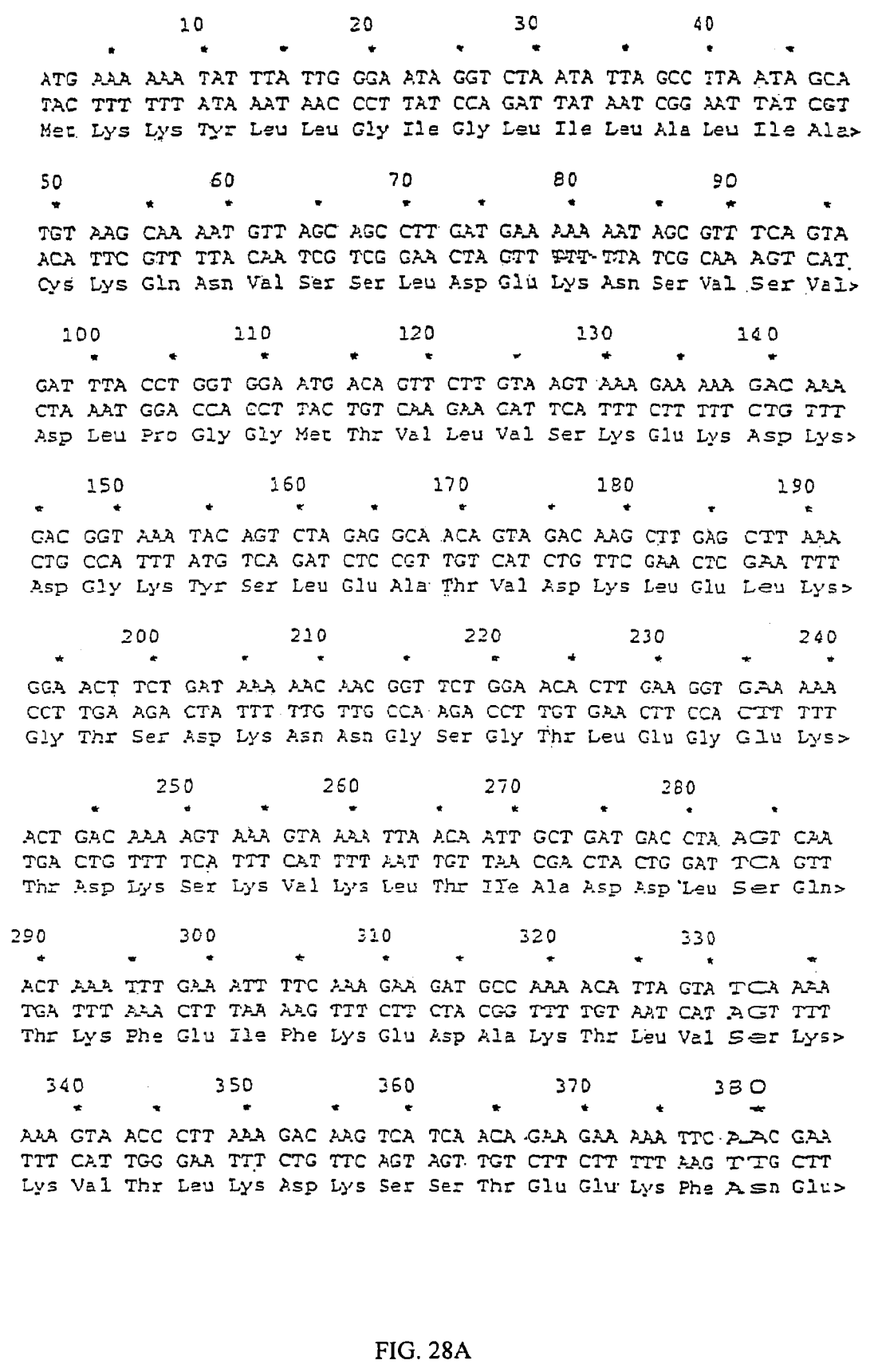

ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50 60 70 80 90

TGT AAG CAA AAT GTT AGC AGC CTT GAT GAA AAA AAT AGC GTT TCA GTA
ACA TTC GTT TTA CAA TCG TCG GAA CTA CTT TTT TTA TCG CAA AGT CAT
Cys Lys Gln Asn Val Ser Ser Leu Asp Glu Lys Asn Ser Val Ser Val>

100 110 120 130 140

GAT TTA CCT GGT GGA ATG ACA GTT CTT GTA AGT AAA GAA AAA GAC AAA
CTA AAT GGA CCA CCT TAC TGT CAA GAA CAT TCA TTT CTT TTT CTG TTT
Asp Leu Pro Gly Gly Met Thr Val Leu Val Ser Lys Glu Lys Asp Lys>

150 160 170 180 190

GAC GGT AAA TAC AGT CTA GAG GCA ACA GTA GAC AAG CTT GAG CTT AAA
CTG CCA TTT ATG TCA GAT CTC CGT TGT CAT CTG TTC GAA CTC GAA TTT
Asp Gly Lys Tyr Ser Leu Glu Ala Thr Val Asp Lys Leu Glu Leu Lys>

200 210 220 230 240

GGA ACT TCT GAT AAA AAC AAC GGT TCT GGA ACA CTT GAA GGT GAA AAA
CCT TGA AGA CTA TTT TTG TTG CCA AGA CCT TGT GAA CTT CCA CTT TTT
Gly Thr Ser Asp Lys Asn Asn Gly Ser Gly Thr Leu Glu Gly Glu Lys>

250 260 270 280

ACT GAC AAA AGT AAA GTA AAA TTA ACA ATT GCT GAT GAC CTA AGT CAA
TGA CTG TTT TCA TTT CAT TTT AAT TGT TAA CGA CTA CTG GAT TCA GTT
Thr Asp Lys Ser Lys Val Lys Leu Thr Ile Ala Asp Asp Leu Ser Gln>

290 300 310 320 330

ACT AAA TTT GAA ATT TTC AAA GAA GAT GCC AAA ACA TTA GTA TCA AAA
TGA TTT AAA CTT TAA AAG TTT CTT CTA CGG TTT TGT AAT CAT AGT TTT
Thr Lys Phe Glu Ile Phe Lys Glu Asp Ala Lys Thr Leu Val Ser Lys>

340 350 360 370 380

AAA GTA ACC CTT AAA GAC AAG TCA TCA ACA GAA GAA AAA TTC AAC GAA
TTT CAT TGG GAA TTT CTG TTC AGT AGT TGT CTT CTT TTT AAG TTG CTT
Lys Val Thr Leu Lys Asp Lys Ser Ser Thr Glu Glu Lys Phe Asn Glu>

FIG. 28A

```
   390         400         410         420         430
*    *     *     *     *     *     *     *     *     *
AAG GGT GAA ACA TCT GAA AAA ACA ATA GTA AGA GCA AAT GGA ACC AGA
TTC CCA CTT TGT AGA CTT TTT TGT TAT CAT TCT CGT TTA CCT TGG TCT
Lys Gly Glu Thr Ser Glu Lys Thr Ile Val Arg Ala Asn Gly Thr Arg>

      440         450         460         470         480
*     *     *     *     *     *     *     *     *     *
CTT GAA TAC ACA GAC ATA AAA AGC GAT GGA TCC GGA AAA GCT AAA GAA
GAA CTT ATG TGT CTG TAT TTT TCG CTA CCT AGG CCT TTT CGA TTT CTT
Leu Glu Tyr Thr Asp Ile Lys Ser Asp Gly Ser Gly Lys Ala Lys Glu>

         490         500         510         520
    *     *     *     *     *     *     *     *     *
GTT TTA AAA GAC TTT ACT CTT GAA GGA ACT CTA GCT GCT GAC GGC AAA
CAA AAT TTT CTG AAA TGA GAA CTT CCT TGA GAT CGA CGA CTG CCG TTT
Val Leu Lys Asp Phe Thr Leu Glu Gly Thr Leu Ala Ala Asp Gly Lys>

530         540         550         560         570
 *     *     *     *     *     *     *     *     *     *
ACA ACA TTG AAA GTT ACA GAA GGC ACT GTT GTT TTA AGC AAG ATT TCA
TGT TGT AAC TTT CAA TGT CTT CCG TGA CAA CAA AAT TCG TTC TAA AGT
Thr Thr Leu Lys Val Thr Glu Gly Thr Val Val Leu Ser Lys Ile Ser>

  580         590         600         610         620
    *     *     *     *     *     *     *     *     *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

    630         640         650         660         670
*     *     *     *     *     *     *     *     *     *
GCT ACT AAA AAA ACT GCA GCT TGG AAT TCA AAA ACT TCC ACT TTA ACA
CGA TGA TTT TTT TGA CGT CGA ACC TTA AGT TTT TGA AGG TGA AAT TGT
Ala Thr Lys Lys Thr Ala Ala Trp Asn Ser Lys Thr Ser Thr Leu Thr>

      680         690         700         710         720
*     *     *     *     *     *     *     *     *     *
ATT AGT GTG AAT AGC CAA AAA ACC AAA AAC CTT GTA TTC ACA AAA GAA
TAA TCA CAC TTA TCG GTT TTT TGG TTT TTG GAA CAT AAG TGT TTT CTT
Ile Ser Val Asn Ser Gln Lys Thr Lys Asn Leu Val Phe Thr Lys Glu>

         730         740         750         760
    *     *     *     *     *     *     *     *     *
GAC ACA ATA ACA GTA CAA AAA TAC GAC TCA GCA GGC ACC AAT CTA GAA
CTG TGT TAT TGT CAT GTT TTT ATG CTG AGT CGT CCG TGG TTA GAT CTT
Asp Thr Ile Thr Val Gln Lys Tyr Asp Ser Ala Gly Thr Asn Leu Glu>
```

FIG. 28B

```
770        780         790         800         810
 *      *    *      *     *     *     *      *    *      *
GGC AAA GCA GTC GAA ATT ACA ACA CTT AAA GAA CTT AAA AAC GCT TTA
CCG TTT CGT CAG CTT TAA TGT TGT GAA TTT CTT GAA TTT TTG CGA AAT
Gly Lys Ala Val Glu Ile Thr Thr Leu Lys Glu Leu Lys Asn Ala Leu>

  820
   *
AAA TAA
TTT ATT
Lys ***>
```

FIG. 28C

```
        10          20          30          40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

  100         110         120         130         140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

    150         160         170         180         190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

      200         210         220         230         240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

          250         260         270         280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290         300         310         320         330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

  340         350         360         370         380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 29A

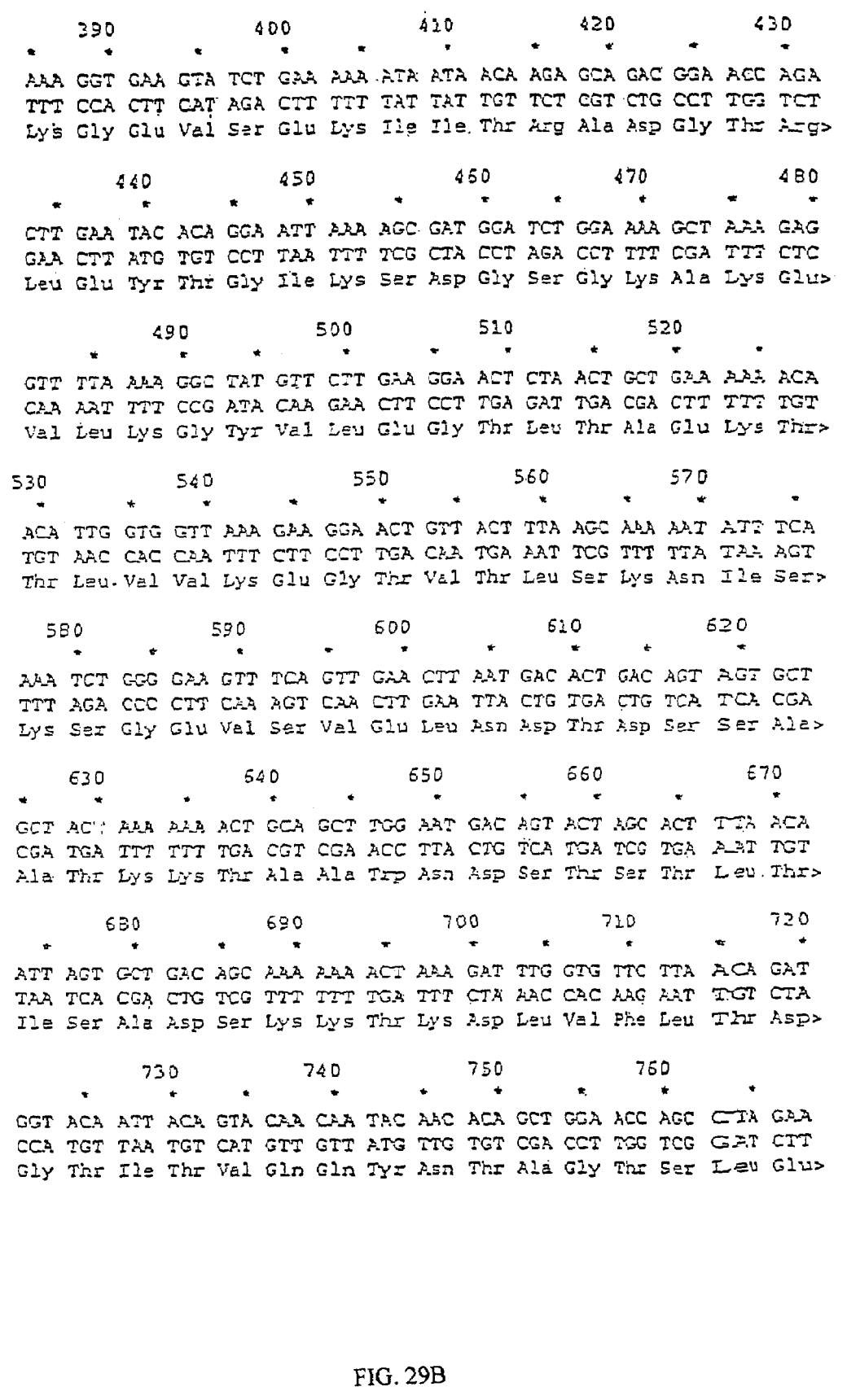

```
     390       400       410       420       430
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

     440       450       460       470       480
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

     490       500       510       520
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530       540       550       560       570
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

 580       590       600       610       620
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

   630       640       650       660       670
GCT ACT AAA AAA ACT GCA GCT TGG AAT GAC AGT ACT AGC ACT TTA ACA
CGA TGA TTT TTT TGA CGT CGA ACC TTA CTG TCA TGA TCG TGA AAT TGT
Ala Thr Lys Lys Thr Ala Ala Trp Asn Asp Ser Thr Ser Thr Leu Thr>

     680       690       700       710       720
ATT AGT GCT GAC AGC AAA AAA ACT AAA GAT TTG GTG TTC TTA ACA GAT
TAA TCA CGA CTG TCG TTT TTT TGA TTT CTA AAC CAC AAG AAT TGT CTA
Ile Ser Ala Asp Ser Lys Lys Thr Lys Asp Leu Val Phe Leu Thr Asp>

       730       740       750       760
GGT ACA ATT ACA GTA CAA CAA TAC AAC ACA GCT GGA ACC AGC CTA GAA
CCA TGT TAA TGT CAT GTT GTT ATG TTG TGT CGA CCT TGG TCG GAT CTT
Gly Thr Ile Thr Val Gln Gln Tyr Asn Thr Ala Gly Thr Ser Leu Glu>
```

FIG. 29B

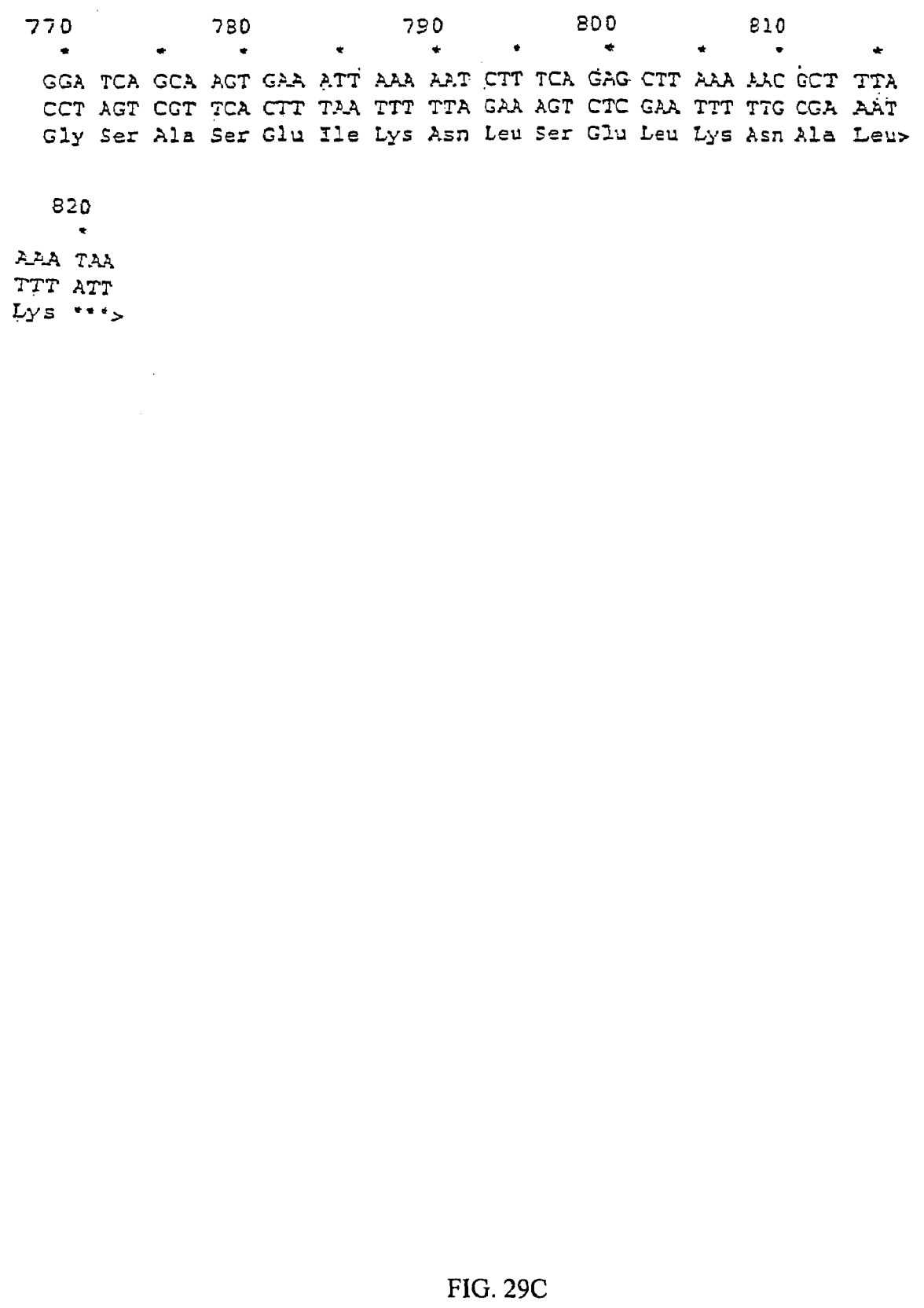

```
770         780         790         800         810
 *     *     *     *     *     *     *     *     *     *
GGA TCA GCA AGT GAA ATT AAA AAT CTT TCA GAG CTT AAA AAC GCT TTA
CCT AGT CGT TCA CTT TAA TTT TTA GAA AGT CTC GAA TTT TTG CGA AAT
Gly Ser Ala Ser Glu Ile Lys Asn Leu Ser Glu Leu Lys Asn Ala Leu>

  820
   *
AAA TAA
TTT ATT
Lys ***>
```

FIG. 29C

```
         10         20         30         40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50         60         70         80         90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

  100        110        120        130        140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

    150        160        170        180        190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

      200        210        220        230        240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

        250        260        270        280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290        300        310        320        330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

  340        350        360        370        380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 30A

```
      390       400       410       420       430
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

        440       450       460       470       480
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

          490       500       510       520
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530       540       550       560       570
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

  580       590       600       610       620
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

    630       640       650       660       670
GCT ACT AAA AAA ACT GCA GCT TGG AAT GAC AGT ACT AGC ACT TTA ACA
CGA TGA TTT TTT TGA CGT CGA ACC TTA CTG TCA TGA TCG TGA AAT TGT
Ala Thr Lys Lys Thr Ala Ala Trp Asn Asp Ser Thr Ser Thr Leu Thr>

      680       690       700       710       720
ATT AGT GCT GAC AGC AAA AAA ACT AAA GAT TTG GTG TTC TTA ACA GAT
TAA TCA CGA CTG TCG TTT TTT TGA TTT CTA AAC CAC AAG AAT TGT CTA
Ile Ser Ala Asp Ser Lys Lys Thr Lys Asp Leu Val Phe Leu Thr Asp>

        730       740       750       760
GGT ACA ATT ACA GTA CAA CAA TAC AAC ACA GCT GGA ACC AGC CTA GAA
CCA TGT TAA TGT CAT GTT GTT ATG TTG TGT CGA CCT TGG TCG GAT CTT
Gly Thr Ile Thr Val Gln Gln Tyr Asn Thr Ala Gly Thr Ser Leu Glu>
```

FIG. 30B

```
770         780          790         800         810
GGA TCA GCA AGT GAA ATT AAA AAT CTT TCA GAG CTT AAA AAC GCT TTA
CCT AGT CGT TCA CTT TAA TTT TTA GAA AGT CTC GAA TTT TTG CGA AAT
Gly Ser Ala Ser Glu Ile Lys Asn Leu Ser Glu Leu Lys Asn Ala Leu>

  820         830         840         850         860
AAA ATG GCT AAT AAT TCA GGG AAA GAT GGG AAT ACA TCT GCA AAT TCT
TTT TAC CGA TTA TTA AGT CCC TTT CTA CCC TTA TGT AGA CGT TTA AGA
Lys Met Ala Asn Asn Ser Gly Lys Asp Gly Asn Thr Ser Ala Asn Ser>

    870         880         890         900         910
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
Ala Asp Glu Ser Val Lys Gly Pro Asn Leu Thr Glu Ile Ser Lys Lys>

      920         930         940         950         960
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
Ile Thr Asp Ser Asn Ala Val Leu Leu Ala Val Lys Glu Val Glu Ala>

        970         980         990         1000
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
Leu Leu Ser Ser Ile Asp Glu Ile Ala Ala Lys Ala Ile Gly Lys Lys>

1010         1020         1030         1040         1050
ATA CAC CAA AAT AAT GGT TTG GAT ACC GAA TAT AAT CAC AAT GGA TCA
TAT GTG GTT TTA TTA CCA AAC CTA TGG CTT ATA TTA GTG TTA CCT AGT
Ile His Gln Asn Asn Gly Leu Asp Thr Glu Tyr Asn His Asn Gly Ser>

 1060         1070         1080         1090         1100
TTG TTA GCG GGA CGT TAT GCA ATA TCA ACC CTA ATA AAA CAA AAA TTA
AAC AAT CGC CCT GCA ATA CGT TAT AGT TGG GAT TAT TTT GTT TTT AAT
Leu Leu Ala Gly Arg Tyr Ala Ile Ser Thr Leu Ile Lys Gln Lys Leu>

   1110         1120         1130         1140         1150
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
Asp Gly Leu Lys Asn Glu Gly Leu Lys Glu Lys Ile Asp Ala Ala Lys>
```

FIG. 30C

```
        1160        1170        1180        1190        1200
  *       *        *     *      *      *    *       *       *    *
AAA TGT TCT GAA ACA TTT ACT AAT AAA TTA AAA GCA AAA CAC ACA GAT
TTT ACA AGA CTT TGT AAA TGA TTA TTT AAT TTT CGT TTT GTG TGT CTA
Lys Cys Ser Glu Thr Phe Thr Asn Lys Leu Lys Ala Lys His Thr Asp>

          1210        1220        1230        1240
      *       *      *       *      *      *      *      *     *
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
Leu Gly Lys Glu Gly Val Thr Asp Ala Asp Ala Lys Glu Ala Ile Leu>

1250        1260        1270        1280        1290
  *       *      *       *      *      *      *      *     *      *
AAA ACA AAT GGT ACT AAA ACT AAA GGT GCT GAA GAA CTT GGA AAA TTA
TTT TGT TTA CCA TGA TTT TGA TTT CCA CGA CTT CTT GAA CCT TTT AAT
Lys Thr Asn Gly Thr Lys Thr Lys Gly Ala Glu Glu Leu Gly Lys Leu>

  1300        1310        1320        1330        1340
      *      *       *       *      *       *      *      *      *
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
Phe Glu Ser Val Glu Val Leu Ser Lys Ala Ala Lys Glu Met Leu Ala>

    1350        1360        1370        1380        1390
  *       *       *       *       *      *      *      *      *      *
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
Asn Ser Val Lys Glu Leu Thr Ser Pro Val Val Ala Glu Ser Pro Lys>

        1400
          *
AAA CCT TAA
TTT GGA ATT
Lys Pro ***>
```

FIG. 30D

```
           10          20          30          40
      *     *     *     *     *     *     *     *     *
ATG AAA AAG AAT ACA TTA AGT GCG ATA TTA ATG ACT TTA TTT TTA TTT
TAC TTT TTC TTA TGT AAT TCA CGC TAT AAT TAC TGA AAT AAA AAT AAA
Met Lys Lys Asn Thr Leu Ser Ala Ile Leu Met Thr Leu Phe Leu Phe>

50          60          70          80          90
 *     *     *     *     *     *     *     *     *     *
ATA TCT TGT AAT AAT TCA GGG AAA GAT GGG AAT ACA TCT GCA AAT TCT
TAT AGA ACA TTA TTA AGT CCC TTT CTA CCC TTA TGT AGA CGT TTA AGA
Ile Ser Cys Asn Asn Ser Gly Lys Asp Gly Asn Thr Ser Ala Asn Ser>

  100         110         120         130         140
   *     *     *     *     *     *     *     *     *
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
Ala Asp Glu Ser Val Lys Gly Pro Asn Leu Thr Glu Ile Ser Lys Lys>

    150         160         170         180         190
 *     *     *     *     *     *     *     *     *     *
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
Ile Thr Asp Ser Asn Ala Val Leu Leu Ala Val Lys Glu Val Glu Ala>

       200         210         220         230         240
   *     *     *     *     *     *     *     *     *     *
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
Leu Leu Ser Ser Ile Asp Glu Ile Ala Ala Lys Ala Ile Gly Lys Lys>

          250         260         270         280
      *     *     *     *     *     *     *     *     *
ATA CAC CAA AAT AAT GGT TTG GAT ACC GAA TAT AAT CAC AAT GGA TCA
TAT GTG GTT TTA TTA CCA AAC CTA TGG CTT ATA TTA GTG TTA CCT AGT
Ile His Gln Asn Asn Gly Leu Asp Thr Glu Tyr Asn His Asn Gly Ser>

290         300         310         320         330
 *     *     *     *     *     *     *     *     *     *
TTG TTA GCG GGA CGT TAT GCA ATA TCA ACC CTA ATA AAA CAA AAA TTA
AAC AAT CGC CCT GCA ATA CGT TAT AGT TGG GAT TAT TTT GTT TTT AAT
Leu Leu Ala Gly Arg Tyr Ala Ile Ser Thr Leu Ile Lys Gln Lys Leu>

  340         350         360         370         380
   *     *     *     *     *     *     *     *     *
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
Asp Gly Leu Lys Asn Glu Gly Leu Lys Glu Lys Ile Asp Ala Ala Lys>
```

FIG. 31A

```
   390        400        410        420        430
 *   *    *    *    *    *    *    *    *    *
AAA TGT TCT GAA ACA TTT ACT AAT AAA TTA AAA GCA AAA CAC ACA GAT
TTT ACA AGA CTT TGT AAA TGA TTA TTT AAT TTT CGT TTT GTG TGT CTA
Lys Cys Ser Glu Thr Phe Thr Asn Lys Leu Lys Ala Lys His Thr Asp>

      440        450        460        470        480
  *    *    *    *    *    *    *    *    *    *
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
Leu Gly Lys Glu Gly Val Thr Asp Ala Asp Ala Lys Glu Ala Ile Leu>

         490        500        510        520
    *    *    *    *    *    *    *    *    *
AAA ACA AAT GGT ACT AAA ACT AAA GGT GCT GAA GAA CTT GGA AAA TTA
TTT TGT TTA CCA TGA TTT TGA TTT CCA CGA CTT CTT GAA CCT TTT AAT
Lys Thr Asn Gly Thr Lys Thr Lys Gly Ala Glu Glu Leu Gly Lys Leu>

530        540        550        560        570
 *    *    *    *    *    *    *    *    *    *
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
Phe Glu Ser Val Glu Val Leu Ser Lys Ala Ala Lys Glu Met Leu Ala>

  580        590        600        610        620
  *    *    *    *    *    *    *    *    *
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
Asn Ser Val Lys Glu Leu Thr Ser Pro Val Val Ala Glu Ser Pro Lys>

    630        640        650        660        670
 *    *    *    *    *    *    *    *    *    *
AAA CCT AAG CAA AAT GTT AGC AGC CTT GAC GAG AAA AAC AGC GTT TCA
TTT GGA TTC GTT TTA CAA TCG TCG GAA CTG CTC TTT TTG TCG CAA AGT
Lys Pro Lys Gln Asn Val Ser Ser Leu Asp Glu Lys Asn Ser Val Ser>

      680        690        700        710        720
  *    *    *    *    *    *    *    *    *    *
GTA GAT TTG CCT GGT GAA ATG AAA GTT CTT GTA AGC AAA GAA AAA AAC
CAT CTA AAC GGA CCA CTT TAC TTT CAA GAA CAT TCG TTT CTT TTT TTG
Val Asp Leu Pro Gly Glu Met Lys Val Leu Val Ser Lys Glu Lys Asn>

         730        740        750        760
    *    *    *    *    *    *    *    *    *
AAA GAC GGC AAG TAC GAT CTA ATT GCA ACA GTA GAC AAG CTT GAG CTT
TTT CTG CCG TTC ATG CTA GAT TAA CGT TGT CAT CTG TTC GAA CTC GAA
Lys Asp Gly Lys Tyr Asp Leu Ile Ala Thr Val Asp Lys Leu Glu Leu>
```

FIG. 31B

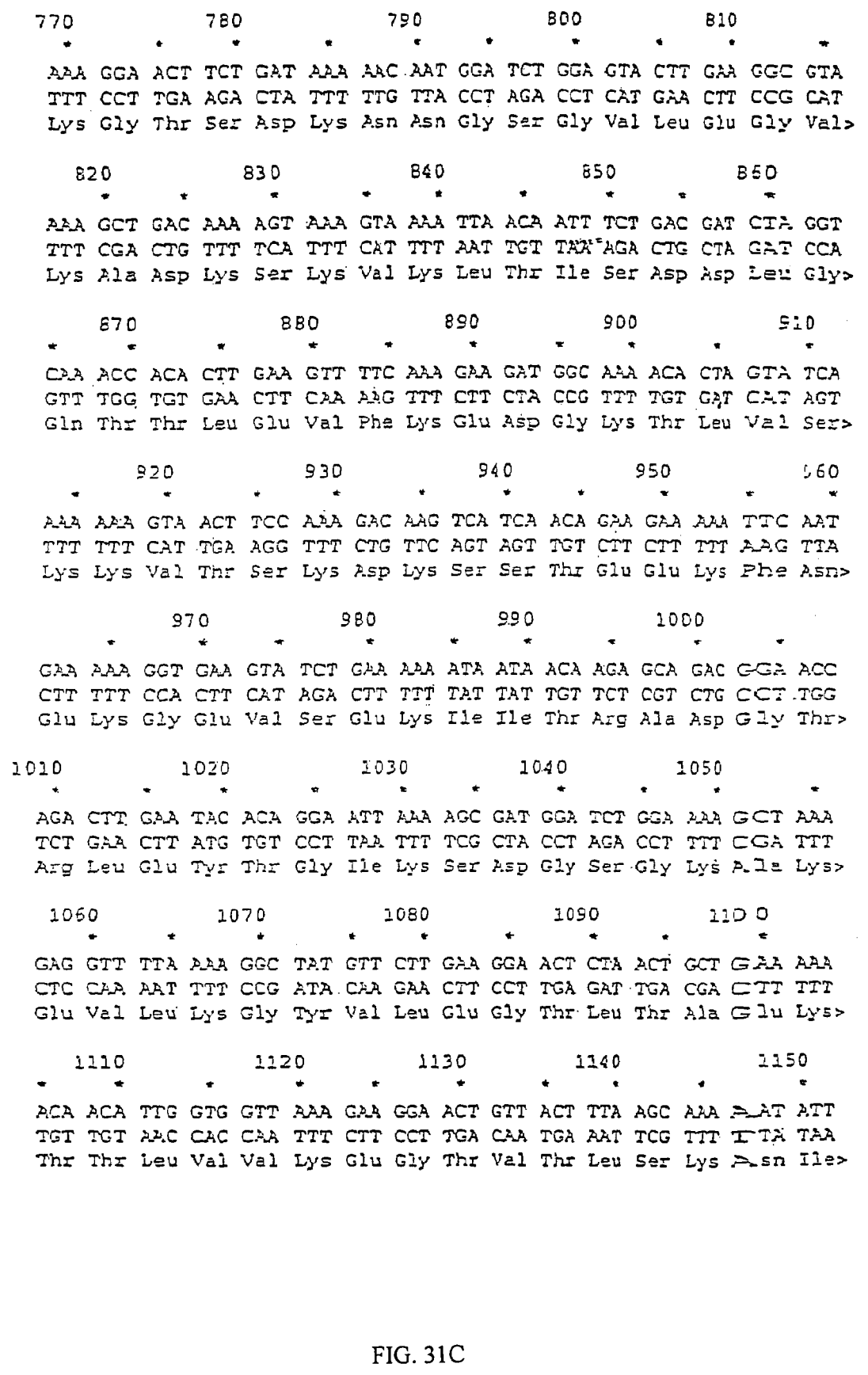

```
770          780          790          800          810
AAA GGA ACT TCT GAT AAA AAC AAT GGA TCT GGA GTA CTT GAA GGC GTA
TTT CCT TGA AGA CTA TTT TTG TTA CCT AGA CCT CAT GAA CTT CCG CAT
Lys Gly Thr Ser Asp Lys Asn Asn Gly Ser Gly Val Leu Glu Gly Val>

  820          830          840          850          860
AAA GCT GAC AAA AGT AAA GTA AAA TTA ACA ATT TCT GAC GAT CTA GGT
TTT CGA CTG TTT TCA TTT CAT TTT AAT TGT TAA AGA CTG CTA GAT CCA
Lys Ala Asp Lys Ser Lys Val Lys Leu Thr Ile Ser Asp Asp Leu Gly>

    870          880          890          900          910
CAA ACC ACA CTT GAA GTT TTC AAA GAA GAT GGC AAA ACA CTA GTA TCA
GTT TGG TGT GAA CTT CAA AAG TTT CTT CTA CCG TTT TGT GAT CAT AGT
Gln Thr Thr Leu Glu Val Phe Lys Glu Asp Gly Lys Thr Leu Val Ser>

      920          930          940          950          960
AAA AAA GTA ACT TCC AAA GAC AAG TCA TCA ACA GAA GAA AAA TTC AAT
TTT TTT CAT TGA AGG TTT CTG TTC AGT AGT TGT CTT CTT TTT AAG TTA
Lys Lys Val Thr Ser Lys Asp Lys Ser Ser Thr Glu Glu Lys Phe Asn>

        970          980          990          1000
GAA AAA GGT GAA GTA TCT GAA AAA ATA ATA ACA AGA GCA GAC GGA ACC
CTT TTT CCA CTT CAT AGA CTT TTT TAT TAT TGT TCT CGT CTG CCT TGG
Glu Lys Gly Glu Val Ser Glu Lys Ile Ile Thr Arg Ala Asp Gly Thr>

1010         1020         1030         1040         1050
AGA CTT GAA TAC ACA GGA ATT AAA AGC GAT GGA TCT GGA AAA GCT AAA
TCT GAA CTT ATG TGT CCT TAA TTT TCG CTA CCT AGA CCT TTT CGA TTT
Arg Leu Glu Tyr Thr Gly Ile Lys Ser Asp Gly Ser Gly Lys Ala Lys>

 1060         1070         1080         1090         1100
GAG GTT TTA AAA GGC TAT GTT CTT GAA GGA ACT CTA ACT GCT GAA AAA
CTC CAA AAT TTT CCG ATA CAA GAA CTT CCT TGA GAT TGA CGA CTT TTT
Glu Val Leu Lys Gly Tyr Val Leu Glu Gly Thr Leu Thr Ala Glu Lys>

   1110         1120         1130         1140         1150
ACA ACA TTG GTG GTT AAA GAA GGA ACT GTT ACT TTA AGC AAA AAT ATT
TGT TGT AAC CAC CAA TTT CTT CCT TGA CAA TGA AAT TCG TTT TTA TAA
Thr Thr Leu Val Val Lys Glu Gly Thr Val Thr Leu Ser Lys Asn Ile>
```

FIG. 31C

```
        1160          1170          1180          1190          1200
   *      *      *      *      *      *      *      *      *      *
TCA AAA TCT GGG GAA GTT TCA GTT GAA CTT AAT GAC ACT GAC AGT AGT
AGT TTT AGA CCC CTT CAA AGT CAA CTT GAA TTA CTG TGA CTG TCA TCA
Ser Lys Ser Gly Glu Val Ser Val Glu Leu Asn Asp Thr Asp Ser Ser>

          1210          1220          1230          1240
      *      *      *      *      *      *      *      *      *
GCT GCT ACT AAA AAA ACT GCA GCT TGG AAT GAC AGT ACT AGC ACT TTA
CGA CGA TGA TTT TTT TGA CGT CGA ACC TTA CTG TCA TGA TCG TGA AAT
Ala Ala Thr Lys Lys Thr Ala Ala Trp Asn Asp Ser Thr Ser Thr Leu>

1250          1260          1270          1280          1290
   *      *      *      *      *      *      *      *      *      *
ACA ATT AGT GCT GAC AGC AAA AAA ACT AAA GAT TTG GTG TTC TTA ACA
TGT TAA TCA CGA CTG TCG TTT TTT TGA TTT CTA AAC CAC AAG AAT TGT
Thr Ile Ser Ala Asp Ser Lys Lys Thr Lys Asp Leu Val Phe Leu Thr>

  1300          1310          1320          1330          1340
      *      *      *      *      *      *      *      *      *
GAT GGT ACA ATT ACA GTA CAA CAA TAC AAC ACA GCT GGA ACC AGC CTA
CTA CCA TGT TAA TGT CAT GTT GTT ATG TTG TGT CGA CCT TGG TCG GAT
Asp Gly Thr Ile Thr Val Gln Gln Tyr Asn Thr Ala Gly Thr Ser Leu>

    1350          1360          1370          1380          1390
  *      *      *      *      *      *      *      *      *      *
GAA GGA TCA GCA AGT GAA ATT AAA AAT CTT TCA GAG CTT AAA AAC GCT
CTT CCT AGT CGT TCA CTT TAA TTT TTA GAA AGT CTC GAA TTT TTG CGA
Glu Gly Ser Ala Ser Glu Ile Lys Asn Leu Ser Glu Leu Lys Asn Ala>

      1400
   *      *
TTA AAA TAA
AAT TTT ATT
Leu Lys ***>
```

FIG. 31D

```
          10          20          30          40
AAG CAA AAT GTT AGC AGC CTT GAC GAG AAA AAC AGC GTT TCA GTA GAT
TTC GTT TTA CAA TCG TCG GAA CTG CTC TTT TTG TCG CAA AGT CAT CTA
 K   Q   N   V   S   S   L   D   E   K   N   S   V   S   V   D>

50          60          70          80          90
TTG CCT GGT GAA ATG AAA GTT CTT GTA AGC AAA GAA AAA AAC AAA GAC
AAC GGA CCA CTT TAC TTT CAA GAA CAT TCG TTT CTT TTT TTG TTT CTG
 L   P   G   E   M   K   V   L   V   S   K   E   K   N   K   D>

 100         110         120         130         140
GGC AAG TAC GAT CTA ATT GCA ACA GTA GAC AAG CTT GAG CTT AAA GGA
CCG TTC ATG CTA GAT TAA CGT TGT CAT CTG TTC GAA CTC GAA TTT CCT
 G   K   Y   D   L   I   A       V   D   K   L   E   L   K   G>

   150         160         170         180         190
ACT TCT GAT AAA AAC AAT GGA TCT GGA GTA CTT GAA GGC GTA AAA GCT
TGA AGA CTA TTT TTG TTA CCT AGA CCT CAT GAA CTT CCG CAT TTT CGA
 T   S   D   K   N   N   G   S   G   V   L   E   G   V   K   A>

       200         210         220         230         240
GAC AAA AGT AAA GTA AAA TTA ACA ATT TCT GAC GAT CTA GGT CAA ACC
CTG TTT TCA TTT CAT TTT AAT TGT TAA AGA CTG CTA GAT CCA GTT TGG
 D   K   S   K   V   K   L   T   I   S   D   D   L   G   Q   T>

         250         260         270         280
ACA CTT GAA GTT TTC AAA GAA GAT GGC AAA ACA CTA GTA TCA AAA AAA
TGT GAA CTT CAA AAG TTT CTT CTA CCG TTT TGT GAT CAT AGT TTT TTT
 T   L   E   V   F   K   E   D   G   K   T   L   V   S   K   K>

290         300         310         320         330
GTA ACT TCC AAA GAC AAG TCA TCA ACA GAA GAA AAA TTC AAT GAA AAA
CAT TGA AGG TTT CTG TTC AGT AGT TGT CTT CTT TTT AAG TTA CTT TTT
 V   T   S   K   D   K   S   S   T   E   E   K   F   N   E   K>

 340         350         360         370         380
GGT GAA GTA TCT GAA AAA ATA ATA ACA AGA GCA GAC GGA ACC AGA CTT
CCA CTT CAT AGA CTT TTT TAT TAT TGT TCT CGT CTG CCT TGG TCT GAA
 G   E   V   S   E   K   I   I   T   R   A   D   G   T   R   L>
```

FIG. 32A

```
     390         400         410         420         430
GAA TAC ACA GGA ATT AAA AGC GAT GGA TCT GGA AAA GCT AAA GAG GTT
CTT ATG TGT CCT TAA TTT TCG CTA CCT AGA CCT TTT CGA TTT CTC CAA
 E   Y   T   G   I   K   S   D   G   S   G   K   A   K   E   V>

      440         450         460         470         480
TTA AAA GGC TAT GTT CTT GAA GGA ACT CTA ACT GCT GAA AAA ACA ACA
AAT TTT CCG ATA CAA GAA CTT CCT TGA GAT TGA CGA CTT TTT TGT TGT
 L   K   G   Y   V   L   E   G   T   L   T   A   E   K   T   T>

       490         500         510         520
TTG GTG GTT AAA GAA GGA ACT GTT ACT TTA AGC AAA AAT ATT TCA AAA
AAC CAC CAA TTT CTT CCT TGA CAA TGA AAT TCG TTT TTA TAA AGT TTT
 L   V   V   K   E   G   T   V   T   L   S   K   N   I   S   K>

530         540         550         560         570
TCT GGG GAA GTT TCA GTT GAA CTT AAT GAC ACT GAC AGT AGT GCT GCT
AGA CCC CTT CAA AGT CAA CTT GAA TTA CTG TGA CTG TCA TCA CGA CGA
 S   G   E   V   S   V   E   L   N   D   T   D   S   S   A   A>

  580         590         600         610         620
ACT AAA AAA ACT GCA GCT TGG AAT TCA GGC ACT TCA ACT TTA ACA ATT
TGA TTT TTT TGA CGT CGA ACC TTA AGT CCG TGA AGT TGA AAT TGT TAA
 T   K   K   T   A   A   W   N   S   G   T   S   T   L   T   I>

    630         640         650         660         670
ACT GTA AAC AGT AAA AAA ACT AAA GAC CTT GTG TTT ACA AAA GAA AAC
TGA CAT TTG TCA TTT TTT TGA TTT CTG GAA CAC AAA TGT TTT CTT TTG
 T   V   N   S   K   K   T   K   D   L   V   F   T   K   E   N>

      680         690         700         710         720
ACA ATT ACA GTA CAA CAA TAC GAC TCA AAT GGC ACC AAA TTA GAG GGG
TGT TAA TGT CAT GTT GTT ATG CTG AGT TTA CCG TGG TTT AAT CTC CCC
 T   I   T   V   Q   Q   Y   D   S   N   G   T   K   L   E   G>

        730         740         750         760
TCA GCA GTT GAA ATT ACA AAA CTT GAT GAA ATT AAA AAC GCT TTA AAA
AGT CGT CAA CTT TAA TGT TTT GAA CTA CTT TAA TTT TTG CGA AAT TTT
 S   A   V   E   I   T   K   L   D   E   I   K   N   A   L   K>
```

FIG. 32B

```
770         780          790          800          810
 *     *     *     *      *     *     *      *     *      *
GGT CAC CCC ATG GAT GAA AAG CTT TTA AAA AGT AAA GAT GAT AAA GCA
CCA GTG GGG TAC CTA CTT TTC GAA AAT TTT TCA TTT CTA CTA TTT CGT
 G   H   P   M   D   E   K   L   L   K   S   K   D   D   K   A>

  820         830          840          850          860
   *     *     *     *      *     *     *      *     *
AGT AAA GAT GGT AAA GCC TTG GAT CTT GAT CGA GAA TTA AAT TCT AAA
TCA TTT CTA CCA TTT CGG AAC CTA GAA CTA GCT CTT AAT TTA AGA TTT
 S   K   D   G   K   A   L   D   L   D   R   E   L   N   S   K>

    870          880          890          900          910
 *     *     *     *      *     *     *      *     *      *
GCT TCT AGC AAA GAA AAA AGT AAA GCC AAG GAA GAA GAA ATA ACC AAG
CGA AGA TCG TTT CTT TTT TCA TTT CGG TTC CTT CTT CTT TAT TGG TTC
 A   S   S   K   E   K   S   K   A   K   E   E   E   I   T   K>

      920          930          940          950          960
  *     *     *     *      *     *     *      *     *      *
GGT AAG TCA CAG AAA AGC TTA GGC GAT TTG AAT AAT GAT GAA AAT CTT
CCA TTC AGT GTC TTT TCG AAT CCG CTA AAC TTA TTA CTA CTT TTA GAA
 G   K   S   Q   K   S   L   G   D   L   N   N   D   E   N   L>

         970          980          990         1000
    *     *     *     *      *     *     *      *     *
ATG ATG CCA GAA GAT CAA AAA TTA CCT GAG GTT AAA AAA TTA GAT AGC
TAC TAC GGT CTT CTA GTT TTT AAT GGA CTC CAA TTT TTT AAT CTA TCG
 M   M   P   E   D   Q   K   L   P   E   V   K   K   L   D   S>

1010        1020         1030         1040         1050
 *     *     *     *      *     *     *      *     *      *
AAA AAA GAA TTT AAA CCT GTT TCT GAG GTT GAG AAA TTA GAT AAG ATT
TTT TTT CTT AAA TTT GGA CAA AGA CTC CAA CTC TTT AAT CTA TTC TAA
 K   K   E   F   K   P   V   S   E   V   E   K   L   D   K   I>

 1060        1070         1080         1090         1100
   *     *     *     *      *     *     *      *     *
TTC AAG TCT AAT AAC AAT GTT GGA GAA TTA TCA CCG TTA GAT AAA TCT
AAG TTC AGA TTA TTG TTA CAA CCT CTT AAT AGT GGC AAT CTA TTT AGA
 F   K   S   N   N   N   V   G   E   L   S   P   L   D   K   S>

   1110        1120         1130         1140         1150
 *     *     *     *      *     *     *      *     *      *
TCT TAT AAA GAC ATT GAT TCA AAA GAG GAG ACA GTT AAT AAA GAT GTT
AGA ATA TTT CTG TAA CTA AGT TTT CTC CTC TGT CAA TTA TTT CTA CAA
 S   Y   K   D   I   D   S   K   E   E   T   V   N   K   D   V>
```

FIG. 32C

```
        1160        1170        1180        1190        1200
AAT TTG CAA AAG ACT AAG CCT CAG GTT AAA GAC CAA GTT ACT TCT TTG
TTA AAC GTT TTC TGA TTC GGA GTC CAA TTT CTG GTT CAA TGA AGA AAC
 N   L   Q   K   T   K   P   Q   V   K   D   Q   V   T   S   L>

        1210        1220        1230        1240
AAT GAA GAT TTG ACT ACT ATG TCT ATA GAT TCC AGT AGT CCT GTA TTT
TTA CTT CTA AAC TGA TGA TAC AGA TAT CTA AGG TCA TCA GGA CAT AAA
 N   E   D   L   T   T   M   S   I   D   S   S   S   P   V   F>

1250        1260        1270        1280        1290
TTA GAG GTT ATT GAT CCA ATT ACA AAT TTA GGA ACT CTT CAA CTT ATT
AAT CTC CAA TAA CTA GGT TAA TGT TTA AAT CCT TGA GAA GTT GAA TAA
 L   E   V   I   D   P   I   T   N   L   G   T   L   Q   L   I>

  1300        1310        1320        1330        1340
GAT TTA AAT ACT GGT GTT AGG CTT AAA GAA AGC ACT CAG CAA GGC ATT
CTA AAT TTA TGA CCA CAA TCC GAA TTT CTT TCG TGA GTC GTT CCG TAA
 D   L   N   T   G   V   R   L   K   E   S   T   Q   Q   G   I>

    1350        1360        1370        1380        1390
CAG CGG TAT GGA ATT TAT GAA CGT GAA AAA GAT TTG GTT GTT ATT AAA
GTC GCC ATA CCT TAA ATA CTT GCA CTT TTT CTA AAC CAA CAA TAA TTT
 Q   R   Y   G   I   Y   E   R   E   K   D   L   V   V   I   K>

      1400        1410        1420        1430        1440
ATG GAT TCA GGA AAA GCT AAG CTT CAG ATA CTT GAT AAA CTT GAA AAT
TAC CTA AGT CCT TTT CGA TTC GAA GTC TAT GAA CTA TTT GAA CTT TTA
 M   D   S   G   K   A   K   L   Q   I   L   D   K   L   E   N>

        1450        1460        1470        1480
TTA AAA GTG GTA TCA GAG TCT AAT TTT GAG ATT AAT AAA AAT TCA TCT
AAT TTT CAC CAT AGT CTC AGA TTA AAA CTC TAA TTA TTT TTA AGT AGA
 L   K   V   V   S   E   S   N   F   E   I   N   K   N   S   S>

1490        1500        1510        1520        1530
CTT TAT GTT GAT TCT AAA ATG ATT TTA GTA GCT GTT AGG GAT AAA GAT
GAA ATA CAA CTA AGA TTT TAC TAA AAT CAT CGA CAA TCC CTA TTT CTA
 L   Y   V   D   S   K   M   I   L   V   A   V   R   D   K   D>
```

FIG. 32D

```
 1540        1550        1560         1570        1580
    *     *     *     *     *     *     *     *     *
AGT AGT AAT GAT TGG AGA TTG GCC AAA TTT TCT CCT AAA AAT TTA GAT
TCA TCA TTA CTA ACC TCT AAC CGG TTT AAA AGA GGA TTT TTA AAT CTA
 S   S   N   D   W   R   L   A   K   F   S   P   K   N   L   D>

   1590         1600        1610        1620         1630
 *     *     *     *     *     *     *     *     *     *
GAG TTT ATT CTT TCA GAG AAT AAA ATT ATG CCT TTT ACT AGC TTT TCT
CTC AAA TAA GAA AGT CTC TTA TTT TAA TAC GGA AAA TGA TCG AAA AGA
 E   F   I   L   S   E   N   K   I   M   P   F   T   S   F   S>

      1640        1650        1660        1670        1680
  *     *     *     *     *     *     *     *     *     *
GTG AGA AAA AAT TTT ATT TAT TTG CAA GAT GAG TTT AAA AGT CTA GTT
CAC TCT TTT TTA AAA TAA ATA AAC GTT CTA CTC AAA TTT TCA GAT CAA
 V   R   K   N   F   I   Y   L   Q   D   E   F   K   S   L   V>

        1690        1700        1710         1720
     *     *     *     *     *     *     *     *
ATT TTA GAT GTA AAT ACT TTA AAA AAA GTT AAG GGT CAC C
TAA AAT CTA CAT TTA TGA AAT TTT TTT CAA TTC CCA GTG G
 I   L   D   V   N   T   L   K   K   V   K   G   H   X>
```

FIG. 32E

```
          10         20         30         40
GCA CAA AAA GGT GCT GAG TCA ATT GGT TCT CAA AAA GAA AAT GAT CTA
CGT GTT TTT CCA CGA CTC AGT TAA CCA AGA GTT TTT CTT TTA CTA GAT
 A   Q   K   G   A   E   S   I   G   S   Q   K   E   N   D   L>

50         60         70         80         90
AAC CTT GAA GAC TCT AGT AAA AAA TCA CAT CAA AAC GCT AAA CAA GAC
TTG GAA CTT CTG AGA TCA TTT TTT AGT GTA GTT TTG CGA TTT GTT CTG
 N   L   E   D   S   S   K   K   S   H   Q   N   A   K   Q   D>

   100        110        120        130        140
CTT CCT GCG GTG ACA GAA GAC TCA GTG TCT TTG TTT AAT GGT AAT AAA
GAA GGA CGC CAC TGT CTT CTG AGT CAC AGA AAC AAA TTA CCA TTA TTT
 L   P   A   V   T   E   D   S   V   S   L   F   N   G   N   K>

     150        160        170        180        190
ATT TTT GTA AGC AAA GAA AAA AAT AGC TCC GGC AAA TAT GAT TTA AGA
TAA AAA CAT TCG TTT CTT TTT TTA TCG AGG CCG TTT ATA CTA AAT TCT
 I   F   V   S   K   E   K   N   S   S   G   K   Y   D   L   R>

        200        210        220        230        240
GCA ACA ATT GAT CAG GTT GAA CTT AAA GGA ACT TCC GAT AAA AAC AAT
CGT TGT TAA CTA GTC CAA CTT GAA TTT CCT TGA AGG CTA TTT TTG TTA
 A   T   I   D   Q   V   E   L   K   G   T   S   D   K   N   N>

           250        260        270        280
GGT TCT GGA ACC CTT GAA GGT TCA AAG CCT GAC AAG AGT AAA GTA AAA
CCA AGA CCT TGG GAA CTT CCA AGT TTC GGA CTG TTC TCA TTT CAT TTT
 G   S   G   T   L   E   G   S   K   P   D   K   S   K   V   K>

290        300        310        320        330
TTA ACA GTT TCT GCT GAT TTA AAC ACA GTA ACC TTA GAA GCA TTT GAT
AAT TGT CAA AGA CGA CTA AAT TTG TGT CAT TGG AAT CTT CGT AAA CTA
 L   T   V   S   A   D   L   N   T   V   T   L   E   A   F   D>

   340        350        360        370        380
GCC AGC AAC CAA AAA ATT TCA AGT AAA GTT ACT AAA AAA CAG GGG TCA
CGG TCG TTG GTT TTT TAA AGT TCA TTT CAA TGA TTT TTT GTC CCC AGT
 A   S   N   Q   K   I   S   S   K   V   T   K   K   Q   G   S>
```

FIG. 33A

```
      390         400         410         420         430
 *     *     *     *     *     *     *     *     *     *
ATA ACA GAG GAA ACT CTC AAA GCT AAT AAA TTA GAC TCA AAG AAA TTA
TAT TGT CTC CTT TGA GAG TTT CGA TTA TTT AAT CTG AGT TTC TTT AAT
 I   T   E   E   T   L   K   A   N   K   L   D   S   K   K   L>

      440         450         460         470         480
 *     *     *     *     *     *     *     *     *     *
ACA AGA TCA AAC GGA ACT ACA CTT GAA TAC TCA CAA ATA ACA GAT GCT
TGT TCT AGT TTG CCT TGA TGT GAA CTT ATG AGT GTT TAT TGT CTA CGA
 T   R   S   N   G   T   T   L   E   Y   S   Q   I   T   D   A>

        490         500         510         520
     *     *     *     *     *     *     *     *     *
GAC AAT GCT ACA AAA GCA GTA GAA ACT CTA AAA AAT AGC ATT AAG CTT
CTG TTA CGA TGT TTT CGT CAT CTT TGA GAT TTT TTA TCG TAA TTC GAA
 D   N   A   T   K   A   V   E   T   L   K   N   S   I   K   L>

530         540         550         560         570
 *     *     *     *     *     *     *     *     *     *
GAA GGA AGT CTT GTA GTC GGA AAA ACA ACA GTG GAA ATT AAA GAA GGT
CTT CCT TCA GAA CAT CAG CCT TTT TGT TGT CAC CTT TAA TTT CTT CCA
 E   G   S   L   V   V   G   K   T   T   V   E   I   K   E   G>

  580         590         600         610         620
   *     *     *     *     *     *     *     *     *
ACT GTT ACT CTA AAA AGA GAA ATT GAA AAA GAT GGA AAA GTA AAA GTC
TGA CAA TGA GAT TTT TCT CTT TAA CTT TTT CTA CCT TTT CAT TTT CAG
 T   V   T   L   K   R   E   I   E   K   D   G   K   V   K   V>

      630         640         650         660         670
 *     *     *     *     *     *     *     *     *     *
TTT TTG AAT GAC ACT GCA GGT TCT AAC AAA AAA ACA GGT AAA TGG GAA
AAA AAC TTA CTG TGA CGT CCA AGA TTG TTT TTT TGT CCA TTT ACC CTT
 F   L   N   D   T   A   G   S   N   K   K   T   G   K   W   E>

      680         690         700         710         720
 *     *     *     *     *     *     *     *     *     *
GAC AGT ACT AGC ACT TTA ACA ATT AGT GCT GAC AGC AAA AAA ACT AAA
CTG TCA TGA TCG TGA AAT TGT TAA TCA CGA CTG TCG TTT TTT TGA TTT
 D   S   T   S   T   L   T   I   S   A   D   S   K   K   T   K>

        730         740         750         760
     *     *     *     *     *     *     *     *     *
GAT TTG GTG TTC TTA ACA GAT GGT ACA ATT ACA GTA CAA CAA TAC AAC
CTA AAC CAC AAG AAT TGT CTA CCA TGT TAA TGT CAT GTT GTT ATG TTG
 D   L   V   F   L   T   D   G   T   I   T   V   Q   Q   Y   N>
```

FIG. 33B

```
770         780         790         800         810
ACA GCT GGA ACC AGC CTA GAA GGA TCA GCA AGT GAA ATT AAA AAT CTT
TGT CGA CCT TGG TCG GAT CTT CCT AGT CGT TCA CTT TAA TTT TTA GAA
 T   A   G   T   S   L   E   G   S   A   S   E   I   K   N   L>

820         830         840         850         860
TCA GAG CTT AAA AAC GCT TTA AAA GGT CAC CCC ATG GCT CAA TAT AAC
AGT CTC GAA TTT TTG CGA AAT TTT CCA GTG GGG TAC CGA GTT ATA TTG
 S   E   L   K   N   A   L   K   G   H   P   M   A   Q   Y   N>

870         880         890         900         910
CAA ATG CAC ATG TTA TCA AAC AAA TCT GCT TCT CAA AAT GTA AGA ACA
GTT TAC GTG TAC AAT AGT TTG TTT AGA CGA AGA GTT TTA CAT TCT TGT
 Q   M   H   M   L   S   N   K   S   A   S   Q   N   V   R   T>

920         930         940         950         960
GCT GAA GAG CTT GGA ATG CAG CCT GCA AAA ATT AAC ACA CCA GCA TCA
CGA CTT CTC GAA CCT TAC GTC GGA CGT TTT TAA TTG TGT GGT CGT AGT
 A   E   E   L   G   M   Q   P   A   K   I   N   T   P   A   S>

970         980         990         1000
CTT TCA GGG CTT CAA GCG TCT TGG ACT TTA AGA GTT CAT GTT GGA GCA
GAA AGT CCC GAA GTT CGC AGA ACC TGA AAT TCT CAA GTA CAA CCT CGT
 L   S   G   L   Q   A   S   W   T   L   R   V   H   V   G   A>

1010        1020        1030        1040        1050
ACC CAA GAT GAA GCT ATT GCT GTA AAT ATT TAT GCA GCT AAT GTT GCA
TGG GTT CTA CTT CGA TAA CGA CAT TTA TAA ATA CGT CGA TTA CAA CGT
 T   Q   D   E   A   I   A   V   N   I   Y   A   A   N   V   A>

1060        1070        1080        1090        1100
AAT CTT TTC TCT GGT GAG GGA GCT CAA ACT GCT CAG GCT GCA CCG GTT
TTA GAA AAG AGA CCA CTC CCT CGA GTT TGA CGA GTC CGA CGT GGC CAA
 N   L   F   S   G   E   G   A   Q   T   A   Q   A   A   P   V>

1110        1120        1130        1140        1150
CAA GAG GGT GTT CAA CAG GAA GGA GCT CAA CAG CCA GCA CCT GCT ACA
GTT CTC CCA CAA GTT GTC CTT CCT CGA GTT GTC GGT CGT GGA CGA TGT
 Q   E   G   V   Q   Q   E   G   A   Q   Q   P   A   P   A   T>
```

FIG. 33C

```
     1160       1170       1180
  *    *    *    *    *    *
GCA CCT TCT CAA GGC GGA GTT GGT CAC C
CGT GGA AGA GTT CCG CCT CAA CCA GTG G
 A   P   S   Q   G   G   V   G   H   X>
```

FIG. 33D

```
          10          20          30          40
GCA CAA AAA GGT GCT GAG TCA ATT GGT TCT CAA AAA GAA AAT GAT CTA
CGT GTT TTT CCA CGA CTC AGT TAA CCA AGA GTT TTT CTT TTA CTA GAT
 A   Q   K   G   A   E   S   I   G   S   Q   K   E   N   D   L>

 50          60          70          80          90
AAC CTT GAA GAC TCT AGT AAA AAA TCA CAT CAA AAC GCT AAA CAA GAC
TTG GAA CTT CTG AGA TCA TTT TTT AGT GTA GTT TTG CGA TTT GTT CTG
 N   L   E   D   S   S   K   K   S   H   Q   N   A   K   Q   D>

   100         110         120         130         140
CTT CCT GCG GTG ACA GAA GAC TCA GTG TCT TTG TTT AAT GGT AAT AAA
GAA GGA CGC CAC TGT CTT CTG AGT CAC AGA AAC AAA TTA CCA TTA TTT
 L   P   A   V   T   E   D   S   V   S   L   F   N   G   N   K>

    150         160         170         180         190
ATT TTT GTA AGC AAA GAA AAA AAT AGC TCC GGC AAA TAT GAT TTA AGA
TAA AAA CAT TCG TTT CTT TTT TTA TCG AGG CCG TTT ATA CTA AAT TCT
 I   F   V   S   K   E   K   N   S   S   G   K   Y   D   L   R>

       200         210         220         230         240
GCA ACA ATT GAT CAG GTT GAA CTT AAA GGA ACT TCC GAT AAA AAC AAT
CGT TGT TAA CTA GTC CAA CTT GAA TTT CCT TGA AGG CTA TTT TTG TTA
 A   T   I   D   Q   V   E   L   K   G   T   S   D   K   N   N>

          250         260         270         280
GGT TCT GGA ACC CTT GAA GGT TCA AAG CCT GAC AAG AGT AAA GTA AAA
CCA AGA CCT TGG GAA CTT CCA AGT TTC GGA CTG TTC TCA TTT CAT TTT
 G   S   G   T   L   E   G   S   K   P   D   K   S   K   V   K>

290         300         310         320         330
TTA ACA GTT TCT GCT GAT TTA AAC ACA GTA ACC TTA GAA GCA TTT GAT
AAT TGT CAA AGA CGA CTA AAT TTG TGT CAT TGG AAT CTT CGT AAA CTA
 L   T   V   S   A   D   L   N   T   V   T   L   E   A   F   D>

  340         350         360         370         380
GCC AGC AAC CAA AAA ATT TCA AGT AAA GTT ACT AAA AAA CAG GGG TCA
CGG TCG TTG GTT TTT TAA AGT TCA TTT CAA TGA TTT TTT GTC CCC AGT
 A   S   N   Q   K   I   S   S   K   V   T   K   K   Q   G   S>
```

FIG. 34A

```
    390         400         410         420         430
ATA ACA GAG GAA ACT CTC AAA GCT AAT AAA TTA GAC TCA AAG AAA TTA
TAT TGT CTC CTT TGA GAG TTT CGA TTA TTT AAT CTG AGT TTC TTT AAT
 I   T   E   E   T   L   K   A   N   K   L   D   S   K   K   L>

    440         450         460         470         480
ACA AGA TCA AAC GGA ACT ACA CTT GAA TAC TCA CAA ATA ACA GAT GCT
TGT TCT AGT TTG CCT TGA TGT GAA CTT ATG AGT GTT TAT TGT CTA CGA
 T   R   S   N   G   T   T   L   E   Y   S   Q   I   T   D   A>

    490         500         510         520
GAC AAT GCT ACA AAA GCA GTA GAA ACT CTA AAA AAT AGC ATT AAG CTT
CTG TTA CGA TGT TTT CGT CAT CTT TGA GAT TTT TTA TCG TAA TTC GAA
 D   N   A   T   K   A   V   E   T   L   K   N   S   I   K   L>

530         540         550         560         570
GAA GGA AGT CTT GTA GTC GGA AAA ACA ACA GTG GAA ATT AAA GAA GGT
CTT CCT TCA GAA CAT CAG CCT TTT TGT TGT CAC CTT TAA TTT CTT CCA
 E   G   S   L   V   V   G   K   T   T   V   E   I   K   E   G>

    580         590         600         610         620
ACT GTT ACT CTA AAA AGA GAA ATT GAA AAA GAT GGA AAA GTA AAA GTC
TGA CAA TGA GAT TTT TCT CTT TAA CTT TTT CTA CCT TTT CAT TTT CAG
 T   V   T   L   K   R   E   I   E   K   D   G   K   V   K   V>

    630         640         650         660         670
TTT TTG AAT GAC ACT GCA GGT TCT AAC AAA AAA ACA GGT AAA TGG GAA
AAA AAC TTA CTG TGA CGT CCA AGA TTG TTT TTT TGT CCA TTT ACC CTT
 F   L   N   D   T   A   G   S   N   K   K   T   G   K   W   E>

    680         690         700         710         720
GAC AGT ACT AGC ACT TTA ACA ATT AGT GCT GAC AGC AAA AAA ACT AAA
CTG TCA TGA TCG TGA AAT TGT TAA TCA CGA CTG TCG TTT TTT TGA TTT
 D   S   T   S   T   L   T   I   S   A   D   S   K   K   T   K>

    730         740         750         760
GAT TTG GTG TTC TTA ACA GAT GGT ACA ATT ACA GTA CAA CAA TAC AAC
CTA AAC CAC AAG AAT TGT CTA CCA TGT TAA TGT CAT GTT GTT ATG TTG
 D   L   V   F   L   T   D   G   T   I   T   V   Q   Q   Y   N>
```

FIG. 34B 770 780 790 800 810
ACA GCT GGA ACC AGC CTA GAA GGA TCA GCA AGT GAA ATT AAA AAT CTT
TGT CGA CCT TGG TCG GAT CTT CCT AGT CGT TCA CTT TAA TTT TTA GAA
T A G T S L E G S A S E I K N L>

820 830 840 850 860
TCA GAG CTT AAA AAC GCT TTA AAA GGT CAC CCC ATG GCT CAA TAT AAC
AGT CTC GAA TTT TTG CGA AAT TTT CCA GTG GGG TAC CGA GTT ATA TTG
S E L K N A L K G H P M A Q Y N>

870 880 890 900 910
CAA ATG CAC ATG TTA TCA AAC AAA TCT GCT TCT CAA AAT GTA AGA ACA
GTT TAC GTG TAC AAT AGT TTG TTT AGA CGA AGA GTT TTA CAT TCT TGT
Q M H M L S N K S A S Q N V R T>

920 930 940 950 960
GCT GAA GAG CTT GGA ATG CAG CCT GCA AAA ATT AAC ACA CCA GCA TCA
CGA CTT CTC GAA CCT TAC GTC GGA CGT TTT TAA TTG TGT GGT CGT AGT
A E E L G M Q P A K I N T P A S>

970 980 990 1000
CTT TCA GGG CTT CAA GCG TCT TGG ACT TTA AGA GTT CAT GTT GGA GCA
GAA AGT CCC GAA GTT CGC AGA ACC TGA AAT TCT CAA GTA CAA CCT CGT
L S G L Q A S W T L R V H V G A>

1010 1020 1030 1040 1050
ACC CAA GAT GAA GCT ATT GCT GTA AAT ATT TAT GCA GCT AAT GTT GCA
TGG GTT CTA CTT CGA TAA CGA CAT TTA TAA ATA CGT CGA TTA CAA CGT
T Q D E A I A V N I Y A A N V A>

1060 1070 1080 1090 1100
AAT CTT TTC TCT GGT GAG GGA GCT CAA ACT GCT CAG GCT GCA CCG GTT
TTA GAA AAG AGA CCA CTC CCT CGA GTT TGA CGA GTC CGA CGT GGC CAA
N L F S G E G A Q T A Q A A P V>

1110 1120 1130 1140 1150
CAA GAG GGT GTT CAA CAG GAA GGA GCT CAA CAG CCA GCA CCT GCT ACA
GTT CTC CCA CAA GTT GTC CTT CCT CGA GTT GTC GGT CGT GGA CGA TGT
Q E G V Q Q E G A Q Q P A P A T>

FIG. 34C

```
        1160          1170          1180          1190          1200
   *     *     *     *     *     *     *     *     *     *
GCA CCT TCT CAA GGC GGA GTT AAT TCT CCT GTT AAT GTT ACA ACT ACA
CGT GGA AGA GTT CCG CCT CAA TTA AGA GGA CAA TTA CAA TGT TGA TGT
 A   P   S   Q   G   G   V   N   S   P   V   N   V   T   T   T>

          1210          1220          1230          1240
     *     *     *     *     *     *     *     *     *
GTT GAT GCT AAT ACA TCA CTT GCT AAA ATT GAA AAT GCT ATT AGA ATG
CAA CTA CGA TTA TGT AGT GAA CGA TTT TAA CTT TTA CGA TAA TCT TAC
 V   D   A   N   T   S   L   A   K   I   E   N   A   I   R   M>

1250          1260          1270          1280          1290
 *     *     *     *     *     *     *     *     *     *
ATA AGT GAT CAA AGG GCA AAT TTA GGT GCT TTC CAA AAT AGA CTT GAA
TAT TCA CTA GTT TCC CGT TTA AAT CCA CGA AAG GTT TTA TCT GAA CTT
 I   S   D   Q   R   A   N   L   G   A   F   Q   N   R   L   E>

 1300          1310          1320          1330          1340
   *     *     *     *     *     *     *     *     *
TCT ATA AAG AAT AGT ACT GAG TAT GCA ATT GAA AAT CTA AAA GCA TCT
AGA TAT TTC TTA TCA TGA CTC ATA CGT TAA CTT TTA GAT TTT CGT AGA
 S   I   K   N   S   T   E   Y   A   I   E   N   L   K   A   S>

    1350          1360
 *     *     *     *
TAT GCT CAA ATA GGT CAC C
ATA CGA GTT TAT CCA GTG G
 Y   A   Q   I   G   H   X>
```

FIG. 34D

Figure 35A:
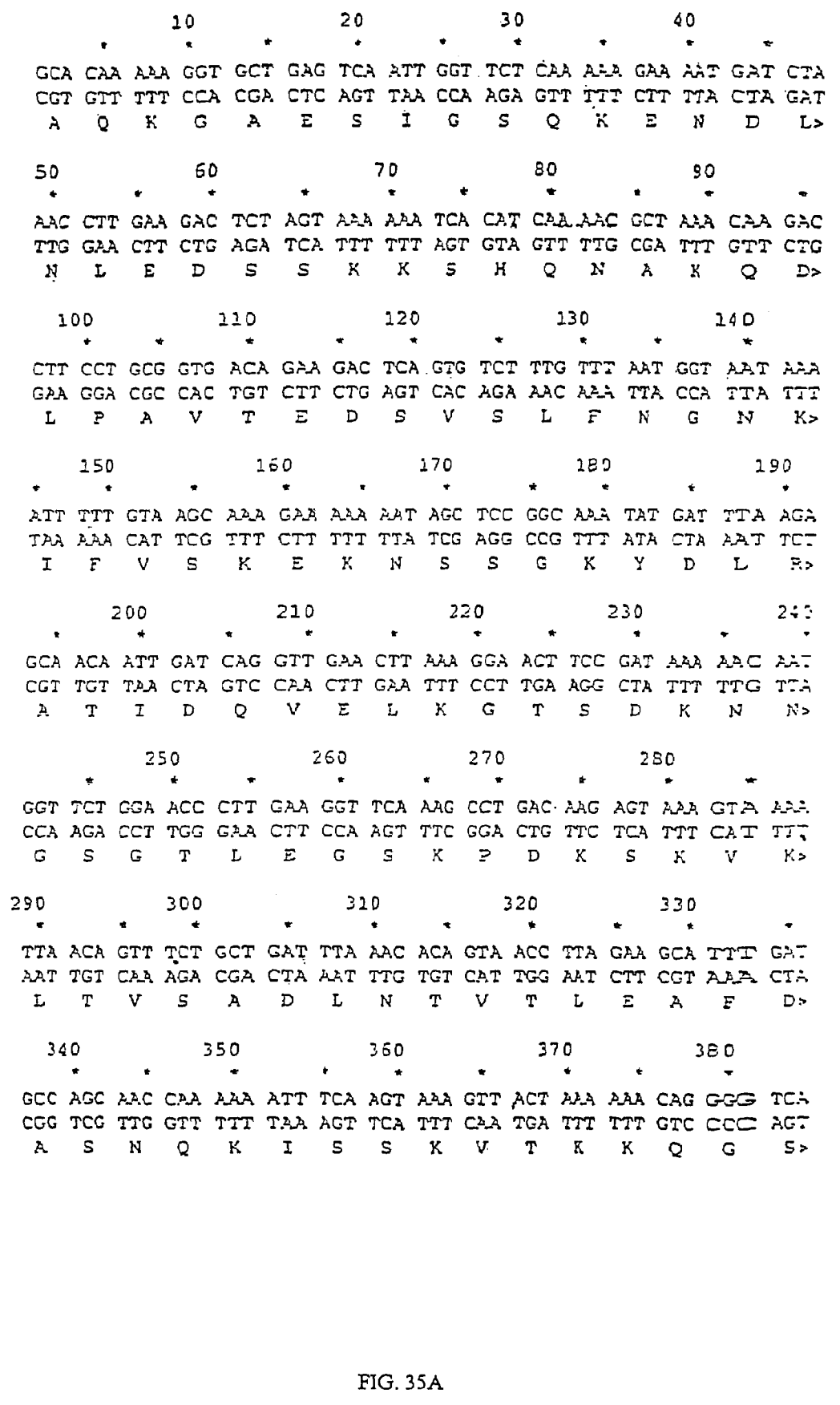

```
        10          20          30          40
GCA CAA AAA GGT GCT GAG TCA ATT GGT TCT CAA AAA GAA AAT GAT CTA
CGT GTT TTT CCA CGA CTC AGT TAA CCA AGA GTT TTT CTT TTA CTA GAT
 A   Q   K   G   A   E   S   I   G   S   Q   K   E   N   D   L>

50          60          70          80          90
AAC CTT GAA GAC TCT AGT AAA AAA TCA CAT CAA AAC GCT AAA CAA GAC
TTG GAA CTT CTG AGA TCA TTT TTT AGT GTA GTT TTG CGA TTT GTT CTG
 N   L   E   D   S   S   K   K   S   H   Q   N   A   K   Q   D>

 100         110         120         130         140
CTT CCT GCG GTG ACA GAA GAC TCA GTG TCT TTG TTT AAT GGT AAT AAA
GAA GGA CGC CAC TGT CTT CTG AGT CAC AGA AAC AAA TTA CCA TTA TTT
 L   P   A   V   T   E   D   S   V   S   L   F   N   G   N   K>

    150         160         170         180         190
ATT TTT GTA AGC AAA GAA AAA AAT AGC TCC GGC AAA TAT GAT TTA AGA
TAA AAA CAT TCG TTT CTT TTT TTA TCG AGG CCG TTT ATA CTA AAT TCT
 I   F   V   S   K   E   K   N   S   S   G   K   Y   D   L   R>

       200         210         220         230         240
GCA ACA ATT GAT CAG GTT GAA CTT AAA GGA ACT TCC GAT AAA AAC AAT
CGT TGT TAA CTA GTC CAA CTT GAA TTT CCT TGA AGG CTA TTT TTG TTA
 A   T   I   D   Q   V   E   L   K   G   T   S   D   K   N   N>

          250         260         270         280
GGT TCT GGA ACC CTT GAA GGT TCA AAG CCT GAC AAG AGT AAA GTA AAA
CCA AGA CCT TGG GAA CTT CCA AGT TTC GGA CTG TTC TCA TTT CAT TTT
 G   S   G   T   L   E   G   S   K   P   D   K   S   K   V   K>

290         300         310         320         330
TTA ACA GTT TCT GCT GAT TTA AAC ACA GTA ACC TTA GAA GCA TTT GAT
AAT TGT CAA AGA CGA CTA AAT TTG TGT CAT TGG AAT CTT CGT AAA CTA
 L   T   V   S   A   D   L   N   T   V   T   L   E   A   F   D>

  340         350         360         370         380
GCC AGC AAC CAA AAA ATT TCA AGT AAA GTT ACT AAA AAA CAG GGG TCA
CGG TCG TTG GTT TTT TAA AGT TCA TTT CAA TGA TTT TTT GTC CCC AGT
 A   S   N   Q   K   I   S   S   K   V   T   K   K   Q   G   S>
```

FIG. 35A 390 400 410 420 430
ATA ACA GAG GAA ACT CTC AAA GCT AAT AAA TTA GAC TCA AAG AAA TTA
TAT TGT CTC CTT TGA GAG TTT CGA TTA TTT AAT CTG AGT TTC TTT AAT
I T E E T L K A N K L D S K K L>

440 450 460 470 480
ACA AGA TCA AAC GGA ACT ACA CTT GAA TAC TCA CAA ATA ACA GAT GCT
TGT TCT AGT TTG CCT TGA TGT GAA CTT ATG AGT GTT TAT TGT CTA CGA
T R S N G T T L E Y S Q I T D A>

490 500 510 520
GAC AAT GCT ACA AAA GCA GTA GAA ACT CTA AAA AAT AGC ATT AAG CTT
CTG TTA CGA TGT TTT CGT CAT CTT TGA GAT TTT TTA TCG TAA TTC GAA
D N A T K A V E T L K N S I K L>

530 540 550 560 570
GAA GGA AGT CTT GTA GTC GGA AAA ACA ACA GTG GAA ATT AAA GAA GGT
CTT CCT TCA GAA CAT CAG CCT TTT TGT TGT CAC CTT TAA TTT CTT CCA
E G S L V V G K T T V E I K E G>

580 590 600 610 620
ACT GTT ACT CTA AAA AGA GAA ATT GAA AAA GAT GGA AAA GTA AAA GTC
TGA CAA TGA GAT TTT TCT CTT TAA CTT TTT CTA CCT TTT CAT TTT CAG
T V T L K R E I E K D G K V K V>

630 640 650 660 670
TTT TTG AAT GAC ACT GCA GGT TCT AAC AAA AAA ACA GGT AAA TGG GAA
AAA AAC TTA CTG TGA CGT CCA AGA TTG TTT TTT TGT CCA TTT ACC CTT
F L N D T A G S N K K T G K W E>

680 690 700 710 720
GAC AGT ACT AGC ACT TTA ACA ATT AGT GCT GAC AGC AAA AAA ACT AAA
CTG TCA TGA TCG TGA AAT TGT TAA TCA CGA CTG TCG TTT TTT TGA TTT
D S T S T L T I S A D S K K T K>

730 740 750 760
GAT TTG GTG TTC TTA ACA GAT GGT ACA ATT ACA GTA CAA CAA TAC AAC
CTA AAC CAC AAG AAT TGT CTA CCA TGT TAA TGT CAT GTT GTT ATG TTG
D L V F L T D G T I T V Q Q Y N>

FIG. 35B

```
770        780         790        800        810
 *     *     *     *     *     *     *     *     *     *
ACA GCT GGA ACC AGC CTA GAA GGA TCA GCA AGT GAA ATT AAA AAT CTT
TGT CGA CCT TGG TCG GAT CTT CCT AGT CGT TCA CTT TAA TTT TTA GAA
 T   A   G   T   S   L   E   G   S   A   S   E   I   K   N   L>

  820        830        840        850        860
   *     *     *     *     *     *     *     *     *
TCA GAG CTT AAA AAC GCT TTA AAA GGT CAC CCC ATG GCT TCT CAA AAT
AGT CTC GAA TTT TTG CGA AAT TTT CCA GTG GGG TAC CGA AGA GTT TTA
 S   E   L   K   N   A   L   K   G   H   P   M   A   S   Q   N>

    870          880        890         900         910
 *     *     *     *     *     *     *     *     *     *
GTA AGA ACA GCT GAA GAG CTT GGA ATG CAG CCT GCA AAA ATT AAC ACA
CAT TCT TGT CGA CTT CTC GAA CCT TAC GTC GGA CGT TTT TAA TTG TGT
 V   R   T   A   E   E   L   G   M   Q   P   A   K   I   N   T>

      920        930        940        950        960
 *     *     *     *     *     *     *     *     *     *
CCA GCA TCA CTT TCA GGG CTT CAA GCG TCT TGG ACT TTA AGA GTT CAT
GGT CGT AGT GAA AGT CCC GAA GTT CGC AGA ACC TGA AAT TCT CAA GTA
 P   A   S   L   S   G   L   Q   A   S   W   T   L   R   V   H>

        970        980        990        1000
     *     *     *     *     *     *     *     *     *
GTT GGA GCA ACC CAA GAT GAA GCT ATT GCT GTA AAT ATT TAT GCA GCT
CAA CCT CGT TGG GTT CTA CTT CGA TAA CGA CAT TTA TAA ATA CGT CGA
 V   G   A   T   Q   D   E   A   I   A   V   N   I   Y   A   A>

1010       1020       1030       1040       1050
 *     *     *     *     *     *     *     *     *     *
AAT GTT GCA AAT CTT TTC TCT GGT GAG GGA GCT CAA ACT GCT CAG GCT
TTA CAA CGT TTA GAA AAG AGA CCA CTC CCT CGA GTT TGA CGA GTC CGA
 N   V   A   N   L   F   S   G   E   G   A   Q   T   A   Q   A>

1060       1070       1080       1090       1100
   *     *     *     *     *     *     *     *     *
GCA CCG GTT CAA GAG GGT GTT CAA CAG GAA GGA GCT CAA CAG CCA GCA
CGT GGC CAA GTT CTC CCA CAA GTT GTC CTT CCT CGA GTT GTC GGT CGT
 A   P   V   Q   E   G   V   Q   Q   E   G   A   Q   Q   P   A>

  1110       1120       1130       1140
 *     *     *     *     *     *     *     *
CCT GCT ACA GCA CCT TCT CAA GGC GGA GTT GGT CAC C
GGA CGA TGT CGT GGA AGA GTT CCG CCT CAA CCA GTG G
 P   A   T   A   P   S   Q   G   G   V   G   H   X>
```

FIG. 35C

```
                10          20          30          40
GCA CAA AAA GGT GCT GAG TCA ATT GGT TCT CAA AAA GAA AAT GAT CTA
CGT GTT TTT CCA CGA CTC AGT TAA CCA AGA GTT TTT CTT TTA CTA GAT
 A   Q   K   G   A   E   S   I   G   S   Q   K   E   N   D   L>

 50          60          70          80          90
AAC CTT GAA GAC TCT AGT AAA AAA TCA CAT CAA AAC GCT AAA CAA GAC
TTG GAA CTT CTG AGA TCA TTT TTT AGT GTA GTT TTG CGA TTT GTT CTG
 N   L   E   D   S   S   K   K   S   H   Q   N   A   K   Q   D>

  100         110         120         130         140
CTT CCT GCG GTG ACA GAA GAC TCA GTG TCT TTG TTT AAT GGT AAT AAA
GAA GGA CGC CAC TGT CTT CTG AGT CAC AGA AAC AAA TTA CCA TTA TTT
 L   P   A   V   T   E   D   S   V   S   L   F   N   G   N   K>

    150         160         170         180         190
ATT TTT GTA AGC AAA GAA AAA AAT AGC TCC GGC AAA TAT GAT TTA AGA
TAA AAA CAT TCG TTT CTT TTT TTA TCG AGG CCG TTT ATA CTA AAT TCT
 I   F   V   S   K   E   K   N   S   S   G   K   Y   D   L   R>

      200         210         220         230         240
GCA ACA ATT GAT CAG GTT GAA CTT AAA GGA ACT TCC GAT AAA AAC AAT
CGT TGT TAA CTA GTC CAA CTT GAA TTT CCT TGA AGG CTA TTT TTG TTA
 A   T   I   D   Q   V   E   L   K   G   T   S   D   K   N   N>

        250         260         270         280
GGT TCT GGA ACC CTT GAA GGT TCA AAG CCT GAC AAG AGT AAA GTA AAA
CCA AGA CCT TGG GAA CTT CCA AGT TTC GGA CTG TTC TCA TTT CAT TTT
 G   S   G   T   L   E   G   S   K   P   D   K   S   K   V   K>

290         300         310         320         330
TTA ACA GTT TCT GCT GAT TTA AAC ACA GTA ACC TTA GAA GCA TTT GAT
AAT TGT CAA AGA CGA CTA AAT TTG TGT CAT TGG AAT CTT CGT AAA CTA
 L   T   V   S   A   D   L   N   T   V   T   L   E   A   F   D>

  340         350         360         370         380
GCC AGC AAC CAA AAA ATT TCA AGT AAA GTT ACT AAA AAA CAG GGG TCA
CGG TCG TTG GTT TTT TAA AGT TCA TTT CAA TGA TTT TTT GTC CCC AGT
 A   S   N   Q   K   I   S   S   K   V   T   K   K   Q   G   S>
```

FIG. 36A 390 400 410 420 430

ATA ACA GAG GAA ACT CTC AAA GCT AAT AAA TTA GAC TCA AAG AAA TTA
TAT TGT CTC CTT TGA GAG TTT CGA TTA TTT AAT CTG AGT TTC TTT AAT
I T E E T L K A N K L D S K K L>

440 450 460 470 480

ACA AGA TCA AAC GGA ACT ACA CTT GAA TAC TCA CAA ATA ACA GAT GCT
TGT TCT AGT TTG CCT TGA TGT GAA CTT ATG AGT GTT TAT TGT CTA CGA
T R S N G T T L E Y S Q I T D A>

490 500 510 520

GAC AAT GCT ACA AAA GCA GTA GAA ACT CTA AAA AAT AGC ATT AAG CTT
CTG TTA CGA TGT TTT CGT CAT CTT TGA GAT TTT TTA TCG TAA TTC GAA
D N A T K A V E T L K N S I K L>

530 540 550 560 570

GAA GGA AGT CTT GTA GTC GGA AAA ACA ACA GTG GAA ATT AAA GAA GGT
CTT CCT TCA GAA CAT CAG CCT TTT TGT TGT CAC CTT TAA TTT CTT CCA
E G S L V V G K T T V E I K E G>

580 590 600 610 620

ACT GTT ACT CTA AAA AGA GAA ATT GAA AAA GAT GGA AAA GTA AAA GTC
TGA CAA TGA GAT TTT TCT CTT TAA CTT TTT CTA CCT TTT CAT TTT CAG
T V T L K R E I E K D G K V K V>

630 640 650 660 670

TTT TTG AAT GAC ACT GCA GGT TCT AAC AAA AAA ACA GGT AAA TGG GAA
AAA AAC TTA CTG TGA CGT CCA AGA TTG TTT TTT TGT CCA TTT ACC CTT
F L N D T A G S N K K T G K W E>

680 690 700 710 720

GAC AGT ACT AGC ACT TTA ACA ATT AGT GCT GAC AGC AAA AAA ACT AAA
CTG TCA TGA TCG TGA AAT TGT TAA TCA CGA CTG TCG TTT TTT TGA TTT
D S T S T L T I S A D S K K T K>

730 740 750 760

GAT TTG GTG TTC TTA ACA GAT GGT ACA ATT ACA GTA CAA CAA TAC AAC
CTA AAC CAC AAG AAT TGT CTA CCA TGT TAA TGT CAT GTT GTT ATG TTG
D L V F L T D G T I T V Q Q Y N>

FIG. 36B

```
770        780        790        800        810
 *     *     *     *     *     *     *     *     *     *
ACA GCT GGA ACC AGC CTA GAA GGA TCA GCA AGT GAA ATT AAA AAT CTT
TGT CGA CCT TGG TCG GAT CTT CCT AGT CGT TCA CTT TAA TTT TTA GAA
 T   A   G   T   S   L   E   G   S   A   S   E   I   K   N   L>

  820        830        840        850        860
   *     *     *     *     *     *     *     *     *
TCA GAG CTT AAA AAC GCT TTA AAA GGT CAC CCC ATG GCT TCT CAA AAT
AGT CTC GAA TTT TTG CGA AAT TTT CCA GTG GGG TAC CGA AGA GTT TTA
 S   E   L   K   N   A   L   K   G   H   P   M   A   S   Q   N>

    870        880        890        900        910
 *     *     *     *     *     *     *     *     *     *
GTA AGA ACA GCT GAA GAG CTT GGA ATG CAG CCT GCA AAA ATT AAC ACA
CAT TCT TGT CGA CTT CTC GAA CCT TAC GTC GGA CGT TTT TAA TTG TGT
 V   R   T   A   E   E   L   G   M   Q   P   A   K   I   N   T>

       920        930        940        950        960
 *     *     *     *     *     *     *     *     *     *
CCA GCA TCA CTT TCA GGG CTT CAA GCG TCT TGG ACT TTA AGA GTT CAT
GGT CGT AGT GAA AGT CCC GAA GTT CGC AGA ACC TGA AAT TCT CAA GTA
 P   A   S   L   S   G   L   Q   A   S   W   T   L   R   V   H>

          970        980        990       1000
   *     *     *     *     *     *     *     *     *
GTT GGA GCA ACC CAA GAT GAA GCT ATT GCT GTA AAT ATT TAT GCA GCT
CAA CCT CGT TGG GTT CTA CTT CGA TAA CGA CAT TTA TAA ATA CGT CGA
 V   G   A   T   Q   D   E   A   I   A   V   N   I   Y   A   A>

1010       1020       1030       1040       1050
 *     *     *     *     *     *     *     *     *     *
AAT GTT GCA AAT CTT TTC TCT GGT GAG GGA GCT CAA ACT GCT CAG GCT
TTA CAA CGT TTA GAA AAG AGA CCA CTC CCT CGA GTT TGA CGA GTC CGA
 N   V   A   N   L   F   S   G   E   G   A   Q   T   A   Q   A>

 1060       1070       1080       1090       1100
   *     *     *     *     *     *     *     *     *
GCA CCG GTT CAA GAG GGT GTT CAA CAG GAA GGA GCT CAA CAG CCA GCA
CGT GGC CAA GTT CTC CCA CAA GTT GTC CTT CCT CGA GTT GTC GGT CGT
 A   P   V   Q   E   G   V   Q   Q   E   G   A   Q   Q   P   A>

   1110       1120       1130       1140       1150
 *     *     *     *     *     *     *     *     *     *
CCT GCT ACA GCA CCT TCT CAA GGC GGA GTT AAT TCT CCT GTT AAT GTT
GGA CGA TGT CGT GGA AGA GTT CCG CCT CAA TTA AGA GGA CAA TTA CAA
 P   A   T   A   P   S   Q   G   G   V   N   S   P   V   N   V>
```

FIG. 36C

```
        1160        1170        1180        1190        1200
 *      *      *      *      *      *      *      *      *      *
ACA ACT ACA GTT GAT GCT AAT ACA TCA CTT GCT AAA ATT GAA AAT GCT
TGT TGA TGT CAA CTA CGA TTA TGT AGT GAA CGA TTT TAA CTT TTA CGA
 T   T   T   V   D   A   N   T   S   L   A   K   I   E   N   A>

          1210        1220        1230        1240
      *      *      *      *      *      *      *      *
ATT AGA ATG ATA AGT GAT CAA AGG GCA AAT TTA GGT GCT TTC CAA AAT
TAA TCT TAC TAT TCA CTA GTT TCC CGT TTA AAT CCA CGA AAG GTT TTA
 I   R   M   I   S   D   Q   R   A   N   L   G   A   F   Q   N>

1250        1260        1270        1280        1290
 *      *      *      *      *      *      *      *      *      *
AGA CTT GAA TCT ATA AAG AAT AGT ACT GAG TAT GCA ATT GAA AAT CTA
TCT GAA CTT AGA TAT TTC TTA TCA TGA CTC ATA CGT TAA CTT TTA GAT
 R   L   E   S   I   K   N   S   T   E   Y   A   I   E   N   L>

 1300        1310        1320
   *      *      *      *      *
AAA GCA TCT TAT GCT CAA ATA GGT CAC C
TTT CGT AGA ATA CGA GTT TAT CCA GTG G
 K   A   S   Y   A   Q   I   G   H   X>
```

FIG. 36D

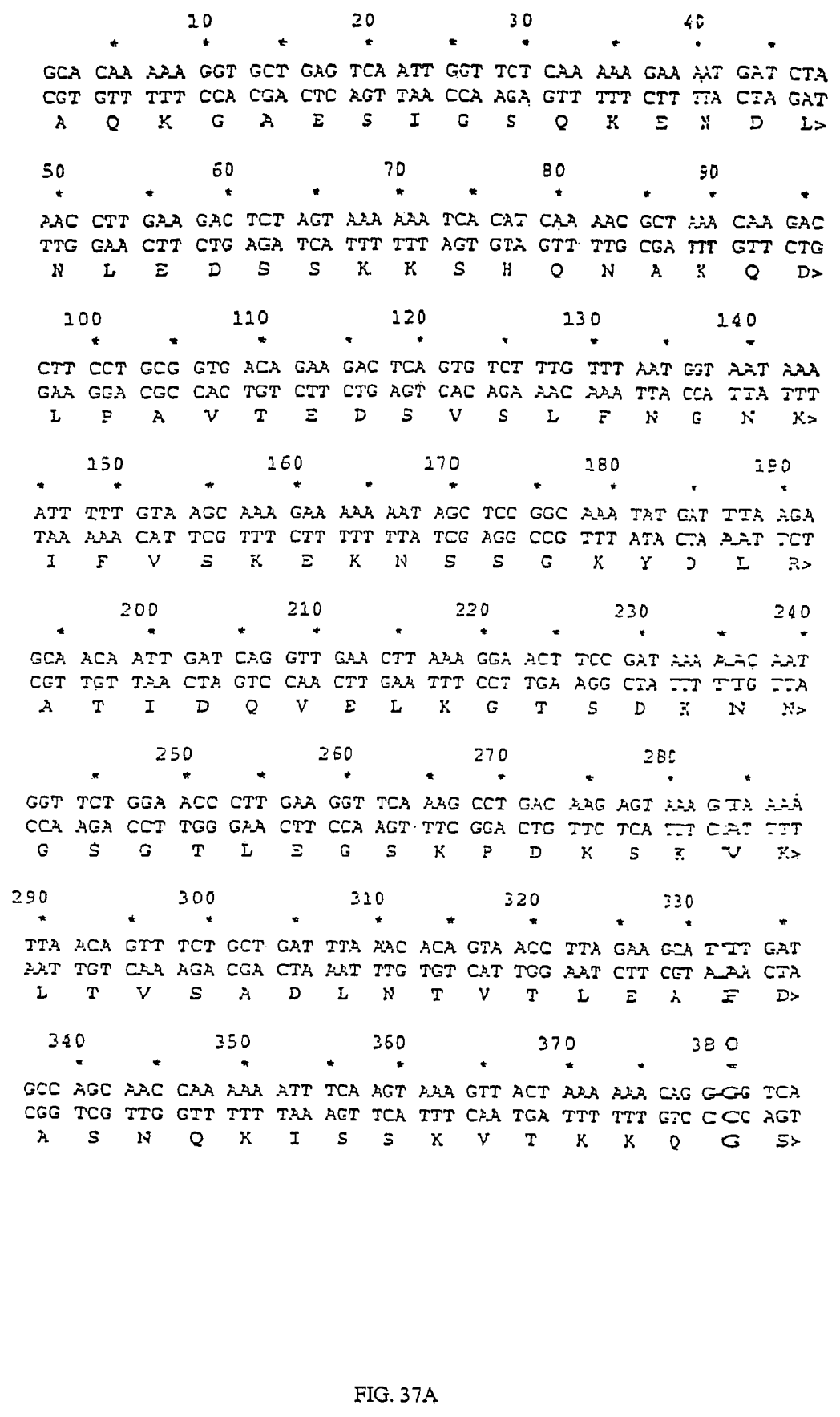

```
        10          20          30          40
GCA CAA AAA GGT GCT GAG TCA ATT GGT TCT CAA AAA GAA AAT GAT CTA
CGT GTT TTT CCA CGA CTC AGT TAA CCA AGA GTT TTT CTT TTA CTA GAT
 A   Q   K   G   A   E   S   I   G   S   Q   K   E   N   D   L>

50          60          70          80          90
AAC CTT GAA GAC TCT AGT AAA AAA TCA CAT CAA AAC GCT AAA CAA GAC
TTG GAA CTT CTG AGA TCA TTT TTT AGT GTA GTT TTG CGA TTT GTT CTG
 N   L   E   D   S   S   K   K   S   H   Q   N   A   K   Q   D>

 100         110         120         130         140
CTT CCT GCG GTG ACA GAA GAC TCA GTG TCT TTG TTT AAT GGT AAT AAA
GAA GGA CGC CAC TGT CTT CTG AGT CAC AGA AAC AAA TTA CCA TTA TTT
 L   P   A   V   T   E   D   S   V   S   L   F   N   G   N   K>

    150         160         170         180         190
ATT TTT GTA AGC AAA GAA AAA AAT AGC TCC GGC AAA TAT GAT TTA AGA
TAA AAA CAT TCG TTT CTT TTT TTA TCG AGG CCG TTT ATA CTA AAT TCT
 I   F   V   S   K   E   K   N   S   S   G   K   Y   D   L   R>

       200         210         220         230         240
GCA ACA ATT GAT CAG GTT GAA CTT AAA GGA ACT TCC GAT AAA AAC AAT
CGT TGT TAA CTA GTC CAA CTT GAA TTT CCT TGA AGG CTA TTT TTG TTA
 A   T   I   D   Q   V   E   L   K   G   T   S   D   K   N   N>

          250         260         270         280
GGT TCT GGA ACC CTT GAA GGT TCA AAG CCT GAC AAG AGT AAA GTA AAA
CCA AGA CCT TGG GAA CTT CCA AGT TTC GGA CTG TTC TCA TTT CAT TTT
 G   S   G   T   L   E   G   S   K   P   D   K   S   K   V   K>

290         300         310         320         330
TTA ACA GTT TCT GCT GAT TTA AAC ACA GTA ACC TTA GAA GCA TTT GAT
AAT TGT CAA AGA CGA CTA AAT TTG TGT CAT TGG AAT CTT CGT AAA CTA
 L   T   V   S   A   D   L   N   T   V   T   L   E   A   F   D>

 340         350         360         370         380
GCC AGC AAC CAA AAA ATT TCA AGT AAA GTT ACT AAA AAA CAG GGG TCA
CGG TCG TTG GTT TTT TAA AGT TCA TTT CAA TGA TTT TTT GTC CCC AGT
 A   S   N   Q   K   I   S   S   K   V   T   K   K   Q   G   S>
```

FIG. 37A

```
     390       400       410       420       430
ATA ACA GAG GAA ACT CTC AAA GCT AAT AAA TTA GAC TCA AAG AAA TTA
TAT TGT CTC CTT TGA GAG TTT CGA TTA TTT AAT CTG AGT TTC TTT AAT
 I   T   E   E   T   L   K   A   N   K   L   D   S   K   K   L>

     440       450       460       470       480
ACA AGA TCA AAC GGA ACT ACA CTT GAA TAC TCA CAA ATA ACA GAT GCT
TGT TCT AGT TTG CCT TGA TGT GAA CTT ATG AGT GTT TAT TGT CTA CGA
 T   R   S   N   G   T   T   L   E   Y   S   Q   I   T   D   A>

     490       500       510       520
GAC AAT GCT ACA AAA GCA GTA GAA ACT CTA AAA AAT AGC ATT AAG CTT
CTG TTA CGA TGT TTT CGT CAT CTT TGA GAT TTT TTA TCG TAA TTC GAA
 D   N   A   T   K   A   V   E   T   L   K   N   S   I   K   L>

530       540       550       560       570
GAA GGA AGT CTT GTA GTC GGA AAA ACA ACA GTG GAA ATT AAA GAA GGT
CTT CCT TCA GAA CAT CAG CCT TTT TGT TGT CAC CTT TAA TTT CTT CCA
 E   G   S   L   V   V   G   K   T   T   V   E   I   K   E   G>

 580       590       600       610       620
ACT GTT ACT CTA AAA AGA GAA ATT GAA AAA GAT GGA AAA GTA AAA GTC
TGA CAA TGA GAT TTT TCT CTT TAA CTT TTT CTA CCT TTT CAT TTT CAG
 T   V   T   L   K   R   E   I   E   K   D   G   K   V   K   V>

     630       640       650       660       670
TTT TTG AAT GAC ACT GCA GGT TCT AAC AAA AAA ACA GGT AAA TGG GAA
AAA AAC TTA CTG TGA CGT CCA AGA TTG TTT TTT TGT CCA TTT ACC CTT
 F   L   N   D   T   A   G   S   N   K   K   T   G   K   W   E>

     680       690       700       710       720
GAC AGT ACT AGC ACT TTA ACA ATT AGT GCT GAC AGC AAA AAA ACT AAA
CTG TCA TGA TCG TGA AAT TGT TAA TCA CGA CTG TCG TTT TTT TGA TTT
 D   S   T   S   T   L   T   I   S   A   D   S   K   K   T   K>

     730       740       750       760
GAT TTG GTG TTC TTA ACA GAT GGT ACA ATT ACA GTA CAA CAA TAC AAC
CTA AAC CAC AAG AAT TGT CTA CCA TGT TAA TGT CAT GTT GTT ATG TTG
 D   L   V   F   L   T   D   G   T   I   T   V   Q   Q   Y   N>
```

FIG. 37B

```
770          780          790          800          810
ACA GCT GGA ACC AGC CTA GAA GGA TCA GCA AGT GAA ATT AAA AAT CTT
TGT CGA CCT TGG TCG GAT CTT CCT AGT CGT TCA CTT TAA TTT TTA GAA
 T   A   G   T   S   L   E   G   S   A   S   E   I   K   N   L>

  820          830          840          850          860
TCA GAG CTT AAA AAC GCT TTA AAA GGT CAC CCC ATG GGA AAT AAT TCA
AGT CTC GAA TTT TTG CGA AAT TTT CCA GTG GGG TAC CCT TTA TTA AGT
 S   E   L   K   N   A   L   K   G   H   P   M   G   N   N   S>

    870          880          890          900          910
GGG AAA GAT GGG AAT ACA TCT GCA AAT TCT GCT GAT GAG TCT GTT AAA
CCC TTT CTA CCC TTA TGT AGA CGT TTA AGA CGA CTA CTC AGA CAA TTT
 G   K   D   G   N   T   S   A   N   S   A   D   E   S   V   K>

       920          930          940          950          960
GGG CCT AAT CTT ACA GAA ATA AGT AAA AAA ATT ACG GAT TCT AAT GCG
CCC GGA TTA GAA TGT CTT TAT TCA TTT TTT TAA TGC CTA AGA TTA CGC
 G   P   N   L   T   E   I   S   K   K   I   T   D   S   N   A>

          970          980          990         1000
GTT TTA CTT GCT GTG AAA GAG GTT GAA GCG TTG CTG TCA TCT ATA GAT
CAA AAT GAA CGA CAC TTT CTC CAA CTT CGC AAC GAC AGT AGA TAT CTA
 V   L   L   A   V   K   E   V   E   A   L   L   S   S   I   D>

1010         1020         1030         1040         1050
GAA ATT GCT GCT AAA GCT ATT GGT AAA AAA ATA CAC CAA AAT AAT GGT
CTT TAA CGA CGA TTT CGA TAA CCA TTT TTT TAT GTG GTT TTA TTA CCA
 E   I   A   A   K   A   I   G   K   K   I   H   Q   N   N   G>

  1060         1070         1080         1090         1100
TTG GAT ACC GAA TAT AAT CAC AAT GGA TCA TTG TTA GCG GGA CGT TAT
AAC CTA TGG CTT ATA TTA GTG TTA CCT AGT AAC AAT CGC CCT GCA ATA
 L   D   T   E   Y   N   H   N   G   S   L   L   A   G   R   Y>

    1110         1120         1130         1140         1150
GCA ATA TCA ACC CTA ATA AAA CAA AAA TTA GAT GGA TTG AAA AAT GAA
CGT TAT AGT TGG GAT TAT TTT GTT TTT AAT CTA CCT AAC TTT TTA CTT
 A   I   S   T   L   I   K   Q   K   L   D   G   L   K   N   E>
```

FIG. 37C

```
        1160         1170         1180         1190         1200
   *     *     *     *     *     *     *     *     *     *
GGA TTA AAG GAA AAA ATT GAT GCG GCT AAG AAA TGT TCT GAA ACA TTT
CCT AAT TTC CTT TTT TAA CTA CGC CGA TTC TTT ACA AGA CTT TGT AAA
 G   L   K   E   K   I   D   A   A   K   K   C   S   E   T   F>

        1210         1220         1230         1240
     *     *     *     *     *     *     *     *     *
ACT AAT AAA TTA AAA GAA AAA CAC ACA GAT CTT GGT AAA GAA GGT GTT
TGA TTA TTT AAT TTT CTT TTT GTG TGT CTA GAA CCA TTT CTT CCA CAA
 T   N   K   L   K   E   K   H   T   D   L   G   K   E   G   V>

1250         1260         1270         1280         1290
   *     *     *     *     *     *     *     *     *     *
ACT GAT GCT GAT GCA AAA GAA GCC ATT TTA AAA ACA AAT GGT ACT AAA
TGA CTA CGA CTA CGT TTT CTT CGG TAA AAT TTT TGT TTA CCA TGA TTT
 T   D   A   D   A   K   E   A   I   L   K   T   N   G   T   K>

  1300         1310         1320         1330         1340
     *     *     *     *     *     *     *     *     *
ACT AAA GGT GCT GAA GAA CTT GGA AAA TTA TTT GAA TCA GTA GAG GTC
TGA TTT CCA CGA CTT CTT GAA CCT TTT AAT AAA CTT AGT CAT CTC CAG
 T   K   G   A   E   E   L   G   K   L   F   E   S   V   E   V>

   1350         1360         1370         1380         1390
  *     *     *     *     *     *     *     *     *     *
TTG TCA AAA GCA GCT AAA GAG ATG CTT GCT AAT TCA GTT AAA GAG CTT
AAC AGT TTT CGT CGA TTT CTC TAC GAA CGA TTA AGT CAA TTT CTC GAA
 L   S   K   A   A   K   E   M   L   A   N   S   V   K   E   L>

        1400         1410         1420         1430         1440
  *     *     *     *     *     *     *     *     *     *
ACA AGC CCT GTT GTG GCA GAA AGT CCA AAA AAA CCT GGT ACC ATG GCT
TGT TCG GGA CAA CAC CGT CTT TCA GGT TTT TTT GGA CCA TGG TAC CGA
 T   S   P   V   V   A   E   S   P   K   K   P   G   T   M   A>

        1450         1460         1470         1480
     *     *     *     *     *     *     *     *     *
CAA TAT AAC CAA ATG CAC ATG TTA TCA AAC AAA TCT GCT TCT CAA AAT
GTT ATA TTG GTT TAC GTG TAC AAT AGT TTG TTT AGA CGA AGA GTT TTA
 Q   Y   N   Q   M   H   M   L   S   N   K   S   A   S   Q   N>

1490         1500         1510         1520         1530
  *     *     *     *     *     *     *     *     *     *
GTA AGA ACA GCT GAA GAG CTT GGA ATG CAG CCT GCA AAA ATT AAC ACA
CAT TCT TGT CGA CTT CTC GAA CCT TAC GTC GGA CGT TTT TAA TTG TGT
 V   R   T   A   E   E   L   G   M   Q   P   A   K   I   N   T>
```

FIG. 37D

```
 1540        1550        1560        1570        1580
   *     *     *     *     *     *     *     *     *
CCA GCA TCA CTT TCA GGG CTT CAA GCG TCT TGG ACT TTA AGA GTT CAT
GGT CGT AGT GAA AGT CCC GAA GTT CGC AGA ACC TGA AAT TCT CAA GTA
 P   A   S   L   S   G   L   Q   A   S   W   T   L   R   V   H>

   1590        1600        1610        1620        1630
 *     *     *     *     *     *     *     *     *     *
GTT GGA GCA ACC CAA GAT GAA GCT ATT GCT GTA AAT ATT TAT GCA GCT
CAA CCT CGT TGG GTT CTA CTT CGA TAA CGA CAT TTA TAA ATA CGT CGA
 V   G   A   T   Q   D   E   A   I   A   V   N   I   Y   A   A>

       1640        1650        1660        1670        1680
 *     *     *     *     *     *     *     *     *     *
AAT GTT GCA AAT CTT TTC TCT GGT GAG GGA GCT CAA ACT GCT CAG GCT
TTA CAA CGT TTA GAA AAG AGA CCA CTC CCT CGA GTT TGA CGA GTC CGA
 N   V   A   N   L   F   S   G   E   G   A   Q   T   A   Q   A>

          1690        1700        1710        1720
     *     *     *     *     *     *     *     *     *
GCA CCG GTT CAA GAG GGT GTT CAA CAG GAA GGA GCT CAA CAG CCA GCA
CGT GGC CAA GTT CTC CCA CAA GTT GTC CTT CCT CGA GTT GTC GGT CGT
 A   P   V   Q   E   G   V   Q   Q   E   G   A   Q   Q   P   A>

1730        1740        1750        1760
 *     *     *     *     *     *     *     *
CCT GCT ACA GCA CCT TCT CAA GGC GGA GTT GGT CAC C
GGA CGA TGT CGT GGA AGA GTT CCG CCT CAA CCA GTG G
 P   A   T   A   P   S   Q   G   G   V   G   H  X>
```

FIG. 37E

```
                        10              20             30              40
                    *       *     *       *        *       *       *       *       *
OspC-B31        ATG AAA AAG AAT ACA TTA AGT GCG ATA TTA ATG ACT TTA TTT TTA TTT
                TAC TTT TTC TTA TGT AAT TCA CGC TAT AAT TAC TGA AAT AAA AAT AAA

 1. OspC-PK             10              20             30              40
[ 1832 ]        ... ... ... ... ... ... ... ... ... ... ... ... ... ... ... ...>

 2. OspC-TR             10              20             30              40
[ 1786 ]        ... ... ... ... ... ... ... ... ... ... ... ... ... ... ... ...>

 3. OspC-K4             10              20             30              40
[ 1774 ]        ... ... ... ... ... ... ... ... ... ... ... ... ... ... ... ...>

                50          60             70              80            90
                *       *      *      *       *       *        *       *       *       *
OspC-B31        ATA TCT TGT AAT AAT TCA GGG AAA GAT GGG AAT ACA TCT GCA AAT TCT
                TAT AGA ACA TTA TTA AGT CCC TTT CTA CCC TTA TGT AGA CGT TTA AGA

                                                                  tgc
                                                                   |
 1. OspC-PK50               60             70              80      |   90
[ 1832 ]        ... ... ... .g. ... ... ... ... .g. ... g.. t.. ... a.t ... c..>

 2. OspC-TR50               60             70                  80              90
[ 1786 ]        ... ... ... ... ... ... ..t ggg ... --- tc. g.. ... a.t ..- ..->

 3. OspC-K450               60             70                  80              90
[ 1774 ]        ... ... ... ... ... ... ..t ggg ... --- .cc g.. ... a.t ..- ..->

                 100          110          120           130          140
                    *       *       *       *       *       *       *       *       *
OspC-B31        GCT GAT GAG TCT GTT AAA GGG CCT AAT CTT ACA GAA ATA AGT AAA AAA
                CGA CTA CTC AGA CAA TTT CCC GGA TTA GAA TGT CTT TAT TCA TTT TTT

 1. OspC-100               110            120             130          140
[ 1832 ]        ... ..c ... ... .cg ... ... ... ... ... ... ... ... ..c ... ...>

 2. OspC-TR              100            110             120          130
[ 1786 ]        -.. ... ... ... .ca ... ..a ... ... ... ..c .t. ... ..c ... ...>

 3.. OspC-K4             100            110             120          130
[ 1774 ]        -.. ... ... ... .ca ... ..a ... ... ... ... .t. ... ..c ... ...>
```

FIG. 38A

```
                 150            160            170           180            190
           *      *       *       *      *       *      *      *       *      *
OspC-B31   ATT ACG GAT TCT AAT GCG GTT TTA CTT GCT GTG AAA GAG GTT GAA GCG
           TAA TGC CTA AGA TTA CGC CAA AAT GAA CGA CAC TTT CTC CAA CTT CGC

 1. OspC-PK150          160           170           180           190
[ 1832 ]   ... ..a ... ... ... ..a t.. g.. ... ... ..t ... ..a ... ..g a.t>

 2. OspC-T140         150           160           170           180
[ 1786 ]   ... ..a ... ... ... ..a t.. ... ..g ... ... ... ..a ... ..g ..t>

 3. OspC-K140         150           160           170           180
[ 1774 ]   ... ..a ... ... ... ..a t.. g.. ..g ... ... ... ..a ... ..g ..t>


                200          210           220          230           240
          *       *       *     *      *       *      *      *      *      *
OspC-B31  TTG CTG TCA TCT ATA GAT GAA ATT GCT GCT AAA GCT ATT GGT AAA AAA
          AAC GAC AGT AGA TAT CTA CTT TAA CGA CGA TTT CGA TAA CCA TTT TTT

 1. OspC-PK   200           210           220           230           240
[ 1832 ]  ... g.t .t. ... ... ... ... c.. ... aag ... ... ... ... c.. ...>

 2. OspC-TR  190           200           210                 220          230
[ 1786 ]  ... ..t ... ... ... ... ... c.. --. -.. ... ... ... ... ... ...>

 3. OspC-K4  190           200           210           220          230
[ 1774 ]  ... a.c ... ... ... ... ... c.. ... aa. ... ... ... ... ... gt.>


                   250          260           270            280
              *       *      *      *      *      *      *      *      *
OspC-B31  ATA CAC CAA AAT AAT GGT TTG GAT ACC GAA TAT AAT CAC AAT GGA TCA
          TAT GTG GTT TTA TTA CCA AAC CTA TGG CTT ATA TTA GTG TTA CCT AGT

 1. OspC-PK       250           260           270           280           290
[ 1832 ]  ... g.. a.t ... ... ... ..a .c. g.t tt. a.. ... ..g ... ... ..g>

                                 tac
                                  |
 2. OspC-TR              240      |250          260           270
[ 1786 ]  ... -.- -.. ... g.. ... ..a ... .a. ... gca ... .ga ..c .a. ...>

 3. OspC-K4    240           250           260          270           280
[ 1774 ]  ... ..t ... ... ... ... ..a a.. g.t a.t gcg gg. ..a ..c ... ...>


            290           300            310          320          330
             *      *      *      *       *      *      *      *     *      *
OspC-B31  TTG TTA GCG GGA CGT TAT GCA ATA TCA ACC CTA ATA AAA CAA  AAA TTA
          AAC AAT CGC CCT GCA ATA CGT TAT AGT TGG GAT TAT TTT GTT  TTT AAT

 1. OspC-PK        300           310           320           330
[ 1832 ]  ... ... ..a ... gcc ... ... ... ... ... ... ... .c. g..  ... ..g>

 2. OspC-280           290           300           310           320
[ 1786 ]  ... a.. ..a ... gc. ... .a. ... ... .aa ... ... .c. ...  ... ...>
```

FIG. 38B

```
 3. OspC-K4        290        300        310        320        330
[ 1774 ]    ... ... ..a ... gcc ... ... ... ... ... ... ... .c. g.. ... ...>

              340        350        360        370        380
               *     *     *     *     *     *     *     *
OspC-B31    GAT GGA TTG AAA AAT GAA GGA TTA AAG GAA AAA ATT GAT GCG GCT AAG
            CTA CCT AAC TTT TTA CTT CCT AAT TTC CTT TTT TAA CTA CGC CGA TTC

                             ttt
                              |
 1. OspC-340          350     | 360        370        380        390
[ 1832 ]    ag. aa. ... ... ..a ... .a. ... ... ac. g.. ... .ca aa. ... ...>

 2. OspC-TR330             340        350        360        370
[ 1786 ]    ag. .t. ... ..t tca ... .a. ... ... a.. ... ... a.a .a. ... ...>

                             ttc
                              |
 3. OspC-K4           340     | 350        360        370        380
[ 1774 ]    ag. aa. ... ... ..a ... .ag ... ..t a.. ... ... ..a .a. ... ...>

               390        400        410        420        430
            *     *     *     *     *     *     *     *     *     *
OspC-B31    AAA TGT TCT GAA ACA TTT ACT AAT AAA TTA AAA GAA AAA CAC ACA GAT
            TTT ACA AGA CTT TGT AAA TGA TTA TTT AAT TTT CTT TTT GTG TGT CTA

 1. OspC-PK           400        410        420        430
[ 1832 ]    ... ... ..c ... ga. ... ... ... ... c.. ... agt ggt ..t g.. ...>

 2. OspC-TR  380        390        400        410        420
[ 1786 ]    g.t ... ..c ... .a. ... ... .c. ..g c.. ... ..t .gt ..t g.. ..g>

 3. OspC-K4         390        400        410        420
[ 1774 ]    ..c ca. ... ... g.. ... ... ... .g. c.. ... .gt tct ..t g.. c.a>

               440        450        460        470        480
            *     *     *     *     *     *     *     *     *
OspC-B31    CTT GGT AAA GAA GGT GTT ACT GAT GCT GAT GCA AAA GAA GCC ATT TTA
            GAA CCA TTT CTT CCA CAA TGA CTA CGA CTA CGT TTT CTT CGG TAA AAT

 1. OspC-P440         450        460        470        480
[ 1832 ]    ... ..c ... c.g .a. .c. ..c ... .a. c.. ... ... .c. ..t ... ...>

 2. OspC-TR     430        440        450        460        470
[ 1786 ]    ... ... .t. c.. a.c ... cag ... .a. a.. ... ... a.. ..t ... ...>

 3. OspC-430          440        450        460        470
[ 1774 ]    ... ..a gtt .ct .c. .c. ... ... .a. c.. ... ... ... ..t ... ...>
```

FIG. 38C

```
                     490         500         510          520
                 *     *      *      *      *     *     *      *      *
OspC-B31     AAA ACA AAT GGT ACT AAA ACT AAA GGT GCT GAA GAA CTT GGA AAA TTA
             TTT TGT TTA CCA TGA TTT TGA TTT CCA CGA CTT CTT GAA CCT TTT AAT

  1. OspC-PK  490         500         510          520          530
[ 1832 ]     ... ... c.. .ca ... .cc ga. ... ... ... a.. ... t.. aa. g.t ...>

  2. OspC-TR        480         490         500         510
[ 1786 ]     ... ... c.. ..a ... ... gac ..g ... ... a.. ... ... .a. g.g ...>

  3. OspC-K4480           490         500         510          520
[ 1774 ]     ..g t.. ... cc. ... ... ga. ..g ... ... a.. .c. ... aa. g.c ...>


            530         540         550         560         570
             *     *     *      *     *      *     *      *    *      *
OspC-B31     TTT GAA TCA GTA GAG GTC TTG TCA AAA GCA GCT AAA GAG ATG CTT GCT
             AAA CTT AGT CAT CTC CAG AAC AGT TTT CGT CGA TTT CTC TAC GAA CGA

  1. OspC-PK     540         550         560         570         580
[.1832 ]     ... ... ... ... ..a .gt ... .t. ... ... ... c.. .ta gca ..a a..>

  2. OspC-520          530         540         550         560
[ 1786 ]    .... a.. ... c.. ..a ag. ... ... ... ... ..g c.. .ca gca t.a a..>

  3. OspC-K4   530         540         -550         560         570
[ 1774 ]     .c. ... ... ... ..a ag. ... g.. ... ... ..g c.. ..a gca t.a ...>


              580         590         600         610         620
                 *     *      *      *     *      *     *     *      *
OspC-B31     AAT TCA GTT AAA GAG CTT ACA AGC CCT GTT GTG GCA GAA AGT CCA AAA
             TTA AGT CAA TTT CTC GAA TGT TCG GGA CAA CAC CGT CTT TCA GGT TTT

  1. OspC-PK        590         600         610         620         630
[ 1832 ]     ... ... ... ... ..a ... ... ..t ... ... ..a ... ... ... ... ...>

  2. OspC-TR570           580         590         600         610
[ 1786 ]     ... ... ... ... ... ....... .at ... ... ... ... ... ... ... ...>

  3. OspC-K4      580         590         600         610         620
[ 1774 ]     ... ... ... ... ..a ... ... .at ... ... ... ... ... ... ... ...>


                 630
             *     *
OspC-B31     AAA CCT TAA
             TTT GGA ATT

  1. OspC-PK
[ 1832 ]     ... ... ...>

  2. OspC-TR   620
[ 1786 ]     ... ... ...>

  3. OspC-K4        630
[ 1774 ]     ... ... ...>
```

FIG. 38D

```
                      10           20           30           40
               *      *     *      *      *     *      *      *      *
B0 ospD      CTA CTG TTA AGT TTA TTT TTA TTG CTC TCA ATA TCT TGT TCT TTA GAT
             GAT GAC AAT TCA AAT AAA AAT AAC GAG AGT TAT AGA ACA AGA AAT CTA

 1. P-Gau o           10           20           30           40
[ 2804 ]     ... ... ... ... ... ... ... ... ... ... ... ... ... .a. ... ...>

 2. DK29 os           10           20           30           40
[ 2786 ]     ... ... c.. ... ... ... ... ... ... ... ... ... g.. ... ... ...>

 3. K48 osp           10           20           30           40
[ 2786 ]     ... ... ... ... ... ... ... ... ... ... ... ... ... ... ... ...>

             50           60           70           80           90
             *      *     *      *     *      *     *      *     *      *
B0 ospD      AAT GAA GGT GTA AAC TCA AAA GAT TAC GAG TCA AAA AAA CAG AGT ATA
             TTA CTT CCA CAT TTG AGT TTT CTA ATG CTC AGT TTT TTT GTC TCA TAT

 1. P-Gau o50         60           70           80           90
[ 2804 ]     ... ... ... ... ... ... ... ... ... ... ... ... ... ... ... ...>

 2. DK29 os50         60           70           80           90
[ 2786 ]     ... ... ... ... ... ... ... ... ... ... ... ... ... ... ... ...>

 3. K48 osp50         60           70           80           90
[ 2786 ]     ... ... ... ... .g. ... ... ... ... ... ... ... ... ... ... ...>

                100          110          120          130          140
                 *      *     *      *     *      *     *      *     *
B0 ospD      CTA GGT GAA TTA AAT CAG CTA TTG GGG CAA ACT ACA AAT TCA CTA AAA
             GAT CCA CTT AAT TTA GTC GAT AAC CCC GTT TGA TGT TTA AGT GAT TTT

 1. P-Gau o 100          110          120          130          140
[ 2804 ]     ... ... ... ... ... ... ... ... ... ... ... ... ... ... ... ...>

 2. DK29 os 100          110          120          130          140
[ 2786 ]     ... ... ... ... ... ... ... ... ... ... ... ... ... ... ... ...>

 3. K48 osp 100          110          120          130          140
[ 2786 ]     ... ... ... ... ... ... ... ... ... ... ... ... ... ... ... ...>

                150          160          170          180          190
```

```
                *     *     *     *     *     *     *     *     *     *
BD ospD        GAA GCA AAA AAT ACA ACA GAT AAT TTA AAT GCA TCA AAT GAG GCA AAT
               CTT CGT TTT TTA TGT TGT CTA TTA AAT TTA CGT AGT TTA CTC CGT TTA

 1. P-Gau o     150          160          170          180          190
[ 2804 ]       ... ... ... ... ... ... ... ... ... ... ... ... ... ... ... ...>

 2. DK29 os     150          160          170          180          190
[ 2786 ]       ... ... ... ... ... ... ... ... ... ... ... ... ... ... ... ...>

 3. K48 osp     150          160          170          180          190
[ 2786 ]       ... ... ... ... ... ... ... ... ... ... ... ... ... ... ... ...>

                    200          210          220          230          240
                *     *     *     *     *     *     *     *     *     *
BD ospD        AAA GTT GTA GAA GCA GTT ATA AGT GTG GTT AAT TTA ATT TCA TCT GCT
               TTT CAA CAT CTT CGT CAA TAT TCA CAC CAA TTA AAT TAA AGT AGA CGA

 1. P-Gau o         200          210          220          230          240
[ 2804 ]       ... ... ... ... ... ... ... ... ... ... ... ... ... ... ... ...>

 2. DK29 os         200          210          220          230          240
[ 2786 ]       ... ... ... ... ... ... ... ... ... ... ... ... ... ... ... ...>

 3. K48 osp         200          210          220          230          240
[ 2786 ]       ... ... ... ... ... ... ... ... ... ... ... ... ... ... ... ...>

                      250          260          270          280
                   *     *     *     *     *     *     *     *
BD ospD        GCA GAT CAG GTA AAA GGT CAA CAA CAA ATA TGC ACG ATT TAG CTC AAA
               CGT CTA GTC CAT TTT CCA GTT GTT GTT TAT ACG TGC TAA ATC GAG TTT

 1. P-Gau o           250          260          270          280
[ 2804 ]       ... ... ... ... ... ... ... ... ... ... ... ... ... ... ... ...>

 2. DK29 os           250          260          270          280
[ 2786 ]       ... ... ... ..g ... ... ... ... ... ... ... ... ... ... ... ...>

 3. K48 osp           250          260          270          280
[ 2786 ]       ... ... ... ..g ... ... ... ... ... ... ... ... ... ... ... ...>

               290          300          310          320          330
                *     *     *     *     *     *     *     *     *     *
BD ospD        TGG CAG AAA TAG ATT TAG AAA AAA TAA AGG AAT CTA GTG ATA AAG TAA
               ACC GTC TTT ATC TAA ATC TTT TTT ATT TCC TTA GAT CAC TAT TTC ATT

 1. P-Gau 290               300          310          320          330
[ 2804 ]       ... ... ... ... ... ... ... ... ... ... ... ... ... ... ... ...>

 2. DK29 o290               300          310          320          330
[ 2786 ]       ... ... ... ... ... ... ... ... ... ... ... ... ... ... ... ...>

 3. K48 os290               300          310          320          330
[ 2786 ]       ... ... ... ... ... ... ... ... ... ... ... ... ... ... ... ...>
```

```
               340         350         360         370         380
                *     *     *     *     *     *     *     *     *
BO ospD        TAG TTG CGG CTA ATG TTG CGA AAG AAG CAT ATA ACC TTA CTA AAG CAG
               ATC AAC GCC GAT TAC AAC GCT TTC TTC GTA TAT TGG AAT GAT TTC GTC

 1. P-Gau o    340         350         360         370         380
[ 2804 ]       ... ... ... ... ... ... ... ... ... ... ... ... ... ... ... ...>

 2. DK29 os    340         350         360         370         380
[ 2786 ]       ... ... ... ... ... ... ... ... ... ... ... ... ... ... ... ...>

 3. K48 osp    340         350         360         370         380
[ 2786 ]       ... ... ... ... ... ... ... ... ... ... ... ... ... ... ... ...>


                   390         400         410         420         430
                *   *     *     *     *     *     *     *     *     *
BO ospD        TAG AAC AAA ATA TGC AAA AAC TGT ACA AAG AGC AAG AAG AGC AAC TAA
               ATC TTG TTT TAT ACG TTT TTG ACA TGT TTC TCG TTC TTC TCG TTG ATT

 1. P-Gau o        390         400         410         420         430
[ 2804 ]       ... ... ... ... ... ... ... ... ... ... ... ... ... ... ... ...>

 2. DK29 os        390         400         410         420         430
[ 2786 ]       ... ... ... ... ... ... ... ... ... ... ... ... ... ... ... ...>

 3. K48 osp        390         400         410         420         430
[ 2786 ]       ... ... ... ... ... ... ... ... ... ... ... ... ... ... ... ...>


                   440         450         460         470         480
                *   *     *     *     *     *     *     *     *     *
BO ospD        AAC ACT ATC TGA TTC TGA TGA AAC AGA ACG AGT TTC TGA TGA AAT AAA
               TTG TGA TAG ACT AAG ACT ACT TTG TCT TGC TCA AAG ACT ACT TTA TTT

 1. P-Gau o        440         450         460         470         480
[ 2804 ]       ... ... ... ... ... ... ... ... ... ... ... ... ... ... ... ...>

 2. DK29 os        440         450         460         470         480
[ 2786 ]       ... ... ... ... ... ... ... .g. ... ... ... ... ... ... ... ...>

 3. K48 osp        440         450         460         470         480
[ 2786 ]       ... ... ... ... ... ... ... .g. ... ... ... ... ... ... ... ...>


                       490         500         510         520
                    *     *     *     *     *     *     *     *     *
BO ospD        ACA AGC TAA AGA GGC TGT AGA AAT AGC TTG GAA AGC CAC AGT AAA AGT
               TGT TCG ATT TCT CCG ACA TCT TTA TCG AAC CTT TCG GTG TCA TTT TCA

 1. P-Gau o        490         500         510         520
[ 2804 ]       ... ... ... ... ... ... ... ... ... ... ... ... ... ... ... ...>

 2. DK29 os        490         500         510         520
[ 2786 ]       ... ... ... ... ... ... ... ... ... ... ... ... ... ... ... ...>

 3. K48 osp        490         500         510         520
```

FIG. 39C

```
                 530         540         550         560         570
                  *     *     *     *     *     *     *     *     *     *
BO ospD          AAA AGA TGA GTT AAT TGA TGT AGA AAA TGC AGT CAA AGA GGC ATT GGA
                 TTT TCT ACT CAA TTA ACT ACA TCT TTT ACG TCA GTT TCT CCG TAA CCT

  1. P-Gau 530               540         550         560         570
[ 2804 ]         ... ... ... ... ... ... ... ... ... ... ... ... ... ... ... ...>

  2. DK29 o530               540         550         560         570
[ 2786 ]         ... ... ... ... ... ... ... ... ... ... ... ... ... ... ... ...>

  3. K48 os530               540         550         560         570
[ 2786 ]         ... ... ... ... ... ... ... ... ... ... ... ... ... ... ... ...>

                     580         590         600         610         620
                      *     *     *     *     *     *     *     *     *
BO ospD          TAA AAT AAA GAC AGA AAC CGC GAA CAA TAC AAA ACT TAC AGA TAT AGA
                 ATT TTA TTT CTG TCT TTG GCG CTT GTT ATG TTT TGA ATG TCT ATA TCT

  1. P-Gau o     580         590         600         610         620
[ 2804 ]         ... ... ... ... ... ... ... ... ... ... ... ... ... ... ... ...>

  2. DK29 os     580         590         600         610         620
[ 2786 ]         ... ... ... ... ... ... ... ... ... ... ... ... ... ... ... ...>

  3. K48 osp     580         590         600         610         620
[ 2786 ]         ... ... ... ... ..g ... ... ... ... ... ... ... ... ... ... ...>

                       630         640         650         660         670
                  *     *     *     *     *     *     *     *     *     *
BO ospD          AGA AGT AGC AGA GTT AGT ATT ACA GAT AGC CAA AAA TGT AGC GGA AAT
                 TCT TCA TCG TCT CAA TCA TAA TGT CTA TCG GTT TTT ACA TCG CCT TTA

  1. P-Gau o     630         640         650         660         670
[ 2804 ]         ... ... ... ... ... ... ... ... a.. ... ... ... ... ... ... ...>

  2. DK29 os     630         640         650         660         670
[ 2786 ]         ... ... ... ... ... ... ... ... a.. ... ... ... ... ... ... ...>

  3. K48 osp     630         640         650         660         670
[ 2786 ]         ... ... ... ... ... ... ... ... a.. ... ... ... ... ... ... ...>

                       680         690         700
                  *     *     *     *     *
BO ospD          AGC GCA AGA AGT TGT GGC CTT GTT AAA TAC TT
                 TCG CGT TCT TCA ACA CCG GAA CAA TTT ATG AA

  1. P-Gau o           680         690         700
[ 2804 ]         ... ... ... ... ... ... ... ... ... ... ..>

  2. DK29 os           680         690         700
[ 2786 ]         ... ... ... ... ... ... ... ... ... ... ..>

  3. K48 osp           680         690         700
[ 2786 ]         ... ... ... ... ... ... ... ... ... ... ..>
```

FIG. 39D

```
              10             20             30             40
         *         *    *         *    *         *    *         *    *
     ATG ATT ATC AAT CAT AAT ACA TCA GCT ATT AAT GCT TCA AGA AAT AAT
     TAC TAA TAG TTA GTA TTA TGT AGT CGA TAA TTA CGA AGT TCT TTA TTA
     Met Ile Ile Asn His Asn Thr Ser Ala Ile Asn Ala Ser Arg Asn Asn>

        50             60             70             80             90
     *         *    *         *    *         *    *         *    *
     GGC ATT AAC GCT GCT AAT CTT AGT AAA ACT CAA GAA AAG CTT TCT AGT
     CCG TAA TTG CGA CGA TTA GAA TCA TTT TGA GTT CTT TTC GAA AGA TCA
     Gly Ile Asn Ala Ala Asn Leu Ser Lys Thr Gln Glu Lys Leu Ser Ser>

       100            110            120            130            140
     *         *    *         *    *         *    *         *    *
     GGC TAC AGA ATT AAT CGA GCT TCT GAT GAT GCT GCT GGC ATG GGA GTT
     CCG ATG TCT TAA TTA GCT CGA AGA CTA CTA CGA CGA CCG TAC CCT CAA
     Gly Tyr Arg Ile Asn Arg Ala Ser Asp Asp Ala Ala Gly Met Gly Val>

       150            160            170            180            190
     *         *    *         *    *         *    *         *    *
     TCT GGT AAG ATT AAT GCT CAA ATA AGA GGT TTG TCA CAA GCT TCT AGA
     AGA CCA TTC TAA TTA CGA GTT TAT TCT CCA AAC AGT GTT CGA AGA TCT
     Ser Gly Lys Ile Asn Ala Gln Ile Arg Gly Leu Ser Gln Ala Ser Arg>

       200            210            220            230            240
     *         *    *         *    *         *    *         *    *
     AAT ACT TCA AAG GCT ATT AAT TTT ATT CAG ACA ACA GAA GGG AAT TTA
     TTA TGA AGT TTC CGA TAA TTA AAA TAA GTC TGT TGT CTT CCC TTA AAT
     Asn Thr Ser Lys Ala Ile Asn Phe Ile Gln Thr Thr Glu Gly Asn Leu>

       250            260            270            280
     *         *    *         *    *         *    *         *    *
     AAT GAA GTA GAA AAA GTC TTA GTA AGA ATG AAG GAA TTG GCA GTT CAA
     TTA CTT CAT CTT TTT CAG AAT CAT TCT TAC TTC CTT AAC CGT CAA GTT
     Asn Glu Val Glu Lys Val Leu Val Arg Met Lys Glu Leu Ala Val Gln>

       290            300            310            320            330
     *         *    *         *    *         *    *         *    *
     TCA GGT AAC GGC ACA TAT TCA GAT GCA GAC AGA GGT TCT ATA CAA ATT
     AGT CCA TTG CCG TGT ATA AGT CTA CGT CTG TCT CCA AGA TAT GTT TAA
     Ser Gly Asn Gly Thr Tyr Ser Asp Ala Asp Arg Gly Ser Ile Gln Ile>

       340            350            360            370            380
     *         *    *         *    *         *    *         *    *
     GAA ATA GAG CAA CTT ACA GAC GAA ATT AAT AGA ATT GCT GAT CAA GCT
     CTT TAT CTC GTT GAA TGT CTG CTT TAA TTA TCT TAA CGA CTA GTT CGA
     Glu Ile Glu Gln Leu Thr Asp Glu Ile Asn Arg Ile Ala Asp Gln Ala>
```

FIG. 40A

```
     390          400          410          420          430
CAA TAT AAC CAA ATG CAC ATG TTA TCA AAC AAA TCT GCT TCT CAA AAT
GTT ATA TTG GTT TAC GTG TAC AAT AGT TTG TTT AGA CGA AGA GTT TTA
Gln Tyr Asn Gln Met His Met Leu Ser Asn Lys Ser Ala Ser Gln Asn>

        440          450          460          470          480
GTA AGA ACA GCT GAA GAG CTT GGA ATG CAG CCT GCA AAA ATT AAC ACA
CAT TCT TGT CGA CTT CTC GAA CCT TAC GTC GGA CGT TTT TAA TTG TGT
Val Arg Thr Ala Glu Glu Leu Gly Met Gln Pro Ala Lys Ile Asn Thr>

           490          500          510          520
CCA GCA TCA CTT TCA GGG CTT CAA GCG TCT TGG ACT TTA AGA GTT CAT
GGT CGT AGT GAA AGT CCC GAA GTT CGC AGA ACC TGA AAT TCT CAA GTA
Pro Ala Ser Leu Ser Gly Leu Gln Ala Ser Trp Thr Leu Arg Val His>

530          540          550          560          570
GTT GGA GCA ACC CAA GAT GAA GCT ATT GCT GTA AAT ATT TAT GCA GCT
CAA CCT CGT TGG GTT CTA CTT CGA TAA CGA CAT TTA TAA ATA CGT CGA
Val Gly Ala Thr Gln Asp Glu Ala Ile Ala Val Asn Ile Tyr Ala Ala>

  580          590          600          610          620
AAT GTT GCA AAT CTT TTC TCT GGT GAG GGA GCT CAA ACT GCT CAG GCT
TTA CAA CGT TTA GAA AAG AGA CCA CTC CCT CGA GTT TGA CGA GTC CGA
Asn Val Ala Asn Leu Phe Ser Gly Glu Gly Ala Gln Thr Ala Gln Ala>

     630          640          650          660          670
GCA CCG GTT CAA GAG GGT GTT CAA CAG GAA GGA GCT CAA CAG CCA GCA
CGT GGC CAA GTT CTC CCA CAA GTT GTC CTT CCT CGA GTT GTC GGT CGT
Ala Pro Val Gln Glu Gly Val Gln Gln Glu Gly Ala Gln Gln Pro Ala>

        680          690          700          710          720
CCT GCT ACA GCA CCT TCT CAA GGC GGA GTT AAT TCT CCT GTT AAT GTT
GGA CGA TGT CGT GGA AGA GTT CCG CCT CAA TTA AGA GGA CAA TTA CAA
Pro Ala Thr Ala Pro Ser Gln Gly Gly Val Asn Ser Pro Val Asn Val>

           730          740          750          760
ACA ACT ACA GTT GAT GCT AAT ACA TCA CTT GCT AAA ATT GAA AAT GCT
TGT TGA TGT CAA CTA CGA TTA TGT AGT GAA CGA TTT TAA CTT TTA CGA
Thr Thr Thr Val Asp Ala Asn Thr Ser Leu Ala Lys Ile Glu Asn Ala>

770          780          790          800          810
ATT AGA ATG ATA AGT GAT CAA AGG GCA AAT TTA GGT GCT TTC CAA AAT
TAA TCT TAC TAT TCA CTA GTT TCC CGT TTA AAT CCA CGA AAG GTT TTA
Ile Arg Met Ile Ser Asp Gln Arg Ala Asn Leu Gly Ala Phe Gln Asn>
```

FIG. 40B

```
  820           830         840          850         860
   *     *       *     *     *     *      *     *     *
AGA CTT GAA TCT ATA AAG AAT AGT ACT GAG TAT GCA ATT GAA AAT CTA
TCT GAA CTT AGA TAT TTC TTA TCA TGA CTC ATA CGT TAA CTT TTA GAT
Arg Leu Glu Ser Ile Lys Asn Ser Thr Glu Tyr Ala Ile Glu Asn Leu>

    870          880         890         900         910
 *     *     *     *     *     *     *     *     *     *
AAA GCA TCT TAT GCT CAA ATA AAA GAT GCT ACA ATG ACA GAT GAG GTT
TTT CGT AGA ATA CGA GTT TAT TTT CTA CGA TGT TAC TGT CTA CTC CAA
Lys Ala Ser Tyr Ala Gln Ile Lys Asp Ala Thr Met Thr Asp Glu Val>

       920         930         940         950         960
 *     *     *     *     *     *     *     *     *     *
GTA GCA GCA ACA ACT AAT ATG ATT TTA ACA CAA TCT GCA ATG GCA ATG
CAT CGT CGT TGT TGA TTA TAC TAA AAT TGT GTT AGA CGT TAC CGT TAC
Val Ala Ala Thr Thr Asn Met Ile Leu Thr Gln Ser Ala Met Ala Met>

          970         980         990        1000
   *     *     *     *     *     *     *     *     *
ATT GCG CAG GCT AAT CAA GTT CCC CAA TAT GTT TTG TCA TTG CTT AGA
TAA CGC GTC CGA TTA GTT CAA GGG GTT ATA CAA AAC AGT AAC GAA TCT
Ile Ala Gln Ala Asn Gln Val Pro Gln Tyr Val Leu Ser Leu Leu Arg>

1010
  *
TAA
ATT
***>
```

FIG. 40C

```
                         10           20           30           40
                    *    *     *      *      *     *      *     *     *
B31-41kD      ATG ATT ATC AAT CAT AAT ACA TCA GCT ATT AAT GCT TCA AGA AAT AAT
              TAC TAA TAG TTA GTA TTA TGT AGT CGA TAA TTA CGA AGT TCT TTA TTA

  1. KA-41kD             10           20           30           40
[ 3996 ]      ... ... ... ... ... ... ... ... ... ... ... ... ... ... ... ...>

  2. P-Gau-4             10           20           30           40
[ 3696 ]      ... ... ... ... ... ... ... ... ... ... ... ... ... ... ... ...>

  3. BO-41kD             10           20           30           40
[ 3684 ]      ... ... ... ... ... ... ... ... ... ... ... ... ... ... ... ...>

  4. DK29-41             10           20           30           40
[ 3672 ]      ... ... ... ... ... ... ... ... ... ... ... ... ... ... ... ...>

  5. PKO-41k             10           20           30           40
[ 3672 ]      ... ... ... ... ... ... ... ... ... ... ... ... ... ... ... ...>

              50           60           70           80           90
              *     *      *     *      *     *      *     *      *      *
B31-41kD      GGC ATT AAC GCT GCT AAT CTT AGT AAA ACT CAA GAA AAG CTT  TCT AGT
              CCG TAA TTG CGA CGA TTA GAA TCA TTT TGA GTT CTT TTC GAA  AGA TCA

 1. KA-41kD50            60           70           80           90
[ 3996 ]      ... ... ... ... ... ... ... ... ... ... ... ... ... ...  ... ...>

 2. P-Gau-450            60           70           80           90
[ 3696 ]      .c. ... ..t ... ... ... ... ... ... ..c ... ..g ... ...  ... ...>

 3. BO-41kD50            60           70           80           90
[ 3684 ]      .c. ... ..t ... ... ... ... ... ... ..c ... ..g ... ...  ... ...>

 4. DK29-4150            60           70           80           90
[ 3672 ]      ..t ... ..t ... ... ... ... ... ... ... ... ..g ... ...  ... ...>

 5. PKO-41k50            60           70           80           90
[ 3672 ]      .c. ... ..t ... ... ... ... ... ... ..c ... ..g ... .c.  ... ...>

                100         110          120          130          140
                 *     *     *     *      *     *     *     *       *
B31-41kD      GGC TAC AGA ATT AAT CGA GCT TCT GAT GAT GCT GCT GGC ATG  GGA GTT
              CCG ATG TCT TAA TTA GCT CGA AGA CTA CTA CGA CGA CCG TAC  CCT CAA
```

```
 1. KA-41kD  100           110           120           130           140
[ 3996 ]    ..g ... ... ... ... ... ... ... ... ... ... ... ... ... ... ... ...>

 2. P-Gau-4  100           110           120           130           140
[ 3696 ]    ..t ... ... ... ... ... ... ... ... ... ... ... ... ..t ... ..g ...>

 3. BO-41kD  100           110           120           130           140
[ 3684 ]    ..t ... ... ... ... ... ... ... ... ... ... ... ... ..t ... ..g ...>

 4. DK29-41  100           110           120           130           140
[ 3672 ]    ..t ... ... ... ... a.. ... ... ... ... ... ... ... ..t ... ..g ...>

 5. PKO-41k  100           110           120           130           140
[ 3672 ]    ..t ... ... ... ... ... ... ... ... ... ... ... ... ..t ... ..g ...>


                 150          160          170          180           190
              *   *       *       *     *     *     *     *     *     *
B31-41kD     TCT GGT AAG ATT AAT GCT CAA ATA AGA GGT TTG TCA CAA GCT TCT AGA
             AGA CCA TTC TAA TTA CGA GTT TAT TCT CCA AAC AGT GTT CGA AGA TCT

 1. KA-41kD      150          160          170          180           190
[ 3996 ]     ... ... ... ... ... ... ... ... ... ... ... ... ... ... ... ...>

 2. P-Gau-4      150          160          170          180           190
[ 3696 ]     ... ..c ... ... ... ... ... ... .c. ..c ..a ... ... ... ... ...>

 3. BO-41kD      150          160          170          180           190
[ 3684 ]     ... ..c ... ... ... ... ... ... ... ..c ..a ... ... ... ... ...>

 4. DK29-41      150          160          170          180           190
[ 3672 ]     ... ..g ... ... ... ... ... ... ... ... ..a ... ... ... ... ...>

 5. PKO-41k      150          160          170          180           190
[ 3672 ]     ... ..c ... ... ... ... ... ... ... ..c ..a ... ... ... ... ...>


                     200          210          220          230           240
              *   *       *       *     *     *     *     *     *     *
B31-41kD     AAT ACT TCA AAG GCT ATT AAT TTT ATT CAG ACA ACA GAA GGG AAT TTA
             TTA TGA AGT TTC CGA TAA TTA AAA TAA GTC TGT TGT CTT CCC TTA AAT

 1. KA-41kD          200          210          220          230           240
[ 3996 ]     ... ... ... ... ... ... ... ... ... ... ... ... ... ... ... ...>

 2. P-Gau-4          200          210          220          230           240
[ 3696 ]     ..c ... ... ..a ... ..c ... ... ... ... ... ... ... ..a ... ...>

 3. BO-41kD          200          210          220          230           240
[ 3684 ]     ..c ... ... ..a ... ..c ... ... ... ... ... ... ... ..a ... ...>

 4. DK29-41          200          210          220          230           240
[ 3672 ]     ..c ... ... ..a ... ... ... ... ... ... ... ... ... ..a ... ..g>

 5. PKO-41k          200          210          220          230           240
[ 3672 ]     ..c ... ... ..a ... ..c ... ... ... ... ... ... ... ..a ... ...>
```

FIG. 41B

```
                       250         260         270         280
                   *    *     *     *     *     *     *     *     *
B31-41kD     AAT GAA GTA GAA AAA GTC TTA GTA AGA ATG AAG GAA TTG GCA GTT CAA
             TTA CTT CAT CTT TTT CAG AAT CAT TCT TAC TTC CTT AAC CGT CAA GTT

 1. KA-41kD             250         260         270         280
[ 3996 ]     ... ... ... ... ... ... ... ... ... ... ... ... ... ... ... ...>

 2. P-Gau-4             250         260         270         280
[ 3696 ]     ... ... ... ... ... ..t ... ... ... ... ..a ... ..a ... ... ...>

 3. BO-41kD             250         260         270         280
[ 3684 ]     ... ... ... ... ... ..t ... ... ... ... ..a ... ..a ... ... ...>

 4. DK29-41             250         260         270         280
[ 3672 ]     ... ... ... ... ... ..t ... ... ... ... ..a ... ..a ... ... ...>

 5. PKO-41k             250         260         270         280
[ 3672 ]     ... ... ... ... ... ..t ... ... ... ... ..a ... ..a ... ... ...>


             290         300         310         320         330
              *     *     *     *     *     *     *     *     *     *
B31-41kD     TCA GGT AAC GGC ACA TAT TCA GAT GCA GAC AGA GGT TCT ATA CAA ATT
             AGT CCA TTG CCG TGT ATA AGT CTA CGT CTG TCT CCA AGA TAT GTT TAA

 1. KA-41k290               300         310         320         330
[ 3996 ]     ... ... ... ... ... ... ... ... ... ... ... ... ... ... ... ...>

 2. P-Gau-290               300         310         320         330
[ 3696 ]     ... ... ... ..a ..g ... ... ..c ... ... ... ... ... ... ..g ...>

 3. BO-41k290               300         310         320         330
[ 3684 ]     ... ... ... ..a ..g ... ... ..c t.. ... ... ... ... ... ..g ...>

 4. DK29-4290               300         310         320         330
[ 3672 ]     ... ... ... ..t ... ... ... ..c ... ... ... ... ... ... ... ...>

 5. PKO-41290               300         310         320         330
[ 3672 ]     ... ... ... ..a ..g ... ... ..c t.. ... ... ... ... ... ..g ...>


               340         350         360         370         380
                *     *     *     *     *     *     *     *     *
B31-41kD     GAA ATA GAG CAA CTT ACA GAC GAA ATT AAT AGA ATT GCT GAT CAA GCT
             CTT TAT CTC GTT GAA TGT CTG CTT TAA TTA TCT TAA CGA CTA GTT CGA

 1. KA-41kD    340         350         360         370         380
[ 3996 ]     ... ... ... ... ... ... ... ... ... ... ... ... ... ... ... ...>

 2. P-Gau-4    340         350         360         370         380
[ 3696 ]     ... ... ... ... ... ... ... ... ... ... ... ... ... ... ..g ...>

 3. BO-41kD    340         350         360         370         380
[ 3684 ]     ... ... ... ... ... ... ... ... ... ... ... ... ... ... ..g ...>

 4. DK29-41    340         350         360         370         380
```

```
 5. PKO-41k  340         350         360         370         380
[ 3672 ]    ... ... ... ... ... ... ... ... ... ... ... ... ... ... ..g ...>

               390         400         410         420         430
            *     *     *     *     *     *     *     *     *
B31-41kD    CAA TAT AAC CAA ATG CAC ATG TTA TCA AAC AAA TCT GCT TCT CAA AAT
            GTT ATA TTG GTT TAC GTG TAC AAT AGT TTG TTT AGA CGA AGA GTT TTA

 1. KA-41kD    390         400         410         420         430
[ 3996 ]    ... ... ... ... ... ... ... ... ... ... ... ... ... ... ... ...>

 2. P-Gau-4    390         400         410         420         430
[ 3696 ]    ... ... ... ... ... ... ... ..g ... ... ... ... ... ..c ... ...>

 3. BO-41kD    390         400         410         420         430
[ 3684 ]    ... ... ... ... ... ... ... ..g ... ... ... ... ... ..c ... ...>

 4. DK29-41    390         400         410         420         430
[ 3672 ]    ... ... ... ... ... ... ... ..g ... ... ... ... ... ..c ... ...>

 5. PKO-41k    390         400         410         420         430
[ 3672 ]    ... ... ... ... ... ... ... ..g ... ... ... ... ... ..c ... ...>

                  440         450         460         470         480
              *     *     *     *     *     *     *     *     *     *
B31-41kD    GTA AGA ACA GCT GAA GAG CTT GGA ATG CAG CCT GCA AAA ATT AAC ACA
            CAT TCT TGT CGA CTT CTC GAA CCT TAC GTC GGA CGT TTT TAA TTG TGT

 1. KA-41kD       440         450         460         470         480
[ 3996 ]    ... ... ... ... ... ... ... ... ... ... ... ... ... ... ... ...>

 2. P-Gau-4       440         450         460         470         480
[ 3696 ]    ... .a. ... ... ... ... ... ... ... ... ... ... ... ... ... ...>

 3. BO-41kD       440         450         460         470         480
[ 3684 ]    ... .a. ... ... ... ... ... ... ... ... ... ... ... ... ... ...>

 4. DK29-41       440         450         460         470         480
[ 3672 ]    ... ... ... ... ... ..a ... ... ... ..a ... ... ... ..c ... ...>

 5. PKO-41k       440         450         460         470         480
[ 3672 ]    ... .a. ... ... ... ... ... ... ... ... ... ... ... ... ... ...>

                     490         500         510         520
                *     *     *     *     *     *     *     *     *
B31-41kD    CCA GCA TCA CTT TCA GGG CTT CAA GCG TCT TGG ACT TTA AGA GTT CAT
            GGT CGT AGT GAA AGT CCC GAA GTT CGC AGA ACC TGA AAT TCT CAA GTA

 1. KA-41kD          490         500         510         520
[ 3996 ]    ... ... ... ... ... ... tc. ... ... ... ... ... ... ... ... ...>

 2. P-Gau-4          490         500         510         520
[ 3696 ]    ... ... ... ... ... ..a tc. ... ..t ... ... ... ... ... ... ...>
```

```
  3. BO-41kD             490              500              510              520
[ 3684 ]     ... ... ... ... ... ..a tc. ... ..t ... ... ... ... ... ... ...>

  4. DK29-41             490              500              510              520
[ 3672 ]     ... ..g ... ... ... ..a tc. ... ..t ... ... ... ... ... ... ...>

  5. PKO-41k             490              500              510              520
[ 3672 ]     ... ... ... ... ... ..a tc. ... ..t ... ... ... ... ... ... ...>

                 530          540          550          560          570
                  *       *       *       *       *       *       *       *       *       *
B31-41kD       GTT GGA GCA ACC CAA GAT GAA GCT ATT GCT GTA AAT ATT TAT GCA GCT
               CAA CCT CGT TGG GTT CTA CTT CGA TAA CGA CAT TTA TAA ATA CGT CGA

  1. KA-41k530          540          550          560          570
[ 3996 ]     ... ... ... .a. ... ... ... ... ... ... ... ... ... ... ... ...>

  2. P-Gau-530          540          550          560          570
[ 3696 ]     ..g ... ... .at ... ... ... ..a ... ... ... ... ... ... t.. ...>

  3. BO-41k530          540          550          560          570
[ 3684 ]     ..g ... ... .at ... ... ... ..a ... ... ... ... ... ... t.. ...>

  4. DK29-4530          540          550          560          570
[ 3672 ]     ..g ... ... .at ... ... ... ..g ... ... ... ... ... ... ..t ...>

  5. PKO-41530          540          550          560          570
[ 3672 ]     ..g ... ... .at ... ... ... ..a ... ... ... ... ... ... t.. ...>

                 580          590          600          610          620
                  *       *       *       *       *       *       *       *       *
B31-41kD       AAT GTT GCA AAT CTT TTC TCT GGT GAG GGA GCT CAA ACT GCT CAG GCT
               TTA CAA CGT TTA GAA AAG AGA CCA CTC CCT CGA GTT TGA CGA GTC CGA

  1. KA-41kD   580          590          600          610          620
[ 3996 ]     ... ... ... ... ... ... ... ... ... ... ... ... ... ... ... ...>

  2. P-Gau-4   580          590          600          610          620
[ 3696 ]     ... ... ... ... ... ..t g.. ... ... ... ... ... g.. ... ... ...>

  3. BO-41kD   580          590          600          610          620
[ 3684 ]     ... ... ... ... ... ..t g.. ... ... ... ... ... g.. ... ... ...>

  4. DK29-41   580          590          600          610          620
[ 3672 ]     ... ... ... ... ..a ... ... ... ..a ... ... ..g g.. ... ... a..>

  5. PKO-41k   580          590          600          610          620
[ 3672 ]     ... ... ... ... ... ..t g.. ... ... ... ... ... g.. ... ... ...>

                    630          640          650          660          670
               *       *       *       *       *       *       *       *       *       *
B31-41kD       GCA CCG GTT CAA GAG GGT GTT CAA CAG GAA GGA GCT CAA CAG CCA GCA
               CGT GGC CAA GTT CTC CCA CAA GTT GTC CTT CCT CGA GTT GTC GGT CGT
```

2. P-Gau-4 630 640 650 660 670
[ 3696 ] ... ..t ... ... ... ... .c. ... g.a ... ... ... ..g ..a ... a..>

3. BO-41kD 630 640 650 660 670
[ 3684 ] ... ..t ... ... ... ... .c. ... g.a ... ... ... ..g ..a ... a..>

4. DK29-41 630 640 650 660 670
[ 3672 ] ... ..t ... ... ..a ... .c. ... ..a ... ... ... ... ..a ... ...>

5. PKO-41k 630 640 650 660 670
[ 3672 ] ... ..t ... ... ... ... .c. ... g.a ... ... ... ..g ..a ... a..>

680 690 700 710 720
* * * * * * * * * *
B31-41kD CCT GCT ACA GCA CCT TCT CAA GGC GGA GTT AAT TCT CCT GTT AAT GTT
GGA CGA TGT CGT GGA AGA GTT CCG CCT CAA TTA AGA GGA CAA TTA CAA

1. KA-41kD 680 690 700 710 720
[ 3996 ] ... ... ... ... ... ... ... ... ... ... ... ... ... ... ... ...>

2. P-Gau-4 680 690 700 710 720
[ 3696 ] ... ... ... ... ... a.. ... ..t ... ... ... ... ... ... ... ...>

3. BO-41kD 680 690 700 710 720
[ 3684 ] ... ... ... ... ... a.. ... ..t ... ... ... ... ... ... ... ...>

4. DK29-41 680 690 700 710 720
[ 3672 ] ... ... ... ..g ... ... g ..t ... ... ... ... ... ... ... ...>

5. PKO-41k 680 690 700 710 720
[ 3672 ] ... ... ... ... ... a.. ... ..t ... ... ... ... ... ... ... ...>

730 740 750 760
* * * * * * * * *
B31-41kD ACA ACT ACA GTT GAT GCT AAT ACA TCA CTT GCT AAA ATT GAA AAT GCT
TGT TGA TGT CAA CTA CGA TTA TGT AGT GAA CGA TTT TAA CTT TTA CGA

1. KA-41kD 730 740 750 760
[ 3996 ] ... ... ... ... ... ... ... ... ... ... ... ... ... ... ... ...>

2. P-Gau-4 730 740 750 760
[ 3696 ] ... ..c ... ... ... ... ... ... ... ... ... ... ..a ... ... ...>

3. BO-41kD 730 740 750 760
[ 3684 ] ... ..c ... ... ... ... ... ... ... ... ... ... ..a ... ... ...>

4. DK29-41 730 740 750 760
[ 3672 ] ... ... ... ... ..c ... ... ... ..t ... ... ... ..a ... ... ...>

5. PKO-41k 730 740 750 760
[ 3672 ] ... ..c ... ... ... ... ... ... ... ... ... ... ..a ... ... ...>

FIG. 41F

```
                770          780          790          800          810
                 *      *     *      *     *      *     *      *     *      *
B31-41kD        ATT AGA ATG ATA AGT GAT CAA AGG GCA AAT TTA GGT GCT TTC CAA AAT
                TAA TCT TAC TAT TCA CTA GTT TCC CGT TTA AAT CCA CGA AAG GTT TTA

 1. KA-41k770                 780          790          800          810
[ 3996 ]        ... ... ... ... ... ... ... ... ... ... ... ... ... ... ... ...>

 2. P-Gau-770                 780          790          800          810
[ 3696 ]        ... ... ... ... ... ... ... ..a ... ... ... ... ... ... ... ...>

 3. BO-41k770                 780          790          800          810
[ 3684 ]        ... ... ... ... ... ... ... ..a ... ... ... ... ... ... ... ...>

 4. DK29-4770                 780          790          800          810
[ 3672 ]        ... ... ... ... ... ... ... ..a ... ... ... ... ... ... ... ...>

 5. PKO-41770                 780          790          800          810
[ 3672 ]        ... ... ... ... ... ... ... ..a ... ... ... ... ... ... ... ...>

                  820          830          840          850          860
                   *      *     *      *     *      *     *      *     *
B31-41kD        AGA CTT GAA TCT ATA AAG AAT AGT ACT GAG TAT GCA ATT GAA AAT CTA
                TCT GAA CTT AGA TAT TTC TTA TCA TGA CTC ATA CGT TAA CTT TTA GAT

 1. KA-41kD       820          830          840          850          860
[ 3996 ]        ... ... ... ... ... ... ... ... ... ... ... ... ... ... ... ...>

 2. P-Gau-4       820          830          840          850          860
[ 3696 ]        ... ... ... ... ... ... ... ..c ... ... ... ..t ... ... ... ...>

 3. BO-41kD       820          830          840          850          860
[ 3684 ]        ... ... ... ... ... ... ... ..c ... ... ... ..t ... ... ... ...>

 4. DK29-41       820          830          840          850          860
[ 3672 ]        ... ... ..g ... ... ... g.. ... ... ... ... ..t ... ... ..c ...>

 5. PKO-41k       820          830          840          850          860
[ 3572 ]        ... ... ... ... ... ... ... ..c ... ... ... ..t ... ... ... ...>

                     870          880          890          900          910
                 *      *     *      *     *      *     *      *     *      *
B31-41kD        AAA GCA TCT TAT GCT CAA ATA AAA GAT GCT ACA ATG ACA GAT GAG GTT
                TTT CGT AGA ATA CGA GTT TAT TTT CTA CGA TGT TAC TGT CTA CTC CAA

 1. KA-41kD          870          880          890          900          910
[ 3996 ]        ... ... ... ... ... ... ... ... ... ... ... ... ... ... ... ...>

 2. P-Gau-4          870          880          890          900          910
[ 3696 ]        ... ... ... ... ... ... ... ... ... ... ... ... ... ... ... ...>

 3. BO-41kD          870          880          890          900          910
[ 3684 ]        ... ... ... ... ... ... ... ... ... ... ... ... ... ... ... ...>

 4. DK29-41          870          880          890          900          910
[ 3672 ]        ... ... ... ... ... ... ... ... ... ... ... ... ... ... ... ...>
```

```
 5. PKO-41k    870          880          890          900          910
[ 3672 ]   ... ... ... ... ... ... ... ... ... ... ... ... ... ... ... ...>

                 920          930          940          950          960
             *    *     *    *     *    *     *    *     *    *
B31-41kD   GTA GCA GCA ACA ACT AAT ATG ATT TTA ACA CAA TCT GCA ATG GCA ATG
           CAT CGT CGT TGT TGA TTA TAC TAA AAT TGT GTT AGA CGT TAC CGT TAC

 1. KA-41kD      920          930          940          950          960
[ 3996 ]   ... ... ... ... ... ... .gt ... ... ... ... ... ... ... ... ...>

 2. P-Gau-4      920          930          940          950          960
[ 3696 ]   ... ... ..t ... ... ... .gt ... ... ..t ... ... ... ... ... ...>

 3. BO-41kD      920          930          940          950          960
[ 3684 ]   ... ... ..t ... ... ... .gt ... ... ..t ... ... ... ... ... ...>

 4. DK29-41      920          930          940          950          960
[ 3672 ]   ... ... ..t ... ... ... .gt ... ... ... ... .g. ... ... ... ...>

 5. PKO-41k      920          930          940          950          960
[ 3672 ]   ... ... ..t ... ... ..a .gt ... ... ..t ... ... ... ... ... ...>

                   970          980          990          1000
               *    *     *    *     *    *     *    *     *
B31-41kD   ATT GCG CAG GCT AAT CAA GTT CCC CAA TAT GTT TTG TCA TTG CTT AGA
           TAA CGC GTC CGA TTA GTT CAA GGG GTT ATA CAA AAC AGT AAC GAA TCT

 1. KA-41kD        970          980          990          1000
[ 3996 ]   ... ... ... ... ... ... ... ... ... ... ... ... ... ... ... ...>

 2. P-Gau-4        970          980          990          1000
[ 3696 ]   ... ..a ... ... ... ... ... ..t ... ... ... ... ... ... ... ...>

 3. BO-41kD        970          980          990          1000
[ 3684 ]   ... ..a ... ... ... ... ... ..t ... ... ... ... ... ... ... ...>

 4. DK29-41        970          980          990          1000
[ 3672 ]   ... ... ..a ... ... ... ... ..t ... ... ... ... ... ... ... ...>

 5. PKO-41k        970          980          990          1000
[ 3672 ]   ... ..a ... ... ... ... ... ..t ... ... ... ... ... ... ... ...>

          1010
            *
B31-41kD   TAA
           ATT

 2. P-Gau1010
[ 3696 ]   ...>
```

FIG. 41H

```
Sequence Range: 1 to 822

                        10          20          30          40
              *     *     *     *     *     *     *     *     *
OspA-B31    ATG AAA AAA TAT TTA TTG GGA ATA GGT CTA ATA TTA GCC TTA ATA GCA
            TAC TTT TTT ATA AAT AAC CCT TAT CCA GAT TAT AAT CGG AAT TAT CGT

OspA-B31                10          20          30          40
[ 3288 ]    ... ... ... ... ... ... ... ... ... ... ... ... ... ... ... ...>

OspA-KA                 10          20          30          40
[ 3288 ]    ... ... ... ... ... ... ... ... ... ... ... ... ... ... ... ...>

OspA-N40                10          20          30          40
[ 3276 ]    ... ... ... ... ... ... ... ... ... ... ... ... ... ... ... ...>

OspA-ZS7                10          20          30          40
[ 3264 ]    ... ... ... ... ... ... ... ... ... ... ... ... ... ... ... ...>

OspA-25015              10          20          30          40
[ 2802 ]    ... ... ... ... ... ... ... ... ... ... ... ... ..t ... ... ...>

OspA-TRO                10          20          30          40
[ 2648 ]    ... ... ... ... ... ... ... ... ... ... ... ... ... ... ... ...>

OspA-K48                10          20          30          40
[ 2584 ]    ... ... ... ... ... ... ... ... ... ... ... ... ... ... ... ...>

OspA-HE 11              10          20          30          40
[ 2580 ]    ... ... ... ... ... ... ... ... ... ... ... ... ... ... ... ...>

OspA-DK29               10          20          30          40
[ 2566 ]    ... ... ... ... ... ... ... ... ... ... ... ... ... ... ... ...>

OspA-Ip90               10          20          30          40
[ 2562 ]    ... ... ... ... ... ... ... ... ... ... ... ... ..a ... ... ...>

OspA-BO                 10          20          30          40
[ 2558 ]    ... ... ... ... ... ... ... ... ... ... ... ... ... ... ... ...>

OSPA-IP3                10          20          30          40
[ 2558 ]    ... ... ... ... ... ... ... ... ... ... ... ... ... ... ... ...>

OspA-PKO                10          20          30          40
[ 2558 ]    ... ... ... ... ... ... ... ... ... ... ... ... ... ... ... ...>

OspA-ACAI               10          20          30          40
[ 2556 ]    ... ... ... ... ... ... ... ... ... ... ... ... ... ... ... ...>

OspA-P-GAU              10          20          30          40
[ 2544 ]    ... ... ... ... ... ... ... ... ... ... ... ... ... ... ... ...>

            50          60          70          80          90
             *     *     *     *     *     *     *     *     *     *
OspA-B31    TGT AAG CAA AAT GTT AGC AGC CTT GAC GAG AAA AAC AGC GTT TCA GTA
            ACA TTC GTT TTA CAA TCG TCG GAA CTG CTC TTT TTG TCG CAA AGT CAT
```

FIG. 42A

```
OspA-B31      50              60              70              80              90
[ 3288 ]      ... ... ... ... ... ... ... ... ... ... ... ... ... ... ... ... ...>

OspA-KA       50              60              70              80              90
[ 3288 ]      ... ... ... ... ... ... ... ... ... ... ... ... ... ... ... ... ...>

OspA-N40      50              60              70              80              90
[ 3276 ]      ... ... ... ... ... ... ... ... ... ... ... ... ... ... ... ... ...>

OspA-ZS7      50              60              70              80              90
[ 3264 ]      ... ... ... ... ... ... ... ... ... ... ... ... ... ... ... ... ...>

OspA-25015    50              60              70              80              90
[ 2802 ]      ... ... ... ... ... ... ... ... ... ... ... ... ... ... ... ... ...>

OspA-TRO      50              60              70              80              90
[ 2648 ]      ... ... ... ... ... ... ... ... ..t ... ... ... ... ... ... ... ...>

OspA-K48      50              60              70              80              90
[ 2584 ]      ... ... ... ... ... ... ... ... ..t ..a ... ..t ... ...     ... ...>

OspA-HE 11    50              60              70              80              90
[ 2580 ]      ... ... ... ... ... ... ... ... ..t ..a ... ..t ... ...     ... ...>

OspA-DK29     50              60              70              80              90
[ 2566 ]      ... ... ... ... ... ... ... ... ..t ..a ... ..t ... ...     ... ...>

OspA-Ip90     50              60              70              80              90
[ 2562 ]      ... ... ... ... ... ... ... ... ..t ..a ... ..t ... ...     ... ...>

OspA-BO       50              60              70              80              90
[ 2558 ]      ..c ... ... ... ... ... ... ... ..t ..a ... ... ... .c.     ... ...>

OSPA-IP3      50              60              70              80              90
[ 2558 ]      ..c ... ... ... ... ... ... ... ..t ..a ... ... ... .c.     ... ...>

OspA-PKO      50              60              70              80              90
[ 2558 ]      ..c ... ... ... ... ... ... ... ..t ..a ... ... ... .c.     ... ...>

OspA-ACAI     50              60              70              80              90
[ 2556 ]      ..c ... ... ... ... ... ... ... ..t ..a ... ... ... .c.     ... ...>

OspA-F-GAU    50              60              70              80              90
[ 2544 ]      ..c ... ... ... ... ... ... ... ..t ..a ... ... ... .c.     ... ...>


                100             110             120             130             140
                 *       *       *       *       *       *       *       *       *
OspA-B31      GAT TTG CCT GGT GAA ATG AAA GTT CTT GTA AGC AAA GAA AAA  AAC AAA
              CTA AAC GGA CCA CTT TAC TTT CAA GAA CAT TCG TTT CTT TTT  TTG TTT

OspA-B31        100             110             120             130             140
[ 3288 ]      ... ... ... ... ... ... ... ... ... ... ... ... ... ...     ... ...>

OspA-KA         100             110             120             130             140
[ 3288 ]      ... ... ... ... ... ... ... ... ... ... ... ... ... ...     ... ...>

OspA-N40        100             110             120             130             140
```

```
[ 3276 ]       ... ... ... ... ... ... ..c ... ... ... ... ... ... ... ... ...>

OspA-ZS7       100            110            120            130            140
[ 3264 ]       ... ... ... ... ... ... ..c ... ... ... ... ... ... ... ... ...>

OspA-25015     100            110            120            130            140
[ 2802 ]       ... ... ... ... ... ... ... ... ... ... ... ... ... ... g.. ...>

OspA-TRO       100            110            120            130            140
[ 2648 ]       ... ..a ... ... ... ... ... ... ... ... ... ... ... ... g.. ...>

OspA-K48       100            110            120            130            140
[ 2584 ]       ... ..a ... ... .g. ... .c. ... ... ... ..t ... ... ... g.. ...>

OspA-HE 11     100            110            120            130            140
[ 2580 ]       ... ..a ... ... .g. ... ... ... ... ... ..t ... ... ... g.. ...>

OspA-DK29      100            110            120            130            140
[ 2566 ]       ... ..a ... ... .g. ... .c. ... ... ... ..t ... ... ... .g.. ...>

OspA-Ip90      100            110            120            130            140
[ 2562 ]       ... ..a ... ... .g. ... c.. ... ... ... ..t ... ... ... g.. ...>

OspA-BO        100            110            120            130            140
[ 2558 ]       ... ... ... ... ..g ... ... ... ... ... ..t ... ... ... g.. ...>

OSPA-IP3       100            110            120            130            140
[ 2558 ]       ... ... ... ... ..g ..t ... ... ... ... ..t ..  ... ... g.. ...>

OspA-PKO       100            110            120            130            140
[ 2558 ]       ... ... ... ... ..g ... ... ... ... ... ..t ... ... ... g.. ...>

OspA-ACAI      100            110            120            130            140
[ 2556 ]       ... ... ... ... ..g ... ... ... ... ... ..t ... ... ... g.. ...>

OspA-P-GAU     100            110            120            130            140
[ 2544 ]       ... ... ... ... ..g ... ... ... ... ... ..t ... ... ... g.. ...>


                   1 0            160            170            180            190
               *   *       *      *      *      *      *      *      *      *
OspA-B31       GAC GGC AAG TAC GAT CTA ATT GCA ACA GTA GAC AAG CTT GAG CTT AAA
               CTG CCG TTC ATG CTA GAT TAA CGT TGT CAT CTG TTC GAA CTC GAA TTT

OspA-B31       150            160            170            180            190
[ 3288 ]       ... ... ... ... ... ... ... ... ... ... ... ... ... ... ... ...>

OspA-KA        150            160            170            180            190
[ 3288 ]       ... ... ... ... ... ... ... ... ... ... ... ... ... ... ... ...>

OspA-N40       150            160            170            180            190
[ 3276 ]       ... ... ... ... ... ... ... ... ... ... ... ... ... ... ... ...>

OspA-ZS7       150            160            170            180            190
[ 3264 ]       ... ... ... ... ... ... ... ... ... ... ... ... ... ... ... ...>

OspA-25015     150            160            170            180            190
[ 2802 ]       ... ... ... ... ag. ... ..g ... ... ... ... ... ... ... ... ...>
```

FIG. 42C

```
OspA-TRO          150            160          170           180           190
[ 2648 ]     ..t ..t ..a ... ag. ... ..g ... ... ... ... ... ..a ... ... ...>

OspA-K48          150            160          170           180           190
[ 2584 ]     ... ..t ..a ... ag. ... gag ... ... ... ... ... ... ... ... ...>

OspA-HE 11        150            160          170           180           190
[ 2580 ]     ..t ..t ..a ... ag. ... ..g ... ... ... ..a ... ... ... ... ...>

OspA-DK29         150            160          170           180           190
[ 2566 ]     ... ..t ..a ... ag. ... gag ... ... ... ... ... ... ... ... ...>

OspA-Ip90         150            160          170           180           190
[ 2562 ]     ..t ..t ..a ... ag. ... ..g ... ... ... ... ... ... ... ... ...>

OspA-BO           150            160          170           180           190
[ 2558 ]     ... ..t ... ... ag. ... .ag ... ... ... ... ... a.. ... ..a ...>

OSPA-IP3          150            160          170           180           190
[ 2558 ]     ... ..t ... ... ag. ... .ag ... ... ... ... ... a.. ... ..a ...>

OspA-PKO          150            160          170           180           190
[ 2558 ]     ... ..t ... ... ag. ... .ag ... ... ... ... ... a.. ... ..a ...>

OspA-ACAI         150            160          170           180           190
[ 2556 ]     ... ..t ... ... ag. ... .ag ... ... ... ... ... a.. ... ..a ...>

ospA-P-GAU        150            160          170           180           190
[ 2544 ]     ... ..t ... ... ag. ... .ag ... ... ... ... ... a.. ... ..a ...>


                      200           210           220           230            240
                *      *      *      *      *      *      *      *      *      *
OspA-B31     GGA ACT TCT GAT AAA AAC AAT GGA TCT GGA GTA CTT GAA GGC GTA AAA
             CCT TGA AGA CTA TTT TTG TTA CCT AGA CCT CAT GAA CTT CCG CAT TTT

OspA-B31              200           210           220           230            240
[ 3288 ]     ... ... ... ... ... ... ... ... ... ... ... ... ... ... ... ...>

OspA-KA               200           210           220           230            240
[ 3288 ]     ... ... ... ... ... ... ... ... ... ... ... ... ... ... ... ...>

OspA-N40              200           210           220           230            240
[ 3276 ]     ... ... ... ... ... ... ... ... ... ... ... ... ... ... ... ...>

OspA-ZS7              200           210           220           230            240
[ 3264 ]     ... ... ... ... ... ... ... ... ... ... ... ... ... ... ... ...>

OspA-25015            200           210           220           230            240
[ 2802 ]     ... ..a ... ... ... ... ... ... ... ..g ..g ... ... ... ... ...>

OspA-TRO              200           210           220           230            240
[ 2648 ]     ... ... ... ... ... .g. ..c ..t ... ... ac. ... ... ..t .a. ...>

OspA-K48              200           210           220           230            240
[ 2584 ]     ... ... ... ... ... ... ..c ..t ... ... ac. ... ... ..t .a. ...>
```

FIG. 42D

```
OspA-HE 11        200          210          220          230          240
[ 2580 ]     ... ... ... ... ... ... ..c ..t ... ... ac. ... ... ..t .a. ...>

OspA-DK29         200          210          220          230          240
[ 2566 ]     ... ... ... ... ... ... ..c ..t ... ... ac. ... ... ..t .a. ...>

OspA-Ip90         200          210          220          230          240
[ 2562 ]     ... ... ... ... ... ... ..c ..t ... ... ac. ... ... ..t .a. ...>

OspA-BO           200          210          220          230          240
[ 2558 ]     ... ... ... ... ... g.. ... ..t ... ..g ..g ... ... ..t ac. ...>

OSPA-IP3          200          210          220          230          240
[ 2558 ]     ... ... ... ... ... g.. ... ..t ... ... ..g ... ... ..t ac. ...>

OspA-PKO          200          210          220          230          240
[ 2558 ]     ... ... ... ... ... g.. ... ..t ... ..g ..g ... ... ..t ac. ...>

OspA-ACAI         200          210          220          230          240
[ 2556 ]     ... ... ... ... ... g.. ... ..t ... ... ..g ... ... ..t ac. ...>

OspA-P-GAU        200          210          220          230          240
[ 2544 ]     ... ... ... ... ... g.. ... ..t ... ... ..g ... ... ..t ac. ...>

                       250           260           270           280
                   *       *     *       *       *     *       *       *
OspA-B31     GCT GAC AAA AGT AAA GTA AAA TTA ACA ATT TCT GAC GAT CTA GGT CAA
             CGA CTG TTT TCA TTT CAT TTT AAT TGT TAA AGA CTG CTA GAT CCA GTT

OspA-B31               250           260           270           280
[ 3288 ]     ... ... ... ... ... ... ... ... ... ... ... ... ... ... ... ...>

OspA-KA                250           260           270           280
[ 3288 ]     ... ... ... ... ... ... ... ... ... ... ... ... ... ... ... ...>

OspA-N40               250           260           270           280
[ 3276 ]     ... ... ... ... ... ... ... ... ... ... ... ... ... ... ... ...>

OspA-ZS7               250           260           270           280
[ 3264 ]     ... ... ... ... ... ... ... ... ... ... ... ... ... ... ... ...>

OspA-25015             250           260           270           280
[ 2802 ]     ... ... ... ..c ... ... ... ... ... g.. ... ... ... ... a.c ac.>

OspA-TRO               250           260           270           280
[ 2648 ]     t.. ... ... ... ... .c. ... ... ... ... ... ..a ... ... a.. a..>

OspA-K48               250           260           270           280
[ 2584 ]     a.. ... ... ... ... ... ... ... ... ... g.. ..t ..c ... a.. ...>

OspA-HE 11             250           260           270           280
[ 2580 ]     a.. ... ... ... ... ... ... ... ... ... g.. ..g ... ... a.. a..>

OspA-DK29              250           260           270           280
[ 2566 ]     a.. ... ... ... ... ... ... .c. ... ... g.. ..t ..c ... a.. ...>

OspA-Ip90              250           260           270           280
```

```
[ 2562 ]      a.. ... ... ... ... .c. ... ... ... ... g.. ..g ... ... a.. a..>

OspA-BO                  250            260            270            280
[ 2558 ]      .a. ... ... ... ... .c. ... ... ... ... g.. ... ... ... ... a..>

OSPA-IP3                 250            260            270            280
[ 2558 ]      .a. ... ... ... ... .c. ... ... ... ... g.. ... ... ... a.. a..>

OspA-PKO                 250            260            270            280
[ 2558 ]      .a. ... ... ... ... .c. ... ... ... ... g.. ... ... ... ... a..>

OspA-ACAI                250            260            270            280
[ 2556 ]      .a. ... ... ... ... .c. ... ... ... ... g.. ... ... ... a.. a..>

OspA-P-GAU               250            260            270.           280
[ 2544 ]      .a. ... ... ... ... .c. ... ... ... ... g.. ... ... ... a.. a..>

              290            300            310            320            330
               *       *       *       *       *       *       *       *       *
OspA-B31      ACC ACA CTT GAA GTT TTC AAA GAA GAT GGC AAA ACA CTA GTA TCA AAA
              TGG TGT GAA CTT CAA AAG TTT CTT CTA CCG TTT TGT GAT CAT AGT TTT

OspA-B31      290            300            310            320            330
[ 3288 ]      ... ... ... ... ... ... ... ... ... ... ... ... ... ... ... ...>

OspA-KA       290            300            310            320            330
[ 3288 ]      ... ... ... ... ... ... ... ... ... ... ... ... ... ... ... ...>

OspA-N40      290            300            310            320            330
[ 3276 ]      ... ... ... ... ... ... ... ... ... ... ... ... ... ... ... ...>

OspA-ZS7      290            300            310            320            330
[ 3264 ]      ... ... ... ... ... ... ... ... ... ... ... ... ... ... ... ...>

OspA-25015    290            300            310            320            330
[ 2802 ]      ... ... ... ... ... ..a ... ... ... ... ... ... t.. ..g ... ...>

OspA-TRO      290            300            310            320            330
[ 2648 ]      ... ... t.. ... a.. ... ... ... ... ... ... ... t.. ... ... ...>

OspA-K48      290            300            310            320            330
[ 2584 ]      ..t .a. t.. ... a.. ... ... ... ... .c. ... ... t.. ... ... ...>

OspA-HE 11    290            300            310            320            330
[ 2580 ]      ... ... t.. ... a.c ... ... ... ... ... ... ... t.. ... ..g ...>

OspA-DK29     290            300            310            320            330
[ 2566 ]      ..t .a. t.. ... a.. ... ... ... ... ... ... ... t.. ... ... ...>

OspA-Ip90     290            300            310            320            330
[ 2562 ]      ... ... t.. ... a.c ... ... ... ... ... ... ... t.. ... ... ...>

OspA-BO       290            300            310            320            330
[ 2558 ]      ... ... t.c ... c.. ... ... ... ... ... ... ... t.. ..g. ... .g.>

OSPA-IP3      290            300            310            320            330
[ 2558 ]      ... ... t.c ... c.. ... ... ... ... ... ... ... t.. ..g ... .g.>
```

FIG. 42F

```
OspA-PKO     290              300            310            320            330
[ 2558 ]     ... ... t.c ... c.. ... ... ... ... ... ... ... t.. ..g ... .g.>

OspA-ACAI    290              300            310            320            330
[ 2556 ]     ... ... t.c ... c.. ... ... ... ... ... ... ... t.. ..g ... .g.>

OspA-P-GAU   290              300            310            320            330
[ 2544 ]     ... ... t.c ... c.. ..a ... ... ... ... ... ... t.. ..g ... .g.>


                 340          350            360            370            380
                  *      *      *       *      *      *      *      *      *
OspA-B31     AAA GTA ACT TCC AAA GAC AAG TCA TCA ACA GAA GAA AAA TTC AAT GAA
             TTT CAT TGA AGG TTT CTG TTC AGT AGT TGT CTT CTT TTT AAG TTA CTT

OspA-B31         340          350            360            370            380
[ 3288 ]     ... ... ... ... ... ... ... ... ... ... ... ... ... ... ... ...>

OspA-KA          340          350            360            370            380
[ 3288 ]     ... ... ... ... ... ... ... ... ... ... ... ... ... ... ... ...>

OspA-N40         340          350            360            370            380
[ 3276 ]     ... ... ... ... ... ... ... ... ... ... ... ... ... ... ... ...>

OspA-ZS7         340          350            360            370            380
[ 3264 ]     ... ... ... ... ... ... ... ... ... ... ... ... ... ... ... ...>

OspA-25015       340          350            360            370            380
[ 2802 ]     ... ag. ... ..t ... ..t ... ... ... ... ... ... ..g ... ... ...>

OspA-TRO         340          350            360            370            380
[ 2648 ]     ... ... .a. ..t ... ..t ... ... ... .t. ... ... ... ... ..c .c.>

OspA-K48         340          350            360            370            380
[ 2584 ]     ... ... ..c ctt ... ... ... ... ... ... ... ... ... ... ..c ...>

OspA-HE 11       340          350            360            370            380
[ 2580 ]     ... ... ..c ctt ... ... ... ... ... ... ... ... ... ... ..c ...>

OspA-DK29        340          350            360            370            380
[ 2566 ]     ... ... ..c ctt ... ... ... ... ... ... ... ... ... ... ..c .g.>

OspA-Ip90        340          350            360            370            380
[ 2562 ]     ... ... ..c ctt ... ... ... ... ... ... ... ... ... ... ..c .c.>

OspA-BO          340          350            360            370            380
[ 2558 ]     ... ... .g. ..t ... ... ..a a.. ... ... ..t ... .tg ... ... ...>

OSPA-IP3         340          350            360            370            380
[ 2558 ]     ... ... .g. ..t ... ... ..a a.. ... ... ..t ... .tg ... ... ...>

OspA-PKO         340          350            360            370            380
[ 2558 ]     ... ... .g. ..t ... ... ..a a.. ... ... ..t ... .tg ... ... ...>

OspA-ACAI        340          350            360            370            380
[ 2556 ]     ... ... .g. ..t ... ... ..a a.. ... ... ..t ... .tg ... ... ...>
```

FIG. 42G

```
OspA-P-GAU       340         350         360         370         380
[ 2544 ]     ... ... .g. ..t .g. ... ..a a.. ... ... ..t ... .tg ... ... ...>

                     390         400         410         420         430
              *   *   *   *   *   *   *   *   *   *
OspA-B31     AAA GGT GAA GTA TCT GAA AAA ATA ATA ACA AGA GCA GAC GGA ACC AGA
             TTT CCA CTT CAT AGA CTT TTT TAT TAT TGT TCT CGT CTG CCT TGG TCT

OspA-B31         390         400         410         420         430
[ 3288 ]     ... ... ... ... ... ... ... ... ... ... ... ... ... ... ... ...>

OspA-KA          390         400         410         420         430
[ 3288 ]     ... ... ... ... ... ... ... ... ... ... ... ... ... ... ... ...>

OspA-N40         390         400         410         420         430
[ 3276 ]     ... ... ... ... ... ... ... ... ... ... ... ... ... ... ... ...>

OspA-ZS7         390         400         410         420         430
[ 3264 ]     ... ... ... ... ... ... ... ... ... ... ... ... ... ... ... ...>

OspA-25015       390         400         410         420         430
[ 2802 ]     ... ..c ... t.. gt. ... ... ... ..g g.. ... ... a.. ... ... .t.>

OspA-TRO         390         400         410         420         430
[ 2648 ]     ... ... ... t.. ... ... ... .c. ... ct. ... ... a.. ... ... ..g>

OspA-K48         390         400         410         420         430
[ 2584 ]     ..g ... ... ac. ... ... ... .c. ... gt. ... ... a.t ... ... ...>

OspA-HE 11       390         400         410         420         430
[ 2580 ]     ..g ... ... a.. ... ... ... .c. ... gt. ... ... a.t ... ... ...>

OspA-DK29        390         400         410         420         430
[ 2566 ]     ..g ... ... ac. ... ... ... .c. ... gt. ... ... a.t ... ... ...>

OspA-Ip90        390         400         410         420         430
[ 2562 ]     ..g ... ... .c. ... ... ... .c. ... gt. ... ... a.t ... ... ...>

OspA-BO          390         400         410         420         430
[ 2558 ]     ... ... ... t.g ... .c. ... .cc ..g ... ... .a. a.t ... ... .a.>

OSPA-IP3         390         400         410         420         430
[ 2558 ]     ... ... ... t.g ... .c. ... .cc ..g ... ... .a. a.t ... ... .a.>

OspA-PKO         390         400         410         420         430
[ 2558 ]     ... ... ... t.g ... .c. ... .cc ..g ... ... .a. a.t ... ... .a.>

OspA-ACAI        390         400         410         420         430
[ 2556 ]     ... ... ... t.g ... .c. ... .cc ..g ... ... .a. a.t ... ... .a.>

ospA-P-GAU       390         400         410         420         430
[ 2544 ]     ... ... ... t.g ... .c. ... .cc ..g ... ... .a. a.t ... ... .a.>

                     440         450         460         470         480
              *   *   *   *   *   *   *   *   *   *
OspA-B31     CTT GAA TAC ACA GGA ATT AAA AGC GAT GGA TCT GGA AAA GCT AAA GAG
```

FIG. 42H

```
                 GAA CTT ATG TGT CCT TAA TTT TCG CTA CCT AGA CCT TTT CGA TTT CTC

OspA-B31             440         450         460         470         480
[ 3288 ]         ... ... ... ... ... ... ... ... ... ... ... ... ... ... ... ...>

OspA-KA              440         450         460         470         480
[ 3288 ]         ... ... ... ... ... ... ... ... ... ... ... ... ... ... ... ...>

OspA-N40             440         450         460         470         480
[ 3276 ]         ... ... ... ... .a. ... ... ... ... ... ... ... ... ... ... ...>

OspA-ZS7             440         450         460         470         480
[ 3264 ]         ... ... ... ... .a. ... ... ... ... ... ... ... ... ... ... ...>

OspA-25015           440         450         460         470         480
[ 2802 ]         ... ... ... ... ... ... ... ... ... ... ..c ... ... ... ... ..a>

OspA-TRO             440         450         460         470         480
[ 2648 ]         ... ... ... ... .a. ..a ... ... ... ... a.c ... ... ... ... ..a>

OspA-K48             440         450         460         470         480
[ 2584 ]         ... ... ... ... .ac ..a ... ... ... ... ..c ... ... ... ... ..a>

OspA-HE 11           440         450         460         470         480
[ 2580 ]         ... ... ... ... .ac ..a ... ... ... aa. a.c ... ... ... ... ..a>

OspA-DK29            440         450         460         470         480
[ 2566 ]         ... ... ... ... .ac ..a ... ... ... ... ..c ... ... ... ... ..a>

OspA-Ip90            440         450         460         470         480
[ 2562 ]         ... ... ... ... .ac ..a ... ... ... aa. a.c ... ... ... ... ..a>

OspA-BO              440         450         460         470         480
[ 2558 ]         ... ... ..t ... .a. ..g ... ... ... ... a.c ... ... ... ... ..a>

OSPA-IP3             440         450         460         470         480
[ 2558 ]         ... ... ..t ... .a. ..g ... ... ... ... a.c ... ... ... ... ..a>

OspA-PKO             440         450         460         470         480
[ 2558 ]         ... ... ..t ... .a. ..g ... ... ... ... a.c ... ... ... ... ..a>

OspA-ACAI            440         450         460         470         480
[ 2556 ]         ... ... ..t ... .a. ..g ... ... ... ... a.c ... ... ... ... ..a>

OspA-P-GAU           440         450         460         470         480
[ 2544 ]         ... ... ..t ... .a. ..g ... ... ... ... a.c ... ... ... ... ..a>


                         490         500         510         520
                  *   *   *   *   *   *   *   *   *
OspA-B31         GTT TTA AAA GGC TAT CTT CTT GAA GGA ACT CTA ACT GCT GAA AAA ACA
                 CAA AAT TTT CCG ATA GAA GAA CTT CCT TGA GAT TGA CGA CTT TTT TGT

OspA-B31             490         500         510         520
[ 3288 ]         ... ... ... ... ... ... ... ... ... ... ... ... ... ... ... ...>

OspA-KA              490         500         510         520
[ 3288 ]         ... ... ... ... ... ... ... ... ... ... ... ... ... ... ... ...>
```

FIG. 42I

```
OspA-N40              490         500         510         520
[ 3276 ]     ... ... ... ... ... ... ... ... ... ... ... ... ... ... ... ...>

OspA-ZS7              490         500         510         520
[ 3264 ]     ... ... ... a.. ... ... ... ... ... ... t.. ... ... ... ... ...>

OspA-25015            490         500         510         520
[ 2802 ]     ac. ... ... .aa ... ... ... ... ... ... ... ... ... ... ... g..>

OspA-TRO              490         500         510         520
[ 2648 ]     .c. ... ... .a. .t. .c. ... ... ... ... ... g.. ..c ..c ... ...>

                                                          cgg
                                                           |
OspA-K48              490         500         510         520|       530
[ 2584 ]     ... ... ... .a. .t. ac. ... ... ... ... ... g.. ... ..c ... ...>

                                                          cgg
                                                           |
OspA-HE 11            490         500         510         520|       530
[ 2580 ]     ... ... ... .a. .t. ac. ... ... ... ... ... g.. ... ..c ... ...>

                                                          cgg
                                                           |
OspA-DK29             490         500         510         520|       530
[ 2566 ]     ... ... ... .a. .t. ac. ... ... ... ... ... g.. ... ..c ... ...>

                                                          cgg
                                                           |
OspA-Ip90             490         500         510         520|       530
[ 2562 ]     ... ... ... .a. .t. .c. ... ... ... ... ... g.. ... ..c ... ...>

OspA-BO               490         500         510         520
[ 2558 ]     ... ... ... aa. .t. ac. ... ... ... .aa g.. g.. aa. ..t ... gt.>

OSPA-IP3              490         500         510         520
[ 2558 ]     ... ... ... aa. .t. ac. ... ... ... .aa g.. g.. aa. ..t ... gt.>

OspA-PKO              490         500         510         520
[ 2558 ]     ... ... ... aa. .t. ac. ... ... ... .aa g.. g.. aa. ..t ... gt.>

OspA-ACAI             490         500         510         520
[ 2556 ]     ... ... ... aa. .t. ac. ... ... ... .aa g.. g.. aa. ..t ... gt.>

ospA-P-GAU            490         500         510         520
[ 2544 ]     ... ... ... aag .t. ac. ... ... ... .aa g.. g.. aa. ..t ... gt.>

            530         540         550         560         570
             *       *       *       *       *       *       *       *       *       *
OspA-B31     ACA TTG GTG GTT AAA GAA GGA ACT GTT ACT TTA AGC AAA AAT ATT TCA
             TGT AAC CAC CAA TTT CTT CCT TGA CAA TGA AAT TCG TTT TTA TAA AGT

OspA-B31     530         540         550         560         570
[ 3288 ]     ... ... ... ... ... ... ... ... ... ... ... ... ... ... ... ...>

OspA-KA      530         540         550         560         570
```

```
[ 3288 ]      ... ... ... ... ... ... ... ... ... ... ... ... ... ... ... ...>

OspA-N40      530         540         550         560         570
[ 3276 ]      ... ... ... ... ... ... ... ... ... ... ... ... ... ... ... ...>

OspA-ZS7      530         540         550         560         570
[ 3264 ]      ... ... ... ... ... ... ... ... ... ... ... ... ... ... ... ...>

OspA-25015    530         540         550         560         570
[ 2802 ]      ... ... ... ... ... ... ... ... ... ... ... ..t ..g c.c ... ...>

OspA-TRO      530         540         550         560         570
[ 2648 ]      ... ... aaa ... .c. ... ..c ... ... gt. ... ... ... c.c ... c..>

OspA-K48                  540         550         560         570
[ 2584 ]      ... ... aaa ... .c. ... ..c ... ... gt. ... ... ..g ..c ... .t.>

OspA-HE II                540         550         560         570
[ 2580 ]      ... ... aaa ... .c. ..g ..c ... ... ... ... ... ..g ..c ... ...>

OspA-DK29                 540         550         560         570
[ 2566 ]      ... ... aaa ... .c. ... ..c ... ... gt. ... ... ..g ..c ... .t.>

OspA-Ip90                 540         550         560         570
[ 2562 ]      ... ..a aaa ... .c. ... ..c ... ... gt. ... ... ... c.c ... ...>

OspA-BO       530         540         550         560         570
[ 2558 ]      ... ... .aa ..a ... ... ... ..c ... ... ... ..t ..g g.a ... g..>

OSPA-IP3      530         540         550         560         570
[ 2558 ]      ... ... .aa ..a ... ... ... ..c ... ... ... ..t ..g g.a ... g..>

OspA-PKO      530         540         550         560         570
[ 2558 ]      ... ... .aa ..a ... ... ... ..c ... ... ... ..t ..g g.a ... g..>

OspA-ACAI     530         540         550         560         570
[ 2556 ]      ... ... .aa ..a ... ... ... ..c ... ... ... ..t ..g g.a ... g..>

OspA-P-GAU    530         540         550         560         570
[ 2544 ]      ... ... .aa ..a ... ... ... ..c ... ... ... ..t ..g g.a ... g..>


                  580         590         600         610         620
                   *     *     *     *     *     *     *     *     *
OspA-B31      AAA TCT GGG GAA GTT TCA GTT GAA CTT AAT GAC ACT GAC AGT AGT GCT
              TTT AGA CCC CTT CAA AGT CAA CTT GAA TTA CTG TGA CTG TCA TCA CGA

OspA-B31          580         590         600         610         620
[ 3288 ]      ... ... ... ... ... ... ... ... ... ... ... ... ... ... ... ...>

OspA-KA           580         590         600         610         620
[ 3288 ]      ... ... ... ... ... ... ... ... ... ... ... ... ... ... ... ...>

OspA-N40          580         590         600         610         620
[ 3276 ]      ... ... ... ... ... ... ... ... ... ... ... ... ... ... ... ...>

OspA-ZS7          580         590         600         610         620
[ 3264 ]      ... ... ... ... ... ... ... ... ... ... ... ... ... ... ... ...>
```

FIG. 42K

```
OspA-25015     580          590          600           610           620
[ 2802 ]   ... ... ..a ... ..a a.. .c. ... ... ... ... ... ... ... .c. caa>

OspA-TRO       580          590          600           610           620
[ 2648 ]   ..c ... ..a ... a.a a.. ... ..g ... ... ... t.. a.. tc. .c. cag>

OspA-K48  580          590          600          610          620
[ 2584 ]   ... ..c ..a ... a.a a.. ... .c. ... g.. ... t.. ... .c. .c. cag>

OspA-HE 1 1580         590          600          610          620
[ 2580 ]   ... ..c ..a ... a.a a.. ... .c. ... g.. ... ... ... tc. .-- ..g>

OspA-DK29 580          590          600          610          620
[ 2566 ]   ... ..c ..a ... a.a a.. .c. .c. ... g.. ... t.. ... .c. .c. cgg>

OspA-Ip90 580          590          600          610          620
[ 2562 ]   ..c ... ..a ... a.a a.. ... ..g ... ... ... t.. ... .c. .c. cag>

OspA-BO        580          590          600          610          620
[ 2558 ]   ... ... ..a ... ..a a.. ... .ct ... ... ... ... a.. .c. .c. cag>

OSPA-IP3       580          590          600          610          620
[ 2558 ]   ... ... ..a ... ..a a.. ... .ct ... ... ... ... a.. .c. .c. cag>

OspA-PKO       580          590          600          610          620
[ 2558 ]   ... ... ..a ... ..a a.. ... .ct ... ... ... ... a.. .c. .c. cag>

OspA-ACAI      580          590          600          610          620
[ 2556 ]   ... ... ..a ... ..a a.. ... .ct ... ... ... ... a.. .c. .c. cag>

ospA-P-GAU     580          590          600          610          620
[ 2544 ]   ... ... ..a ... ..a a.. ... .ct ... ... ... ... a.. .c. .c. cag>


                 630          640          650          660          670
            *     *     *     *     *     *     *     *     *     *
OspA-B31    GCT ACT AAA AAA ACT GCA GCT TGG AAT TCA GGC ACT TCA ACT TTA ACA
            CGA TGA TTT TTT TGA CGT CGA ACC TTA AGT CCG TGA AGT TGA AAT TGT

OspA-B31         630          640          650          660          670
[ 3288 ]    ... ... ... ... ... ... ... ... ... ... ... ... ... ... .-. ...>

OspA-KA          630          640          650          660          670
[ 3288 ]    ... ... ... ... ... ... ... ... ... ... ... ... ... ... .-. ...>

OspA-N40         630          640          650          660          670
[ 3276 ]    ... ... ... ... ... ... ... ... ... ... ... ... ... ... .-. ...>

OspA-ZS7         630          640          650          660          670
[ 3264 ]    ... ... ... ... ... ... ... ... ... ... ... ... ... ... .-. ...>

OspA-25015       630          640          650          660          670
[ 2802 ]    ... ... ... ... ... .gg aaa ... g.. g.. ... ... ... ... .-. ...>

OspA-TRO         630          640          650          660          670
[ 2648 ]    ... ... ... ... ... .g. aaa ... g.. ... aat ... ..c ... .-. ...>
```

FIG. 42L

```
OspA-K48   630         640         650         660         670
[ 2584 ]   ... ... ... ... ... .g. aaa ... g.. ... aaa ... ..c ... ... ...>

OspA-HE 11     630         640         650         660         670
[ 2580 ]   ..- .a. ... ... t.c .g. a.a ... g.. ... ..t ... ..t ... ... ...>

OspA-DK29  630         640         650         660         670
[ 2566 ]   ... ... ... ... ... .g. aaa ... g.. ... aag ... ..c ... ... ...>

OspA-Ip90  630         640         650         660         670
[ 2562 ]   ... ... ... ... ... .g. a.a ... g.. ... aag ... ..c ... ... ...>

OspA-BO        630         640         650         660         670
[ 2558 ]   ... ... ... ... ... .gc ..a ... g.. ... aaa ... ..t ... ... ...>

OSPA-IP3       630         640         650         660         670
[ 2558 ]   ... ... ... ... ... .gc ..a ... g.. ... aaa ... ..t ... ... ...>

OspA-PKO       630         640         650         660         670
[ 2558 ]   ... ... ... ... ... .gc ..a ... g.. ... aaa ... ..t ... ... ...>

OspA-ACAI      630         640         650         660         670
[ 2556 ]   ... ... ... ... ... .gc ..a ... g.. ... aaa ... ..t ... ... ...>

OspA-P-GAU     630         640         650         660         670
[ 2544 ]   ... ... ... ... ... .gc ..a ... g.. ... aaa ... ..t ... ... ...>


                   680         690         700         710         720
            *   *   *   *   *   *   *   *   *   *
OspA-B31   ATT ACT GTA AAC AGT AAA AAA ACT AAA GAC CTT GTG TTT ACA AAA GAA
           TAA TGA CAT TTG TCA TTT TTT TGA TTT CTG GAA CAC AAA TGT TTT CTT

OspA-B31           680         690         700         710         720
[ 3288 ]   ... ... ... ... ... ... ... ... ... ... ... ... ... ... ... ...>

OspA-KA            680         690         700         710         720
[ 3288 ]   ... ... ... ... ... ... ... ... ... ... ... ... ... ... ... ...>

OspA-N40           680         690         700         710         720
[ 3276 ]   ... ... ... ... ... ... ... ... ... ... ... ... ... ... ... ...>

OspA-ZS7           680         690         700         710         720
[ 3264 ]   ... ... ... ... ... ... ... ... ... ... ... ... ... ... ... ...>

OspA-25015         680         690         700         710         720
[ 2802 ]   ... ... ... ... .ac ... ... ... ... .c. ... ..a ... ... ... c..>

OspA-TRO           680         690         700         710         720
[ 2648 ]   ... .g. ..g ..t ..c ... ... ... ... a.. a.. ..a ... ... ... ...>

OspA-K48       680         690         700         710         720
[ 2584 ]   ... .g. ..g ..t ..c c.. ... ..c ... a.. ... ..a ..c ... ... ...>

OspA-HE 11         680         690         700         710         720
[ 2580 ]   ... .g. aa. ... ..a c.. ... ... ... c.a ... ..a ..c ... ... ...>

OspA-DK29      680         690         700         710         720
```

```
[ 2566 ]    . ... .g. ..g ..t ..c c.. ... ..c ... a.. ... ..a ..c ... ... ...>

OspA-Ip90      680        690         700        710         720
[ 2562 ]    ... .g. ..g ..t ..c cg. ... ..c ... a.. ... ..a ..c ... ... ...>

OspA-BO          680         690         700         710         720
[ 2558 ]    ... .g. ..t ... ..c ... ... ... .c. c.a ... ... ... ..t ... c..>

OSPA-IP3         680         690         700         710         720
[ 2558 ]    ... .g. ..t ... ... ... ... ... .c. c.a ... ... ... ..t ... c..>

OspA-PKO         680         690         700         710         720
[ 2558 ]    ... .g. ..t ... ..c ... ... ... .c. c.a ... ... ... ..t ... c..>

OspA-ACAI        680         690         700         710         720
[ 2556 ]    ... .g. ..t ... ..c ... ... ... .c. c.a ... ... ... ..t ... c..>

ospA-P-GAU       680         690         700         710         720
[ 2544 ]    ... .g. ..t ... ..c ... ... ... .c. c.a ... ... ... ..t ... c..>

                      730         740         750         760
                       *     *     *     *     *     *     *     *     *
OspA-B31    AAC ACA ATT ACA GTA CAA CAA TAC GAC TCA AAT GGC ACC AAA TTA GAG
            TTG TGT TAA TGT CAT GTT GTT ATG CTG AGT TTA CCG TGG TTT AAT CTC

OspA-B31              730         740         750         760
[ 3288 ]    ... ... ... ... ... ... ... ... ... ... ... ... ... ... ... ...>

OspA-KA               730         740         750         760
[ 3288 ]    ... ... ... ... ... ... ... ... ... ... ... ... ... ... ... ...>

OspA-N40              730         740         750         760
[ 3276 ]    ... ... ... ... ... ... ... ... ... ... ... ... ... ... ... ...>

OspA-ZS7              730         740         750         760
[ 3264 ]    ... ... ... ... ... ... ... ... ... ... ... ... ... ... ... ...>

OspA-25015            730         740         750         760
[ 2802 ]    g.. ... ... ... tc. ... a.. ... ... ..gca ..a ... ..c ..g ..a>

OspA-TRO              730         740         750         760
[ 2648 ]    g.. ... ..a ... ... ... a.. ... ... ... gca ... ... ..t c.. ..a>

OspA-K48        730         740         750         760         770
[ 2584 ]    g.. ... ..a ... ... ... a.. ... ... ... gca ... ... ..t c.. ..a>

OspA-HE 11            730         740         750         760
[ 2580 ]    g.. ... ..a ... ... ... a.c ... ... ... gca ... ... ..t c.. ..a>

OspA-DK29       730         740         750         760         770
[ 2566 ]    g.. ... ..a ... ... ... ag. ... ... ... gca ... ... ..t c.. ..a>

OspA-Ip90       730         740         750         760         770
[ 2562 ]    g.. ... ..a ... ... ... a.. ... ... ... gca ... ... ..t c.. ..a>

OspA-BO               730         740         750         760
[ 2558 ]    g.. ... ..a ..t ... ... a.. ... ... ..c gca ..t ... ..t ... ..a>
```

FIG. 42N

```
OSPA-IP3                730         740         750         760
[ 2558 ]     g.. ... ..a..t ... ... a.. ... ... ..c gca ..t ... ..t ... ..a>

OspA-PKO                730         740         750         760
[ 2558 ]     g.. ... ..a ..t ... ... a.. ... ... ..c gca ..t ......t ... ..a>

OspA-ACAI               730         740         750         760
[ 2556 ]     g.. ... ..a ..t ... ... a.. ... ... ..c gca ..t ... ..t ... ..a>

ospA-P-GAU              730         740         750         760
[ 2544 ]     t.. ... ..a ..t ... a.. ... ... ... ..c gca ..t ... ..t ... ..a>

           770.        780         790         800         810
            *     *     *     *     *     *     *     *     *     *
OspA-B31     GGG TCA GCA GTT GAA ATT ACA AAA CTT GAT GAA ATT AAA AAC GCT TTA
             CCC AGT CGT CAA CTT TAA TGT TTT GAA CTA CTT TAA TTT TTG CGA AAT

OspA-B31   770         780         790         800         810
[ 3288 ]     ... ... ... ... ... ... ... ... ... ... ... ... ... ... ... ...>

OspA-KA    770         780         790         800         810
[ 3288 ]     ... ... ... ... ... ... ... ... ... ... ... ... ... ... ... ...>

OspA-N40   770         780         790         800         810
[ 3276 ]     ... ... ... ... ... ... ... ... ... ... ... ... ... ... ... ...>

OspA-ZS7   770         780         790         800         810
[ 3264 ]     ... ... ... ... ... ... ... ... ... ... ... ... ... ... ... ...>

OspA-25015 770         780         790         800         810
[ 2802 ]     ..c a.. ... ..c ... ... .a. .c. ... ... ... c.. ... ... ... ...>

OspA-TRO   770         780         790         800         810
[ 2648 ]     ..c aac ... ..c ... ... .a. .c. ... ... ... c.. ... ... ... ...>

OspA-K48               780         790         800         810
[ 2584 ]     ..c aa. ... ..c ... ... ... .c. ... a.a ... c.. ... ... ... ...>

OspA-HE 11 770         780         790         800         810
[ 2580 ]     ..c aa. ... ..c ... ... ... .c. ... a.a ... c.. ... ... ... ...>

OspA-DK29              780         790         800         810
[ 2566 ]     ..c aa. ... ..c ... ... ... .c. ... a.a ... c.. ... ... ... ...>

OspA-Ip90              780         790         800         810
[ 2562 ]     ..c aa. ... ..c ... ... ... .cg ... a.a ... c.. ... g.t ... ...>

OspA-BO    770         780         790         800         810
[ 2558 ]     ..c a.. ... ..c ... ... .a. .c. ... ... ... c.. ... ... ... ...>

OSPA-IP3   770         780         790         800         810
[ 2558 ]     ..c a.. ... ..c ... ... .a. .c. ... ... ... c.. ... ... ... ...>

OspA-PKO   770         780         790         800         810
[ 2558 ]     ..c a.. ... ..c ... ... .a. .c. ... ... ... c.. ... ... ... ...>
```

FIG. 42O

```
OspA-ACAI  770        780          790          800         810
[ 2556 ]   ..c a.. ... ..c ... ... .a. .c. ... ... ... c.. ... ... ... ..g>

ospA-P-GAU 770        780          790          800         810
[ 2544 ]   ..c a.. ... ..c ... ... .a. .c. ... ... ... c.. ... ... ... ...>


                820
                 *
OspA-B31      AAA TAA
              TTT ATT

OspA-B31        820
[ 3288 ]      ... ...>

OspA-KA         820
[ 3288 ]      ... ...>

OspA-N40        820
[ 3276 ]      ... ...>

OspA-ZS7        820
[ 3264 ]      ... ...>

OspA-25015
[ 2802 ]      .g.>

OspA-TRO        820
[ 2648 ]      ... ..>

OspA-K48   820
[ 2584 ]      ... ...>

OspA-HE 11      820
[ 2580 ]      ... ..>

OspA-DK29 820
[ 2566 ]      ... ...>

OspA-Ip90 820
[ 2562 ]      ... ..>

OspA-BO         820
[ 2558 ]      ... ..>

OSPA-IP3        820
[ 2558 ]      ... ..>

OspA-PKO        820
[ 2558 ]      ... ..>

OspA-ACAI       820
[ 2556 ]      ... ...>

ospA-P-GAU      820
[ 2544 ]      ... ...>
```

FIG. 42P

```
              10             20             30             40
     *        *       *      *       *      *       *      *      *
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT

    50             60             70             80             90
     *        *       *      *       *      *       *      *      *
GCA TGT AAG CAA AAT GTT AGC AGC CTT GAT GAA AAA AAT AGC GTT
CGT ACA TTC GTT TTA CAA TCG TCG GAA CTA CTT TTT TTA TCG CAA

             100            110            120            130
     *        *       *      *       *      *       *      *      *
TCA GTA GAT TTA CCT GGT GGA ATG ACA GTT CTT GTA AGT AAA GAA
AGT CAT CTA AAT GGA CCA CCT TAC TGT CAA GAA CAT TCA TTT CTT

   140            150            160            170            180
     *        *       *      *       *      *       *      *      *
AAA GAC AAA GAC GGT AAA TAC AGT CTA GAG GCA ACA GTA GAC AAG
TTT CTG TTT CTG CCA TTT ATG TCA GAT CTC CGT TGT CAT CTG TTC

             190            200            210            220
     *        *       *      *       *      *       *      *      *
CTT GAG CTT AAA GGA ACT TCT GAT AAA AAC AAC GGT TCT GGA ACA
GAA CTC GAA TTT CCT TGA AGA CTA TTT TTG TTG CCA AGA CCT TGT

   230            240            250            260            270
     *        *       *      *       *      *       *      *      *
CTT GAA GGT GAA AAA ACT GAC AAA AGT AAA GTA AAA TTA ACA ATT
GAA CTT CCA CTT TTT TGA CTG TTT TCA TTT CAT TTT AAT TGT TAA

             280            290            300            310
     *        *       *      *       *      *       *      *      *
GCT GAT GAC CTA AGT CAA ACT AAA TTT GAA ATT TTC AAA GAA GAT
CGA CTA CTG GAT TCA GTT TGA TTT AAA CTT TAA AAG TTT CTT CTA

   320            330            340            350            360
     *        *       *      *       *      *       *      *      *
GCC AAA ACA TTA GTA TCA AAA AAA GTA ACC CTT AAA GAC AAG TCA
CGG TTT TGT AAT CAT AGT TTT TTT CAT TGG GAA TTT CTG TTC AGT

             370            380            390            400
     *        *       *      *       *      *       *      *      *
TCA ACA GAA GAA AAA TTC AAC GAA AAG GGT GAA ACA TCT GAA AAA
AGT TGT CTT CTT TTT AAG TTG CTT TTC CCA CTT TGT AGA CTT TTT

   410            420            430            440            450
     *        *       *      *       *      *       *      *      *
ACA ATA GTA AGA GCA AAT GGA ACC AGA CTT GAA TAC ACA GAC ATA
TGT TAT CAT TCT CGT TTA CCT TGG TCT GAA CTT ATG TGT CTG TAT

             460            470            480            490
     *        *       *      *       *      *       *      *      *
AAA AGC GAT GGA TCC GGA AAA GCT AAA GAA GTT TTA AAA GAC TTT
TTT TCG CTA CCT AGG CCT TTT CGA TTT CTT CAA AAT TTT CTG AAA

   500            510            520            530            540
     *        *       *      *       *      *       *      *      *
ACT CTT GAA GGA ACT CTA GCT GCT GAC GGC AAA ACA ACA TTG AAA
TGA GAA CTT CCT TGA GAT CGA CGA CTG CCG TTT TGT TGT AAC TTT

             550            560            570            580
     *        *       *      *       *      *       *      *      *
GTT ACA GAA GGC ACT GTT GTT TTA AGC AAG AAC ATT TTA AAA TCC
```

FIG. 43A

```
CAA TGT CTT CCG TGA CAA CAA AAT TCG TTC TTG TAA AAT TTT AGG

   590          600           610          620          630
    *      *     *      *      *     *      *      *      *
GGA GAA ATA ACA GTT GCA CTT GAT GAC TCT GAC ACT ACT CAG GCT
CCT CTT TAT TGT CAA CGT GAA CTA CTG AGA CTG TGA TGA GTC CGA

          640          650          660          670
    *      *     *      *      *     *      *      *      *
ACT AAA AAA ACT GGA AAA TGG GAT TCA AAT ACT TCC ACT TTA ACA
TGA TTT TTT TGA CCT TTT ACC CTA AGT TTA TGA AGG TGA AAT TGT

   680          690           700          710          720
    *      *     *      *      *     *      *      *      *
ATT AGT GTG AAT AGC AAA AAA ACT AAA AAC ATT GTA TTT ACA AAA
TAA TCA CAC TTA TCG TTT TTT TGA TTT TTG TAA CAT AAA TGT TTT

          730          740          750          760
    *      *     *      *      *     *      *      *      *
GAA GAC ACA ATA ACA GTA CAA AAA TAC GAC TCA GCA GGC ACC AAT
CTT CTG TGT TAT TGT CAT GTT TTT ATG CTG AGT CGT CCG TGG TTA

   770          780           790          800          810
    *      *     *      *      *     *      *      *      *
CTA GAA GGC AAC GCA GTC GAA ATT AAA ACA CTT GAT GAA CTT AAA
GAT CTT CCG TTG CGT CAG CTT TAA TTT TGT GAA CTA CTT GAA TTT

          820
    *      *     *
AAC GCT TTA AAA TAG
TTG CGA AAT TTT ATC
```

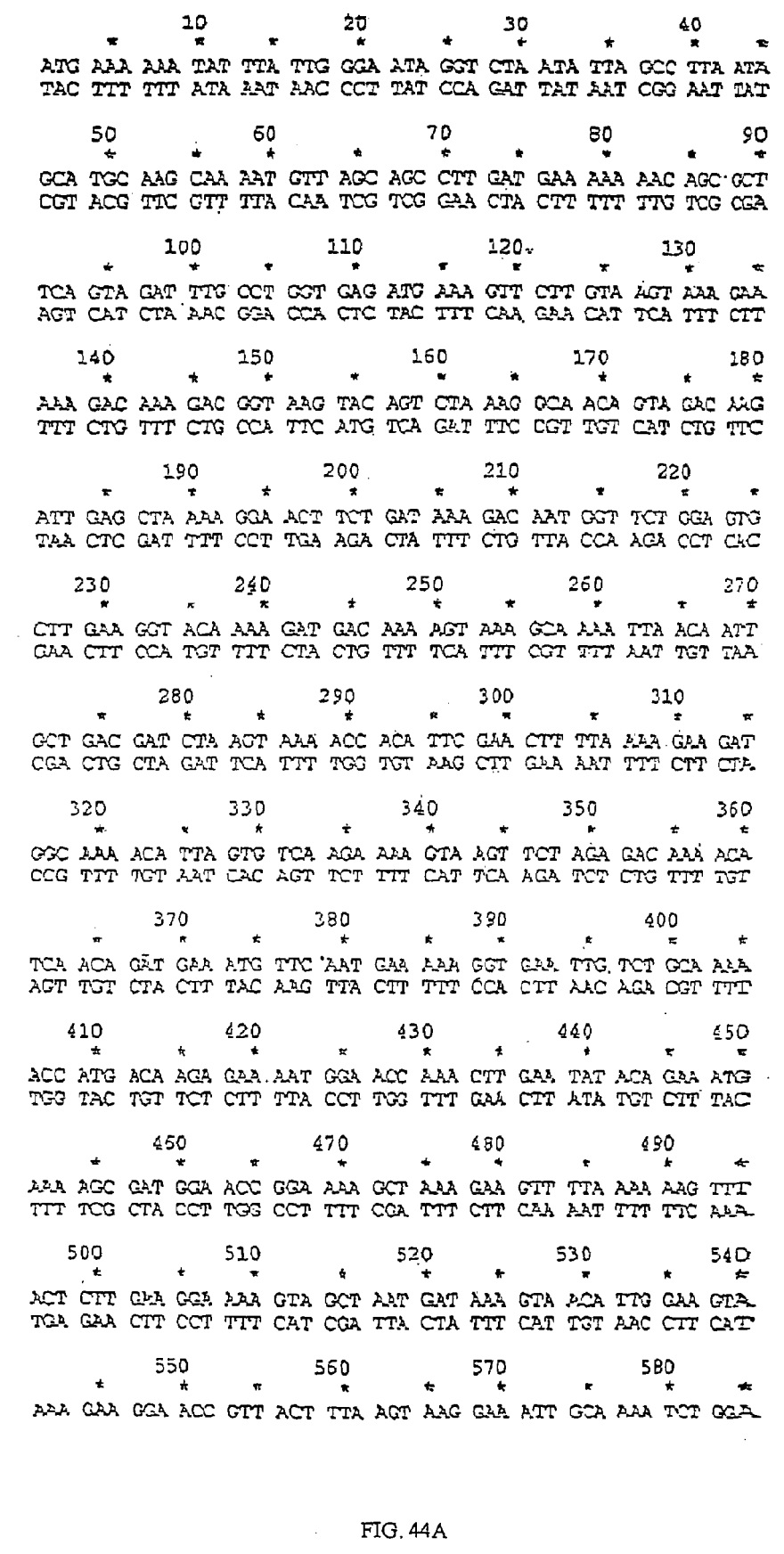

FIG. 43B 10 20 30 40
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT 50 60 70 80 90
GCA TGC AAG CAA AAT GTT AGC AGC CTT GAT GAA AAA AAC AGC GCT
CGT ACG TTC GTT TTA CAA TCG TCG GAA CTA CTT TTT TTG TCG CGA 100 110 120 130
TCA GTA GAT TTG CCT GGT GAG ATG AAA GTT CTT GTA AGT AAA GAA
AGT CAT CTA AAC GGA CCA CTC TAC TTT CAA GAA CAT TCA TTT CTT 140 150 160 170 180
AAA GAC AAA GAC GGT AAG TAC AGT CTA AAG GCA ACA GTA GAC AAG
TTT CTG TTT CTG CCA TTC ATG TCA GAT TTC CGT TGT CAT CTG TTC 190 200 210 220
ATT GAG CTA AAA GGA ACT TCT GAT AAA GAC AAT GGT TCT GGA GTG
TAA CTC GAT TTT CCT TGA AGA CTA TTT CTG TTA CCA AGA CCT CAC 230 240 250 260 270
CTT GAA GGT ACA AAA GAT GAC AAA AGT AAA GCA AAA TTA ACA ATT
GAA CTT CCA TGT TTT CTA CTG TTT TCA TTT CGT TTT AAT TGT TAA 280 290 300 310
GCT GAC GAT CTA AGT AAA ACC ACA TTC GAA CTT TTA AAA GAA GAT
CGA CTG CTA GAT TCA TTT TGG TGT AAG CTT GAA AAT TTT CTT CTA 320 330 340 350 360
GGC AAA ACA TTA GTG TCA AGA AAA GTA AGT TCT AGA GAC AAA ACA
CCG TTT TGT AAT CAC AGT TCT TTT CAT TCA AGA TCT CTG TTT TGT 370 380 390 400
TCA ACA GAT GAA ATG TTC AAT GAA AAA GGT GAA TTG TCT GCA AAA
AGT TGT CTA CTT TAC AAG TTA CTT TTT CCA CTT AAC AGA CGT TTT 410 420 430 440 450
ACC ATG ACA AGA GAA AAT GGA ACC AAA CTT GAA TAT ACA GAA ATG
TGG TAC TGT TCT CTT TTA CCT TGG TTT GAA CTT ATA TGT CTT TAC 460 470 480 490
AAA AGC GAT GGA ACC GGA AAA GCT AAA GAA GTT TTA AAA AAG TTT
TTT TCG CTA CCT TGG CCT TTT CGA TTT CTT CAA AAT TTT TTC AAA 500 510 520 530 540
ACT CTT GAA GGA AAA GTA GCT AAT GAT AAA GTA ACA TTG GAA GTA
TGA GAA CTT CCT TTT CAT CGA TTA CTA TTT CAT TGT AAC CTT CAT 550 560 570 580
AAA GAA GGA ACC GTT ACT TTA AGT AAG GAA ATT GCA AAA TCT GGA

FIG. 44A

TTT CTT CCT TGG CAA TGA AAT TCA TTC CTT TAA CGT TTT AGA CCT 590 600 610 620 630

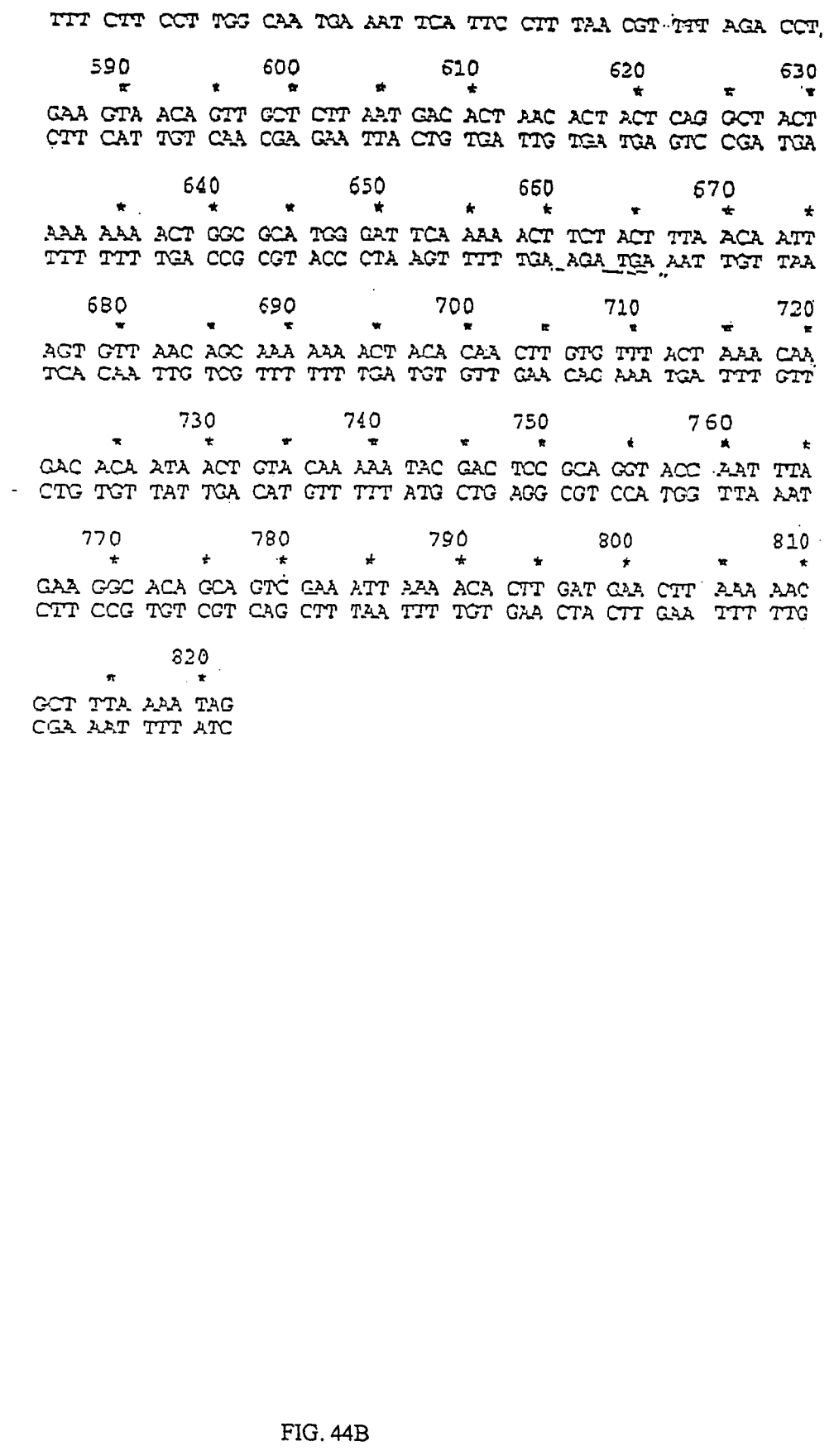

GAA GTA ACA GTT GCT CTT AAT GAC ACT AAC ACT ACT CAG GCT ACT
CTT CAT TGT CAA CGA GAA TTA CTG TGA TTG TGA TGA GTC CGA TGA 640 650 660 670

AAA AAA ACT GGC GCA TGG GAT TCA AAA ACT TCT ACT TTA ACA ATT
TTT TTT TGA CCG CGT ACC CTA AGT TTT TGA AGA TGA AAT TGT TAA 680 690 700 710 720

AGT GTT AAC AGC AAA AAA ACT ACA CAA CTT GTG TTT ACT AAA CAA
TCA CAA TTG TCG TTT TTT TGA TGT GTT GAA CAC AAA TGA TTT GTT 730 740 750 760

GAC ACA ATA ACT GTA CAA AAA TAC GAC TCC GCA GGT ACC AAT TTA
CTG TGT TAT TGA CAT GTT TTT ATG CTG AGG CGT CCA TGG TTA AAT 770 780 790 800 810

GAA GGC ACA GCA GTC GAA ATT AAA ACA CTT GAT GAA CTT AAA AAC
CTT CCG TGT CGT CAG CTT TAA TTT TGT GAA CTA CTT GAA TTT TTG

820

GCT TTA AAA TAG
CGA AAT TTT ATC

FIG. 44B

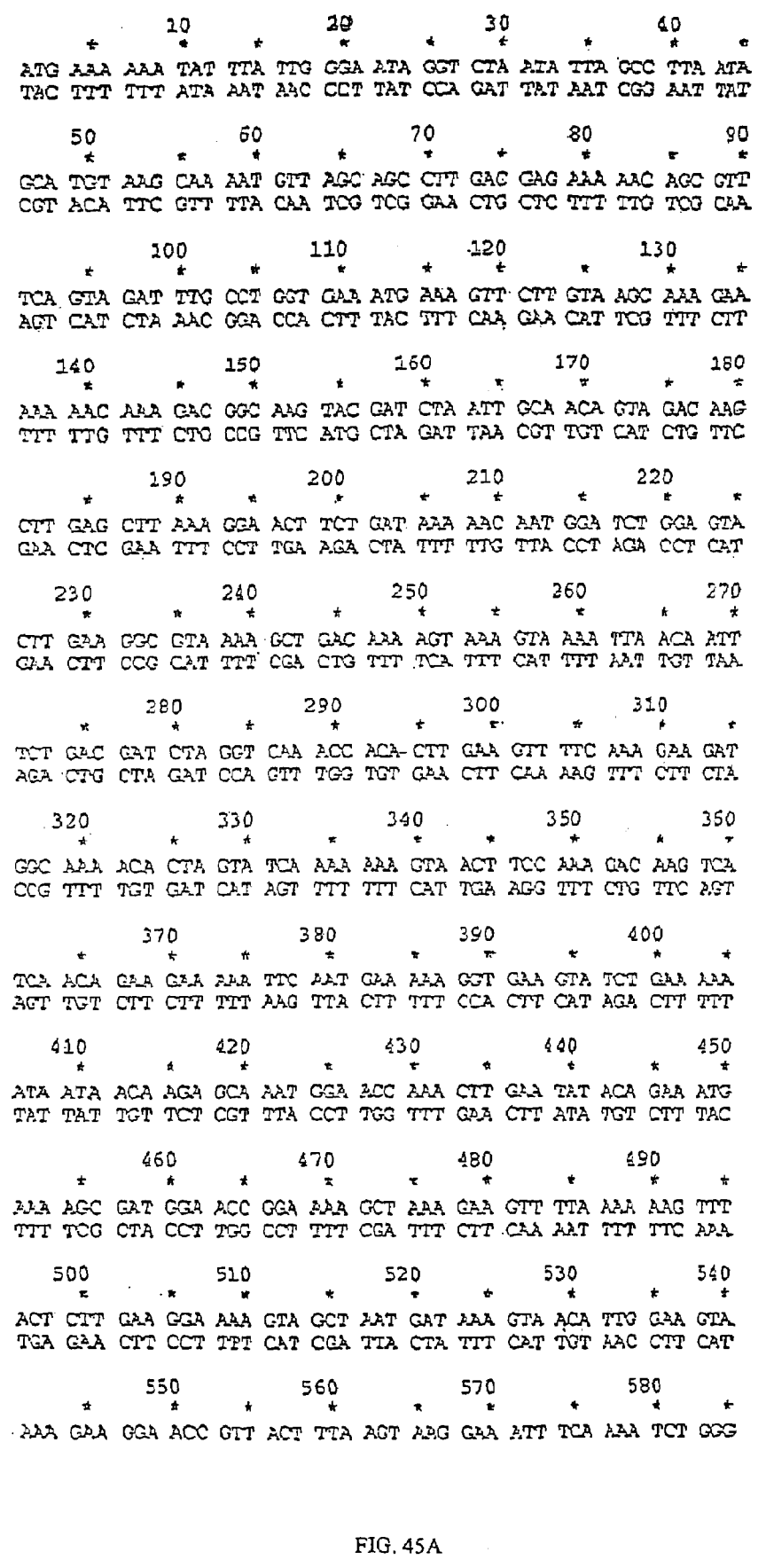

```
                 10                  20                  30                  40
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT

       50                  60                  70                  80                  90
GCA TGT AAG CAA AAT GTT AGC AGC CTT GAC GAG AAA AAC AGC GTT
CGT ACA TTC GTT TTA CAA TCG TCG GAA CTG CTC TTT TTG TCG CAA

                100                 110                 120                 130
TCA GTA GAT TTG CCT GGT GAA ATG AAA GTT CTT GTA AGC AAA GAA
AGT CAT CTA AAC GGA CCA CTT TAC TTT CAA GAA CAT TCG TTT CTT

      140                 150                 160                 170                 180
AAA AAC AAA GAC GGC AAG TAC GAT CTA ATT GCA ACA GTA GAC AAG
TTT TTG TTT CTG CCG TTC ATG CTA GAT TAA CGT TGT CAT CTG TTC

                190                 200                 210                 220
CTT GAG CTT AAA GGA ACT TCT GAT AAA AAC AAT GGA TCT GGA GTA
GAA CTC GAA TTT CCT TGA AGA CTA TTT TTG TTA CCT AGA CCT CAT

      230                 240                 250                 260                 270
CTT GAA GGC GTA AAA GCT GAC AAA AGT AAA GTA AAA TTA ACA ATT
GAA CTT CCG CAT TTT CGA CTG TTT TCA TTT CAT TTT AAT TGT TAA

                280                 290                 300                 310
TCT GAC GAT CTA GGT CAA ACC ACA CTT GAA GTT TTC AAA GAA GAT
AGA CTG CTA GAT CCA GTT TGG TGT GAA CTT CAA AAG TTT CTT CTA

      320                 330                 340                 350                 360
GGC AAA ACA CTA GTA TCA AAA AAA GTA ACT TCC AAA GAC AAG TCA
CCG TTT TGT GAT CAT AGT TTT TTT CAT TGA AGG TTT CTG TTC AGT

                370                 380                 390                 400
TCA ACA GAA GAA AAA TTC AAT GAA AAA GGT GAA GTA TCT GAA AAA
AGT TGT CTT CTT TTT AAG TTA CTT TTT CCA CTT CAT AGA CTT TTT

      410                 420                 430                 440                 450
ATA ATA ACA AGA GCA AAT GGA ACC AAA CTT GAA TAT ACA GAA ATG
TAT TAT TGT TCT CGT TTA CCT TGG TTT GAA CTT ATA TGT CTT TAC

                460                 470                 480                 490
AAA AGC GAT GGA ACC GGA AAA GCT AAA GAA GTT TTA AAA AAG TTT
TTT TCG CTA CCT TGG CCT TTT CGA TTT CTT CAA AAT TTT TTC AAA

      500                 510                 520                 530                 540
ACT CTT GAA GGA AAA GTA GCT AAT GAT AAA GTA ACA TTG GAA GTA
TGA GAA CTT CCT TTT CAT CGA TTA CTA TTT CAT TGT AAC CTT CAT

                550                 560                 570                 580
AAA GAA GGA ACC GTT ACT TTA AGT AAG GAA ATT TCA AAA TCT GGG
```

FIG. 45A

```
TTT CTT CCT TGG CAA TGA AAT TCA .TC CTT TAA AGT TTT AGA CCC

    590             600             610             620             630
     *       *       *       *       *       *       *       *       *
GAA GTT TCA GTT GAA CTT AAT GAC ACT GAC AGT AGT GCT GCT ACT
CTT CAA AGT CAA CTT GAA TTA CTG TGA CTG TCA TCA CGA CGA TGA

            640             650             660             670
     *       *       *       *       *       *       *       *       *
AAA AAA ACT GCA GCT TGG AAT TCA AAA ACT TCC ACT TTA ACA ATT
TTT TTT TGA CGT CGA ACC TTA AGT TTT TGA AGG TGA AAT TGT TAA

    680             690             700             710             720
     *       *       *       *       *       *       *       *       *
AGT GTG AAT AGC CAA AAA ACC AAA AAC CTT GTA TTC ACA AAA GAA
TCA CAC TTA TCG GTT TTT TGG TTT TTG GAA CAT AAG TGT TTT CTT

            730             740             750             760
     *       *       *       *       *       *       *       *       *
GAC ACA ATA ACA GTA CAA AAA TAC GAC TCA GCA GGC ACC AAT CTA
CTG TGT TAT TGT CAT GTT TTT ATG CTG AGT CGT CCG TGG TTA GAT

    770             780             790             800             810
     *       *       *       *       *       *       *       *       *
GAA GGC AAA GCA GTC GAA ATT ACA ACA CTT AAA GAA CTT AAA AAC
CTT CCG TTT CGT CAG CTT TAA TGT TGT GAA TTT CTT GAA TTT TTG

            820
     *       *
GCT TTA AAA TAA
CGA AAT TTT ATT
```

FIG. 45B

```
         10          20          30          40
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT

 50          60          70          80          90
GCA TGC AAG CAA AAT GTT AGC AGC CTT GAT GAA AAA AAC AGC GCT
CGT ACG TTC GTT TTA CAA TCG TCG GAA CTA CTT TTT TTG TCG CGA

        100         110         120         130
TCA GTA GAT TTG CCT GGT GAG ATG AAA GTT CTT GTA AGT AAA GAA
AGT CAT CTA AAC GGA CCA CTC TAC TTT CAA GAA CAT TCA TTT CTT

140         150         160         170         180
AAA GAC AAA GAC GGT AAG TAC AGT CTA AAG GCA ACA GTA GAC AAG
TTT CTG TTT CTG CCA TTC ATG TCA GAT TTC CGT TGT CAT CTG TTC

        190         200         210         220
ATT GAG CTA AAA GGA ACT TCT GAT AAA GAC AAT GGT TCT GGA GTG
TAA CTC GAT TTT CCT TGA AGA CTA TTT CTG TTA CCA AGA CCT CAC

230         240         250         260         270
CTT GAA GGT ACA AAA GAT GAC AAA AGT AAA GCA AAA TTA ACA ATT
GAA CTT CCA TGT TTT CTA CTG TTT TCA TTT CGT TTT AAT TGT TAA

        280         290         300         310
GCT GAC GAT CTA AGT AAA ACC ACA TTC GAA CTT TTA AAA GAA GAT
CGA CTG CTA GAT TCA TTT TGG TGT AAG CTT GAA AAT TTT CTT CTA

320         330         340         350         360
GGC AAA ACA TTA GTG TCA AGA AAA GTA AGT TCT AGA GAC AAA ACA
CCG TTT TGT AAT CAC AGT TCT TTT CAT TCA AGA TCT CTG TTT TGT

        370         380         390         400
TCA ACA GAT GAA ATG TTC AAT GAA AAA GGT GAA TTG TCT GCA AAA
AGT TGT CTA CTT TAC AAG TTA CTT TTT CCA CTT AAC AGA CGT TTT

410         420         430         440         450
ACC ATG ACA AGA GAA AAT GGA ACC AAA CTT GAA TAT ACA GAA ATG
TGG TAC TGT TCT CTT TTA CCT TGG TTT GAA CTT ATA TGT CTT TAC

        460         470         480         490
AAA AGC GAT GGA ACC GGA AAA GCT AAA GAA GTT TTA AAA AAG TTT
TTT TCG CTA CCT TGG CCT TTT CGA TTT CTT CAA AAT TTT TTC AAA

500         510         520         530         540
ACT CTT GAA GGA AAA GTA GCT AAT GAT AAA GTA ACA TTG GAA GTA
TGA GAA CTT CCT TTT CAT CGA TTA CTA TTT CAT TGT AAC CTT CAT

        550         560         570         580
AAA GAA GGA ACC GTT ACT TTA AGT AAG GAA ATT TCA AAA TCT GGG
```

FIG. 46A

```
TTT CTT CCT TGG CAA TGA AAT TCA TTC CTT TAA AGT TTT AGA CCC

   590         600         610         620         630
    *     *     *     *     *     *     *     *     *
GAA GTT TCA GTT GAA CTT AAT GAC ACT GAC AGT AGT GCT GCT ACT
CTT CAA AGT CAA CTT GAA TTA CTG TGA CTG TCA TCA CGA CGA TGA

         640         650         660         670
    *     *     *     *     *     *     *     *     *
AAA AAA ACT GCA GCT TGG AAT TCA AAA ACT TCC ACT TTA ACA ATT
TTT TTT TGA CGT CGA ACC TTA AGT TTT TGA AGG TGA AAT TGT TAA

   680         690         700         710         720
    *     *     *     *     *     *     *     *     *
AGT GTG AAT AGC CAA AAA ACC AAA AAC CTT GTA TTC ACA AAA GAA
TCA CAC TTA TCG GTT TTT TGG TTT TTG GAA CAT AAG TGT TTT CTT

         730         740         750         760
    *     *     *     *     *     *     *     *     *
GAC ACA ATA ACA GTA CAA AAA TAC GAC TCA GCA GGC ACC AAT CTA
CTG TGT TAT TGT CAT GTT TTT ATG CTG AGT CGT CCG TGG TTA GAT

   770         780         790         800         810
    *     *     *     *     *     *     *     *     *
GAA GGC AAA GCA GTC GAA ATT ACA ACA CTT AAA GAA CTT AAA AAC
CTT CCG TTT CGT CAG CTT TAA TGT TGT GAA TTT CTT GAA TTT TTG

         820
    *     *
GCT TTA AAA TAA
CGA AAT TTT ATT
```

FIG. 46B

```
                10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

 50             60                  70                  80                  90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
 A   D   E   S   V   K   G   P   N   L   T   E   I   N   K   K>

  100               110                 120                 130               140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

    150               160                 170                 180               190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

        200                 210                 220                 230             240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
 I   H   Q   N   N   G   L   D   T   E   N   N   H   N   G   S>

            250                 260                 270                 280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290             300                 310                 320                 330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

 340                350                 360                 370                 380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

    390                 400                 410                 420                 430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

        440                 450                 460                 470             480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
 K   A   N   G   T   K   T   K   G   A   E   E   L   G   K   L>

            490                 500                 510                 520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

FIG. 55A 530 540 550 560 570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
N S V K E L T S P V V A E S P K>

580 590 600 610 620
AAA CCT TCC ATG GCC AAG CAA AAT GTT AGC AGC CTT GAC GAG AAA AAC
TTT GGA AGG TAC CGG TTC GTT TTA CAA TCG TCG GAA CTG CTC TTT TTG
K P S M A K Q N V S S L D E K N>

630 640 650 660 670
AGC GTT TCA GTA GAT TTG CCT GGT GAA ATG AAA GTT CTT GTA AGC AAA
TCG CAA AGT CAT CTA AAC GGA CCA CTT TAC TTT CAA GAA CAT TCG TTT
S V S V D L P G E M K V L V S K>

680 690 700 710 720
GAA AAA AAC AAA GAC GGC AAG TAC GAT CTA ATT GCA ACA GTA GAC AAG
CTT TTT TTG TTT CTG CCG TTC ATG CTA GAT TAA CGT TGT CAT CTG TTC
E K N K D G K Y D L I A T V D K>

730 740 750 760
CTT GAG CTT AAA GGA ACT TCT GAT AAA AAC AAT GGA TCT GGA GTA CTT
GAA CTC GAA TTT CCT TGA AGA CTA TTT TTG TTA CCT AGA CCT CAT GAA
L E L K G T S D K N N G S G V L>

770 780 790 800 810
GAA GGC GTA AAA GCT GAC AAA AGT AAA GTA AAA TTA ACA ATT TCT GAC
CTT CCG CAT TTT CGA CTG TTT TCA TTT CAT TTT AAT TGT TAA AGA CTG
E G V K A D K S K V K L T I S D>

820 830 840 850 860
GAT CTA GGT CAA ACC ACA CTT GAA GTT TTC AAA GAA GAT GGC AAA ACA
CTA GAT CCA GTT TGG TGT GAA CTT CAA AAG TTT CTT CTA CCG TTT TGT
D L G Q T T L E V F K E D G K T>

870 880 890 900 910
CTA GTA TCA AAA AAA GTA ACT TCC AAA GAC AAG TCA TCA ACA GAA GAA
GAT CAT AGT TTT TTT CAT TGA AGG TTT CTG TTC AGT AGT TGT CTT CTT
L V S K K V T S K D K S S T E E>

920 930 940 950 960
AAA TTC AAT GAA AAA GGT GAA GTA TCT GAA AAA ATA ATA ACA AGA GCA
TTT AAG TTA CTT TTT CCA CTT CAT AGA CTT TTT TAT TAT TGT TCT CGT
K F N E K G E V S E K I I T R A>

970 980 990 1000
GAC GGA ACC AGA CTT GAA TAC ACA GGA ATT AAA AGC GAT GGA TCT GGA
CTG CCT TGG TCT GAA CTT ATG TGT CCT TAA TTT TCG CTA CCT AGA CCT
D G T R L E Y T G I K S D G S G>

1010 1020 1030 1040 1050
AAA GCT AAA GAG GTT TTA AAA GGC TAT GTT CTT GAA GGA ACT CTA ACT
TTT CGA TTT CTC CAA AAT TTT CCG ATA CAA GAA CTT CCT TGA GAT TGA
K A K E V L K G Y V L E G T L T>

1060 1070 1080 1090 1100
GCT GAA AAA ACA ACA TTG GTG GTT AAA GAA GGA ACT GTT ACT TTA AGC

FIG. 55B

```
CGA CTT TTT TGT TGT AAC CAC CAA TTT CTT CCT TGA CAA TGA AAT TCG
A   E   K   T   T   L   V   V   K   E   G   T   V   T   L   S>

 1110            1120           1130          1140          1150
AAA AAT ATT TCA AAA TCT GGG GAA GTT TCA GTT GAA CTT AAT GAC ACT
TTT TTA TAA AGT TTT AGA CCC CTT CAA AGT CAA CTT GAA TTA CTG TGA
K   N   I   S   K   S   G   E   V   S   V   E   L   N   D   T>

    1160          1170           1180          1190          1200
GAC AGT AGT GCT GCT ACT AAA AAA ACT GCA GCT TGG AAT TCA GGC ACT
CTG TCA TCA CGA CGA TGA TTT TTT TGA CGT CGA ACC TTA AGT CCG TGA
D   S   S   A   A   T   K   K   T   A   A   W   N   S   G   T>

        1210          1220          1230          1240
TCA ACT TTA ACA ATT ACT GTA AAC AGT AAA AAA ACT AAA GAC CTT GTG
AGT TGA AAT TGT TAA TGA CAT TTG TCA TTT TTT TGA TTT CTG GAA CAC
S   T   L   T   I   T   V   N   S   K   K   T   K   D   L   V>

1250        1260          1270          1280          1290
TTT ACA AAA GAA AAC ACA ATT ACA GTA CAA CAA TAC GAC TCA AAT GGC
AAA TGT TTT CTT TTG TGT TAA TGT CAT GTT GTT ATG CTG AGT TTA CCG
F   T   K   E   N   T   I   T   V   Q   Q   Y   D   S   N   G>

1300          1310          1320          1330          1340
ACC AAA TTA GAG GGG TCA GCA GTT GAA ATT ACA AAA CTT GAT GAA ATT
TGG TTT AAT CTC CCC AGT CGT CAA CTT TAA TGT TTT GAA CTA CTT TAA
T   K   L   E   G   S   A   V   E   I   T   K   L   D   E   I>

  1350          1360
AAA AAC GCT TTA AAA TAA
TTT TTG CGA AAT TTT ATT
K   N   A   L   K   *>
```

FIG. 55C

```
                 10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50                  60                  70                  80                  90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
 A   D   E   S   V   K   G   P   N   L   T   E   I   N   K   K>

   100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

      150                 160                 170                 180                 190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

         200                 210                 220                 230                 240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
 I   H   Q   N   N   G   L   D   T   E   N   N   H   N   G   S>

            250                 260                 270                 280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290                 300                 310                 320                 330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

   340                 350                 360                 370                 380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

      390                 400                 410                 420                 430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

         440                 450                 460                 470                 480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
 K   A   N   G   T   K   T   K   G   A   E   E   L   G   K   L>

            490                 500                 510                 520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

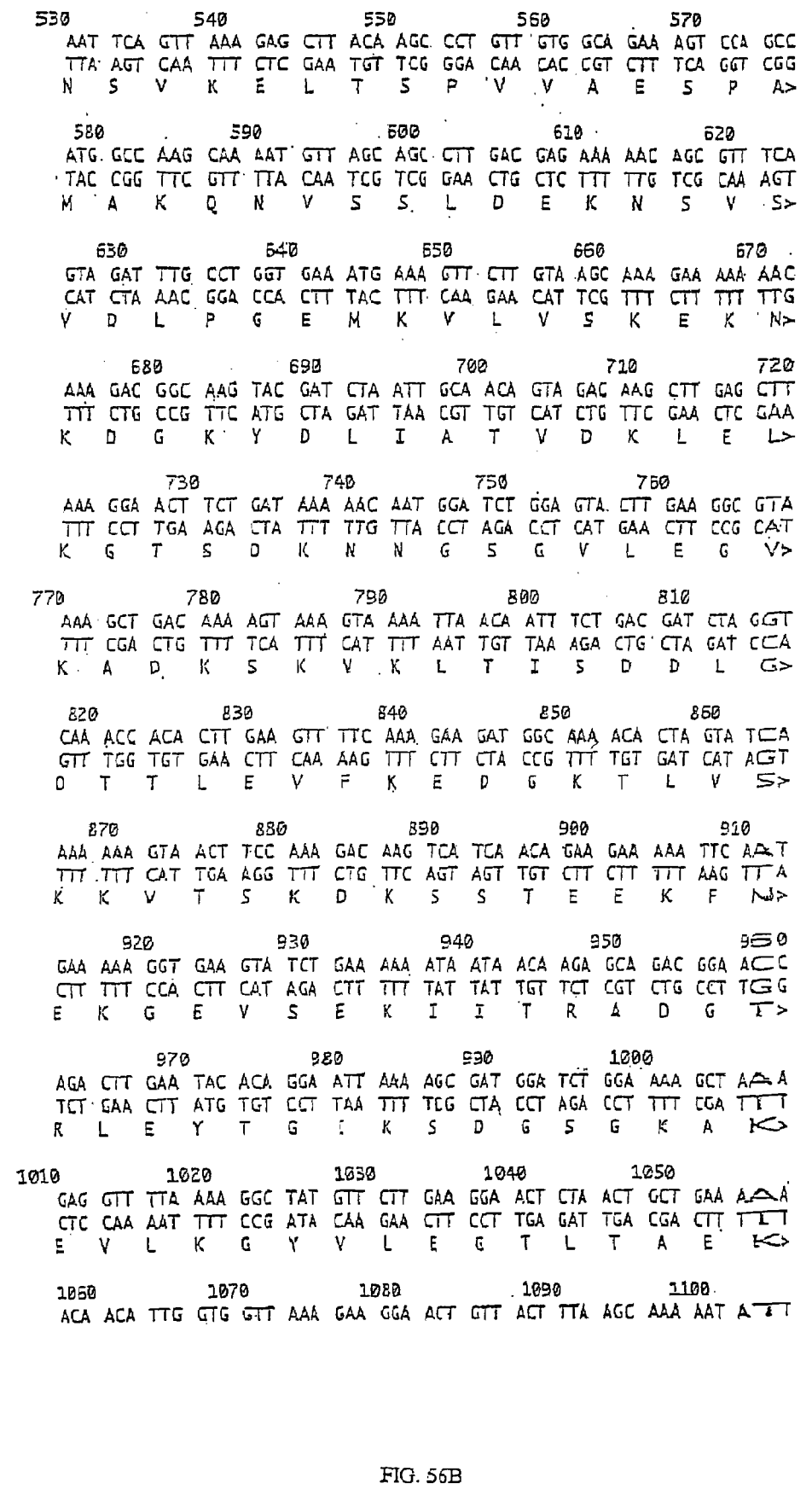

FIG. 56A 530 540 550 560 570
AAT TCA GTT AAA GAG CTT ACA AGC CCT GTT GTG GCA GAA AGT CCA GCC
TTA AGT CAA TTT CTC GAA TGT TCG GGA CAA CAC CGT CTT TCA GGT CGG
N S V K E L T S P V V A E S P A>

580 590 600 610 620
ATG GCC AAG CAA AAT GTT AGC AGC CTT GAC GAG AAA AAC AGC GTT TCA
TAC CGG TTC GTT TTA CAA TCG TCG GAA CTG CTC TTT TTG TCG CAA AGT
M A K Q N V S S L D E K N S V S>

630 640 650 660 670
GTA GAT TTG CCT GGT GAA ATG AAA GTT CTT GTA AGC AAA GAA AAA AAC
CAT CTA AAC GGA CCA CTT TAC TTT CAA GAA CAT TCG TTT CTT TTT TTG
V D L P G E M K V L V S K E K N>

680 690 700 710 720
AAA GAC GGC AAG TAC GAT CTA ATT GCA ACA GTA GAC AAG CTT GAG CTT
TTT CTG CCG TTC ATG CTA GAT TAA CGT TGT CAT CTG TTC GAA CTC GAA
K D G K Y D L I A T V D K L E L>

730 740 750 760
AAA GGA ACT TCT GAT AAA AAC AAT GGA TCT GGA GTA CTT GAA GGC GTA
TTT CCT TGA AGA CTA TTT TTG TTA CCT AGA CCT CAT GAA CTT CCG CAT
K G T S D K N N G S G V L E G V>

770 780 790 800 810
AAA GCT GAC AAA AGT AAA GTA AAA TTA ACA ATT TCT GAC GAT CTA GGT
TTT CGA CTG TTT TCA TTT CAT TTT AAT TGT TAA AGA CTG CTA GAT CCA
K A D K S K V K L T I S D D L G>

820 830 840 850 860
CAA ACC ACA CTT GAA GTT TTC AAA GAA GAT GGC AAA ACA CTA GTA TCA
GTT TGG TGT GAA CTT CAA AAG TTT CTT CTA CCG TTT TGT GAT CAT AGT
Q T T L E V F K E D G K T L V S>

870 880 890 900 910
AAA AAA GTA ACT TCC AAA GAC AAG TCA TCA ACA GAA GAA AAA TTC AAT
TTT TTT CAT TGA AGG TTT CTG TTC AGT AGT TGT CTT CTT TTT AAG TTA
K K V T S K D K S S T E E K F N>

920 930 940 950 960
GAA AAA GGT GAA GTA TCT GAA AAA ATA ATA ACA AGA GCA GAC GGA ACC
CTT TTT CCA CTT CAT AGA CTT TTT TAT TAT TGT TCT CGT CTG CCT TGG
E K G E V S E K I I T R A D G T>

970 980 990 1000
AGA CTT GAA TAC ACA GGA ATT AAA AGC GAT GGA TCT GGA AAA GCT AAA
TCT GAA CTT ATG TGT CCT TAA TTT TCG CTA CCT AGA CCT TTT CGA TTT
R L E Y T G I K S D G S G K A K>

1010 1020 1030 1040 1050
GAG GTT TTA AAA GGC TAT GTT CTT GAA GGA ACT CTA ACT GCT GAA AAA
CTC CAA AAT TTT CCG ATA CAA GAA CTT CCT TGA GAT TGA CGA CTT TTT
E V L K G Y V L E G T L T A E K>

1060 1070 1080 1090 1100
ACA ACA TTG GTG GTT AAA GAA GGA ACT GTT ACT TTA AGC AAA AAT ATT

FIG. 56B

```
TGT TGT AAC CAC CAA TTT CTT CCT TGA CAA TGA AAT TCG TTT TTA TAA
 T   T   L   V   V   K   E   G   T   V   T   L   S   K   N   I>

  1110          1120          1130          1140          1150
TCA AAA TCT GGG GAA GTT TCA GTT GAA CTT AAT GAC ACT GAC AGT AGT
AGT TTT AGA CCC CTT CAA AGT CAA CTT GAA TTA CTG TGA CTG TCA TCA
 S   K   S   G   E   V   S   V   E   L   N   D   T   D   S   S>

      1160          1170          1180          1190          1200
GCT GCT ACT AAA AAA ACT GCA GCT TGG AAT TCA GGC ACT TCA ACT TTA
CGA CGA TGA TTT TTT TGA CGT CGA ACC TTA AGT CCG TGA AGT TGA AAT
 A   A   T   K   K   T   A   A   W   N   S   G   T   S   T   L>

          1210          1220          1230          1240
ACA ATT ACT GTA AAC AGT AAA AAA ACT AAA GAC CTT GTG TTT ACA AAA
TGT TAA TGA CAT TTG TCA TTT TTT TGA TTT CTG GAA CAC AAA TGT TTT
 T   I   T   V   N   S   K   K   T   K   D   L   V   F   T   K>

1250          1260          1270          1280          1290
GAA AAC ACA ATT ACA GTA CAA CAA TAC GAC TCA AAT GGC ACC AAA TTA
CTT TTG TGT TAA TGT CAT GTT GTT ATG CTG AGT TTA CCG TGG TTT AAT
 E   N   T   I   T   Y   Q   Q   Y   D   S   N   G   T   K   L>

1300          1310          1320          1330          1340
GAG GGG TCA GCA GTT GAA ATT ACA AAA CTT GAT GAA ATT AAA AAC GCT
CTC CCC AGT CGT CAA CTT TAA TGT TTT GAA CTA CTT TAA TTT TTG CGA
 E   G   S   A   V   E   I   T   K   L   D   E   I   K   N   A>

  1350
TTA AAA TAA
AAT TTT ATT
 L   K   *>
```

FIG. 56C

```
            10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50                  60                  70                  80                  90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
A   D   E   S   V   K   G   P   N   L   T   E   I   S   K   K>

  100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

    150                 160                 170                 180                 190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
L   L   S   S   I   D   E   L   A   K   A   I   G   K   K   I>

        200                 210                 220                 230                 240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
K   N   D   G   S   L   D   N   E   A   N   R   N   E   S   L>

            250                 260                 270                 280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
L   A   G   A   Y   T   I   S   T   L   I   T   Q   K   L   S>

290                 300                 310                 320                 330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
K   L   N   G   S   E   G   L   K   E   K   I   A   A   A   K>

 340                 350                 360                 370                 380
AAA TGC TCT GAA GAG TTT AGT ACT AAA CTA AAA GAT AAT CAT GCA CAG
TTT ACG AGA CTT CTC AAA TCA TGA TTT GAT TTT CTA TTA GTA CGT GTC
K   C   S   E   E   F   S   T   K   L   K   D   N   H   A   Q>

   390                 400                 410                 420                 430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
L   G   I   Q   G   V   T   D   E   N   A   K   K   A   I   L>

        440                 450                 460                 470                 480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
K   A   N   A   A   G   K   D   K   G   V   E   E   L   E   K>

            490                 500                 510                 520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
L   S   G   S   L   E   S   L   S   K   A   A   K   E   M   L>
```

FIG. 57A

```
530            540            550            560            570
GCT AAT TCA GTT AAA GAG CTT ACA AGC CCT GTT GTC CAT GGC AAG CAA
CGA TTA AGT CAA TTT CTC GAA TGT TCG GGA CAA CAG GTA CCG TTC GTT
 A   N   S   V   K   E   L   T   S   P   V   V   H   G   K   Q>

 580            590            600            610            620
AAT GTT AGC AGC CTT GAC GAG AAA AAC AGC GTT TCA GTA GAT TTG CCT
TTA CAA TCG TCG GAA CTG CTC TTT TTG TCG CAA AGT CAT CTA AAC GGA
 N   V   S   S   L   D   E   K   N   S   V   S   V   D   L   P>

    630            640            650            660            670
GGT GAA ATG AAA GTT CTT GTA AGC AAA GAA AAA AAC AAA GAC GGC AAG
CCA CTT TAC TTT CAA GAA CAT TCG TTT CTT TTT TTG TTT CTG CCG TTC
 G   E   M   K   V   L   V   S   K   E   K   N   K   D   G   K>

        680            690            700            710            720
TAC GAT CTA ATT GCA ACA GTA GAC AAG CTT GAG CTT AAA GGA ACT TCT
ATG CTA GAT TAA CGT TGT CAT CTG TTC GAA CTC GAA TTT CCT TGA AGA
 Y   D   L   I   A   T   V   D   K   L   E   L   K   G   T   S>

            730            740            750            760
GAT AAA AAC AAT GGA TCT GGA GTA CTT GAA GGC GTA AAA GCT GAC AAA
CTA TTT TTG TTA CCT AGA CCT CAT GAA CTT CCG CAT TTT CGA CTG TTT
 D   K   N   N   G   S   G   V   L   E   G   V   K   A   D   K>

770            780            790            800            810
AGT AAA GTA AAA TTA ACA ATT TCT GAC GAT CTA GGT CAA ACC ACA CTT
TCA TTT CAT TTT AAT TGT TAA AGA CTG CTA GAT CCA GTT TGG TGT GAA
 S   K   V   K   L   T   I   S   D   D   L   G   Q   T   T   L>

 820            830            840            850            860
GAA GTT TTC AAA GAA GAT GGC AAA ACA CTA GTA TCA AAA AAA GTA ACT
CTT CAA AAG TTT CTT CTA CCG TTT TGT GAT CAT AGT TTT TTT CAT TGA
 E   V   F   K   E   D   G   K   T   L   V   S   K   K   V   T>

    870            880            890            900            910
TCC AAA GAC AAG TCA TCA ACA GAA GAA AAA TTC AAT GAA AAA GGT GAA
AGG TTT CTG TTC AGT AGT TGT CTT CTT TTT AAG TTA CTT TTT CCA CTT
 S   K   D   K   S   S   T   E   E   K   F   N   E   K   G   E>

        920            930            940            950            960
GTA TCT GAA AAA ATA ATA ACA AGA GCA GAC GGA ACC AGA CTT GAA TAC
CAT AGA CTT TTT TAT TAT TGT TCT CGT CTG CCT TGG TCT GAA CTT ATG
 V   S   E   K   I   I   T   R   A   D   G   T   R   L   E   Y>

            970            980            990            1000
ACA GGA ATT AAA AGC GAT GGA TCT GGA AAA GCT AAA GAG GTT TTA AAA
TGT CCT TAA TTT TCG CTA CCT AGA CCT TTT CGA TTT CTC CAA AAT TTT
 T   G   I   K   S   D   G   S   G   K   A   K   E   V   L   K>

1010           1020           1030           1040           1050
GGC TAT GTT CTT GAA GGA ACT CTA ACT GCT GAA AAA ACA ACA TTG GTG
CCG ATA CAA GAA CTT CCT TGA GAT TGA CGA CTT TTT TGT TGT AAC CAC
 G   Y   V   L   E   G   T   L   T   A   E   K   T   T   L   V>

1060           1070           1080           1090           1100
GTT AAA GAA GGA ACT GTT ACT TTA AGC AAA AAT ATT TCA AAA TCT GGG
```

FIG.57B

```
CAA TTT CTT CCT TGA CAA TGA AAT TCG TTT TTA TAA AGT TTT AGA CCC
V   K   E   G   T   V   T   L   S   K   N   I   S   K   S   G>

    1110            1120            1130            1140            1150
GAA GTT TCA GTT GAA CTT AAT GAC ACT GAC AGT AGT GCT GCT ACT AAA
CTT CAA AGT CAA CTT GAA TTA CTG TGA CTG TCA TCA CGA CGA TGA TTT
E   V   S   V   E   L   N   D   T   D   S   S   A   A   T   K>

        1160            1170            1180            1190            1200
AAA ACT GCA GCT TGG AAT TCA GGC ACT TCA ACT TTA ACA ATT ACT GTA
TTT TGA CGT CGA ACC TTA AGT CCG TGA AGT TGA AAT TGT TAA TGA CAT
K   T   A   A   W   N   S   G   T   S   T   L   T   I   T   V>

            1210            1220            1230            1240
AAC AGT AAA AAA ACT AAA GAC CTT GTG TTT ACA AAA GAA AAC ACA ATT
TTG TCA TTT TTT TGA TTT CTG GAA CAC AAA TGT TTT CTT TTG TGT TAA
N   S   K   K   T   K   D   L   V   F   T   K   E   N   T   I>

1250            1260            1270            1280            1290
ACA GTA CAA CAA TAC GAC TCA AAT GGC ACC AAA TTA GAG GGG TCA GCA
TGT CAT GTT GTT ATG CTG AGT TTA CCG TGG TTT AAT CTC CCC AGT CGT
T   V   Q   Q   Y   D   S   N   G   T   K   L   E   G   S   A>

1300            1310            1320            1330            1340
GTT GAA ATT ACA AAA CTT GAT GAA ATT AAA AAC GCT TTA AAA TAA
CAA CTT TAA TGT TTT GAA CTA CTT TAA TTT TTG CGA AAT TTT ATT
V   E   I   T   K   L   D   E   I   K   N   A   L   K   *>
```

FIG. 57C

```
            10              20              30              40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50            60              70              80              90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
A   D   E   S   V   K   G   P   N   L   T   E   I   N   K   K>

  100             110             120             130             140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

    150             160             170             180             190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
L   L   S   S   I   D   E   I   A   A   K   A   I   G   K   K>

        200             210             220             230             240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
I   H   Q   N   N   G   L   D   T   E   N   N   H   N   G   S>

          250             260             270             280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
L   L   A   G   A   Y   A   I   S   T   L   I   K   Q   K   L>

290           300             310             320             330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
D   G   L   K   N   E   G   L   K   E   K   I   D   A   A   K>

 340             350             360             370             380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
K   C   S   E   T   F   T   N   K   L   K   E   K   H   T   D>

   390             400             410             420             430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
L   G   K   E   G   V   T   D   A   D   A   K   E   A   I   L>

      440             450             460             470             480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
K   A   N   G   T   K   T   K   G   A   E   E   L   G   K   L>

          490             500             510             520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
F   E   S   V   E   V   L   S   K   A   A   K   E   M   L   A>
```

FIG. 58A

```
530          540          550          560          570
 AAT TCA GTT AAA GAG CTT ACA AGC CCT GTT GTG GCA GAA AGT CCA AAA
 TTA AGT CAA TTT CTC GAA TGT TCG GGA CAA CAC CGT CTT TCA GGT TTT
 N   S   V   K   E   L   T   S   P   V   V   A   E   S   P   K>

 580          590          600          610          620
 AAA CCT TCC ATG GCC AAG CAA AAT GTT AGC AGC CTT GAC GAG AAA AAC
 TTT GGA AGG TAC CGG TTC GTT TTA CAA TCG TCG GAA CTG CTC TTT TTG
 K   P   S   M   A   K   Q   N   V   S   S   L   D   E   K   N>

 630          640          650          660          670
 AGC GTT TCA GTA GAT TTG CCT GGT GAA ATG AAA GTT CTT GTA AGC AAA
 TCG CAA AGT CAT CTA AAC GGA CCA CTT TAC TTT CAA GAA CAT TCG TTT
 S   V   S   V   D   L   P   G   E   M   K   V   L   V   S   K>

 680          690          700          710          720
 GAA AAA AAC AAA GAC GGC AAG TAC GAT CTA ATT GCA ACA GTA GAC AAG
 CTT TTT TTG TTT CTG CCG TTC ATG CTA GAT TAA CGT TGT CAT CTG TTC
 E   K   N   K   D   G   K   Y   D   L   I   A   T   V   D   K>

 730          740          750          760
 CTT GAG CTT AAA GGA ACT TCT GAT AAA AAC AAT GGA TCT GGA GTA CTT
 GAA CTC GAA TTT CCT TGA AGA CTA TTT TTG TTA CCT AGA CCT CAT GAA
 L   E   L   K   G   T   S   D   K   N   N   G   S   G   V   L>

770          780          790          800          810
 GAA GGC GTA AAA GCT GAC AAA AGT AAA GTA AAA TTA ACA ATT TCT GAC
 CTT CCG CAT TTT CGA CTG TTT TCA TTT CAT TTT AAT TGT TAA AGA CTG
 E   G   V   K   A   D   K   S   K   V   K   L   T   I   S   D>

 820          830          840          850          860
 GAT CTA GGT CAA ACC ACA CTT GAA GTT TTC AAA GAA GAT GGC AAA ACA
 CTA GAT CCA GTT TGG TGT GAA CTT CAA AAG TTT CTT CTA CCG TTT TGT
 D   L   G   Q   T   T   L   E   V   F   K   E   D   G   K   T>

 870          880          890          900          910
 CTA GTA TCA AAA AAA GTA ACT TCC AAA GAC AAG TCA TCA ACA GAA GAA
 GAT CAT AGT TTT TTT CAT TGA AGG TTT CTG TTC AGT AGT TGT CTT CTT
 L   V   S   K   K   V   T   S   K   D   K   S   S   T   E   E>

 920          930          940          950          960
 AAA TTC AAT GAA AAA GGT GAA GTA TCT GAA AAA ATA ATA ACA AGA GCA
 TTT AAG TTA CTT TTT CCA CTT CAT AGA CTT TTT TAT TAT TGT TCT CGT
 K   F   N   E   K   G   E   V   S   E   K   I   I   T   R   A>

 970          980          990          1000
 GAC GGA ACC AGA CTT GAA TAC ACA GGA ATT AAA AGC GAT GGA TCT GGA
 CTG CCT TGG TCT GAA CTT ATG TGT CCT TAA TTT TCG CTA CCT AGA CCT
 D   G   T   R   L   E   Y   T   G   I   K   S   D   G   S   G>

1010         1020         1030         1040         1050
 AAA GCT AAA GAG GTT TTA AAA GGC TAT GTT CTT GAA GGA ACT CTA ACT
 TTT CGA TTT CTC CAA AAT TTT CCG ATA CAA GAA CTT CCT TGA GAT TGA
 K   A   K   E   V   L   K   G   Y   V   L   E   G   T   L   T>

 1060         1070         1080         1090         1100
 GCT GAA AAA ACA ACA TTG GTG GTT AAA GAA GGA ACT GTT ACT TTA AGC
```

FIG. 58B

```
CGA CTT TTT TGT TGT AAC CAC CAA TTT CTT CCT TGA CAA TGA AAT TCG
A   E   K   T   T   L   V   V   K   E   G   T   V   T   L   S>

 1110            1120           1130           1140            1150
AAA AAT ATT TCA AAA TCT GGG GAA GTT TCA GTT GAA CTT AAT GAC ACT
TTT TTA TAA AGT TTT AGA CCC CTT CAA AGT CAA CTT GAA TTA CTG TGA
K   N   I   S   K   S   G   E   V   S   V   E   L   N   D   T>

    1160           1170           1180           1190           1200
GAC AGT AGT GCT GCT ACT AAA AAA ACT GCA GCT TGG AAT TCA AAA ACT
CTG TCA TCA CGA CGA TGA TTT TTT TGA CGT CGA ACC TTA AGT TTT TGA
D   S   S   A   A   T   K   K   T   A   A   W   N   S   K   T>

        1210           1220           1230           1240
TCC ACT TTA ACA ATT AGT GTG AAT AGC CAA AAA ACC AAA AAC CTT GTA
AGG TGA AAT TGT TAA TCA CAC TTA TCG GTT TTT TGG TTT TTG GAA CAT
S   T   L   T   I   S   V   N   S   Q   K   T   K   N   L   V>

1250        1260           1270           1280           1290
TTC ACA AAA GAA GAC ACA ATA ACA GTA CAA AAA TAC GAC TCA GCA GGC
AAG TGT TTT CTT CTG TGT TAT TGT CAT GTT TTT ATG CTG AGT CGT CCG
F   T   K   E   D   T   I   T   V   Q   K   Y   D   S   A   G>

1300           1310           1320           1330           1340
ACC AAT CTA GAA GGC AAA GCA GTC GAA ATT ACA ACA CTT AAA GAA CTT
TGG TTA GAT CTT CCG TTT CGT CAG CTT TAA TGT TGT GAA TTT CTT GAA
T   N   L   E   G   K   A   V   E   I   T   T   L   K   E   L>

   1350          1360
AAA AAC GCT TTA AAA TAA
TTT TTG CGA AAT TTT ATT
K   N   A   L   K   *>
```

FIG. 58C

```
                10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50                  60                  70                  80                  90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
A   D   E   S   V   K   G   P   N   L   T   E   I   S   K   K>

  100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

    150                 160                 170                 180                 190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
L   L   S   S   I   D   E   L   A   K   A   I   G   K   K   I>

        200                 210                 220                 230                 240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
K   N   D   G   S   L   D   N   E   A   N   R   N   E   S   L>

            250                 260                 270                 280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
L   A   G   A   Y   T   I   S   T   L   I   T   Q   K   L   S>

290                 300                 310                 320                 330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
K   L   N   G   S   E   G   L   K   E   K   I   A   A   A   K>

340                 350                 360                 370                 380
AAA TGC TCT GAA GAG TTT AGT ACT AAA CTA AAA GAT AAT CAT GCA CAG
TTT ACG AGA CTT CTC AAA TCA TGA TTT GAT TTT CTA TTA GTA CGT GTC
K   C   S   E   E   F   S   T   K   L   K   D   N   H   A   Q>

  390                 400                 410                 420                 430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
L   G   I   Q   G   V   T   D   E   N   A   K   K   A   I   L>

      440                 450                 460                 470                 480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
K   A   N   A   A   G   K   D   K   G   V   E   E   L   E   K>

          490                 500                 510                 520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
L   S   G   S   L   E   S   L   S   K   A   A   K   E   M   L>
```

FIG. 59A

```
530         540         550         560         570
GCT AAT TCA GTT AAA GAG CTT ACA AGC CCT GTT GTC CAT GGC AAG CAA
CGA TTA AGT CAA TTT CTC GAA TGT TCG GGA CAA CAG GTA CCG TTC GTT
 A   N   S   V   K   E   L   T   S   P   V   V   H   G   K   Q>

580         590         600         610         620
AAT GTT AGC AGC CTT GAC GAG AAA AAC AGC GTT TCA GTA GAT TTG CCT
TTA CAA TCG TCG GAA CTG CTC TTT TTG TCG CAA AGT CAT CTA AAC GGA
 N   V   S   S   L   D   E   K   N   S   V   S   V   D   L   P>

630         640         650         660         670
GGT GAA ATG AAA GTT CTT GTA AGC AAA GAA AAA AAC AAA GAC GGC AAG
CCA CTT TAC TTT CAA GAA CAT TCG TTT CTT TTT TTG TTT CTG CCG TTC
 G   E   M   K   V   L   V   S   K   E   K   N   K   D   G   K>

680         690         700         710         720
TAC GAT CTA ATT GCA ACA GTA GAC AAG CTT GAG CTT AAA GGA ACT TCT
ATG CTA GAT TAA CGT TGT CAT CTG TTC GAA CTC GAA TTT CCT TGA AGA
 Y   D   L   I   A   T   V   D   K   L   E   L   K   G   T   S>

730         740         750         760
GAT AAA AAC AAT GGA TCT GGA GTA CTT GAA GGC GTA AAA GCT GAC AAA
CTA TTT TTG TTA CCT AGA CCT CAT GAA CTT CCG CAT TTT CGA CTG TTT
 D   K   N   N   G   S   G   V   L   E   G   V   K   A   D   K>

770         780         790         800         810
AGT AAA GTA AAA TTA ACA ATT TCT GAC GAT CTA GGT CAA ACC ACA CTT
TCA TTT CAT TTT AAT TGT TAA AGA CTG CTA GAT CCA GTT TGG TGT GAA
 S   K   V   K   L   T   I   S   D   D   L   G   Q   T   T   L>

820         830         840         850         860
GAA GTT TTC AAA GAA GAT GGC AAA ACA CTA GTA TCA AAA AAA GTA ACT
CTT CAA AAG TTT CTT CTA CCG TTT TGT GAT CAT AGT TTT TTT CAT TGA
 E   V   F   K   E   D   G   K   T   L   V   S   K   K   V   T>

870         880         890         900         910
TCC AAA GAC AAG TCA TCA ACA GAA GAA AAA TTC AAT GAA AAA GGT GAA
AGG TTT CTG TTC AGT AGT TGT CTT CTT TTT AAG TTA CTT TTT CCA CTT
 S   K   D   K   S   S   T   E   E   K   F   N   E   K   G   E>

920         930         940         950         960
GTA TCT GAA AAA ATA ATA ACA AGA GCA GAC GGA ACC AGA CTT GAA TAC
CAT AGA CTT TTT TAT TAT TGT TCT CGT CTG CCT TGG TCT GAA CTT ATG
 V   S   E   K   I   I   T   R   A   D   G   T   R   L   E   Y>

970         980         990         1000
ACA GGA ATT AAA AGC GAT GGA TCT GGA AAA GCT AAA GAG GTT TTA AAA
TGT CCT TAA TTT TCG CTA CCT AGA CCT TTT CGA TTT CTC CAA AAT TTT
 T   G   I   K   S   D   G   S   G   K   A   K   E   V   L   K>

1010        1020        1030        1040        1050
GGC TAT GTT CTT GAA GGA ACT CTA ACT GCT GAA AAA ACA ACA TTG GTG
CCG ATA CAA GAA CTT CCT TGA GAT TGA CGA CTT TTT TGT TGT AAC CAC
 G   Y   V   L   E   G   T   L   T   A   E   K   T   T   L   V>

1060        1070        1080        1090        1100
GTT AAA GAA GGA ACT GTT ACT TTA AGC AAA AAT ATT TCA AAA TCT GGG
```

FIG. 59B

```
CAA TTT CTT CCT TGA CAA TGA AAT TCG TTT TTA TAA AGT TTT AGA CCC
 V   K   E   G   T   V   T   L   S   K   N   I   S   K   S   G>

     1110            1120            1130            1140            1150
GAA GTT TCA GTT GAA CTT AAT GAC ACT GAC AGT AGT GCT GCT ACT AAA
CTT CAA AGT CAA CTT GAA TTA CTG TGA CTG TCA TCA CGA CGA TGA TTT
 E   V   S   V   E   L   N   D   T   D   S   S   A   A   T   K>

         1160            1170            1180            1190            1200
AAA ACT GCA GCT TGG AAT TCA AAA ACT TCC ACT TTA ACA ATT AGT GTG
TTT TGA CGT CGA ACC TTA AGT TTT TGA AGG TGA AAT TGT TAA TCA CAC
 K   T   A   A   W   N   S   K   T   S   T   L   T   I   S   V>

             1210            1220            1230            1240
AAT AGC CAA AAA ACC AAA AAC CTT GTA TTC ACA AAA GAA GAC ACA ATA
TTA TCG GTT TTT TGG TTT TTG GAA CAT AAG TGT TTT CTT CTG TGT TAT
 N   S   Q   K   T   K   N   L   V   F   T   K   E   D   T   I>

1250             1260            1270            1280            1290
ACA GTA CAA AAA TAC GAC TCA GCA GGC ACC AAT CTA GAA GGC AAA GCA
TGT CAT GTT TTT ATG CTG AGT CGT CCG TGG TTA GAT CTT CCG TTT CGT
 T   V   Q   K   Y   D   S   A   G   T   N   L   E   G   K   A>

1300             1310            1320            1330            1340
GTC GAA ATT ACA ACA CTT AAA GAA CTT AAA AAC GCT TTA AAA TAA
CAG CTT TAA TGT TGT GAA TTT CTT GAA TTT TTG CGA AAT TTT ATT
 V   E   I   T   T   L   K   E   L   K   N   A   L   K   *>
```

FIG. 59C

```
         10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50                  60                  70                  80                  90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
 A   D   E   S   V   K   G   P   N   L   T   E   I   N   K   K>

 100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

    150                 160                 170                 180                 190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

        200                 210                 220                 230                 240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
 I   H   Q   N   N   G   L   D   T   E   N   N   H   N   G   S>

            250                 260                 270                 280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290                 300                 310                 320                 330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

 340                 350                 360                 370                 380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

   390                 400                 410                 420                 430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

       440                 450                 460                 470                 480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
 K   A   N   G   T   K   T   K   G   A   E   E   L   G   K   L>

           490                 500                 510                 520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

FIG. 60A

```
530         540         550         560         570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
N   S   V   K   E   L   T   S   P   V   V   A   E   S   P   K>

580         590         600         610         620
AAA CCT TCC ATG GCC AAG CAA AAT GTT AGC AGC CTT GAC GAG AAA AAC
TTT GGA AGG TAC CGG TTC GTT TTA CAA TCG TCG GAA CTG CTC TTT TTG
K   P   S   M   A   K   Q   N   V   S   S   L   D   E   K   N>

630         640         650         660         670
AGC GTT TCA GTA GAT TTG CCT GGT GAA ATG AAA GTT CTT GTA AGC AAA
TCG CAA AGT CAT CTA AAC GGA CCA CTT TAC TTT CAA GAA CAT TCG TTT
S   V   S   V   D   L   P   G   E   M   K   V   L   V   S   K>

680         690         700         710         720
GAA AAA AAC AAA GAC GGC AAG TAC GAT CTA ATT GCA ACA GTA GAC AAG
CTT TTT TTG TTT CTG CCG TTC ATG CTA GAT TAA CGT TGT CAT CTG TTC
E   K   N   K   D   G   K   Y   D   L   I   A   T   V   D   K>

730         740         750         760
CTT GAG CTT AAA GGA ACT TCT GAT AAA AAC AAT GGA TCT GGA GTA CTT
GAA CTC GAA TTT CCT TGA AGA CTA TTT TTG TTA CCT AGA CCT CAT GAA
L   E   L   K   G   T   S   D   K   N   N   G   S   G   V   L>

770         780         790         800         810
GAA GGC GTA AAA GCT GAC AAA AGT AAA GTA AAA TTA ACA ATT TCT GAC
CTT CCG CAT TTT CGA CTG TTT TCA TTT CAT TTT AAT TGT TAA AGA CTG
E   G   V   K   A   D   K   S   K   V   K   L   T   I   S   D>

820         830         840         850         860
GAT CTA GGT CAA ACC ACA CTT GAA GTT TTC AAA GAA GAT GGC AAA ACA
CTA GAT CCA GTT TGG TGT GAA CTT CAA AAG TTT CTT CTA CCG TTT TGT
D   L   G   Q   T   T   L   E   V   F   K   E   D   G   K   T>

870         880         890         900         910
CTA GTA TCA AAA AAA GTA ACT TCC AAA GAC AAG TCA TCA ACA GAA GAA
GAT CAT AGT TTT TTT CAT TGA AGG TTT CTG TTC AGT AGT TGT CTT CTT
L   V   S   K   K   V   T   S   K   D   K   S   S   T   E   E>

920         930         940         950         960
AAA TTC AAT GAA AAA GGT GAA GTA TCT GAA AAA ATA ATA ACA AGA GCA
TTT AAG TTA CTT TTT CCA CTT CAT AGA CTT TTT TAT TAT TGT TCT CGT
K   F   N   E   K   G   E   V   S   E   K   I   I   T   R   A>

970         980         990         1000
GAC GGA ACC AGA CTT GAA TAC ACA GGA ATT AAA AGC GAT GGA TCT GGA
CTG CCT TGG TCT GAA CTT ATG TGT CCT TAA TTT TCG CTA CCT AGA CCT
D   G   T   R   L   E   Y   T   G   I   K   S   D   G   S   G>

1010        1020        1030        1040        1050
AAA GCT AAA GAG GTT TTA AAA GGC TAT GTT CTT GAA GGA ACT CTA ACT
TTT CGA TTT CTC CAA AAT TTT CCG ATA CAA GAA CTT CCT TGA GAT TGA
K   A   K   E   V   L   K   G   Y   V   L   E   G   T   L   T>

1060        1070        1080        1090        1100
GCT GAA AAA ACA ACA TTG GTG GTT AAA GAA GGA ACT GTT ACT TTA AGC
```

FIG. 60B

```
CGA CTT TTT TGT TGT AAC CAC CAA TTT CTT CCT TGA CAA TGA AAT TCG
A   E   K   T   T   L   V   V   K   E   G   T   V   T   L   S>

   1110          1120          1130          1140          1150
AAA AAT ATT TCA AAA TCT GGG GAA GTT TCA GTT GAA CTT AAT GAC ACT
TTT TTA TAA AGT TTT AGA CCC CTT CAA AGT CAA CTT GAA TTA CTG TGA
K   N   I   S   K   S   G   E   V   S   V   E   L   N   D   T>

       1160          1170          1180          1190          1200
GAC AGT AGT GCT GCT ACT AAA AAA ACT GCA GCT TGG AAT TCA AAA ACT
CTG TCA TCA CGA CGA TGA TTT TTT TGA CGT CGA ACC TTA AGT TTT TGA
D   S   S   A   A   T   K   K   T   A   A   W   N   S   K   T>

           1210          1220          1230          1240
TCT ACT TTA ACA ATT AGT GTT AAC AGC AAA AAA ACT ACA CAA CTT GTG
AGA TGA AAT TGT TAA TCA CAA TTG TCG TTT TTT TGA TGT GTT GAA CAC
S   T   L   T   I   S   V   N   S   K   K   T   T   Q   L   V>

1250          1260          1270          1280          1290
TTT ACT AAA CAA GAC ACA ATA ACT GTA CAA AAA TAC GAC TCC GCA GGT
AAA TGA TTT GTT CTG TGT TAT TGA CAT GTT TTT ATG CTG AGG CGT CCA
F   T   K   Q   D   T   I   T   V   Q   K   Y   D   S   A   G>

1300          1310          1320          1330          1340
ACC AAT TTA GAA GGC ACA GCA GTC GAA ATT AAA ACA CTT GAT GAA CTT
TGG TTA AAT CTT CCG TGT CGT CAG CTT TAA TTT TGT GAA CTA CTT GAA
T   N   L   E   G   T   A   V   E   I   K   T   L   D   E   L>

  1350          1360
AAA AAC GCT TTA AAA TAA
TTT TTG CGA AAT TTT ATT
K   N   A   L   K   *>
```

FIG. 60C 10 20 30 40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M A C N N S G K D G N T S A N S>

50 60 70 80 90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
A D E S V K G P N L T E I S K K>

100 110 120 130 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I T D S N A V L L A V K E V E A>

150 160 170 180 190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
L L S S I D E L A K A I G K K I>

200 210 220 230 240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
K N D G S L D N E A N R N E S L>

250 260 270 280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
L A G A Y T I S T L I T Q K L S>

290 300 310 320 330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
K L N G S E G L K E K I A A A K>

340 350 360 370 380
AAA TGC TCT GAA GAG TTT AGT ACT AAA CTA AAA GAT AAT CAT GCA CAG
TTT ACG AGA CTT CTC AAA TCA TGA TTT GAT TTT CTA TTA GTA CGT GTC
K C S E E F S T K L K D N H A Q>

390 400 410 420 430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
L G I Q G V T D E N A K K A I L>

440 450 460 470 480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
K A N A A G K D K G V E E L E K>

490 500 510 520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
L S G S L E S L S K A A K E M L>

FIG. 61A

```
530              540              550              560              570
   GCT AAT TCA GTT AAA GAG CTT ACA AGC CCT GTT GTC CAT GGC AAG CAA
   CGA TTA AGT CAA TTT CTC GAA TGT TCG GGA CAA CAG GTA CCG TTC GTT
   A   N   S   V   K   E   L   T   S   P   V   V   H   G   K   Q>

    580              590              600              610              620
   AAT GTT AGC AGC CTT GAC GAG AAA AAC AGC GTT TCA GTA GAT TTG CCT
   TTA CAA TCG TCG GAA CTG CTC TTT TTG TCG CAA AGT CAT CTA AAC GGA
   N   V   S   S   L   D   E   K   N   S   V   S   V   D   L   P>

       630              640              650              660              670
   GGT GAA ATG AAA GTT CTT GTA AGC AAA GAA AAA AAC AAA GAC GGC AAG
   CCA CTT TAC TTT CAA GAA CAT TCG TTT CTT TTT TTG TTT CTG CCG TTC
   G   E   M   K   V   L   V   S   K   E   K   N   K   D   G   K>

          680              690              700              710              720
   TAC GAT CTA ATT GCA ACA GTA GAC AAG CTT GAG CTT AAA GGA ACT TCT
   ATG CTA GAT TAA CGT TGT CAT CTG TTC GAA CTC GAA TTT CCT TGA AGA
   Y   D   L   I   A   T   V   D   K   L   E   L   K   G   T   S>

             730              740              750              760
   GAT AAA AAC AAT GGA TCT GGA GTA CTT GAA GGC GTA AAA GCT GAC AAA
   CTA TTT TTG TTA CCT AGA CCT CAT GAA CTT CCG CAT TTT CGA CTG TTT
   D   K   N   N   G   S   G   V   L   E   G   V   K   A   D   K>

770              780              790              800              810
   AGT AAA GTA AAA TTA ACA ATT TCT GAC GAT CTA GGT CAA ACC ACA CTT
   TCA TTT CAT TTT AAT TGT TAA AGA CTG CTA GAT CCA GTT TGG TGT GAA
   S   K   V   K   L   T   I   S   D   D   L   G   Q   T   T   L>

    820              830              840              850              860
   GAA GTT TTC AAA GAA GAT GGC AAA ACA CTA GTA TCA AAA AAA GTA ACT
   CTT CAA AAG TTT CTT CTA CCG TTT TGT GAT CAT AGT TTT TTT CAT TGA
   E   V   F   K   E   D   G   K   T   L   V   S   K   K   V   T>

       870              880              890              900              910
   TCC AAA GAC AAG TCA TCA ACA GAA GAA AAA TTC AAT GAA AAA GGT GAA
   AGG TTT CTG TTC AGT AGT TGT CTT CTT TTT AAG TTA CTT TTT CCA CTT
   S   K   D   K   S   S   T   E   E   K   F   N   E   K   G   E>

          920              930              940              950              960
   GTA TCT GAA AAA ATA ATA ACA AGA GCA GAC GGA ACC AGA CTT GAA TAC
   CAT AGA CTT TTT TAT TAT TGT TCT CGT CTG CCT TGG TCT GAA CTT ATG
   V   S   E   K   I   I   T   R   A   D   G   T   R   L   E   Y>

             970              980              990             1000
   ACA GGA ATT AAA AGC GAT GGA TCT GGA AAA GCT AAA GAG GTT TTA AAA
   TGT CCT TAA TTT TCG CTA CCT AGA CCT TTT CGA TTT CTC CAA AAT TTT
   T   G   I   K   S   D   G   S   G   K   A   K   E   V   L   K>

1010             1020             1030             1040             1050
   GGC TAT GTT CTT GAA GGA ACT CTA ACT GCT GAA AAA ACA ACA TTG GTG
   CCG ATA CAA GAA CTT CCT TGA GAT TGA CGA CTT TTT TGT TGT AAC CAC
   G   Y   V   L   E   G   T   L   T   A   E   K   T   T   L   V>

1060             1070             1080             1090             1100
   GTT AAA GAA GGA ACT GTT ACT TTA AGC AAA AAT ATT TCA AAA TCT GGG
```

FIG. 61B

```
CAA TTT CTT CCT TGA CAA TGA AAT TCG TTT TTA TAA AGT TTT AGA CCC
V   K   E   G   T   V   T   L   S   K   N   I   S   K   S   C>

 1110            1120            1130            1140            1150
GAA GTT TCA GTT GAA CTT AAT GAC ACT GAC AGT AGT GCT GCT ACT AAA
CTT CAA AGT CAA CTT GAA TTA CTG TGA CTG TCA TCA CGA CGA TGA TTT
E   V   S   V   E   L   N   D   T   D   S   S   A   A   T   K>

    1160            1170            1180            1190            1200
AAA ACT GCA GCT TGG AAT TCA AAA ACT TCT ACT TTA ACA ATT AGT GTT
TTT TGA CGT CGA ACC TTA AGT TTT TGA AGA TGA AAT TGT TAA TCA CAA
K   T   A   A   W   N   S   K   T   S   T   L   T   I   S   V>

       1210            1220            1230            1240
AAC AGC AAA AAA ACT ACA CAA CTT GTG TTT ACT AAA CAA TAC ACA ATA
TTG TCG TTT TTT TGA TGT GTT GAA CAC AAA TGA TTT GTT ATG TGT TAT
N   S - K   K   T   T   Q   L   V   F   T   K   Q   Y   T   I>

1250           1260            1270            1280            1290
ACT GTA AAA CAA TAC GAC TCC GCA GGT ACC AAT TTA GAA GGC ACA GCA
TGA CAT TTT GTT ATG CTG AGG CGT CCA TGG TTA AAT CTT CCG TGT CGT
T   V   K   Q   Y   D   S   A   G   T   N   L   E   G   T   A>

1300            1310            1320            1330            1340
GTC GAA ATT AAA ACA CTT GAT GAA CTT AAA AAC GCT TTA AAA TAA
CAG CTT TAA TTT TGT GAA CTA CTT GAA TTT TTG CGA AAT TTT ATT
V   E   I   K   T   L   D   E   L   K   N   A   L   K   *>
```

FIG. 61C 10 20 30 40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M A C N N S G K D G N T S A N S>

50 60 70 80 90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
A D E S V K G P N L T E I S K K>

100 110 120 130 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I T D S N A V L L A V K E V E A>

150 160 170 180 190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
L L S S I D E I A A K A I G K K>

200 210 220 230 240
ATA CAC CAA AAT AAT GGT TTG GAT ACC GAA TAT AAT CAC AAT GGA TCA
TAT GTG GTT TTA TTA CCA AAC CTA TGG CTT ATA TTA GTG TTA CCT AGT
I H Q N N G L D T E Y N H N G S>

250 260 270 280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
L L A G A Y A I S T L I K Q K L>

290 300 310 320 330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
D G L K N E G L K E K I D A A K>

340 350 360 370 380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
K C S E T F T N K L K E K H T D>

390 400 410 420 430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
L G K E G V T D A D A K E A I L>

440 450 460 470 480
AAA ACA AAT GGT ACT AAA ACT AAA GGT GCT GAA GAA CTT GGA AAA TTA
TTT TGT TTA CCA TGA TTT TGA TTT CCA CGA CTT CTT GAA CCT TTT AAT
K T N G T K T K G A E E L G K L>

490 500 510 520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
F E S V E V L S K A A K E M L A>

FIG. 62A 530 540 550 560 570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
N S V K E L T S P V V A E S P K>

580 590 600 610 620
AAA CCT TCC ATG GCC AAG CAA AAT GTT AGC AGC CTT GAT GAA AAA AAT
TTT GGA AGG TAC CGG TTC GTT TTA CAA TCG TCG GAA CTA CTT TTT TTA
K P S M A K Q N V S S L D E K N>

630 640 650 660 670
AGC GTT TCA GTA GAT TTA CCT GGT GGA ATG ACA GTT CTT GTA AGT AAA
TCG CAA AGT CAT CTA AAT GGA CCA CCT TAC TGT CAA GAA CAT TCA TTT
S V S V D L P G G M T V L V S K>

680 690 700 710 720
GAA AAA GAC AAA GAC GGT AAA TAC AGT CTA GAG GCA ACA GTA GAC AAG
CTT TTT CTG TTT CTG CCA TTT ATG TCA GAT CTC CGT TGT CAT CTG TTC
E K D K D G K Y S L E A T V D K>

730 740 750 760
CTT GAG CTT AAA GGA ACT TCT GAT AAA AAC AAC GGT TCT GGA ACA CTT
GAA CTC GAA TTT CCT TGA AGA CTA TTT TTG TTG CCA AGA CCT TGT GAA
L E L K G T S D K N N G S G T L>

770 780 790 800 810
GAA GGT GAA AAA ACT GAC AAA AGT AAA GTA AAA TTA ACA ATT GCT GAT
CTT CCA CTT TTT TGA CTG TTT TCA TTT CAT TTT AAT TGT TAA CGA CTA
E G E K T D K S K V K L T I A D>

820 830 840 850 860
GAC CTA AGT CAA ACT AAA TTT GAA ATT TTC AAA GAA GAT GCC AAA ACA
CTG GAT TCA GTT TGA TTT AAA CTT TAA AAG TTT CTT CTA CGG TTT TGT
D L S Q T K F E I F K E D A K T>

870 880 890 900 910
TTA GTA TCA AAA AAA GTA ACC CTT AAA GAC AAG TCA TCA ACA GAA GAA
AAT CAT AGT TTT TTT CAT TGG GAA TTT CTG TTC AGT AGT TGT CTT CTT
L V S K K V T L K D K S S T E E>

920 930 940 950 960
AAA TTC AAC GAA AAG GGT GAA ACA TCT GAA AAA ACA ATA GTA AGA GCA
TTT AAG TTG CTT TTC CCA CTT TGT AGA CTT TTT TGT TAT CAT TCT CGT
K F N E K G E T S E K T I V R A>

970 980 990 1000
AAT GGA ACC AGA CTT GAA TAC ACA GAC ATA AAA AGC GAT GGA TCC GGA
TTA CCT TGG TCT GAA CTT ATG TGT CTG TAT TTT TCG CTA CCT AGG CCT
N G T R L E Y T D I K S D G S G>

1010 1020 1030 1040 1050
AAA GCT AAA GAA GTT TTA AAA GAC TTT ACT CTT GAA GGA ACT CTA GCT
TTT CGA TTT CTT CAA AAT TTT CTG AAA TGA GAA CTT CCT TGA GAT CGA
K A K E V L K D F T L E G T L A>

1060 1070 1080 1090 1100
GCT GAC GGC AAA ACA ACA TTG AAA GTT ACA GAA GGC ACT GTT GTT TTA

FIG. 62B

```
 CGA CTG CCG TTT TGT TGT AAC TTT CAA TGT CTT CCG TGA CAA CAA AAT
 A   D   G   K   T   T   L   K   V   T   E   G   T   V   V   L>

   1110           1120         1130         1140         1150
 AGC AAG AAC ATT TTA AAA TCC GGA GAA ATA ACA GTT GCA CTT GAT GAC
 TCG TTC TTG TAA AAT TTT AGG CCT CTT TAT TGT CAA CGT GAA CTA CTG
 S   K   N   I   L   K   S   G   E   I   T   V   A   L   D   D>

      1160         1170         1180         1190         1200
 TCT GAC ACT ACT CAG GCT ACT AAA AAA ACT GGA AAA TGG GAT TCA AAT
 AGA CTG TGA TGA GTC CGA TGA TTT TTT TGA CCT TTT ACC CTA AGT TTA
 S   D   T   T   Q   A   T   K   K   T   G   K   W   D   S   N>

          1210         1220         1230         1240
 ACT TCC ACT TTA ACA ATT AGT GTG AAT AGC AAA AAA ACT AAA AAC ATT
 TGA AGG TGA AAT TGT TAA TCA CAC TTA TCG TTT TTT TGA TTT TTG TAA
 T   S   T   L   T   I   S   V   N   S   K   K   T   K   N   I>

1250          1260         1270         1280         1290
 GTA TTT ACA AAA GAA GAC ACA ATA ACA GTA CAA AAA TAC GAC TCA GCA
 CAT AAA TGT TTT CTT CTG TGT TAT TGT CAT GTT TTT ATG CTG AGT CGT
 V   F   T   K   E   D   T   I   T   V   Q   K   Y   D   S   A>

 1300         1310         1320         1330         1340
 GGC ACC AAT CTA GAA GGC AAC GCA GTC GAA ATT AAA ACA CTT GAT GAA
 CCG TGG TTA GAT CTT CCG TTG CGT CAG CTT TAA TTT TGT GAA CTA CTT
 G   T   N   L   E   G   N   A   V   E   I   K   T   L   D   E>

   1350         1360
 CTT AAA AAC GCT TTA AAA TAG
 GAA TTT TTG CGA AAT TTT ATC
 L   K   N   A   L   K   *>
```

FIG. 62C

```
                 10                  20                  30                   40
 ATG GCT TGT AAT AAT TCA GGG AAA GAT GGG AAT ACA TCT GCA AAT TCT
 TAC CGA ACA TTA TTA AGT CCC TTT CTA CCC TTA TGT AGA CGT TTA AGA
 M   A   C   N   N   S   G   K   D   G   N   T   S   A   N   S>

50                60                  70                  80                  90
 GCT GAT GAG TCT GTT AAA GGG CCT AAT CTT ACA GAA ATA AGT AAA AAA
 CGA CTA CTC AGA CAA TTT CCC GGA TTA GAA TGT CTT TAT TCA TTT TTT
 A   D   E   S   V   K   G   P   N   L   T   E   I   S   K   K>

 100                110                 120                 130                 140
 ATT ACG GAT TCT AAT GCG GTT TTA CTT GCT GTG AAA GAG GTT GAA GCG
 TAA TGC CTA AGA TTA CGC CAA AAT GAA CGA CAC TTT CTC CAA CTT CGC
 I   T   D   S   N   A   V   L   L   A   V   K   E   V   E   A>

   150                160                 170                 180                 190
 TTG CTG TCA TCT ATA GAT GAG CTT GCT AAA GCT ATT GGT AAA AAA ATA
 AAC GAC AGT AGA TAT CTA CTC GAA CGA TTT CGA TAA CCA TTT TTT TAT
 L   L   S   S   I   D   E   L   A   K   A   I   G   K   K   I>

        200                 210                 220                 230             240
 AAA AAC GAT GGT AGT TTA GAT AAT GAA GCA AAT CGC AAC GAG TCA TTG
 TTT TTG CTA CCA TCA AAT CTA TTA CTT CGT TTA GCG TTG CTC AGT AAC
 K   N   D   G   S   L   D   N   E   A   N   R   N   E   S   L>

          250                 260                 270                 280
 TTA GCA GGA GCT TAT ACA ATA TCA ACC TTA ATA ACA CAA AAA TTA AGT
 AAT CGT CCT CGA ATA TGT TAT AGT TGG AAT TAT TGT GTT TTT AAT TCA
 L   A   G   A   Y   T   I   S   T   L   I   T   Q   K   L   S>

290             300                 310                 320                 330
 AAA TTA AAC GGA TCA GAA GGT TTA AAG GAA AAG ATT GCC GCA GCT AAG
 TTT AAT TTG CCT AGT CTT CCA AAT TTC CTT TTC TAA CGG CGT CGA TTC
 K   L   N   G   S   E   G   L   K   E   K   I   A   A   A   K>

 340                350                 360                 370                 380
 AAA TGC TCT GAA GAG TTT AGT ACT AAA CTA AAA GAT AAT CAT GCA CAG
 TTT ACG AGA CTT CTC AAA TCA TGA TTT GAT TTT CTA TTA GTA CGT GTC
 K   C   S   E   E   F   S   T   K   L   K   D   N   H   A   Q>

   390                400                 410                 420                 430
 CTT GGT ATA CAG GGC GTT ACT GAT GAA AAT GCA AAA AAA GCT ATT TTA
 GAA CCA TAT GTC CCG CAA TGA CTA CTT TTA CGT TTT TTT CGA TAA AAT
 L   G   I   Q   G   V   T   D   E   N   A   K   K   A   I   L>

        440                 450                 460                 470             480
 AAA GCA AAT GCA GCG GGT AAA GAT AAG GGC GTT GAA GAA CTT GAA AAG
 TTT CGT TTA CGT CGC CCA TTT CTA TTC CCG CAA CTT CTT GAA CTT TTC
 K   A   N   A   A   G   K   D   K   G   V   E   E   L   E   K>

          490                 500                 510                 520
 TTG TCC GGA TCA TTA GAA AGC TTA TCA AAA GCA GCT AAA GAG ATG CTT
 AAC AGG CCT AGT AAT CTT TCG AAT AGT TTT CGT CGA TTT CTC TAC GAA
 L   S   G   S   L   E   S   L   S   K   A   A   K   E   M   L>
```

FIG. 63A

```
530         540         550         560         570
GCT AAT TCA GTT AAA GAG CTT ACA AGC CCT GTT GTC CAT GGC AAG CAA
CGA TTA AGT CAA TTT CTC GAA TGT TCG GGA CAA CAG GTA CCG TTC GTT
A   N   S   V   K   E   L   T   S   P   V   V   H   G   K   Q>

580         590         600         610         620
AAT GTT AGC AGC CTT GAT GAA AAA AAT AGC GTT TCA GTA GAT TTA CCT
TTA CAA TCG TCG GAA CTA CTT TTT TTA TCG CAA AGT CAT CTA AAT GGA
N   V   S   S   L   D   E   K   N   S   V   S   V   D   L   P>

630         640         650         660         670
GGT GGA ATG ACA GTT CTT GTA AGT AAA GAA AAA GAC AAA GAC GGT AAA
CCA CCT TAC TGT CAA GAA CAT TCA TTT CTT TTT CTG TTT CTG CCA TTT
G   G   M   T   V   L   V   S   K   E   K   D   K   D   G   K>

680         690         700         710         720
TAC AGT CTA GAG GCA ACA GTA GAC AAG CTT GAG CTT AAA GGA ACT TCT
ATG TCA GAT CTC CGT TGT CAT CTG TTC GAA CTC GAA TTT CCT TGA AGA
Y   S   L   E   A   T   V   D   K   L   E   L   K   G   T   S>

730         740         750         760
GAT AAA AAC AAC GGT TCT GGA ACA CTT GAA GGT GAA AAA ACT GAC AAA
CTA TTT TTG TTG CCA AGA CCT TGT GAA CTT CCA CTT TTT TGA CTG TTT
D   K   N   N   G   S   G   T   L   E   G   E   K   T   D   K>

770         780         790         800         810
AGT AAA GTA AAA TTA ACA ATT GCT GAT GAC CTA AGT CAA ACT AAA TTT
TCA TTT CAT TTT AAT TGT TAA CGA CTA CTG GAT TCA GTT TGA TTT AAA
S   K   V   K   L   T   I   A   D   D   L   S   Q   T   K   F>

820         830         840         850         860
GAA ATT TTC AAA GAA GAT GCC AAA ACA TTA GTA TCA AAA AAA GTA ACC
CTT TAA AAG TTT CTT CTA CGG TTT TGT AAT CAT AGT TTT TTT CAT TGG
E   I   F   K   E   D   A   K   T   L   V   S   K   K   V   T>

870         880         890         900         910
CTT AAA GAC AAG TCA TCA ACA GAA GAA AAA TTC AAC GAA AAG GGT GAA
GAA TTT CTG TTC AGT AGT TGT CTT CTT TTT AAG TTG CTT TTC CCA CTT
L   K   D   K   S   S   T   E   E   K   F   N   E   K   G   E>

920         930         940         950         960
ACA TCT GAA AAA ACA ATA GTA AGA GCA AAT GGA ACC AGA CTT GAA TAC
TGT AGA CTT TTT TGT TAT CAT TCT CGT TTA CCT TGG TCT GAA CTT ATG
T   S   E   K   T   I   V   R   A   N   G   T   R   L   E   Y>

970         980         990         1000
ACA GAC ATA AAA AGC GAT GGA TCC GGA AAA GCT AAA GAA GTT TTA AAA
TGT CTG TAT TTT TCG CTA CCT AGG CCT TTT CGA TTT CTT CAA AAT TTT
T   D   I   K   S   D   G   S   G   K   A   K   E   V   L   K>

1010        1020        1030        1040        1050
GAC TTT ACT CTT GAA GGA ACT CTA GCT GCT GAC GGC AAA ACA ACA TTG
CTG AAA TGA GAA CTT CCT TGA GAT CGA CGA CTG CCG TTT TGT TGT AAC
D   F   T   L   E   G   T   L   A   A   D   G   K   T   T   L>

1060        1070        1080        1090        1100
AAA GTT ACA GAA GGC ACT GTT GTT TTA AGC AAG AAC ATT TTA AAA TCC
```

FIG. 63B

```
TTT CAA TGT CTT CCG TGA CAA CAA AAT TCG TTC TTG TAA AAT TTT AGG
K   V   T   E   G   T   V   V   L   S   K   N   I   L   K   S>

 1110            1120           1130          1140           1150
GGA GAA ATA ACA GTT GCA CTT GAT GAC TCT GAC ACT ACT CAG GCT ACT
CCT CTT TAT TGT CAA CGT GAA CTA CTG AGA CTG TGA TGA GTC CGA TGA
G   E   I   T   V   A   L   D   D   S   D   T   T   Q   A   T>

     1160           1170           1180          1190           1200
AAA AAA ACT GGA AAA TGG GAT TCA AAT ACT TCC ACT TTA ACA ATT AGT
TTT TTT TGA CCT TTT ACC CTA AGT TTA TGA AGG TGA AAT TGT TAA TCA
K   K   T   G   K   W   D   S   N   T   S   T   L   T   I   S>

        1210           1220           1230           1240
GTG AAT AGC AAA AAA ACT AAA AAC ATT GTA TTT ACA AAA GAA GAC ACA
CAC TTA TCG TTT TTT TGA TTT TTG TAA CAT AAA TGT TTT CTT CTG TGT
V   N   S   K   K   T   K   N   I   V   F   T   K   E   D   T>

1250          1260           1270          1280           1290
ATA ACA GTA CAA AAA TAC GAC TCA GCA GGC ACC AAT CTA GAA GGC AAC
TAT TGT CAT GTT TTT ATG CTG AGT CGT CCG TGG TTA GAT CTT CCG TTG
I   T   V   Q   K   Y   D   S   A   G   T   N   L   E   G   N>

1300          1310           1320           1330          1340
GCA GTC GAA ATT AAA ACA CTT GAT GAA CTT AAA AAC GCT TTA AAA TAG
CGT CAG CTT TAA TTT TGT GAA CTA CTT GAA TTT TTG CGA AAT TTT ATC
A   V   E   I   K   T   L   D   E   L   K   N   A   L   K   *>
```

FIG. 63C

```
               10                20                30                40
 ATG GCT TGT AAT AAT TCA GGA AAA GAT GGG AAT ACA TCT GCA AAT TCT
 TAC CGA ACA TTA TTA AGT CCT TTT CTA CCC TTA TGT AGA CGT TTA AGA
 M   A   C   N   N   S   G   K   D   G   N   T   S   A   N   S>

50             60                70                80                90
 GCT GAT GAG TCT GTT AAA GGG CCT AAT CTT ACA GAA ATA AGT AAA AAA
 CGA CTA CTC AGA CAA TTT CCC GGA TTA GAA TGT CTT TAT TCA TTT TTT
 A   D   E   S   V   K   G   P   N   L   T   E   I   S   K   K>

   100               110               120               130               140
 ATT ACA GAA TCT AAC GCA GTT GTT CTG GCT GTG AAA GAA ATT GAA ACT
 TAA TGT CTT AGA TTG CGT CAA CAA GAC CGA CAC TTT CTT TAA CTT TGA
 I   T   E   S   N   A   V   V   L   A   V   K   E   I   E   T>

     150               160               170               180               190
 TTG CTT GCA TCT ATA GAT GAA CTT GCT ACT AAA GCT ATT GGT AAA AAA
 AAC GAA CGT AGA TAT CTA CTT GAA CGA TGA TTT CGA TAA CCA TTT TTT
 L   L   A   S   I   D   E   L   A   T   K   A   I   G   K   K>

         200               210               220               230               240
 ATA CAA CAA AAT GGT GGT TTA GCT GTC GAA GCG GGG CAT AAT GGA ACA
 TAT GTT GTT TTA CCA CCA AAT CGA CAG CTT CGC CCC GTA TTA CCT TGT
 I   Q   Q   N   G   G   L   A   V   E   A   G   H   N   G   T>

             250               260               270               280
 TTG TTA GCA GGT GCT TAT ACA ATA TCA AAA CTA ATA ACA CAA AAA TTA
 AAC AAT CGT CCA CGA ATA TGT TAT AGT TTT GAT TAT TGT GTT TTT AAT
 L   L   A   G   A   Y   T   I   S   K   L   I   T   Q   K   L>

290            300               310               320               330
 GAT GGA TTG AAA AAT TCA GAA AAA TTA AAG GAA AAA ATT GAA AAT GCT
 CTA CCT AAC TTT TTA AGT CTT TTT AAT TTC CTT TTT TAA CTT TTA CGA
 D   G   L   K   N   S   E   K   L   K   E   K   I   E   N   A>

 340               350               360               370               380
 AAG AAA TGT TCT GAA GAT TTT ACT AAA AAA CTA GAA GGA GAA CAT GCG
 TTC TTT ACA AGA CTT CTA AAA TGA TTT TTT GAT CTT CCT CTT GTA CGC
 K   K   C   S   E   D   F   T   K   K   L   E   G   E   H   A>

   390               400               410               420               430
 CAA CTT GGA ATT GAA AAT GTT ACT GAT GAG AAT GCA AAA AAA GCT ATT
 GTT GAA CCT TAA CTT TTA CAA TGA CTA CTC TTA CGT TTT TTT CGA TAA
 Q   L   G   I   E   N   V   T   D   E   N   A   K   K   A   I>

       440               450               460               470               480
 TTA ATA ACA GAT GCA GCT AAA GAT AAG GGC GCT GCA GAG CTT GAA AAG
 AAT TAT TGT CTA CGT CGA TTT CTA TTC CCG CGA CGT CTC GAA CTT TTC
 L   I   T   D   A   A   K   D   K   G   A   A   E   L   E   K>

           490               500               510               520
 CTA TTT AAA GCA GTA GAA AAC TTG GCA AAA GCA GCT AAA GAG ATG CTT
 GAT AAA TTT CGT CAT CTT TTG AAC CGT TTT CGT CGA TTT CTC TAC GAA
 L   F   K   A   V   E   N   L   A   K   A   A   K   E   M   L>
```

FIG. 64A

```
530 540 550 560 570
GCT AAT TCA GTT AAA GAG CTT ACA AGT CCT ATT GTG CAT GGC GTT TCA
CGA TTA AGT CAA TTT CTC GAA TGT TCA GGA TAA CAC GTA CCG CAA AGT
A   N   S   V   K   E   L   T   S   P   I   V   H   G   V   S>

580 590 600 610 620
GTA GAT TTG CCT GGT GAA ATG AAA GTT CTT GTA AGC AAA GAA AAA AAC
CAT CTA AAC GGA CCA CTT TAC TTT CAA GAA CAT TCG TTT CTT TTT TTG
V   D   L   P   G   E   M   K   V   L   V   S   K   E   K   N>

630 640 650 660 670
AAA GAC GGC AAG TAC GAT CTA ATT GCA ACA GTA GAC AAG CTT GAG CTT
TTT CTG CCG TTC ATG CTA GAT TAA CGT TGT CAT CTG TTC GAA CTC GAA
K   D   G   K   Y   D   L   I   A   T   V   D   K   L   E   L>

680 690 700 710 720
AAA GGA ACT TCT GAT AAA AAC AAT GGA TCT GGA GTA CTT GAA GGC GTA
TTT CCT TGA AGA CTA TTT TTG TTA CCT AGA CCT CAT GAA CTT CCG CAT
K   G   T   S   D   K   N   N   G   S   G   V   L   E   G   V>

730 740 750 760
AAA GCT GAC AAA AGT AAA GTA AAA TTA ACA ATT TCT GAC GAT CTA GGT
TTT CGA CTG TTT TCA TTT CAT TTT AAT TGT TAA AGA CTG CTA GAT CCA
K   A   D   K   S   K   V   K   L   T   I   S   D   D   L   G>

770 780 790 800 810
CAA ACC ACA CTT GAA GTT TTC AAA GAA GAT GGC AAA ACA CTA GTA TCA
GTT TGG TGT GAA CTT CAA AAG TTT CTT CTA CCG TTT TGT GAT CAT AGT
Q   T   T   L   E   V   F   K   E   D   G   K   T   L   V   S>

820 830 840 850 860
AAA AAA GTA ACT TCC AAA GAC AAG TCA TCA ACA GAA GAA AAA TTC AAT
TTT TTT CAT TGA AGG TTT CTG TTC AGT AGT TGT CTT CTT TTT AAG TTA
K   K   V   T   S   K   D   K   S   S   T   E   E   K   F   N>

870 880 890 900 910
GAA AAA GGT GAA GTA TCT GAA AAA ATA ATA ACA AGA GCA GAC GGA ACC
CTT TTT CCA CTT CAT AGA CTT TTT TAT TAT TGT TCT CGT CTG CCT TGG
E   K   G   E   V   S   E   K   I   I   T   R   A   D   G   T>

920 930 940 950 960
AGA CTT GAA TAC ACA GGA ATT AAA AGC GAT GGA TCT GGA AAA GCT AAA
TCT GAA CTT ATG TGT CCT TAA TTT TCG CTA CCT AGA CCT TTT CGA TTT
R   L   E   Y   T   G   I   K   S   D   G   S   G   K   A   K>

970 980 990 1000
GAG GTT TTA AAA AAA TTT ACT CTT GAA GGA AAA GTA GCT AAT GAT AAA
CTC CAA AAT TTT TTT AAA TGA GAA CTT CCT TTT CAT CGA TTA CTA TTT
E   V   L   K   K   F   T   L   E   G   K   V   A   N   D   K>

1010 1020 1030 1040 1050
GTA ACA TTG GAA GTA AAA GAA GGA ACC GTT ACT TTA AGT AAG AAC ATT
CAT TGT AAC CTT CAT TTT CTT CCT TGG CAA TGA AAT TCA TTC TTG TAA
V   T   L   E   V   K   E   G   T   V   T   L   S   K   N   I>

1060 1070 1080 1090 1100
TCA AAA TCT GGG GAA GTT TCA GTT GAA CTT AAT GAC ACT GAC AGT AGT
```

FIG. 64B

```
 AGT TTT AGA CCC CTT CAA AGT CAA CTT GAA TTA CTG TGA CTG TCA TCA
 S   K   S   G   E   V   S   V   E   L   N   D   T   D   S   S>

   1110            1120           1130           1140           1150
 GCT GCT ACT AAA AAA ACT GCA GCT TGG AAT TCA GGC ACT TCA ACT TTA
 CGA CGA TGA TTT TTT TGA CGT CGA ACC TTA AGT CCG TGA AGT TGA AAT
 A   A   T   K   K   T   A   A   W   N   S   G   T   S   T   L>

       1160           1170           1180           1190           1200
 ACA ATT ACT GTA AAC AGT AAA AAA ACT AAA GAC CTT GTG TTT ACA AAA
 TGT TAA TGA CAT TTG TCA TTT TTT TGA TTT CTG GAA CAC AAA TGT TTT
 T   I   T   V   N   S   K   K   T   K   D   L   V   F   T   K>

          1210           1220           1230           1240
 GAA AAC ACA ATT ACA GTA CAA CAA TAC GAC TCA AAT GGC ACC AAA TTA
 CTT TTG TGT TAA TGT CAT GTT GTT ATG CTG AGT TTA CCG TGG TTT AAT
 E   N   T   I   T   V   Q   Q   Y   D   S   N   G   T   K   L>

1250          1260           1270           1280          1290
 GAG GGG TCA GCA GTT GAA ATT ACA AAA CTT GAT GAA ATT AAA AAC GCT
 CTC CCC AGT CGT CAA CTT TAA TGT TTT GAA CTA CTT TAA TTT TTG CGA
 E   G   S   A   V   E   I   T   K   L   D   E   I   K   N   A>

  1300
 TTA AAA TAA
 AAT TTT ATT
 L   K   *>
```

FIG. 64C

```
          10              20              30              40
ATG GCT TGT AGT AAT TCA GGG AAA GGT GGG GAT TCT GCA TCT ACT AAT
TAC CGA ACA TCA TTA AGT CCC TTT CCA CCC CTA AGA CGT AGA TGA TTA
 M   A   C   S   N   S   G   K   G   G   D   S   A   S   T   N>

50            60              70              80              90
CCT GCT GAC GAG TCT GCG AAA GGG CCT AAT CTT ACA GAA ATA AGC AAA
GGA CGA CTG CTC AGA CGC TTT CCC GGA TTA GAA TGT CTT TAT TCG TTT
 P   A   D   E   S   A   K   G   P   N   L   T   E   I   S   K>

 100             110             120             130             140
AAA ATT ACA GAT TCT AAT GCA TTT GTA CTT GCT GTT AAA GAA GTT GAG
TTT TAA TGT CTA AGA TTA CGT AAA CAT GAA CGA CAA TTT CTT CAA CTC
 K   I   T   D   S   N   A   F   V   L   A   V   K   E   V   E>

    150             160             170             180             190
ACT TTG GTT TTA TCT ATA GAT GAA CTT GCT AAG AAA GCT ATT GGT CAA
TGA AAC CAA AAT AGA TAT CTA CTT GAA CGA TTC TTT CGA TAA CCA GTT
 T   L   V   L   S   I   D   E   L   A   K   K   A   I   G   Q>

        200             210             220             230         240
AAA ATA GAC AAT AAT AAT GGT TTA GCT GCT TTA AAT AAT CAG AAT GGA
TTT TAT CTG TTA TTA TTA CCA AAT CGA CGA AAT TTA TTA GTC TTA CCT
 K   I   D   N   N   N   G   L   A   A   L   N   N   Q   N   G>

            250             260             270             280
TCG TTG TTA GCA GGA GCC TAT GCA ATA TCA ACC CTA ATA ACA GAA AAA
AGC AAC AAT CGT CCT CGG ATA CGT TAT AGT TGG GAT TAT TGT CTT TTT
 S   L   L   A   G   A   Y   A   I   S   T   L   I   T   E   K>

290             300             310             320             330
TTG AGT AAA TTG AAA AAT TTA GAA GAA TTA AAG ACA GAA ATT GCA AAG
AAC TCA TTT AAC TTT TTA AAT CTT CTT AAT TTC TGT CTT TAA CGT TTC
 L   S   K   L   K   N   L   E   E   L   K   T   E   I   A   K>

 340             350             360             370             380
GCT AAG AAA TGT TCC GAA GAA TTT ACT AAT AAA CTA AAA AGT GGT CAT
CGA TTC TTT ACA AGG CTT CTT AAA TGA TTA TTT GAT TTT TCA CCA GTA
 A   K   K   C   S   E   E   F   T   N   K   L   K   S   G   H>

    390             400             410             420             430
GCA GAT CTT GGC AAA CAG GAT GCT ACC GAT GAT CAT GCA AAA GCA GCT
CGT CTA GAA CCG TTT GTC CTA CGA TGG CTA CTA GTA CGT TTT CGT CGA
 A   D   L   G   K   Q   D   A   T   D   D   H   A   K   A   A>

        440             450             460             470         480
ATT TTA AAA ACA CAT GCA ACT ACC GAT AAA GGT GCT AAA GAA TTT AAA
TAA AAT TTT TGT GTA CGT TGA TGG CTA TTT CCA CGA TTT CTT AAA TTT
 I   L   K   T   H   A   T   T   D   K   G   A   K   E   F   K>

            490             500             510             520
GAT TTA TTT GAA TCA GTA GAA GGT TTG TTA AAA GCA GCT CAA GTA GCA
CTA AAT AAA CTT AGT CAT CTT CCA AAC AAT TTT CGT CGA GTT CAT CGT
 D   L   F   E   S   V   E   G   L   L   K   A   A   Q   V   A>
```

FIG. 65A

```
530            540            550            560            570
CTA ACT AAT TCA GTT AAA GAA CTT ACA AGT CCT GTT GTA GCA GAA AGT
GAT TGA TTA AGT CAA TTT CTT GAA TGT TCA GGA CAA CAT CGT CTT TCA
L   T   N   S   V   K   E   L   T   S   P   V   V   A   E   S>

 580            590            600            610            620
CCA AAA AAA CCT TCC ATG GCC GTT TCA GTA GAT TTG CCT GGT GAA ATG
GGT TTT TTT GGA AGG TAC CGG CAA AGT CAT CTA AAC GGA CCA CTT TAC
P   K   K   P   S   M   A   V   S   V   D   L   P   G   E   M>

   630            640            650            660            670
AAA GTT CTT GTA AGC AAA GAA AAA AAC AAA GAC GGC AAG TAC GAT CTA
TTT CAA GAA CAT TCG TTT CTT TTT TTG TTT CTG CCG TTC ATG CTA GAT
K   V   L   V   S   K   E   K   N   K   D   G   K   Y   D   L>

      680            690            700            710            720
ATT GCA ACA GTA GAC AAG CTT GAG CTT AAA GGA ACT TCT GAT AAA AAC
TAA CGT TGT CAT CTG TTC GAA CTC GAA TTT CCT TGA AGA CTA TTT TTG
I   A   T   V   D   K   L   E   L   K   G   T   S   D   K   N>

         730            740            750            760
AAT GGA TCT GGA GTA CTT GAA GGC GTA AAA GCT GAC AAA AGT AAA GTA
TTA CCT AGA CCT CAT GAA CTT CCG CAT TTT CGA CTG TTT TCA TTT CAT
N   G   S   G   V   L   E   G   V   K   A   D   K   S   K   V>

770            780            790            800            810
AAA TTA ACA ATT TCT GAC GAT CTA GGT CAA ACC ACA CTT GAA GTT TTC
TTT AAT TGT TAA AGA CTG CTA GAT CCA GTT TGG TGT GAA CTT CAA AAG
K   L   T   I   S   D   D   L   G   Q   T   T   L   E   V   F>

 820            830            840            850            860
AAA GAA GAT GGC AAA ACA CTA GTA TCA AAA AAA GTA ACT TCC AAA GAC
TTT CTT CTA CCG TTT TGT GAT CAT AGT TTT TTT CAT TGA AGG TTT CTG
K   E   D   G   K   T   L   V   S   K   K   V   T   S   K   D>

   870            880            890            900            910
AAG TCA TCA ACA GAA GAA AAA TTC AAT GAA AAA GGT GAA GTA TCT GAA
TTC AGT AGT TGT CTT CTT TTT AAG TTA CTT TTT CCA CTT CAT AGA CTT
K   S   S   T   E   E   K   F   N   E   K   G   E   V   S   E>

      920            930            940            950            960
AAA ATA ATA ACA AGA GCA GAC GGA ACC AGA CTT GAA TAC ACA GGA ATT
TTT TAT TAT TGT TCT CGT CTG CCT TGG TCT GAA CTT ATG TGT CCT TAA
K   I   I   T   R   A   D   G   T   R   L   E   Y   T   G   I>

         970            980            990            1000
AAA AGC GAT GGA TCT GGA AAA GCT AAA GAG GTT TTA AAA AAA TTT ACT
TTT TCG CTA CCT AGA CCT TTT CGA TTT CTC CAA AAT TTT TTT AAA TGA
K   S   D   G   S   G   K   A   K   E   V   L   K   K   F   T>

1010           1020           1030           1040           1050
CTT GAA GGA AAA GTA GCT AAT GAT AAA GTA ACA TTG GAA GTA AAA GAA
GAA CTT CCT TTT CAT CGA TTA CTA TTT CAT TGT AAC CTT CAT TTT CTT
L   E   G   K   V   A   N   D   K   V   T   L   E   V   K   E>

1060           1070           1080           1090           1100
GGA ACC GTT ACT TTA AGT AAG AAT ATT TCA AAA TCT GGG GAA GTT TCA
```

FIG. 65B

```
              CCT TGG CAA TGA AAT TCA TTC TTA TAA AGT TTT AGA CCC CTT CAA AGT
               G   T   V   T   L   S   K   N   I   S   K   S   G   E   V   S>

                 1110        1120        1130        1140        1150
              GTT GAA CTT AAT GAC ACT GAC AGT AGT GCT GCT ACT AAA AAA ACT GCA
              CAA CTT GAA TTA CTG TGA CTG TCA TCA CGA CGA TGA TTT TTT TGA CGT
               V   E   L   N   D   T   D   S   S   A   A   T   K   K   T   A>

                 1160        1170        1180        1190        1200
              GCT TGG AAT TCA AAA ACT TCC ACT TTA ACA ATT AGT GTG AAT AGC CAA
              CGA ACC TTA AGT TTT TGA AGG TGA AAT TGT TAA TCA CAC TTA TCG GTT
               A   W   N   S   K   T   S   T   L   T   I   S   V   N   S   Q>

                 1210        1220        1230        1240
              AAA ACC AAA AAC CTT GTA TTC ACA AAA GAA GAC ACA ATA ACA GTA CAA
              TTT TGG TTT TTG GAA CAT AAG TGT TTT CTT CTG TGT TAT TGT CAT GTT
               K   T   K   N   L   V   F   T   K   E   D   T   I   T   V   Q>

        1250        1260        1270        1280        1290
        AAA TAC GAC TCA GCA GGC ACC AAT CTA GAA GGC AAA GCA GTC GAA ATT
        TTT ATG CTG AGT CGT CCG TGG TTA GAT CTT CCG TTT CGT CAG CTT TAA
         K   Y   D   S   A   G   T   N   L   E   G   K   A   V   E   I>

        1300        1310        1320        1330
        ACA ACA CTT AAA GAA CTT AAA AAC GCT TTA AAA TAA
        TGT TGT GAA TTT CTT GAA TTT TTG CGA AAT TTT ATT
         T   T   L   K   E   L   K   N   A   L   K   *>
```

FIG. 65C

```
            10                  20                  30                  40
ATG GCT TGT AAT AAT TCA GGT GGG GAT TCT GCA TCT ACT AAT CCT GAT
TAC CGA ACA TTA TTA AGT CCA CCC CTA AGA CGT AGA TGA TTA GGA CTA
 M   A   C   N   N   S   G   G   D   S   A   S   T   N   P   D>

50          60                  70                  80                  90
GAG TCT GCA AAA GGA CCT AAT CTT ACC GTA ATA AGC AAA AAA ATT ACA
CTC AGA CGT TTT CCT GGA TTA GAA TGG CAT TAT TCG TTT TTT TAA TGT
 E   S   A   K   G   P   N   L   T   V   I   S   K   K   I   T>

  100               110                 120                 130                 140
GAT TCT AAT GCA TTT TTA CTG GCT GTG AAA GAA GTT GAG GCT TTG CTT
CTA AGA TTA CGT AAA AAT GAC CGA CAC TTT CTT CAA CTC CGA AAC GAA
 D   S   N   A   F   L   L   A   V   K   E   V   E   A   L   L>

    150                 160                 170                 180                 190
TCA TCT ATA GAT GAA CTT TCT AAA GCT ATT GGT AAA AAA ATA AAA AAT
AGT AGA TAT CTA CTT GAA AGA TTT CGA TAA CCA TTT TTT TAT TTT TTA
 S   S   I   D   E   L   S   K   A   I   G   K   K   I   K   N>

        200                 210                 220                 230                 240
GAT GGT ACT TTA GAT AAC GAA GCA AAT CGA AAC GAA TCA TTG ATA GCA
CTA CCA TGA AAT CTA TTG CTT CGT TTA GCT TTG CTT AGT AAC TAT CGT
 D   G   T   L   D   N   E   A   N   R   N   E   S   L   I   A>

            250                 260                 270                 280
GGA GCT TAT GAA ATA TCA AAA CTA ATA ACA CAA AAA TTA AGT GTA TTG
CCT CGA ATA CTT TAT AGT TTT GAT TAT TGT GTT TTT AAT TCA CAT AAC
 G   A   Y   E   I   S   K   L   I   T   Q   K   L   S   V   L>

290             300                 310                 320                 330
AAT TCA GAA GAA TTA AAG GAA AAA ATT AAA GAG GCT AAG GAT TGT TCC
TTA AGT CTT CTT AAT TTC CTT TTT TAA TTT CTC CGA TTC CTA ACA AGG
 N   S   E   E   L   K   E   K   I   K   E   A   K   D   C   S>

  340               350                 360                 370                 380
GAA AAA TTT ACT ACT AAG CTA AAA GAT AGT CAT GCA GAG CTT GGT ATA
CTT TTT AAA TGA TGA TTC GAT TTT CTA TCA GTA CGT CTC GAA CCA TAT
 E   K   F   T   T   K   L   K   D   S   H   A   E   L   G   I>

    390                 400                 410                 420                 430
CAA AGC GTT CAG GAT GAT AAT GCA AAA AAA GCT ATT TTA AAA ACA CAT
GTT TCG CAA GTC CTA CTA TTA CGT TTT TTT CGA TAA AAT TTT TGT GTA
 Q   S   V   Q   D   D   N   A   K   K   A   I   L   K   T   H>

        440                 450                 460                 470                 480
GGA ACT AAA GAC AAG GGT GCT AAA GAA CTT GAA GAG TTA TTT AAA TCA
CCT TGA TTT CTG TTC CCA CGA TTT CTT GAA CTT CTC AAT AAA TTT AGT
 G   T   K   D   K   G   A   K   E   L   E   E   L   F   K   S>

            490                 500                 510                 520
CTA GAA AGC TTG TCA AAA GCA GCG CAA GCA GCA TTA ACT AAT TCA GTT
GAT CTT TCG AAC AGT TTT CGT CGC GTT CGT CGT AAT TGA TTA AGT CAA
 L   E   S   L   S   K   A   A   Q   A   A   L   T   N   S   V>
```

FIG. 66A

```
530         540         550         560         570
AAA GAG CTT ACA AAT CCT GTT GTG GCA GAA AGT CCA AAA AAA CCT TCC
TTT CTC GAA TGT TTA GGA CAA CAC CGT CTT TCA GGT TTT TTT GGA AGG
K   E   L   T   N   P   V   V   A   E   S   P   K   K   P   S>

580         590         600         610         620
ATG GCC GTT TCA GTA GAT TTG CCT GGT GAA ATG AAA GTT CTT GTA AGC
TAC CGG CAA AGT CAT CTA AAC GGA CCA CTT TAC TTT CAA GAA CAT TCG
M   A   V   S   V   D   L   P   G   E   M   K   V   L   V   S>

630         640         650         660         670
AAA GAA AAA AAC AAA GAC GGC AAG TAC GAT CTA ATT GCA ACA GTA GAC
TTT CTT TTT TTG TTT CTG CCG TTC ATG CTA GAT TAA CGT TGT CAT CTG
K   E   K   N   K   D   G   K   Y   D   L   I   A   T   V   D>

680         690         700         710         720
AAG CTT GAG CTT AAA GGA ACT TCT GAT AAA AAC AAT GGA TCT GGA GTA
TTC GAA CTC GAA TTT CCT TGA AGA CTA TTT TTG TTA CCT AGA CCT CAT
K   L   E   L   K   G   T   S   D   K   N   N   G   S   G   V>

730         740         750         760
CTT GAA GGC GTA AAA GCT GAC AAA AGT AAA GTA AAA TTA ACA ATT TCT
GAA CTT CCG CAT TTT CGA CTG TTT TCA TTT CAT TTT AAT TGT TAA AGA
L   E   G   V   K   A   D   K   S   K   V   K   L   T   I   S>

770         780         790         800         810
GAC GAT CTA GGT CAA ACC ACA CTT GAA GTT TTC AAA GAA GAT GGC AAA
CTG CTA GAT CCA GTT TGG TGT GAA CTT CAA AAG TTT CTT CTA CCG TTT
D   D   L   G   Q   T   T   L   E   V   F   K   E   D   G   K>

820         830         840         850         860
ACA CTA GTA TCA AAA AAA GTA ACT TCC AAA GAC AAG TCA TCA ACA GAA
TGT GAT CAT AGT TTT TTT CAT TGA AGG TTT CTG TTC AGT AGT TGT CTT
T   L   V   S   K   K   V   T   S   K   D   K   S   S   T   E>

870         880         890         900         910
GAA AAA TTC AAT GAA AAA GGT GAA GTA TCT GAA AAA ATA ATA ACA AGA
CTT TTT AAG TTA CTT TTT CCA CTT CAT AGA CTT TTT TAT TAT TGT TCT
E   K   F   N   E   K   G   E   V   S   E   K   I   I   T   R>

920         930         940         950         960
GCA GAC GGA ACC AGA CTT GAA TAC ACA GGA ATT AAA AGC GAT GGA TCT
CGT CTG CCT TGG TCT GAA CTT ATG TGT CCT TAA TTT TCG CTA CCT AGA
A   D   G   T   R   L   E   Y   T   G   I   K   S   D   G   S>

970         980         990         1000
GGA AAA GCT AAA GAG GTT TTA AAA AAA TTT ACT CTT GAA GGA AAA GTA
CCT TTT CGA TTT CTC CAA AAT TTT TTT AAA TGA GAA CTT CCT TTT CAT
G   K   A   K   E   V   L   K   K   F   T   L   E   G   K   V>

1010        1020        1030        1040        1050
GCT AAT GAT AAA GTA ACA TTG GAA GTA AAA GAA GGA ACC GTT ACT TTA
CGA TTA CTA TTT CAT TGT AAC CTT CAT TTT CTT CCT TGG CAA TGA AAT
A   N   D   K   V   T   L   E   V   K   E   G   T   V   T   L>

1060        1070        1080        1090        1100
AGT AAG AAC ATT TCA AAA TCT GGG GAA GTT TCA GTT GAA CTT AAT GAC
```

FIG. 66B

```
TCA TTC TTG TAA AGT TTT AGA CCC CTT CAA AGT CAA CTT GAA TTA CTG
S   K   N   I   S   K   S   G   E   V   S   V   E   L   N   D>

   1110          1120          1130          1140          1150
ACT GAC AGT AGT GCT GCT ACT AAA AAA ACT GCA GCT TGG AAT TCA AAA
TGA CTG TCA TCA CGA CGA TGA TTT TTT TGA CGT CGA ACC TTA AGT TTT
T   D   S   S   A   A   T   K   K   T   A   A   W   N   S   K>

      1160          1170          1180          1190          1200
ACT TCT ACT TTA ACA ATT AGT GTT AAC AGC AAA AAA ACT ACA CAA CTT
TGA AGA TGA AAT TGT TAA TCA CAA TTG TCG TTT TTT TGA TGT GTT GAA
T   S   T   L   T   I   S   V   N   S   K   K   T   T   Q   L>

         1210          1220          1230          1240
GTG TTT ACT AAA CAA GAC ACA ATA ACT GTA CAA AAA TAC GAC TCC GCA
CAC AAA TGA TTT GTT CTG TGT TAT TGA CAT GTT TTT ATG CTG AGG CGT
V   F   T   K   Q   D   T   I   T   V   Q   K   Y   D   S   A>

1250          1260          1270          1280          1290
GGT ACC AAT TTA GAA GGC ACA GCA GTC GAA ATT AAA ACA CTT GAT GAA
CCA TGG TTA AAT CTT CCG TGT CGT CAG CTT TAA TTT TGT GAA CTA CTT
G   T   N   L   E   G   T   A   V   E   I   K   T   L   D   E>

1300          1310
CTT AAA AAC GCT TTA AAA TAA
GAA TTT TTG CGA AAT TTT ATT
L   K   N   A   L   K   *>
```

FIG. 66C

```
          10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50                  60                  70                  80                  90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
A   D   E   S   V   K   G   P   N   L   T   E   I   N   K   K>

 100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

    150                 160                 170                 180                 190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
L   L   S   S   I   D   E   I   A   A   K   A   I   G   K   K>

       200                 210                 220                 230                 240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
I   H   Q   N   N   G   L   D   T   E   N   N   H   N   G   S>

           250                 260                 270                 280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
L   L   A   G   A   Y   A   I   S   T   L   I   K   Q   K   L>

290                 300                 310                 320                 330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
D   G   L   K   N   E   G   L   K   E   K   I   D   A   A   K>

340                 350                 360                 370                 380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
K   C   S   E   T   F   T   N   K   L   K   E   K   H   T   D>

   390                 400                 410                 420                 430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
L   G   K   E   G   V   T   D   A   D   A   K   E   A   I   L>

      440                 450                 460                 470                 480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
K   A   N   G   T   K   T   K   G   A   E   E   L   G   K   L>

          490                 500                 510                 520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
F   E   S   V   E   V   L   S   K   A   A   K   E   M   L   A>
```

FIG. 67A

```
530        540        550        560        570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
N   S   V   K   E   L   T   S   P   V   V   A   E   S   P   K>

580        590        600        610        620
AAA CCT TCC ATG GCC AAG CAA AAT GTT TCT GAA AAA ATA ATA ACA AGA
TTT GGA AGG TAC CGG TTC GTT TTA CAA AGA CTT TTT TAT TAT TGT TCT
K   P   S   M   A   K   Q   N   V   S   E   K   I   I   T   R>

630        640        650        660        670
GCA GAC GGA ACC AGA CTT GAA TAC ACA GGA ATT AAA AGC GAT GGA TCT
CGT CTG CCT TGG TCT GAA CTT ATG TGT CCT TAA TTT TCG CTA CCT AGA
A   D   G   T   R   L   E   Y   T   G   I   K   S   D   G   S>

680        690        700        710        720
GGA AAA GCT AAA GAG GTT TTA AAA GGC TAT GTT CTT GAA GGA ACT CTA
CCT TTT CGA TTT CTC CAA AAT TTT CCG ATA CAA GAA CTT CCT TGA GAT
G   K   A   K   E   V   L   K   G   Y   V   L   E   G   T   L>

730        740        750        760
ACT GCT GAA AAA ACA ACA TTG GTG GTT AAA GAA GGA ACT GTT ACT TTA
TGA CGA CTT TTT TGT TGT AAC CAC CAA TTT CTT CCT TGA CAA TGA AAT
T   A   E   K   T   T   L   V   V   K   E   G   T   V   T   L>

770        780        790        800        810
AGC AAA AAT ATT TCA AAA TCT GGG GAA GTT TCA GTT GAA CTT AAT GAC
TCG TTT TTA TAA AGT TTT AGA CCC CTT CAA AGT CAA CTT GAA TTA CTG
S   K   N   I   S   K   S   G   E   V   S   V   E   L   N   D>

820        830        840        850        860
ACT GAC AGT AGT GCT GCT ACT AAA AAA ACT GCA GCT TGG AAT TCA GGC
TGA CTG TCA TCA CGA CGA TGA TTT TTT TGA CGT CGA ACC TTA AGT CCG
T   D   S   S   A   A   T   K   K   T   A   A   W   N   S   G>

870        880        890        900        910
ACT TCA ACT TTA ACA ATT ACT GTA AAC AGT AAA AAA ACT AAA GAC CTT
TGA AGT TGA AAT TGT TAA TGA CAT TTG TCA TTT TTT TGA TTT CTG GAA
T   S   T   L   T   I   T   V   N   S   K   K   T   K   D   L>

920        930        940        950        960
GTG TTT ACA AAA GAA AAC ACA ATT ACA GTA CAA CAA TAC GAC TCA AAT
CAC AAA TGT TTT CTT TTG TGT TAA TGT CAT GTT GTT ATG CTG AGT TTA
V   F   T   K   E   N   T   I   T   V   Q   Q   Y   D   S   N>

970        980        990        1000
GGC ACC AAA TTA GAG GGG TCA GCA GTT GAA ATT ACA AAA CTT GAT GAA
CCG TGG TTT AAT CTC CCC AGT CGT CAA CTT TAA TGT TTT GAA CTA CTT
G   T   K   L   E   G   S   A   V   E   I   T   K   L   D   E>

1010       1020
ATT AAA AAC GCT TTA AAA TAA
TAA TTT TTG CGA AAT TTT ATT
I   K   N   A   L   K   *>
```

FIG. 67B

```
           10          20          30          40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50          60          70          80          90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
A   D   E   S   V   K   G   P   N   L   T   E   I   N   K   K>

  100         110         120         130         140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

    150         160         170         180         190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
L   L   S   S   I   D   E   I   A   A   K   A   I   G   K   K>

      200         210         220         230         240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
I   H   Q   N   N   G   L   D   T   E   N   N   H   N   G   S>

        250         260         270         280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
L   L   A   G   A   Y   A   I   S   T   L   I   K   Q   K   L>

290         300         310         320         330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
D   G   L   K   N   E   G   L   K   E   K   I   D   A   A   K>

340         350         360         370         380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
K   C   S   E   T   F   T   N   K   L   K   E   K   H   T   D>

  390         400         410         420         430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
L   G   K   E   G   V   T   D   A   D   A   K   E   A   I   L>

    440         450         460         470         480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
K   A   N   G   T   K   T   K   G   A   E   E   L   G   K   L>

      490         500         510         520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
F   E   S   V   E   V   L   S   K   A   A   K   E   M   L   A>
```

FIG. 68A

```
530         540          550         560         570
 AAT TCA GTT AAA GAG CTT ACA AGC CCT GTT GTG GCA GAA AGT CCA AAA
 TTA AGT CAA TTT CTC GAA TGT TCG GGA CAA CAC CGT CTT TCA GGT TTT
 N   S   V   K   E   L   T   S   P   V   V   A   E   S   P   K>

 580         590          600         610         620
AAA CCT TCC ATG GCC AAG CAA AAT GTA TCT GAA AAA ATA ATA ACA AGA
TTT GGA AGG TAC CGG TTC GTT TTA CAT AGA CTT TTT TAT TAT TGT TCT
K   P   S   M   A   K   Q   N   V   S   E   K   I   I   T   R>

   630         640         650         660         670
GCA GAC GGA ACC AGA CTT GAA TAC ACA GGA ATT AAA AGC GAT GGA TCT
CGT CTG CCT TGG TCT GAA CTT ATG TGT CCT TAA TTT TCG CTA CCT AGA
A   D   G   T   R   L   E   Y   T   G   I   K   S   D   G   S>

      680         690         700         710         720
GGA AAA GCT AAA GAG GTT TTA AAA GGC TAT GTT CTT GAA GGA ACT CTA
CCT TTT CGA TTT CTC CAA AAT TTT CCG ATA CAA GAA CTT CCT TGA GAT
G   K   A   K   E   V   L   K   G   Y   V   L   E   G   T   L>

         730         740         750         760
ACT GCT GAA AAA ACA ACA TTG GTG GTT AAA GAA GGA ACT GTT ACT TTA
TGA CGA CTT TTT TGT TGT AAC CAC CAA TTT CTT CCT TGA CAA TGA AAT
T   A   E   K   T   T   L   V   V   K   E   G   T   V   T   L>

770         780         790         800         810
 AGC AAA AAT ATT TCA AAA TCT GGG GAA GTT TCA GTT GAA CTT AAT GAC
 TCG TTT TTA TAA AGT TTT AGA CCC CTT CAA AGT CAA CTT GAA TTA CTG
 S   K   N   I   S   K   S   G   E   V   S   V   E   L   N   D>

 820         830         840         850         860
ACT GAC AGT AGT GCT GCT ACT AAA AAA ACT GCA GCT TGG AAT TCA AAA
TGA CTG TCA TCA CGA CGA TGA TTT TTT TGA CGT CGA ACC TTA AGT TTT
T   D   S   S   A   A   T   K   K   T   A   A   W   N   S   K>

   870         880         890         900         910
ACT TCC ACT TTA ACA ATT AGT GTG AAT AGC CAA AAA ACC AAA AAC CTT
TGA AGG TGA AAT TGT TAA TCA CAC TTA TCG GTT TTT TGG TTT TTG GAA
T   S   T   L   T   I   S   V   N   S   Q   K   T   K   N   L>

      920         930         940         950         960
GTA TTC ACA AAA GAA GAC ACA ATA ACA GTA CAA AAA TAC GAC TCA GCA
CAT AAG TGT TTT CTT CTG TGT TAT TGT CAT GTT TTT ATG CTG AGT CGT
V   F   T   K   E   D   T   I   T   V   Q   K   Y   D   S   A>

         970         980         990         1000
GGC ACC AAT CTA GAA GGC AAA GCA GTC GAA ATT ACA ACA CTT AAA GAA
CCG TGG TTA GAT CTT CCG TTT CGT CAG CTT TAA TGT TGT GAA TTT CTT
G   T   N   L   E   G   K   A   V   E   I   T   T   L   K   E>

1010        1020
 CTT AAA AAC GCT TTA AAA TAA
 GAA TTT TTG CGA AAT TTT ATT
 L   K   N   A   L   K   *>
```

FIG. 68B

```
                10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50                  60                  70                  80                  90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
A   D   E   S   V   K   G   P   N   L   T   E   I   N   K   K>

 100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

   150                 160                 170                 180                 190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
L   L   S   S   I   D   E   I   A   A   K   A   I   G   K   K>

        200                 210                 220                 230                 240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
I   H   Q   N   N   G   L   D   T   E   N   N   H   N   G   S>

            250                 260                 270                 280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
L   L   A   G   A   Y   A   I   S   T   L   I   K   Q   K   L>

290             300                 310                 320                 330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
D   G   L   K   N   E   G   L   K   E   K   I   D   A   A   K>

340             350                 360                 370                 380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
K   C   S   E   T   F   T   N   K   L   K   E   K   H   T   D>

  390                 400                 410                 420                 430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
L   G   K   E   G   V   T   D   A   D   A   K   E   A   I   L>

      440                 450                 460                 470                 480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
K   A   N   G   T   K   T   K   G   A   E   E   L   G   K   L>

          490                 500                 510                 520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
F   E   S   V   E   V   L   S   K   A   A   K   E   M   L   A>
```

FIG. 69A

```
530          540           550          560          570
 AAT TCA GTT AAA GAG CTT ACA AGC CCT GTT GTG GCA GAA AGT CCA AAA
 TTA AGT CAA TTT CTC GAA TGT TCG GGA CAA CAC CGT CTT TCA GGT TTT
 N   S   V   K   E   L   T   S   P   V   V   A   E   S   P   K>

 580          590          600          610          620
 AAA CCT TCC ATG GCC AAG CAA AAT GTA TCT GAA AAA ATA ATA ACA AGA
 TTT GGA AGG TAC CGG TTC GTT TTA CAT AGA CTT TTT TAT TAT TGT TCT
 K   P   S   M   A   K   Q   N   V   S   E   K   I   I   T   R>

   630          640          650          660          670
 GCA GAC GGA ACC AGA CTT GAA TAC ACA GGA ATT AAA AGC GAT GGA TCT
 CGT CTG CCT TGG TCT GAA CTT ATG TGT CCT TAA TTT TCG CTA CCT AGA
 A   D   G   T   R   L   E   Y   T   G   I   K   S   D   G   S>

       680          690          700          710          720
 GGA AAA GCT AAA GAG GTT TTA AAA GGC TAT GTT CTT GAA GGA ACT CTA
 CCT TTT CGA TTT CTC CAA AAT TTT CCG ATA CAA GAA CTT CCT TGA GAT
 G   K   A   K   E   V   L   K   G   Y   V   L   E   G   T   L>

         730          740          750          760
 ACT GCT GAA AAA ACA ACA TTG GTG GTT AAA GAA GGA ACT GTT ACT TTA
 TGA CGA CTT TTT TGT TGT AAC CAC CAA TTT CTT CCT TGA CAA TGA AAT
 T   A   E   K   T   T   L   V   V   K   E   G   T   V   T   L>

770          780          790          800          810
 AGC AAA AAT ATT TCA AAA TCT GGG GAA GTT TCA GTT GAA CTT AAT GAC
 TCG TTT TTA TAA AGT TTT AGA CCC CTT CAA AGT CAA CTT GAA TTA CTG
 S   K   N   I   S   K   S   G   E   V   S   V   E   L   N   D>

 820          830          840          850          860
 ACT GAC AGT AGT GCT GCT ACT AAA AAA ACT GCA GCT TGG AAT TCA AAA
 TGA CTG TCA TCA CGA CGA TGA TTT TTT TGA CGT CGA ACC TTA AGT TTT
 T   D   S   S   A   A   T   K   K   T   A   A   W   N   S   K>

  870          880          890          900          910
 ACT TCT ACT TTA ACA ATT AGT GTT AAC AGC AAA AAA ACT ACA CAA CTT
 TGA AGA TGA AAT TGT TAA TCA CAA TTG TCG TTT TTT TGA TGT GTT GAA
 T   S   T   L   T   I   S   V   N   S   K   K   T       Q   L>

     920          930          940          950          960
 GTG TTT ACT AAA CAA GAC ACA ATA ACT GTA CAA AAA TAC GAC TCC GCA
 CAC AAA TGA TTT GTT CTG TGT TAT TGA CAT GTT TTT ATG CTG AGG CGT
 V   F   T   K   Q   D   T   I   T   V   Q   K   Y   D   S   A>

         970          980          990          1000
 GGT ACC AAT TTA GAA GGC ACA GCA GTC GAA ATT AAA ACA CTT GAT GAA
 CCA TGG TTA AAT CTT CCG TGT CGT CAG CTT TAA TTT TGT GAA CTA CTT
 G   T   N   L   E   G   T   A   V   E   I   K   T   L   D   E>

1010         1020
 CTT AAA AAC GCT TTA AAA TAA
 GAA TTT TTG CGA AAT TTT ATT
 L   K   N   A   L   K   *>
```

FIG. 69B

```
                 10                 20                 30                 40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50                 60                 70                 80                 90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
A   D   E   S   V   K   G   P   N   L   T   E   I   S   K   K>

   100                110                120                130                140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

    150                160                170                180                190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
L   L   S   S   I   D   E   I   A   A   K   A   I   G   K   K>

        200                210                220                230                240
ATA CAC CAA AAT AAT GGT TTG GAT ACC GAA TAT AAT CAC AAT GGA TCA
TAT GTG GTT TTA TTA CCA AAC CTA TGG CTT ATA TTA GTG TTA CCT AGT
I   H   Q   N   N   G   L   D   T   E   Y   N   H   N   G   S>

            250                260                270                280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
L   L   A   G   A   Y   A   I   S   T   L   I   K   Q   K   L>

290                300                310                320                330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
D   G   L   K   N   E   G   L   K   E   K   I   D   A   A   K>

  340                350                360                370                380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
K   C   S   E   T   F   T   N   K   L   K   E   K   H   T   D>

     390                400                410                420                430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
L   G   K   E   G   V   T   D   A   D   A   K   E   A   I   L>

        440                450                460                470                480
AAA ACA AAT GGT ACT AAA ACT AAA GGT GCT GAA GAA CTT GGA AAA TTA
TTT TGT TTA CCA TGA TTT TGA TTT CCA CGA CTT CTT GAA CCT TTT AAT
K   T   N   G   T   K   T   K   G   A   E   E   L   G   K   L>

            490                500                510                520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
F   E   S   V   E   V   L   S   K   A   A   K   E   M   L   A>
```

FIG. 70A

```
530        540        550        560        570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
N   S   V   K   E   L   T   S   P   V   V   A   E   S   P   K>

 580        590        600        610        620
AAA CCT TCC ATG GCC AAG CAA AAT GTT ACA TCT GAA AAA ACA ATA GTA
TTT GGA AGG TAC CGG TTC GTT TTA CAA TGT AGA CTT TTT TGT TAT CAT
K   P   S   M   A   K   Q   N   V   T   S   E   K   T   I   V>

   630        640        650        660        670
AGA GCA AAT GGA ACC AGA CTT GAA TAC ACA GAC ATA AAA AGC GAT GGA
TCT CGT TTA CCT TGG TCT GAA CTT ATG TGT CTG TAT TTT TCG CTA CCT
R   A   N   G   T   R   L   E   Y   T   D   I   K   S   D   G>

      680        690        700        710        720
TCC GGA AAA GCT AAA GAA GTT TTA AAA GAC TTT ACT CTT GAA GGA ACT
AGG CCT TTT CGA TTT CTT CAA AAT TTT CTG AAA TGA GAA CTT CCT TGA
S   G   K   A   K   E   V   L   K   D   F   T   L   E   G   T>

         730        740        750        760
CTA GCT GCT GAC GGC AAA ACA ACA TTG AAA GTT ACA GAA GGC ACT GTT
GAT CGA CGA CTG CCG TTT TGT TGT AAC TTT CAA TGT CTT CCG TGA CAA
L   A   A   D   G   K   T   T   L   K   V   T   E   G   T   V>

770        780        790        800        810
GTT TTA AGC AAG AAC ATT TTA AAA TCC GGA GAA ATA ACA GTT GCA CTT
CAA AAT TCG TTC TTG TAA AAT TTT AGG CCT CTT TAT TGT CAA CGT GAA
V   L   S   K   N   I   L   K   S   G   E   I   T   V   A   L>

 820        830        840        850        860
GAT GAC TCT GAC ACT ACT CAG GCT ACT AAA AAA ACT GGA AAA TGG GAT
CTA CTG AGA CTG TGA TGA GTC CGA TGA TTT TTT TGA CCT TTT ACC CTA
D   D   S   D   T   T   Q   A   T   K   K   T   G   K   W   D>

   870        880        890        900        910
TCA AAT ACT TCC ACT TTA ACA ATT AGT GTG AAT AGC AAA AAA ACT AAA
AGT TTA TGA AGG TGA AAT TGT TAA TCA CAC TTA TCG TTT TTT TGA TTT
S   N   T   S   T   L   T   I   S   V   N   S   K   K   T   K>

      920        930        940        950        960
AAC ATT GTA TTT ACA AAA GAA GAC ACA ATA ACA GTA CAA AAA TAC GAC
TTG TAA CAT AAA TGT TTT CTT CTG TGT TAT TGT CAT GTT TTT ATG CTG
N   I   V   F   T   K   E   D   T   I   T   V   Q   K   Y   D>

         970        980        990        1000
TCA GCA GGC ACC AAT CTA GAA GGC AAC GCA GTC GAA ATT AAA ACA CTT
AGT CGT CCG TGG TTA GAT CTT CCG TTG CGT CAG CTT TAA TTT TGT GAA
S   A   G   T   N   L   E   G   N   A   V   E   I   K   T   L>

1010       1020       1030
GAT GAA CTT AAA AAC GCT TTA AAA TAG
CTA CTT GAA TTT TTG CGA AAT TTT ATC
D   E   L   K   N   A   L   K   *>
```

FIG. 70B

```
        10          20          30          40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50          60          70          80          90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
 A   D   E   S   V   K   G   P   N   L   T   E   I   N   K   K>

 100         110         120         130         140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

  150         160         170         180         190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

     200         210         220         230         240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
 I   H   Q   N   N   G   L   D   T   E   N   N   H   N   G   S>

        250         260         270         280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290         300         310         320         330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

340         350         360         370         380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

  390         400         410         420         430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

     440         450         460         470         480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
 K   A   N   G   T   K   T   K   G   A   E   E   L   G   K   L>

        490         500         510         520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

FIG. 71A 530 540 550 560 570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
N S V K E L T S P V V A E S P K>

580 590 600 610 620
AAA CCT TCC ATG GCC GTT TCA GTA GAT TTG CCT GGT GAA ATG AAA GTT
TTT GGA AGG TAC CGG CAA AGT CAT CTA AAC GGA CCA CTT TAC TTT CAA
K P S M A V S V D L P G E M K V>

630 640 650 660 670
CTT GTA AGC AAA GAA AAA AAC AAA GAC GGC AAG TAC GAT CTA ATT GCA
GAA CAT TCG TTT CTT TTT TTG TTT CTG CCG TTC ATG CTA GAT TAA CGT
L V S K E K N K D G K Y D L I A>

680 690 700 710 720
ACA GTA GAC AAG CTT GAG CTT AAA GGA ACT TCT GAT AAA AAC AAT GGA
TGT CAT CTG TTC GAA CTC GAA TTT CCT TGA AGA CTA TTT TTG TTA CCT
T V D K L E L K G T S D K N N G>

730 740 750 760
TCT GGA GTA CTT GAA GGC GTA AAA GCT GAC AAA AGT AAA GTA AAA TTA
AGA CCT CAT GAA CTT CCG CAT TTT CGA CTG TTT TCA TTT CAT TTT AAT
S G V L E G V K A D K S K V K L>

770 780 790 800 810
ACA ATT TCT GAC GAT CTA GGT CAA ACC ACA CTT GAA GTT TTC AAA GAA
TGT TAA AGA CTG CTA GAT CCA GTT TGG TGT GAA CTT CAA AAG TTT CTT
T I S D D L G Q T T L E V F K E>

820 830 840 850 860
GAT GGC AAA ACA CTA GTA TCA AAA AAA GTA ACT TCC AAA GAC AAG TCA
CTA CCG TTT TGT GAT CAT AGT TTT TTT CAT TGA AGG TTT CTG TTC AGT
D G K T L V S K K V T S K D K S>

870 880 890 900 910
TCA ACA GAA GAA AAA TTC AAT GAA AAA GGT GAA GTA TCT GAA AAA ATA
AGT TGT CTT CTT TTT AAG TTA CTT TTT CCA CTT CAT AGA CTT TTT TAT
S T E E K F N E K G E V S E K I>

920 930 940 950 960
ATA ACA AGA GCA GAC GGA ACC AGA CTT GAA TAC ACA GGA ATT AAA AGC
TAT TGT TCT CGT CTG CCT TGG TCT GAA CTT ATG TGT CCT TAA TTT TCG
I T R A D G T R L E Y T G I K S>

970 980 990 1000
GAT GGA TCT GGA AAA GCT AAA GAG GTT TTA AAA GGC TTT ACT CTT GAA
CTA CCT AGA CCT TTT CGA TTT CTC CAA AAT TTT CCG AAA TGA GAA CTT
D G S G K A K E V L K G F T L E>

1010 1020 1030 1040 1050
GGA AAA GTA GCT AAT GAT AAA GTA ACA TTG GAA GTA AAA GAA GGA ACC
CCT TTT CAT CGA TTA CTA TTT CAT TGT AAC CTT CAT TTT CTT CCT TGG
G K V A N D K V T L E V K E G T>

1060 1070 1080 1090 1100
GTT ACT TTA AGT AAG ATT TCA AAA TCT GGG GAA GTT TCA GTT GAA CTT

FIG. 71B

```
CAA TGA AAT TCA TTC TAA AGT TTT AGA CCC CTT CAA AGT CAA CTT GAA
V   T   L   S   K   I   S   K   S   G   E   V   S   V   E   L>

 1110            1120          1130          1140          1150
AAT GAC ACT GAC AGT AGT GCT GCT ACT AAA AAA ACT GCA GCT TGG AAT
TTA CTG TGA CTG TCA TCA CGA CGA TGA TTT TTT TGA CGT CGA ACC TTA
N   D   T   D   S   S   A   A   T   K   K   T   A   A   W   N>

     1160          1170           1180          1190          1200
TCA AAA ACT TCT ACT TTA ACA ATT AGT GTT AAC AGC AAA AAA ACT ACA
AGT TTT TGA AGA TGA AAT TGT TAA TCA CAA TTG TCG TTT TTT TGA TGT
S   K   T   S   T   L   T   I   S   V   N   S   K   K   T   T>

         1210          1220          1230          1240
CAA CTT GTG TTT ACT AAA CAA GAC ACA ATA ACT GTA CAA AAA TAC GAC
GTT GAA CAC AAA TGA TTT GTT CTG TGT TAT TGA CAT GTT TTT ATG CTG
Q   L   V   F   T   K   Q   D   T   I   T   V   Q   K   Y   D>

1250          1260          1270          1280          1290
    TCC GCA GGT ACC AAT TTA GAA GGC ACA GCA GTC GAA ATT AAA ACA CTT
    AGG CGT CCA TGG TTA AAT CTT CCG TGT CGT CAG CTT TAA TTT TGT GAA
    S   A   G   T   N   L   E   G   T   A   V   E   I   K   T   L>

1300          1310          1320
GAT GAA CTT AAA AAC GCT TTA AAA TAA
CTA CTT GAA TTT TTG CGA AAT TTT ATT
D   E   L   K   N   A   L   K   *>
```

FIG. 71C 10 20 30 40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M A C N N S G K D G N T S A N S>

50 60 70 80 90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
A D E S V K G P N L T E I S K K>

100 110 120 130 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I T D S N A V L L A V K E V E A>

150 160 170 180 190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
L L S S I D E L A K A I G K K I>

200 210 220 230 240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
K N D G S L D N E A N R N E S L>

250 260 270 280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
L A G A Y T I S T L I T Q K L S>

290 300 310 320 330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
K L N G S E G L K E K I A A A K>

340 350 360 370 380
AAA TGC TCT GAA GAG TTT AGT ACT AAA CTA AAA GAT AAT CAT GCA CAG
TTT ACG AGA CTT CTC AAA TCA TGA TTT GAT TTT CTA TTA GTA CGT GTC
K C S E E F S T K L K D N H A Q>

390 400 410 420 430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
L G I Q G V T D E N A K K A I L>

440 450 460 470 480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
K A N A A G K D K G V E E L E K>

490 500 510 520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
L S G S L E S L S K A A K E M L>

FIG. 72A

```
530          540          550          560          570
GCT AAT TCA GTT AAA GAG CTT ACA AGC CCT GTT GTC CAT GGC GTT TCA
CGA TTA AGT CAA TTT CTC GAA TGT TCG GGA CAA CAG GTA CCG CAA AGT
 A   N   S   V   K   E   L   T   S   P   V   V   H   G   V   S>

 580          590          600          610          620
GTA GAT TTG CCT GGT GAA ATG AAA GTT CTT GTA AGC AAA GAA AAA AAC
CAT CTA AAC GGA CCA CTT TAC TTT CAA GAA CAT TCG TTT CTT TTT TTG
 V   D   L   P   G   E   M   K   V   L   V   S   K   E   K   N>

     630          640          650          660          670
AAA GAC GGC AAG TAC GAT CTA ATT GCA ACA GTA GAC AAG CTT GAG CTT
TTT CTG CCG TTC ATG CTA GAT TAA CGT TGT CAT CTG TTC GAA CTC GAA
 K   D   G   K   Y   D   L   I   A   T   V   D   K   L   E   L>

         680          690          700          710          720
AAA GGA ACT TCT GAT AAA AAC AAT GGA TCT GGA GTA CTT GAA GGC GTA
TTT CCT TGA AGA CTA TTT TTG TTA CCT AGA CCT CAT GAA CTT CCG CAT
 K   G   T   S   D   K   N   N   G   S   G   V   L   E   G   V>

             730          740          750          760
AAA GCT GAC AAA AGT AAA GTA AAA TTA ACA ATT TCT GAC GAT CTA GGT
TTT CGA CTG TTT TCA TTT CAT TTT AAT TGT TAA AGA CTG CTA GAT CCA
 K   A   D   K   S   K   V   K   L   T   I   S   D   D   L   G>

770          780          790          800          810
CAA ACC ACA CTT GAA GTT TTC AAA GAA GAT GGC AAA ACA CTA GTA TCA
GTT TGG TGT GAA CTT CAA AAG TTT CTT CTA CCG TTT TGT GAT CAT AGT
 Q   T   T   L   E   V   F   K   E   D   G   K   T   L   V   S>

 820          830          840          850          860
AAA AAA GTA ACT TCC AAA GAC AAG TCA TCA ACA GAA GAA AAA TTC AAT
TTT TTT CAT TGA AGG TTT CTG TTC AGT AGT TGT CTT CTT TTT AAG TTA
 K   K   V   T   S   K   D   K   S   S   T   E   E   K   F   N>

     870          880          890          900          910
GAA AAA GGT GAA GTA TCT GAA AAA ATA ATA ACA AGA GCA GAC GGA ACC
CTT TTT CCA CTT CAT AGA CTT TTT TAT TAT TGT TCT CGT CTG CCT TGG
 E   K   G   E   V   S   E   K   I   I   T   R   A   D   G   T>

         920          930          940          950          960
AGA CTT GAA TAC ACA GGA ATT AAA AGC GAT GGA TCT GGA AAA GCT AAA
TCT GAA CTT ATG TGT CCT TAA TTT TCG CTA CCT AGA CCT TTT CGA TTT
 R   L   E   Y   T   G   I   K   S   D   G   S   G   K   A   K>

             970          980          990          1000
GAG GTT TTA AAA GGC TTT ACT CTT GAA GGA AAA GTA GCT AAT GAT AAA
CTC CAA AAT TTT CCG AAA TGA GAA CTT CCT TTT CAT CGA TTA CTA TTT
 E   V   L   K   G   F   T   L   E   G   K   V   A   N   D   K>

1010         1020         1030         1040         1050
GTA ACA TTG GAA GTA AAA GAA GGA ACC GTT ACT TTA AGT AAG ATT TCA
CAT TGT AAC CTT CAT TTT CTT CCT TGG CAA TGA AAT TCA TTC TAA AGT
 V   T   L   E   V   K   E   G   T   V   T   L   S   K   I   S>

1060         1070         1080         1090         1100
AAA TCT GGG GAA GTT TCA GTT GAA CTT AAT GAC ACT GAC AGT AGT GCT
```

FIG. 72B

```
TTT AGA CCC CTT CAA AGT CAA CTT GAA TTA CTG TGA CTG TCA TCA CGA
K   S   G   E   V   S   V   E   L   N   D   T   D   S   S   A>

 1110        1120        1130        1140        1150
GCT ACT AAA AAA ACT GCA GCT TGG AAT TCA AAA ACT TCT ACT TTA ACA
CGA TGA TTT TTT TGA CGT CGA ACC TTA AGT TTT TGA AGA TGA AAT TGT
A   T   K   K   T   A   A   W   N   S   K   T   S   T   L   T>

  1160        1170        1180        1190        1200
ATT AGT GTT AAC AGC AAA AAA ACT ACA CAA CTT GTG TTT ACT AAA CAA
TAA TCA CAA TTG TCG TTT TTT TGA TGT GTT GAA CAC AAA TGA TTT GTT
I   S   V   N   S   K   K   T   T   Q   L   V   F   T   K   Q>

      1210        1220        1230        1240
GAC ACA ATA ACT GTA CAA AAA TAC GAC TCC GCA GGT ACC AAT TTA GAA
CTG TGT TAT TGA CAT GTT TTT ATG CTG AGG CGT CCA TGG TTA AAT CTT
D   T   I   T   V   Q   K   Y   D   S   A   G   T   N   L   E>

1250        1260        1270        1280        1290
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
G   T   A   V   E   I   K   T   L   D   E   L   K   N   A   L>

 1300
AAA TAA
TTT ATT
```

FIG. 72C

RECOMBINANT CONSTRUCTS OF *BORRELIA BURGDORFERI*

RELATED APPLICATIONS

This application is a divisional of 10/369,100, filed Feb. 18, 2003, which is a continuation of International Application No. PCT/US01/24736, filed Aug. 7, 2001, published in English, which claims the benefit of U.S. Provisional Application No. 60/226,484, filed Aug. 18, 2000, said International Application No. PCT/US01/24736 also being a continuation-in-part of U.S. Ser. No. 09/666,017, filed Sep. 19, 2000 (abandoned), which is itself a continuation-in-part of U.S. Ser. No. 08/235,836 (now U.S. Pat. No. 6,248,562), filed Apr. 29, 1994, which is itself a continuation-in-part of U.S. Ser. No. 08/148,191, filed Nov. 1, 1993 (abandoned). The teachings of all of these applications are incorporated herein by reference in their entirety.

GOVERNMENT SUPPORT

The invention was supported, in whole or in part, by Grant 2R01AI37256-05A1 from the National Institute of Allergy and Infectious Diseases. The Government has certain rights in the invention.

BACKGROUND OF THE INVENTION

Lyme disease (Lyme borreliosis) is the most common tick-borne infectious disease in North America and Europe, and has been found in Russia, Japan, China and Australia. Lyme disease begins at the site of a tick bite, producing a primary infection with spread of the organism to secondary sites occurring during the course of infection. The causative bacterial agent of this disease is the spirochete *Borrelia burgdorferi*, which was first isolated and cultivated in 1982 (Burgdorferi, W. A. et al., *Science* 216: 1317–1319 (1982); Steere, A. R. et al., *N. Engl. J. Med.* 308: 733–740 (1983)). With that discovery, a wide array of clinical syndromes, described in both the European and American literature since the early 20th century, could be attributed to infection by *B. burgdorferi* (Afzelius, A., *Acta Derm. Venereol.* 2: 120–125 (1921); Bannwarth, A., *Arch. Psychiatr. Nervenkrankh.* 117: 161–185 (1944); Garin, C. and A. Bujadouz, *J. Med. Lyon* 71: 765–767 (1922); Herxheimer, K. and K. Hartmann, *Arch. Dermatol. Syphilol.* 61: 57–76, 255–300 (1902)).

Three pathogenic genospecies of *Borrelia, B. burgdorferi* sensu stricto (*B. burgdorferi* or B.b.s.s.), *B. afzelii* and *B. garinii* have been described (Baranton, G., et al., *Int. J. Syst. Bacteriol.* 42:378–383 (1992)). These are members of a species complex, *B. burgdorferi* sensu lato, which consists of at least 10 different genospecies (Piken, R. N., et al., *J. Invest. Dermatol.,* 110:211–214 (1998); Postic, D., et al., *Int. J. Syst. Bacteriol.* 44:743–752 (1994); Valsangiacomo, C. T., et al., *Int. J. Syst. Bacteriol.* 47:1–10 (1997)). The three genospecies, *B. burgdorferi* sensu stricto, *B. afzelii* and *B. garinii*, all are thought to be pathogenic and all are found in Europe. However, in North America, *B. burgdorferi* sensu stricto is the only identified pathogenic genospecies. Each of these three genospecies is associated with distinct clinical manifestations (Van Dam, A. P. et al., *Clin. Infect. Dis.* 17:708–717 (1993)). This implies that differences in genospecies may play an important role in the wide array of clinical manifestations observed in Lyme Disease.

OspA is a basic lipoprotein of approximately 31 kd, which is encoded on a large linear plasmid along with OspB, a basic lipoprotein of approximately 34 kd (Szczepanski, A., and J. L. Benach, *Microbiol. Rev.* 55:21 (1991)). Analysis of isolates of *B. burgdorferi* obtained from North America and Europe has demonstrated that OspA has antigenic variability, and that several distinct groups can be serologically and genotypically defined (Wilske, B., et al., *World J. Microbiol.* 7: 130 (1991)). Other *Borrelia* proteins demonstrate similar antigenic variability. Surprisingly, the immune response to these outer surface proteins tends to occur late in the disease, if at all (Craft, J. E. et al., *J Clin Invest.* 78: 934–939 (1986); Dattwyler, R. J. and B. J. Luft, *Rheum. Clin. North Am.* 15: 727–734 (1989)). Furthermore, patients acutely and chronically infected with *B. burgdorferi* respond variably to the different antigens, including OspA, OspB, OspC, OspD, p39, p41 and p93.

As an infected tick begins to feed on a mammal, the synthesis of another outer surface protein, outer surface protein C or OspC, is induced (Schwan, T. G., et al., *Proc. Natl. Acad. Sci.* 2:2909–2913 (1995)). Thus, in early infection, OspC is the major outer membrane protein expressed by the spirochete (Fung, B. P., et al., *Infect. Immun.* 62:3213–3221 (1994); Padula, S. J., et al., *J. Clin. Microbiol.,* 32:1733–1738 (1994)). Even through OspC has been demonstrated to have limited surface exposure (Cox, D. L., et al., *Proc. Natl. Acad. Sci.,* 93:7973–7978 (1996); Mathiesen, M. M., et al., *Infect. Immun.* 66:4073–4079 (1998)), OspC is a potent immunogen. Immunization with OspC is protective against tick-transmitted *Borrelia* infection (Gilmore Jr., R. D., *Infect. Immun.* 64:2234–2239 (1999)). However, because OspC is highly variable in its sequence, the protection is limited to the *Borrelia burgdorferi* strain expressing the same allele of OspC. Challenge with heterologous isolates, expressing other ospC alleles results in infection (Probert, W. S., et al., *J. Infect. D.,* 175:400–405 (1997)). OspC is a very diverse genetic locus (Jauris-Heipke, S., et al., *Med. Microbiol. Immunol.* 182:37–50 (1993)) as evidenced by the fact that Livey et al. found thirty-four alleles of OspC in seventy-six *B. burgdorferi* sensu lato isolates (Livey, I., et al., *Mol. Microbiol.* 18:257–269 (1995)).

Currently, Lyme Disease is treated with a range of antibiotics, e.g., tetracyclines, penicillin and cephalosporins. However, such treatment is not always successful in clearing the infection. Treatment is often delayed due to improper diagnosis with the deleterious effect that the infection proceeds to a chronic condition, where treatment with antibiotics is often not useful. One of the factors contributing to delayed treatment is the lack of effective diagnostic tools.

Vaccines against Lyme borreliosis have been attempted. Mice immunized with a recombinant form of OspA are protected from challenge with the same strain of *B. burgdorferi* from which the protein was obtained (Fikrig, E., et al., *Science* 250: 553–556 (1990)). Furthermore, passively transferred anti-OspA monoclonal antibodies (MAbs) have been shown to be protective in mice, and vaccination with a recombinant protein induced protective immunity against subsequent infection with the homologous strain of *B. burgdorferi* (Simon, M. M., et al., *J. Infect. Dis.* 164: 123 (1991)). In addition, there have been two independent trials of first generation vaccines for the prevention of Lyme disease that have studied the efficacy and safety of a vaccine based on recombinant outer surface protein A (OspA) (Sigal, L. H. et al., *N. Engl. J. Med* 339:216–222, 1998; Steere, A. C. et al., *N. Engl. J. Med.* 339:209–215, (1998)). However, a vaccine that consists of recombinant OspA may require frequent booster immunizations. An additional concern of OspA-based vaccines is the recent identification of a putative autoreactive OspA domain with a high degree of similarity to a region of human leukocyte function-associated antigen-1 (hLFA-1) (Gross, D. M. et al., *Science,* 281: 703–706 (1998)).

It has been noted that immunization with a single protein from a particular strain of *Borrelia* often does not confer resistance to that strain in all individuals (Fikrig, E. et al., *J. Immunol.* 7: 2256–1160 (1992)). There is considerable variation displayed in OspA, OspB and OspC, as well as p93, including the regions conferring antigenicity. Therefore, the degree and frequency of protection from vaccination with a protein from a single strain depend upon the response of the immune system to the particular variation, as well as the frequency of genetic variation in *B. burgdorferi*. In the case of vaccines directed against OspA, the vaccine is typically only effective against strains of *Borrelia* that express OspA that is homologous to OspA from which the vaccine was derived.

Another limitation of current OspA Lyme Disease vaccines is that they are directed against an antigen that is expressed predominantly in the tick vector. Indeed, recent reports have indicated that *Borrelia burgdorferi* in infected ticks alter their surface expression by increasing expression of OspC during ingestion of a blood meal (Schwan, T. G. et al., *Proc. Natl. Acad. Sci. USA,* 92: 2909–2913 (1995)). Thus, it seems that natural infection with *B. burgdorferi* does not elicit an antibody response to OspA, as it does against OspC.

Given the heterogeneity of antigenic determinants present in *Borrelia* proteins, a need exists for a vaccine and diagnostic tool which can provide immunogenicity to various strains and/or genospecies of *Borrelia burgdorferi*, as well as to more epitopes within a strain or genospecies. There is also a need for vaccines and diagnostic tools which detect antibody responses against immunoprotective targets that are expressed at different stages of the life cycle of *Borrelia burgdorferi*. This would allow for diagnosis and/or vaccination against all, or most forms, of *Borrelia* that cause systemic disease.

SUMMARY OF THE INVENTION

The current invention pertains to chimeric *Borrelia* proteins which include two or more antigenic *Borrelia* polypeptides which do not occur naturally (in nature) in the same protein in *Borrelia*, as well as the nucleic acids encoding such chimeric proteins. The proteins from which the antigenic polypeptides are derived can be from the same strain or genospecies of *Borrelia*, from different strains or genospecies, or from combinations of proteins from the same and from different strains or genospecies. Particular chimeric proteins, and the nucleotide sequences encoding them, are set forth in FIGS. 30–37 and 55–72.

The chimeric proteins of the current invention provide antigenic polypeptides of a variety of *Borrelia* strains and/or proteins within a single protein. Such proteins are particularly useful in immunodiagnostic assays to detect the presence of antibodies to native *Borrelia* in potentially infected individuals as well as to measure T-cell reactivity, and can therefore be used as immunodiagnostic reagents. These chimeric proteins are also useful in the generation of immune responses (such as antibody production) against proteins expressed by *Borrelia burgdorferi*. The chimeric proteins of the current invention are additionally useful as vaccine immunogens against *Borrelia* infection.

In one embodiment of the present invention, the chimeric proteins are made up of polypeptide fragments from Lyme Disease-causing strains of *Borrelia*. In another embodiment, the polypeptide fragments that make up the chimeric protein are from outer surface protein A (OspA) and outer surface protein C (OspC), which have the general structure of OspC linked via a peptide bond to the N-terminus of OspA. The present invention encompasses both lipidated and unlipidated chimeric proteins. In one embodiment, the OspA and OspC portions of the chimeric protein possess a lipidation signal. In other embodiments, either the OspA polypeptide portion, the OspC polypeptide portion, or both, do not include a lipidation signal.

The OspA portion of the chimeric polypeptide can itself comprise OspA portions from two or more strains of Lyme Disease-causing *Borrelia* as described herein and provided, for example, in FIGS. 23–29 and 43–46. In another embodiment, the OspA polypeptide comprises OspA portions from two or more genospecies of Lyme Disease-causing *Borrelia*, for example, wherein the genospecies are defined as *Borrelia burgdorferi* sensu stricto, *Borrelia afzelii* and *Borrelia garinii*. In this manner, the OspC and OspA polypeptide fragments that make up the chimeric protein can be from the same strain or genospecies of *Borrelia*, from different strains or genospecies of *Borrelia*, or from combinations of proteins from the same and from different strains or genospecies of *Borrelia.*

The present invention is also drawn to nucleic acids which encode a *Borrelia* chimeric protein. In a particular embodiment, the composition comprises a nucleic acid that encodes a chimeric protein of at least two polypeptides, wherein the first polypeptide comprises *Borrelia burgdorferi* OspC, and the second polypeptide comprises *Borrelia burgdorferi* OspA, such that OspC is upstream of OspA. The OspC and OspA nucleic acid fragments that make up the chimeric protein can be from the same strain or genospecies of *Borrelia*, from different strains or genospecies of *Borrelia*, or from combinations of proteins that are from the same and/or different strains or genospecies of *Borrelia.*

The present invention is also drawn to expression vectors which comprise an isolated DNA encoding a *Borrelia* chimeric protein. In one embodiment, the composition includes an expression vector comprising an isolated DNA which encodes an OspC/OspA chimeric protein as described herein. The present invention also encompasses host cells which comprise a recombinant nucleic acid encoding an OspC/OspA chimeric protein as described herein.

The present invention is also drawn to methods of making the *Borrelia* chimeric polypeptides described herein. In one embodiment, the method of making a chimeric *Borrelia* protein comprises selecting a polynucleotide sequence encoding OspC, or an antigenic portion thereof, selecting a polynucleotide sequence encoding OspA, or an antigenic portion thereof, and ligating these polynucleotide sequences together.

The present invention is also drawn to methods of delivering the *Borrelia* chimeric polypeptides described herein. In one embodiment, the method comprises administering the chimeric protein in a physiologically-acceptable carrier to an individual. As a result of the administration of the chimeric protein, the individual develops at least some immune response to the chimeric protein, e.g., the individual generates a humoral immune response, wherein antibodies are produced by the individual that recognize at least a portion of said chimeric polypeptide.

The present invention is also drawn to methods of delivering nucleic acids which encode the chimeric polypeptides described herein. In one embodiment, the method comprises administering the nucleic acid in a physiologically-acceptable carrier to an individual. As a result of the administration of the nucleic acid, the individual expresses the chimeric protein at least transiently and develops at least some immune response to the chimeric protein encoded by the nucleic acid, e.g., the individual generates a humoral immune response, wherein antibodies that recognize at least a portion of the chimeric polypeptide produced from the nucleic acid, are produced by the individual.

The invention also encompasses methods of using the chimeric proteins described herein in a diagnostic assay. As described herein, the method can be used to detect the presence of OspA- and/or OspC-specific antibodies in a sample, e.g., a host sample of interest. The method comprises contacting a sample, e.g., a host sample of interest, with the chimeric protein, under conditions, wherein antibodies, if present in the host sample, bind to the chimeric protein thereby forming antigen-antibody complexes. The antigen-antibody complexes are then detected. In this manner, the chimeric proteins of the present invention can be used to detect an immune response to Lyme Disease causing *Borrelia*.

The present invention is also drawn to diagnostic kits which comprise the chimeric polypeptides described herein. In one embodiment, the kit comprises a *Borrelia burgdorferi* OspC/OspA chimeric protein. The kit also includes reagents for detecting antibody-antigen complexes that are formed between the OspC/OspA chimeric protein and antibodies that are present in a sample, e.g., a user-supplied host sample.

The present invention is also drawn to pharmaceutical compositions which can be used to vaccinate and/or treat *Borrelia* infection in an animal or human. The pharmaceutical composition can be administered together with a physiologically-acceptable carrier and/or with suitable excipients and/or adjuvants.

The present invention is also drawn to methods of immunizing an animal or human against Lyme disease. In a particular embodiment, the method comprises administering a *Borrelia* chimeric OspC/OspA protein. The chimeric protein can be administered together with a physiologically-acceptable carrier, a suitable excipient and/or a suitable adjuvant, to an animal or human such that the animal or human develops an immune response to at least one of the OspC and/or OspA polypeptides of the composition.

By incorporating polypeptide fragments from multiple *Borrelia burgdorferi* proteins, the present invention provides a composition that has great utility for vaccines and diagnostic kits. As a result of the present invention, there exist diagnostic tools and vaccines that comprise both OspA and OspC antigens from various *Borrelia burgdorferi* strains and/or genospecies in a single protein. Since OspA is primarily expressed in the tick vector, and OspC is upregulated in response to the feeding of an infected tick on a mammal, this allows for a diagnostic tool or vaccine that can recognize antigens that are expressed at different stages of the life cycle of *Borrelia burgdorferi*. Thus, the chimeric proteins of the present invention can act at the level of the tick as well as the level of the host, in preventing infection and/or disease caused by *Borrelia*. Moreover, by incorporating unique polypeptide fragments from pathogenic families of *Borrelia*, such as *Borrelia burgdorferi* sensu stricto, *Borrelia* afzelii and *Borrelia* garinii, an improved diagnostic tool or vaccine is produced which can detect clinically important exposure to a wider variety of pathogenic *Borrelia*, while overlooking the remainder of non-pathogenic families of *Borrelia*. Furthermore, OspC polypeptides can be selected from strains of *Borrelia* that are associated with disseminated disease, as described in WO 00/78966, the teachings of which are incorporated herein in their entirety.

The present invention also provides a combination of *Borrelia* antigens in a single polypeptide that, when used as a vaccine, are expected to prevent Lyme disease from becoming systemic. The chimeric proteins of the present invention can be effective in preventing Lyme disease, as well as having a therapeutic effect on established infection, for example after the tick bite is noticed by the patient.

The present invention is drawn to both lipidated and unlipidated chimeric proteins. Unlipidated chimeric proteins, such as the OspC/OspA chimeric proteins described herein, have certain advantages over their lipidated counterparts. These advantages include simpler production methods, improved yields of protein and simpler purification methods. While the lack of a lipidation signal provides several advantages, it had been thought that the lipidation signal was required for immunogenicity. However, as described herein, the non-lipidated OspC/OspA chimeric proteins of the present invention elicit an immune response that is at least as broadly reactive as that of lipidated OspA and lipidated OspC control proteins. Moreover, the unlipidated OspC/OspA chimeric proteins of the present invention unexpectedly elicit an immune response to more than one genospecies and/or strain of Lyme disease-causing *Borrelia*, including genospecies and/or strains that were not used to generate the particular chimeric OspC/OspA immunogen.

For a better understanding of the present invention together with other and further objects, reference is made to the following description, taken together with the accompanying drawings.

BRIEF DESCRIPTION OF THE DRAWINGS

FIG. 2 is a comparison of the antigenic domains depicted in FIG. 1, for OspA in nine strains of *B. burgdorferi*. In Domain 1, A-B31 is SEQ ID NO: 187, A-TRo is SEQ ID NO: 187; A-K48 is SEQ ID NO: 188; A-DK29 is SEQ ID NO: 188; A-P/Gau is SEQ ID NO: 187; A-PKo is SEQ ID NO: 187; A-IP3 is SEQ ID NO: 189; A-IP90 is SEQ ID NO: 194; and A-25015 is SEQ ID NO: 187. In Domain 2, A-B31 is SEQ ID NO: 191, A-TRo is SEQ ID NO: 192; A-K48 is SEQ ID NO: 193; A-DK29 is SEQ ID NO: 193; A-P/Gau is SEQ ID NO: 194; A-PKo is SEQ ID NO: 194; A-IP3 is SEQ ID NO: 195; A-IP90 is SEQ ID NO: 192; and A-25015 is SEQ ID NO: 191. In Domain 3, A-B31 is SEQ ID NO: 196, A-TRo is SEQ ID NO: 197; A-K48 is SEQ ID NO: 198; A-DK29 is SEQ ID NO: 199; A-P/Gau is SEQ ID NO: 200; A-PKo is SEQ ID NO: 200; A-IP3 is SEQ ID NO: 200; A-IP90 is SEQ ID NO: 201; and A-25015 is SEQ ID NO: 202. In Domain 4, A-B31 is SEQ ID NO: 203, A-TRo is SEQ ID NO: 294; A-K48 is SEQ ID NO: 205; A-DK29 is SEQ ID NO: 205; A-P/Gau is SEQ ID NO: 206; A-PKo is SEQ ID NO: 206; A-IP3 is SEQ ID NO: 206; A-IP90 is SEQ ID NO: 205; and A-25015 is SEQ ID NO: 206.

FIG. 4 depicts the amino acid alignment of residues 200 through 220 for OspAs from strains B31 (SEQ ID NO: 207) and K48 (SEQ ID NO: 208) as well as for the site-directed mutants 613 (SEQ ID NO: 209), 625 (SEQ ID NO: 210), 640 (SEQ ID NO: 211), 613/625 (SEQ ID NO: 212), and 613/640 (SEQ ID NO: 213). The arrow indicates Trp216. Amino acid changes are underlined.

FIGS. 7A and 7B depict the nucleic acid sequence of OspA-B31 (SEQ ID NO. 6), and the encoded protein sequence (SEQ ID NO. 7).

FIGS. 8A, 8B and 8C depict the nucleic acid sequence of OspA-K48 (SEQ ID NO. 8), and the encoded protein sequence (SEQ ID NO. 9).

FIGS. 9A, 9B and 9C depict the nucleic acid sequence of OspA-PGau (SEQ ID NO. 10), and the encoded protein sequence (SEQ ID NO. 11).

FIGS. 10A and 10B depict the nucleic acid sequence of a portion of an OspA gene (SEQ ID NO. 185) and its encoded protein sequence (SEQ ID NO. 186).

FIGS. 11A, 11B and 11C depict the nucleic acid sequence of OspB-B31 (SEQ ID NO. 21), and the encoded protein sequence (SEQ ID NO. 22).

FIGS. 12A and 12B depict the nucleic acid sequence of OspC-B31 (SEQ ID NO. 29), and the encoded protein sequence (SEQ ID NO. 30).

FIGS. 13A and 13B depict the nucleic acid sequence of OspC-K48 (SEQ ID NO. 31), and the encoded protein sequence (SEQ ID NO. 32).

FIGS. 14A and 14B depict the nucleic acid sequence of OspC-PKo (SEQ ID NO. 33), and the encoded protein sequence (SEQ ID NO. 34).

FIGS. 15A and 15B depict the nucleic acid sequence of OspC-PTrob (SEQ ID NO. 35) and the encoded protein sequence (SEQ ID NO. 36).

FIGS. 16A, 16B, 16C, 16D and 16E depict the nucleic acid sequence of p93-B31 (SEQ ID NO. 65) and the encoded protein sequence (SEQ ID NO. 66).

FIG. 17 depicts the nucleic acid sequence of p93-K48 (SEQ ID NO. 67).

FIG. 18 depicts the nucleic acid sequence of p93-PBo (SEQ ID NO. 69).

FIG. 19 depicts the nucleic acid sequence of p93-PTrob (SEQ ID NO. 71).

FIG. 20 depicts the nucleic acid sequence of p93-PGAU (SEQ ID NO. 73).

FIG. 21 depicts the nucleic acid sequence of p93–25015 (SEQ ID NO. 77).

FIG. 22 depicts the nucleic acid sequence of p93-PKo (SEQ ID NO. 75).

FIGS. 23A, 23B and 23C depict the nucleic acid sequence of the OspA-K48/OspA-PGAU chimer (SEQ ID NO. 85) and the encoded chimeric protein sequence (SEQ ID NO. 86).

FIGS. 24A, 24B and 24C depict the nucleic acid sequence of the OspA-B31/OspA-PGAU chimer (SEQ ID NO. 88) and the encoded chimeric protein sequence (SEQ ID NO. 89).

FIGS. 25A and 25B depict the nucleic acid sequence of the OspA-B31/OspA-K48 chimer (SEQ ID NO. 91) and the encoded chimeric protein sequence (SEQ ID NO. 92).

FIGS. 26A, 26B and 26C depict the nucleic acid sequence of the OspA-B31/OspA-25015 chimer (SEQ ID NO. 94) and the encoded chimeric protein sequence (SEQ ID NO. 95).

FIGS. 27A, 27B and 27C depict the nucleic acid sequence of the OspA-K48/OspA-B31/OspA-K48 chimer (SEQ ID NO. 97) and the encoded chimeric protein sequence (SEQ ID NO. 98).

FIGS. 28A, 28B and 28C depict the nucleic acid sequence of the OspA-B31/OspA-K48/OspA-B31/OspA-K48 chimer (SEQ ID NO. 100) and the encoded chimeric protein sequence (SEQ ID NO. 101).

FIGS. 29A, 29B and 29C depict the nucleic acid sequence of the OspA-B31/OspB-B31 chimer (SEQ ID NO. 103) and the encoded chimeric protein sequence (SEQ ID NO. 104).

FIGS. 30A, 30B, 30C and 30D depict the nucleic acid sequence of the OspA-B31/OspB-B31/OspC-B31 chimer (SEQ ID NO. 106) and the encoded chimeric protein sequence (SEQ ID NO. 107).

FIGS. 31A, 31B, 31C and 31D depict the nucleic acid sequence of the OspC-B31/OspA-B31/OspB-B31 chimer (SEQ ID NO. 109) and the encoded chimeric protein sequence (SEQ ID NO. 110).

FIGS. 32A, 32B, 32C, 32D and 32E depict the nucleic acid sequence of the OspA-B31/p93-B31 chimer (SEQ ID NO. 111) and the encoded chimeric protein sequence (SEQ ID NO. 112).

FIGS. 33A, 33B, 33C and 33D depict the nucleic acid sequence of the OspB-B31/p41-B31 (122–234) chimer (SEQ ID NO. 113) and the encoded chimeric protein sequence (SEQ ID NO. 114).

FIGS. 34A, 34B, 34C and 34D depict the nucleic acid sequence of the OspB-B31/p41-B31 (122–295) chimer (SEQ ID NO. 115) and the encoded chimeric protein sequence (SEQ ID NO. 116).

FIGS. 35A, 35B and 35C depict the nucleic acid sequence of the OspB-B331/p41-B31 (140–234) chimer (SEQ ID NO. 117) and the encoded chimeric protein sequence (SEQ ID NO. 118).

FIGS. 36A, 36B, 36C and 36D depict the nucleic acid sequence of the OspB-B31/p41-B31 (140–295) chimer (SEQ ID NO. 119) and the encoded chimeric protein sequence (SEQ ID NO. 120).

FIGS. 37A, 37B, 37C, 37D and 37E depict the nucleic acid sequence of the OspB-B31/p41-B31 (122–234)/OspC-B31 chimer (SEQ ID NO. 121) and the encoded chimeric protein sequence (SEQ ID NO. 122).

FIGS. 38A, 38B, 38C and 38D depict an alignment of the nucleic acid sequences for OspC-B31 (SEQ ID NO. 29), OspC-PKo (SEQ ID NO. 33), OspC-PTrob (SEQ ID NO. 35), and OspC-K48 (SEQ ID NO. 31). Nucleic acids which are identical to those in the lead nucleic acid sequence (here, OspC-B31) are represented by a period (.); differing nucleic acids are shown in lower case letters.

FIGS. 39A, 39B, 39C and 39D depict an alignment of the nucleic acid sequences for OspD-PBo (SEQ ID NO. 123), OspD-PGAU (SEQ ID NO. 124), OspD-DK29 (SEQ ID NO. 125), and OspD-K48 (SEQ ID NO. 126). Nucleic acids which are identical to those in the lead nucleic acid sequence (here, OspD-PBo) are represented by a period (.); differing nucleic acids are shown in lower case letters.

FIGS. 40A, 40B and 40C depict the nucleic acid sequence of p41-B31 (SEQ ID NO. 127) and then encoded protein sequence (SEQ ID NO. 128).

FIGS. 41A, 41B, 41C, 41D, 41E, 41F, 41G and 41H depict an alignment of the nucleic acid sequences for p41-B31 (SEQ ID NO. 127), p41-PKa1 (SEQ ID NO. 129), p41-PGAU (SEQ ID NO. 51), p41-PBo (SEQ ID NO. 130), p41-DK29 (SEQ ID NO. 53), and p41-PKo (SEQ ID NO. 131). Nucleic acids which are identical to those in the lead nucleic acid sequence (here, p41-B31) are represented by a period (.); differing nucleic acids are shown in lower case letters.

FIGS. 42A, 42B, 42C, 42D, 42E, 42F, 42G, 42H, 42I, 42J, 42K, 42L, 42M, 42N, 42O and 42P depict an alignment of the nucleic acid sequences for OspA-B31 (SEQ ID NO. 6), OspA-PKa1 (SEQ ID NO. 132), OspA-N40 (SEQ ID NO. 133), OspA-ZS7 (SEQ ID NO. 134), OspA-25015 (SEQ ID NO. 12), OspA-PTrob (SEQ ID NO. 135), OspA-K48 (SEQ ID NO. 8), OspA-Hei (SEQ ID NO. 136), OspA-DK29 (SEQ ID NO. 49), OspA-Ip90 (SEQ ID NO. 50), OspA-PBo (Seq ID NO. 55), OspA-Ip3 (SEQ ID NO. 56), OspA-PKo (SEQ ID NO. 57), OspA-ACAI (SEQ ID NO. 58), and OspA-PGAU (SEQ ID NO. 10). Nucleic acids which are identical to those in the lead nucleic acid sequence (here, OspA-B31) are represented by a period (.); differing nucleic acids are shown in lower case letters.

FIGS. 43A and 43B depict the nucleic acid sequence of the OspA-Tro/OspA-Bo chimer (SEQ ID NO. 137) which encodes the chimeric protein sequence SEQ ID NO. 138.

FIGS. 44A and 44B depict the nucleic acid sequence of the OspA-PGAU/OspA-Bo chimer (SEQ ID NO. 139) which encodes the chimeric protein sequence SEQ ID NO. 140.

FIGS. 45A and 45B depict the nucleic acid sequence of the OspA-B31/OspA-PGAU/OspA-B31/OspA-K48 chimer (SEQ ID NO. 143) which encodes the chimeric protein sequence SEQ ID NO. 144.

FIGS. 46A and 46B depict the nucleic acid sequence of the OspA-PGAU/OspA-B31/OspA-K48 chimer (SEQ ID NO. 141) which encodes the chimeric protein sequence SEQ ID NO. 142.

FIGS. 55A, 55B and 55C depict the nucleic acid sequence of the OspC-B31 (bp 55–633)/OspA-B31 (bp 52–822) chimer (SEQ ID NO. 145) and the encoded chimeric protein sequence (SEQ ID NO. 146).

FIGS. 56A, 56B and 56C depict the nucleic acid sequence of the OspC-B31 (bp 55–624)/OspA-B31 (bp 52–822) chimer (SEQ ID NO. 147) and the encoded chimeric protein sequence (SEQ ID NO. 148).

FIGS. 57A, 57B and 57C depict the nucleic acid sequence of the OspC-C2 (bp 55–612)/OspA-B31 (bp 52–822) chimer (SEQ ID NO. 149) and the encoded chimeric protein sequence (SEQ ID NO. 150).

FIGS. 58A, 58B and 58C depict the nucleic acid sequence of the OspC-B31 (bp 55–633)/OspA-B31 (bp 52–651)/OspA-K48 (bp 652–820) chimer (SEQ ID NO. 151) and the encoded chimeric protein sequence (SEQ ID NO. 152).

FIGS. 59A, 59B and 59C depict the nucleic acid sequence of the OspC-C2 (bp 55–612)/OspA-B31 (bp 52–651)/OspA-K48 (bp 652–820) chimer (SEQ ID NO. 153) and the encoded chimeric protein sequence (SEQ ID NO. 154).

FIGS. 60A, 60B and 60C depict the nucleic acid sequence of the OspC-B31 (bp 55–633)/OspA-B31 (bp 52–651)/OspA-PKo (bp 652–820) chimer (SEQ ID NO. 155) and the encoded chimeric protein sequence (SEQ ID NO. 156).

FIGS. 61A, 61B and 61C depict the nucleic acid sequence of the OspC-C2 (bp 55–612)/OspA-B31 (bp 52–651)/OspA-PKo (bp 652–820) chimer (SEQ ID NO. 157) and the encoded chimeric protein sequence (SEQ ID NO. 158).

FIGS. 62A, 62B and 62C depict the nucleic acid sequence of the OspC-B31 (bp 55–633)/OspA-K48 (bp 52–654)/OspA-Tro (bp 655–819) chimer (SEQ ID NO. 159) and the encoded chimeric protein sequence (SEQ ID NO. 160).

FIGS. 63A, 63B and 63C depict the nucleic acid sequence of the OspC-C2 (bp 55–612)/OspA-K48 (bp 52–654)/OspA-Tro (bp 655–819) chimer (SEQ ID NO. 161) and the encoded chimeric protein sequence (SEQ ID NO. 162).

FIGS. 64A, 64B and 64C depict the nucleic acid sequence of the OspC-C 12 (bp 55–612)/OspA-B31 (bp 88–492)/OspA-PKo (bp 493–537)/OspA-B31 (bp 538–822) chimer (SEQ ID NO. 163) and the encoded chimeric protein sequence (SEQ ID NO. 164).

FIGS. 65A, 65B and 65C depict the nucleic acid sequence of the OspC-PKo (bp 55–639)/OspA-B31 (bp 88–492)/OspA-PKo (bp 493–537)/OspA-B31 (bp 538–651)/OspA-K48 (bp 652–825) chimer (SEQ ID NO. 165) and the encoded chimeric protein sequence (SEQ ID NO. 166).

FIGS. 66A, 66B and 66C depict the nucleic acid sequence of the OspC-Tro (bp 55–624)/OspA-B31 (bp 88–492)/OspA-PKo (bp 493–537)/OspA-B31 (bp 538–651)/OspA-PKo (bp 652–822) chimer (SEQ ID NO. 167) and the encoded chimeric protein sequence (SEQ ID NO. 168).

FIGS. 67A and 67B depict the nucleic acid sequence of the OspC-B31 (bp 55–633)/OspA-B31 (bp 394–820) chimer (SEQ ID NO. 169) and the encoded chimeric protein sequence (SEQ ID NO. 170).

FIGS. 68A and 68B depict the nucleic acid sequence of the OspC-B31 (bp 55–631)/OspA-B31 (bp 394–651)/OspA-K48 (bp 652–820) chimer (SEQ ID NO. 171) and the encoded chimeric protein sequence (SEQ ID NO. 172).

FIGS. 69A and 69B depict the nucleic acid sequence of the OspC-B31 (bp 55–633)/OspA-B31 (bp 394–651)/OspA-PKo (bp 652–820) chimer (SEQ ID NO. 173) and the encoded chimeric protein sequence (SEQ ID NO. 174).

FIGS. 70A and 70B depict the nucleic acid sequence of the OspC-B31 (bp 55–633)/OspA-K48 (bp 394–654)/OspA-Tro (bp 655–819) chimer (SEQ ID NO. 175) and the encoded chimeric protein sequence (SEQ ID NO. 176).

FIGS. 71A, 71B and 71C depict the nucleic acid sequence of the OspC-B31 (bp 55–633)/OspA-B31 (bp 88–492)/OspA-PKo (bp 493–537)/OspA-B31 (bp 541–651)/OspA-PKo (bp 652–822) chimer (SEQ ID NO. 177) and the encoded chimeric protein sequence (SEQ ID NO. 178); a variant of this sequence was also generated, where the N at position 190 of B31 OspA was deleted.

FIGS. 72A, 72B and 72C depict the nucleic acid sequence of the OspC-C2 (bp 55–612)/OspA-B31 (bp 88–492)/OspA-PKo (bp 493–537)/OspA-B31 (bp 541-651)/OspA-PKo (bp 652–822) chimer (SEQ ID NO. 179) and the encoded chimeric protein sequence (SEQ ID NO. 180); a variant of this sequence was also generated, where the N at position 190 of B31 OspA was deleted.

DETAILED DESCRIPTION OF THE INVENTION

Figure 1:
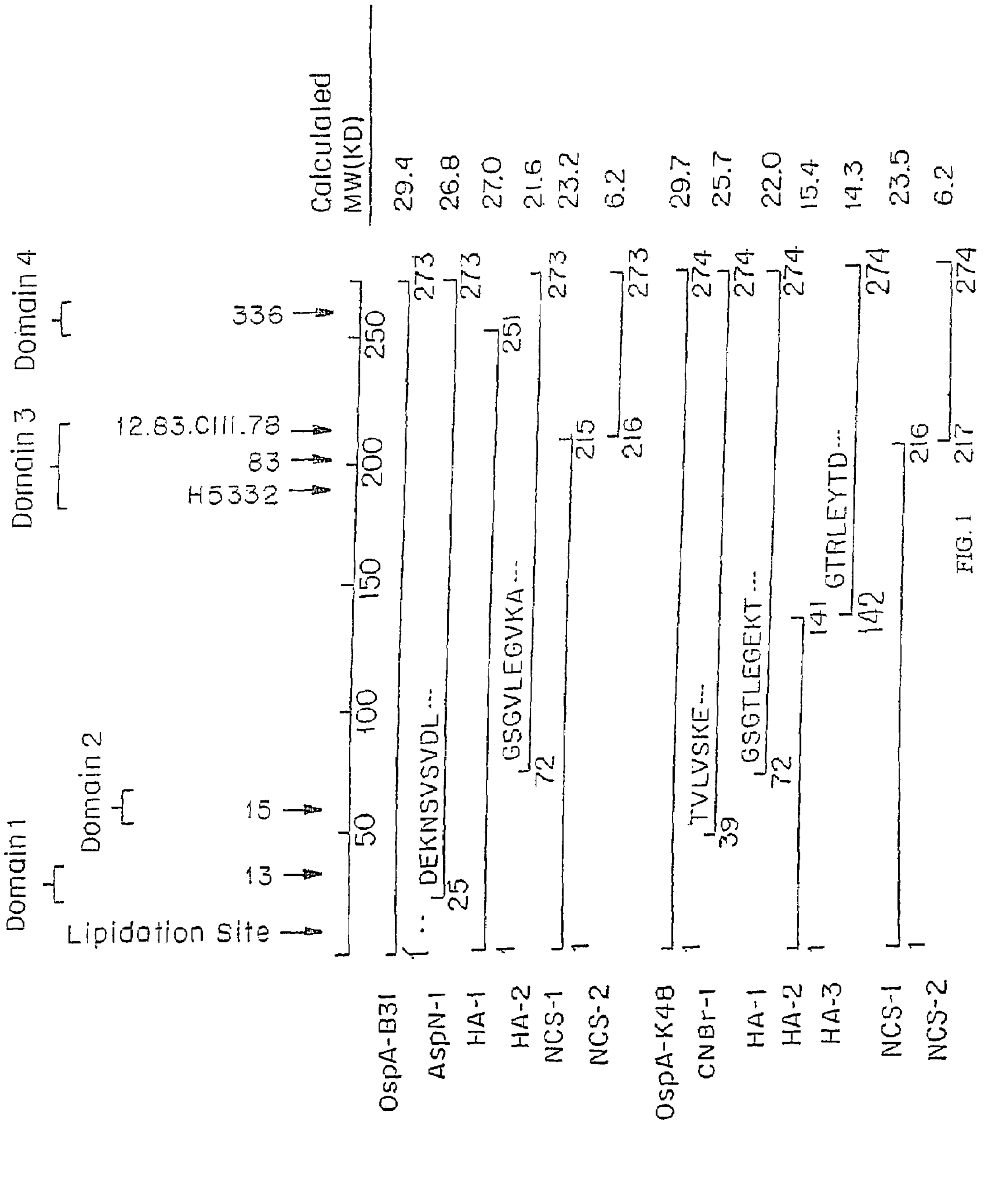
FIG. 1 summarizes peptides and antigenic domains localized by proteolytic and chemical fragmentation of OspA.

The present invention pertains to chimeric proteins comprising various antigenic *Borrelia* polypeptides. In a preferred embodiment, the chimeric protein comprises *Borrelia* outer surface protein C (OspC) and outer surface protein A (OspA). These chimeric proteins have the general structure of OspC linked to OspA via a peptide bond. Each of the OspA and OspC portions of the chimeric OspC/OspA protein can be lipidated or unlipidated. In a preferred embodiment, the OspC/OspA chimer comprises OspC and OspA polypeptide fragments that do not possess their lipidation signals.

The chimeric forms of the OspA and OspC proteins described herein were bioengineered such that the resultant chimeric protein maintained at least some antigenicity of one or both of the parent molecules. As described herein, antigenic refers to the ability of a compound to bind products of an immune response, such as antibodies, T-cell receptors or both. Such responses can be measured using standard antibody detection assays, such as ELISA or standard T-cell activation assays. In a particular embodiment, the chimeric OspC/OspA proteins comprise OspA polypeptides which lack the putative autoreactive domain that has similarity to a region of human leukocyte function-associated antigen-1 (hLFA-1) (Gross, D. M. et al., *Science,* 281: 703–706 (1998)).

The current invention pertains to chimeric proteins comprising antigenic *Borrelia* polypeptides which do not occur in nature in the same *Borrelia* protein. The chimeric proteins are a combination of two or more antigenic polypeptides derived from *Borrelia* proteins. The antigenic polypeptides can be derived from different proteins from the same species of *Borrelia*, or different proteins from different *Borrelia* species, as well as from corresponding proteins from different species. As used herein, the term “chimeric protein” describes a protein comprising two or more polypeptides which are derived from corresponding and/or non-corresponding native *Borrelia* protein. A polypeptide “derived from” a native *Borrelia* protein is a polypeptide which has an amino acid sequence the same as an amino acid sequence present in a *Borrelia* protein, an amino acid sequence equivalent to the amino acid sequence of a naturally occurring *Borrelia* protein, or an amino acid sequence substantially similar to the amino acid sequence of a naturally occurring *Borrelia* protein (e.g., differing by a few amino acids), such as when a nucleic acid encoding a protein is subjected to site-directed mutagenesis. “Corresponding” proteins are equivalent proteins from different species or strains of *Borrelia*, such as outer surface protein A (OspA) from strain B31 and OspA from strain K48. The invention additionally pertains to nucleic acids encoding these chimeric proteins.

In one embodiment, the present invention is drawn to chimeric proteins comprising antigenic polypeptides from Lyme Disease-causing strains of *Borrelia*. In another embodiment, the chimeric proteins described herein comprise antigenic polypeptides from different pathogenic genospecies of *Borrelia*, such as *Borrelia burgdorferi* sensu stricto, *Borrelia afzelii* and *Borrelia garinii*. In a preferred embodiment, the chimeric proteins comprise antigenic polypeptides from each of the pathogenic genospecies of *Borrelia*, including *Borrelia burgdorferi* sensu stricto, *Borrelia afzelii* and *Borrelia garinii.*

The OspA portion of the chimeric molecules of the present invention can themselves be chimeric combinations of more than one OspA polypeptide. Similarly, the OspC portion of the chimeric molecules of the present invention can themselves be chimeric combinations of more than one OspC polypeptide. As described below, Applicants have identified two separate antigenic domains of OspA and OspB which flank the sole conserved tryptophan present in OspA and in OspB. These domains share cross-reactivity with different genospecies of *Borrelia*. The precise amino acids responsible for antigenic variability were determined through site-directed mutagenesis, so that proteins with specific amino acid substitutions are available for the development of chimeric versions of OspA which can be included in the OspC/OspA chimeric proteins of the present invention. Furthermore, Applicants have identified immunologically important hypervariable domains in OspA proteins, as described below in Example 2. The first hypervariable domain of interest for chimeric proteins, Domain A, includes amino acid residues 120–140 of OspA, the second hypervariable domain, Domain B, includes residues 150–180 and the third hypervariable domain, Domain C, includes residues 200–216 or 217 (depending on the position of the sole conserved tryptophan residue in the OspA of that particular species of *Borrelia*) (see FIG. 3). In addition, Applicants have sequenced the genes for several *Borrelia* proteins.

These discoveries have aided in the development of novel recombinant *Borrelia* proteins which include two or more amino acid regions or sequences which do not occur in the same *Borrelia* protein in nature. The recombinant proteins comprise polypeptides from a variety of *Borrelia* proteins, including, but not limited to, OspA, OspB, OspC, OspD, p12, p39, p41, p66, and p93. Preferred combinations include all or a portion of OspC linked to all or a portion of OspA. Antigenically relevant polypeptides from each of a number of proteins are combined into a single chimeric protein.

In one embodiment of the current invention, chimeras are now available which include antigenic OspA polypeptides flanking a tryptophan residue. OspB has a similar primary structure as OspA and is included in the following discussion. The antigenic polypeptides are derived from either the proximal portion from the tryptophan (the portion of the OspA protein present between the amino terminus and the conserved tryptophan of the protein), or the distal portion from the tryptophan (the portion of the OspA protein present between the conserved tryptophan of the protein and the carboxy terminus) in OspA. The resultant chimeras can be OspA-OspA chimeras (e.g., chimeras incorporating polypeptides derived from OspA from different strains of *Borrelia*), OspA-OspB chimeras, or OspB-OspB chimeras, and are constructed such that amino acid residues amino-proximal to an invariant tryptophan are from one protein and residues carboxy-proximal to the invariant tryptophan are from the other protein. For example, one available chimer consists of a polypeptide derived from the amino-proximal region of OspA from strain B31, followed by the tryptophan residue, followed by a polypeptide derived from the carboxy-proximal region of OspA from strain K48 (SEQ ID NO. 92). Another available chimer includes a polypeptide derived from the amino-proximal region of OspA from strain B31, and a polypeptide derived from the carboxy-proximal region of OspB from strain B31 (SEQ ID NO. 104). If the polypeptide proximal to the tryptophan of these chimeric proteins is derived from OspA, the proximal polypeptide can be further subdivided into the three hypervariable domains (Domains A, B, and C), each of which can be derived from OspA from a different strain of *Borrelia*. These chimeric proteins can further comprise antigenic polypeptides from another protein, e.g., OspC, in addition to the antigenic polypeptides flanking the tryptophan residue.

In one embodiment, the chimeric OspC/OspA proteins of the present invention comprise at least a first and a second polypeptide, wherein the first polypeptide comprises *Borrelia burgdorferi* OspC and wherein the second polypeptide comprises *Borrelia burgdorferi* OspA, such that OspC comprises the N-terminus of the protein.

In a particular embodiment, the first polypeptide comprises a *Borrelia burgdorferi* OspC polypeptide from about amino acid residue 19 to about amino acid residue 213, and the second polypeptide comprises a *Borrelia burgdorferi* OspA polypeptide. In another embodiment, the first polypeptide comprises a *Borrelia burgdorferi* OspC polypeptide from about amino acid residue 19 to about amino acid residue 211. In another embodiment, the first polypeptide comprises a *Borrelia burgdorferi* OspC polypeptide from about amino acid residue 19 to about amino acid residue 208. In another embodiment, the first polypeptide comprises a *Borrelia burgdorferi* OspC polypeptide from about amino acid residue 19 to about amino acid residue 204. The numbering of the OspC residues is according to the numbering of SEQ ID NO: 30 (FIGS. 12 A and 12B). It is evident that the person of skill in the art recognizes that OspC genes from different strains and/or genospecies may differ in their primary sequence and that based on homology, similar regions of such OspC proteins could be identified and used in the present invention with no or only routine experimentation.

In one embodiment, the invention is drawn to chimeric OspC/OspA proteins wherein the first polypeptide comprises a *Borrelia burgdorferi* OspC polypeptide and the second polypeptide comprises a *Borrelia burgdorferi* OspA polypeptide from about amino acid residue 18 to about amino acid residue 273. In other embodiments, the chimeric OspC/OspA protein comprises a first polypeptide which is a *Borrelia burgdorferi* OspC polypeptide and a second polypeptide which is a *Borrelia burgdorferi* OspA polypeptide selected from the group consisting of an OspA polypeptide from about amino acid residue 132 to about amino acid residue 216, an OspA polypeptide from about amino acid residue 218 to about amino acid residue 273, an OspA polypeptide from about amino acid residue 18 to about amino acid residue 216 and an OspA polypeptide from about 132 to about amino acid residue 273. The numbering of the OspA residues is according to the numbering of SEQ ID NO: 7 (FIGS. 7A and 7B). It is evident that the person of skill in the art recognizes that OspA genes from different strains and/or genospecies may differ in their primary sequence and that based on homology, similar regions of such OspA proteins could be identified and used in the present invention with no or only routine experimentation.

The present invention is also drawn to OspC/OspA chimeric proteins wherein the first polypeptide comprises a *Borrelia burgdorferi* OspC polypeptide and the second polypeptide comprises a *Borrelia burgdorferi* OspA polypeptide, wherein the OspA polypeptide comprises two or more OspA polypeptide fragments as described above. In a preferred embodiment, the OspA polypeptide comprises portions of OspA from two or more strains of *Borrelia*. In another preferred embodiment, the OspA polypeptide comprises portions of OspA from two or more Lyme Disease-causing genospecies of *Borrelia*, e.g., wherein the genospecies are *Borrelia burgdorferi* sensu stricto, *Borrelia afzelii* and/or *Borrelia garinii*. In still another preferred embodiment, the OspC/OspA chimeric protein comprises one or more polypeptides from each of the pathogenic genospecies, *Borrelia burgdorferi* sensu stricto, *Borrelia afzelii* and *Borrelia garinii*.

The chimeras described herein can be produced so that they are highly soluble, hyper-produced in *E. coli*, and non-lipidated. Lipidated chimeric proteins can also be produced. In addition, the chimeric proteins can be designed to end in an affinity tag (His-tag) to facilitate purification. The recombinant proteins described herein have been constructed to maintain antigenicity of at least one of the parent polypeptides. In addition, recombinant proteins specific for the various genospecies of *Borrelia* that cause Lyme disease are now available, because the genes from each of the major genospecies have been sequenced. These recombinant proteins with their novel biophysical and antigenic properties will be important diagnostic reagent and vaccine candidates.

The chimeric proteins of the current invention are advantageous in that they retain at least some specific reactivity to monoclonal or polyclonal antibodies that recognize wild-type *Borrelia* proteins. The proteins are immunogenic, and elicit antibodies that inhibit growth and/or induce lysis of *Borrelia* in vitro. Furthermore, in some embodiments, the proteins provide antigenic domains of two or more *Borrelia* strains and/or proteins within a single protein. Such proteins are particularly useful in immunodiagostic assays. For example, proteins of the present invention can be used as reagents in assays to detect the presence of antibodies to native *Borrelia* in potentially infected individuals. These proteins can also be used as immunodiagnostic reagents, such as in dot blots, Western blots, enzyme-linked immunosorbent assays (ELISA), or agglutination assays. The chimeric proteins of the present invention can be produced by known techniques, such as by recombinant methodology, polymerase chain reaction, or mutagenesis.

Furthermore, the proteins of the current invention are useful as vaccine immunogens against *Borrelia* infection. Because *Borrelia* has been shown to be clonal, a protein comprising antigenic polypeptides from a variety of *Borrelia* proteins and/or species, will provide immunoprotection for a considerable time when used in a vaccine. The lack of significant intragenic recombination, a process which might rapidly generate novel epitopes with changed antigenic properties, ensures that *Borrelia* can only change antigenic type by accumulating mutational change, which is slow when compared with recombination in generating different antigenic types. The chimeric protein can be combined with a physiologically-acceptable carrier and administered to a vertebrate animal through standard methods (e.g., intravenously or intramuscularly, for example).

In addition to the chimeric proteins described herein, the present invention is also drawn to nucleic acids which encode the *Borrelia* chimeric protein described herein. In one embodiment of the present invention, the composition comprises a nucleic acid that encodes a chimeric protein of at least two polypeptides, wherein the first polypeptide comprises *Borrelia burgdorferi* OspC, and the second polypeptide comprises *Borrelia burgdorferi* OspA, such that OspC is upstream of OspA. The OspC and OspA nucleic acid fragments that make up the chimeric protein can be from the same strain or genospecies of *Borrelia*, from different strains or genospecies of *Borrelia*, or from combinations of nucleic acids that are from the same and/or different strains or genospecies of *Borrelia*.

It is understood that the nucleic acids that encode the polypeptides that comprise the chimeric protein can include extra nucleotides or fewer nucleotides in order to simplify the construction of the gene encoding the chimeric polypeptide, e.g., to allow for the use of convenient restriction endonuclease sites or to allow the ligation of the gene fragments such that a contiguous coding region is created. Based on the guidance provided herein, one of ordinary skill in the art would readily be able to add or remove nucleotides from the termini of the gene fragments encoding the polypeptides of the chimeric OspC/OspA protein in order to generate the chimeric proteins of the present invention with no or only routine experimentation. Furthermore, there can be an extra about 1 to about 10 amino acids on the N- and/or C-terminus of the polypeptides and chimeric proteins of the present invention and still retain the properties of the present invention. It is also understood that those of skill in the art, using art-known methods and/or the methods described herein, could generate additional OspC-OspA chimeric proteins, and that these chimeric proteins are encompassed by the invention.

The present invention is also drawn to expression vectors which comprise an isolated DNA encoding the *Borrelia* chimeric protein described herein. In one embodiment, the composition includes an expression vector comprising an isolated DNA which encodes an OspC/OspA chimeric protein, wherein the OspC portion of the protein is upstream of the OspA portion. The present invention also encompasses host cells which comprise a recombinant nucleic acid that encodes an OspC/OspA chimeric protein, as described herein.

The present invention is also drawn to methods of making the *Borrelia* chimeric polypeptides described herein. In one embodiment, the method of making a chimeric *Borrelia* protein comprises selecting a polynucleotide sequence encoding OspC, or an antigenic portion thereof, selecting a polynucleotide sequence encoding OspA, or an antigenic portion thereof, and ligating these polynucleotide sequences together, such that OspC comprises the N-terminus of the protein. The polypeptides of the present invention can also be recombinantly expressed in suitable microbial hosts, wherein said hosts include, but are not limited to, bacterial hosts, such as *E. coli*, fungal hosts, such as *S. cerevisiae* or cell culture hosts, such as those of mammalian cell culture or insect cell culture.

The present invention is also drawn to methods of delivering the *Borrelia* chimeric polypeptides described herein. In one embodiment, the method comprises administering the chimeric protein in a physiologically-acceptable carrier to an individual. The individual develops at least some immune response to the chimeric protein. As an example, the individual could generate a humoral immune response, wherein antibodies that recognize at least a portion of said chimeric polypeptide are produced by the individual. The antibodies that recognize the chimeric polypeptide can be of any class of immunoglobulin, such as IgM, IgD, IgA and IgG or combinations thereof.

The present invention is also drawn to methods of delivering a nucleic acid which encodes a chimeric polypeptide described herein. In one embodiment, the method comprises administering the nucleic acid in a physiologically-acceptable carrier to an individual using art-accepted methods of DNA delivery, including but not limited to, biolistic delivery and lipid encapsulation. The chimeric polypeptide is at least transiently expressed and the individual develops at least some immune response to the chimeric protein encoded by the nucleic acid.

The invention also encompasses methods of using the chimeric proteins described herein in diagnostic assays. In one embodiment, the method can be used to detect the presence of OspA- and/or OspC-specific antibodies in a sample, e.g., a host sample of interest. In one embodiment, the method comprises contacting a host sample of interest with the chimeric OspC/OspA protein, under conditions, wherein antibodies, if present in the host sample, bind to the chimeric protein thereby forming antigen-antibody complexes. The antigen-antibody complexes are then detected. In this manner, an immune response to Lyme-Disease causing *Borrelia* can be detected.

As described herein, the chimeric proteins of the present invention incorporate antigenic domains from different *Borrelia* proteins, as well as from different *Borrelia* strains and/or genospecies. As such, they are useful in the detection or diagnosis of the presence of Lyme disease-causing *Borrelia*, especially *Borrelia* from groups capable of causing disseminated symptoms of Lyme disease. Disseminated symptoms refer to infection outside of the erythema migrans skin lesion, e.g., infection in blood, CNS or synovia.

The chimeric polypeptides of the present invention elicit specific immune responses to OspC and OspA. In one embodiment, the chimeric polypeptides elicit immune responses to strains of Lyme disease-causing *Borrelia* of the same genospecies as that represented by the OspC/OspA chimeric protein. In another embodiment, the chimeric polypeptides elicit immune responses to strains of Lyme disease-causing *Borrelia* of different genospecies than that represented by the OspC/OspA chimeric protein, as well as to Lyme disease-causing *Borrelia* of the same genospecies as that represented by the OspC/OspA chimeric protein. The immune response includes, but is not limited to, a humoral response, a secretory response, a cell-mediated response, or any combination thereof.

The immunogenic compositions of the present invention can also be used to immunize animals, e.g., mammals, including humans. Immunization is understood to elicit specific immunogenic responses as described herein. In one embodiment, administration of an immunogenic composition, e.g., an OspC/OspA chimeric protein, an OspC/OspA chimeric nucleic acid, to an animal results in the animal developing immunity to infection by Lyme disease-causing *Borrelia*, e.g., *Borrelia burgdorferi, Borrelia afzelii* and/or *Borrelia garinii*.

Immunity, as described herein, is understood to mean the ability of the treated animal to resist infection (e.g., systemic infection), to overcome infection (e.g., systemic infection) or to overcome infection (e.g., systemic infection) more easily and/or more quickly when compared to non-immunized and/or non-treated individuals. Immunity can also include an improved ability of the treated individual to sustain an infection with reduced or no clinical symptoms of systemic infection. The individual may be treated with the chimeric proteins of the present invention either proactively, e.g., once a year or alternatively after sustaining a tick bite.

In one embodiment, the OspC/OspA chimeric protein of the present invention, together with suitable excipients and/or adjuvants, is administered to an animal such that the animal develops an immune response to at least one of the OspC and/or OspA polypeptides of the composition. The pharmaceutical composition can also be administered with other components suitable for in vitro and/or in vivo use. These additional components include buffers, carrier proteins, adjuvants, excipients, preservatives and combinations thereof.

The present invention is also drawn to pharmaceutical compositions which can be used to vaccinate and/or treat *Borrelia* infection in an animal or human. In a particular embodiment, the pharmaceutical composition comprises a *Borrelia burgdorferi* OspC/OspA chimeric protein. The pharmaceutical composition can also be administered together with a physiologically-acceptable carrier, an excipient and/or an adjuvant. Suitable adjuvants are well known in the art (see for example PCT Publication WO 96/40290, the entire teachings of which are incorporated herein by reference), and can be used, for example, to enhance immunogenicity, potency or half-life of the chimeric proteins in the treated animal.

The pharmaceutical compositions used to vaccinate and/or treat *Borrelia* infection can be prepared using methods for preparing vaccines which are well known in the art. For example, the OspC/OspA chimeric proteins described herein can be isolated and/or purified by known techniques, such as by size exclusion chromatography, affinity chromatography, ion exchange chromatography, preparative electrophoresis, selective precipitation or combinations thereof. The prepared chimeric proteins can be mixed with suitable other reagents as described herein, such that the chimeric protein is at a suitable concentration. The dosage of the chimeric protein will vary and depends upon the age, weight and/or physical condition of the animal, e.g., mammal, human, to be treated. The optimal dosage can be determined by routine optimization techniques, using suitable animal models.

Administration of the pharmaceutical composition to be used as a vaccine can be by any suitable technique. Suitable techniques for administration of the pharmaceutical composition include, but are not limited to, injection, e.g., subcutaneous injection, intramuscular injection, intravenous injection, intra peritoneal injection; mucosal administration, e.g., exposing nasal mucosa to nose drops containing the proteins or chimeric proteins of the present invention; oral administration; and DNA immunization.

The incorporation of polypeptide fragments from different strains and/or genospecies of *Borrelia burgdorferi* allows for a greater detection range and a more effective vaccination tool. The present invention provides a chimeric combination of proteins that, when used as a vaccine, can prevent Lyme disease from becoming systemic. The chimeric proteins of the present invention can be effective in preventing Lyme disease, as well as having a therapeutic effect on established infection, for example, after the tick bite is noticed by the patient. Since the chimeric proteins of the present invention comprise both OspC and OspA polypeptides, they are expected to act at the level of the tick as well as the level of the host in preventing both infection and disease due to *Borrelia burgdorferi, Borrelia afzelii* and/or *Borrelia garinii*.

The present invention is also drawn to diagnostic kits which comprise the chimeric polypeptides described herein. In one embodiment, the kit comprises a chimeric protein comprising at least a first and a second polypeptide, wherein the first polypeptide comprises *Borrelia burgdorferi* OspC and wherein the second polypeptide comprises *Borrelia burgdorferi* OspA, such that OspC comprises the N-terminus of the protein. The kit also includes reagents for detecting antibody-antigen complexes that are formed between the OspC/OspA chimeric protein and antibodies that are present in a sample, e.g., a user-supplied host sample.

As a result of the present invention, it is now possible to prepare improved diagnostic tools comprising both OspA and OspC antigens from various *Borrelia burgdorferi* strains and/or genospecies. Since OspA is primarily expressed in the tick vector, and OspC is upregulated in response to the feeding of an infected tick on a mammal, the diagnostic compositions of the invention can recognize antigens that are expressed at different stages of the life cycle of *Borrelia burgdorferi*. Moreover, by incorporating unique polypeptide fragments from pathogenic families of *Borrelia*, the present invention allows for improved diagnostic compositions which can detect clinically important exposure to pathogenic *Borrelia* while overlooking the remainder of non-pathogenic families of *Borrelia*.

As described herein, the OspC/OspA chimeric proteins were bioengineered such that the protective domains of each protein were maintained. In experiments described herein, mice were either immunized with OspA, OspC or OspC/OspA chimeric proteins in aluminum hydroxide. Mice were then bled and tested for antibody responses against OspC and OspA derived from various strains of *Borrelia*. In additional experiments, these immunized mice were challenged with ticks infected with *Borrelia burgdorferi* and transmission of infection was assessed.

Figure 47:
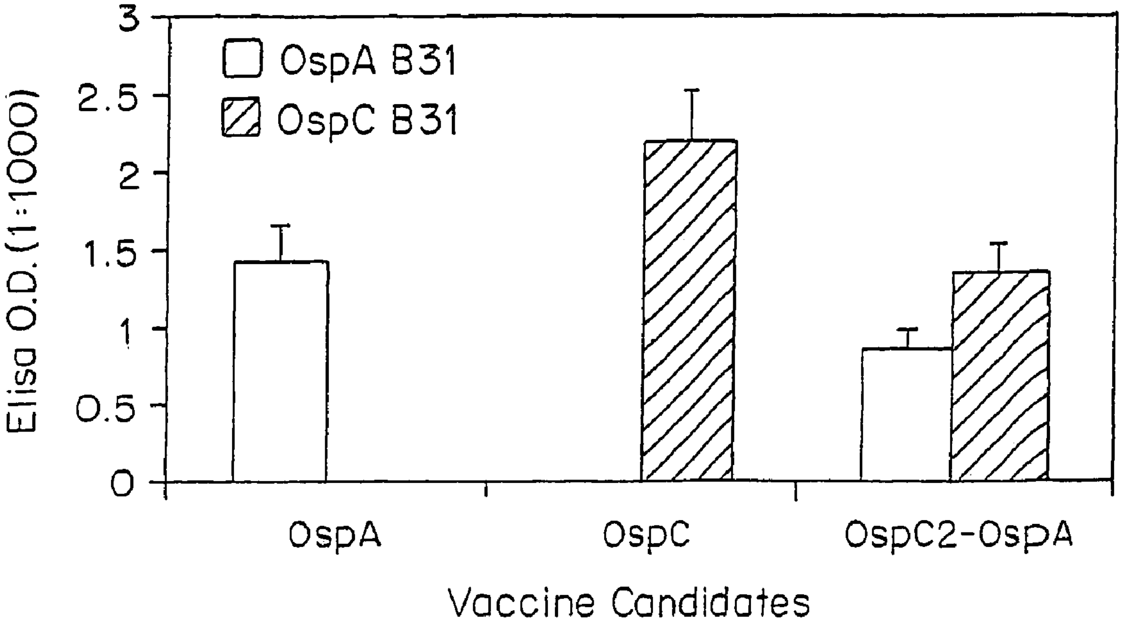
FIG. 47 is a bar graph showing the reactivity (as measured by ELISA) of sera from mice immunized with the indicated *Borrelia* protein (OspA or OspC) or recombinant chimeric protein (OspC2-OspA) (X-axis) against OspA B31 or OspC B31 antigens (legend).
Figure 48:
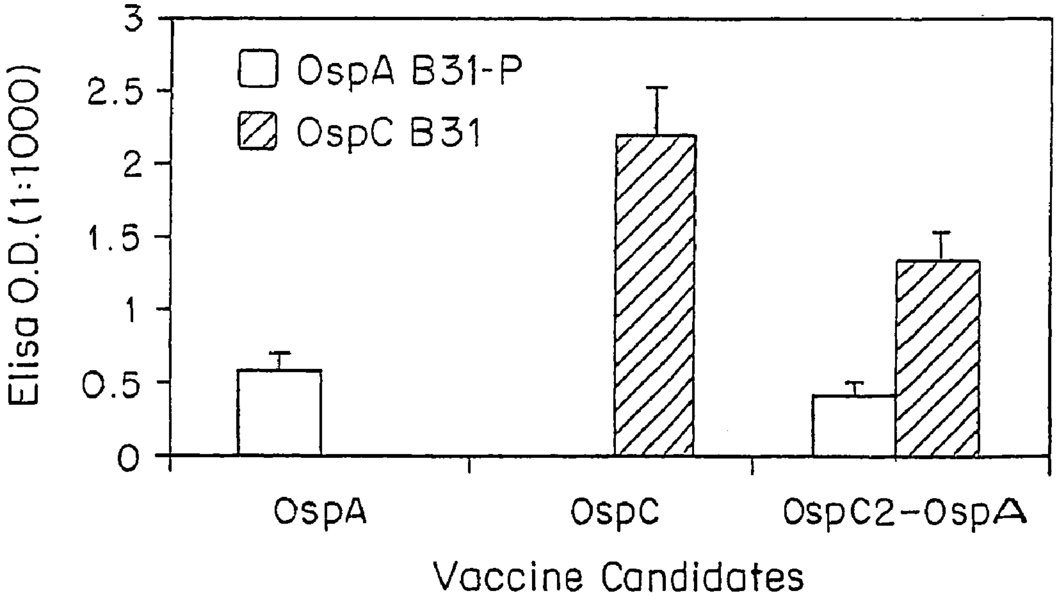
FIG. 48 is a bar graph showing the reactivity (as measured by ELISA) of sera from mice immunized with the indicated *Borrelia* protein (OspA or OspC) or recombinant chimeric protein (OspC2-OspA) (X-axis) against OspA B31 or OspC B31 antigens (legend). For the ELISA results to the B31 OspA antigen, a purified fragment of B31 OspA (amino acids 18–139) was added in excess to the sera so that the detected immune response was specific for the C-terminal region of OspA.

Mice immunized with the OspC/OspA chimeric protein gave a remarkable and equivalent antibody response to both OspA and OspC, as compared to mice immunized with OspA and OspC control proteins (FIGS. 47 and 48). In addition, antibodies in the sera of mice immunized with the OspC/OspA chimeric protein were also reactive against antigens derived from different strains of *Borrelia burgdorferi* (FIGS. 49–50 and 52–54). Chimer-immunized mice were fully protected against challenge with ticks infected with *Borrelia burgdorferi*, as compared to sham-vaccinated controls (infection rates of 100%) (Table VI).

Figure 49:
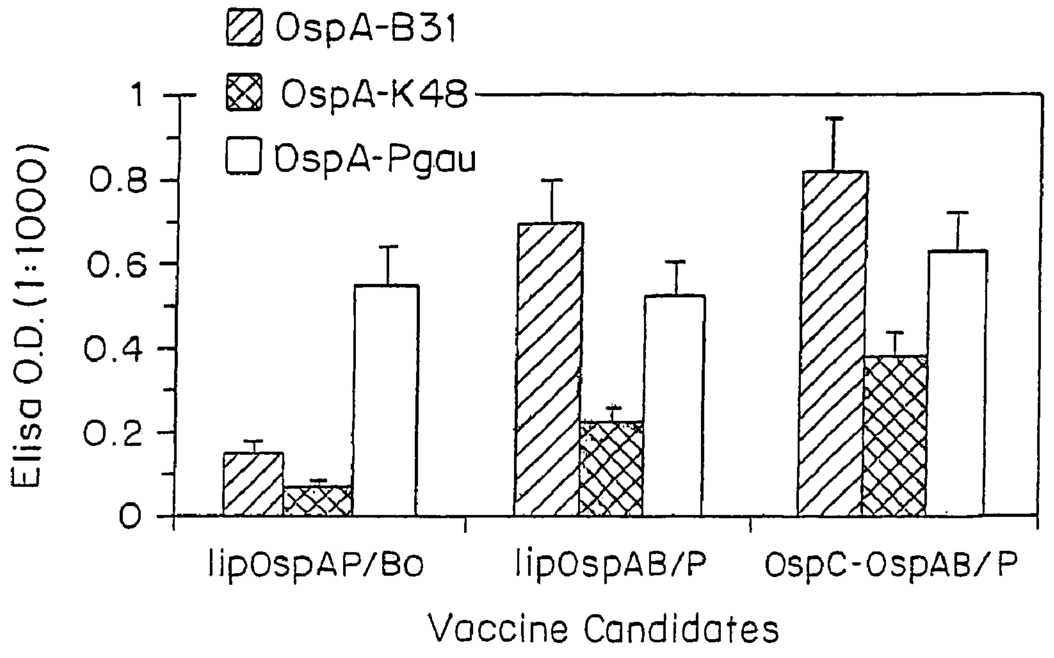
FIG. 49 is a bar graph showing the reactivity of sera from mice immunized with the indicated *Borrelia* chimeric protein (lipOspA/Bo, lipOspAB/P or OspC-OspAB/P) (X-axis) against the indicated OspA antigens (legend) from strains B31 (*Borrelia burgdorferi* sensu stricto), K48 (*Borrelia garinii*) and PGau (*Borrelia afzelli*).
Figure 50:
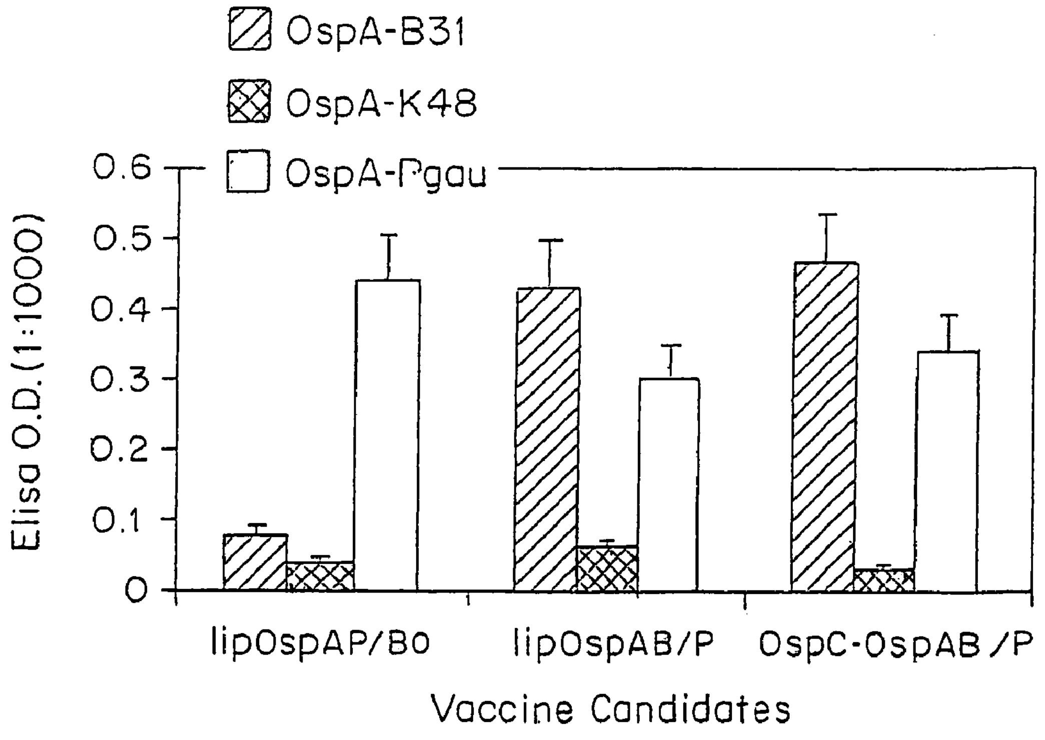
FIG. 50 is a bar graph showing the reactivity of sera from mice immunized with the indicated *Borrelia* chimeric protein (lipOspAP/Bo, lipOspAB/P) or OspC-OspAB/P) (X-axis) against the indicated OspA (legend) from strains B31 (*Borrelia burgdorferi* sensu stricto), K48 (*Borrelia garinii*) and PGau (*Borrelia afzelli*). In all cases, a purified fragment of B31 OspA (amino acids 18–139) was added in excess to the sera so that the detected immune response is specific for the C-terminal region of OspA.
Figure 51:
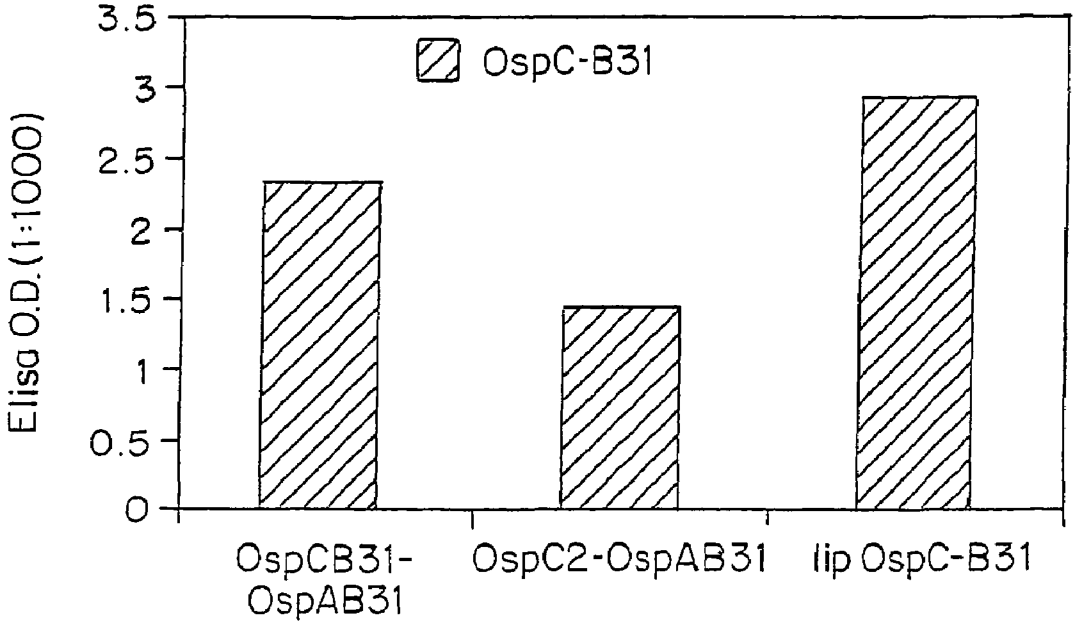
FIG. 51 is a bar graph showing the reactivity of sera from mice immunized with the indicated *Borrelia* chimeric protein (OspCB31-OspAB31, OspC2-OspAB31 or lip OspC-B31) (X-axis) against the indicated OspC antigen (legend) from the strain B31 (*Borrelia burgdorferi* sensu stricto).

In other experiments described herein, mice were either immunized with a lipidated OspA chimeric protein, a lipidated OspC chimeric protein, or a non-lipidated OspC/OspA chimeric protein, once again in the presence of aluminum hydroxide. Mice were then bled and tested for antibody responses against OspA and OspC derived from various strains of *Borrelia*. Surprisingly, the results of these studies indicate that mice immunized with the non-lipidated OspC/OspA chimeric protein have antibody responses to OspA and OspC that are equivalent or greater than those generated by mice immunized with the corresponding lipidated OspA or lipidated OspC chimeric proteins (FIGS. 49–51).

The results of the studies presented herein indicate that mice immunized with OspC-OspA chimeric proteins generate a potent antibody response against two immunoprotective targets that are expressed at different stages of the life cycle of *Borrelia burgdorferi.*

The current invention is illustrated by the following Examples, which are not to be construed to be limiting in any way.

EXEMPLIFICATION

Example 1

Purification of *Borrelia Burgdorferi* Outer Surface Protein A and Analysis of Antibody Binding Domains This example details a method for the purification of large amounts of native outer surface protein A (OspA) to homogeneity, and describes mapping of the antigenic specificities of several anti-OspA MAbs. OspA was purified to homogeneity by exploiting its resistance to trypsin digestion. Intrinsic labeling with $^{14}$C-palmitic acid confirmed that OspA was lipidated, and partial digestion established lipidation at the amino-terminal cysteine of the molecule.

The reactivity of seven anti-OspA murine monoclonal antibodies to nine different *Borrelia* isolates was ascertained by Western blot analysis. Purified OspA was fragmented by enzymatic or chemical cleavage, and the monoclonal antibodies were able to define four distinct immunogenic domains (see FIG. 1). Domain 3, which included residues 190–220 of OspA, was reactive with protective antibodies known to agglutinate the organism in vitro, and included distinct specificities, some of which were not restricted to a genotype of *B. burgdorferi.*

A. Purification of Native OspA

Detergent solubilization of *B. burgdorferi* strips the outer surface proteins and yields partially-purified preparations containing both OspA and outer surface protein B (OspB) (Barbour, A. G. et al., *Infect. Immun.* 52 (5): 549–554 (1986); Coleman, J. L. and J. L. Benach, *J Infect. Dis.* 155 (4): 756–765 (1987); Cunningham, T. M. et al., *Ann. NY Acad. Sci.* 539: 376–378 (1988); Brandt, M. E. et al., *Infect. Immun.* 58: 983–991 (1990); Sambri, V. and R. Cevenini, *Microbiol.* 14: 307–314 (1991)). Although both OspA and OspB are sensitive to proteinase K digestion, in contrast to OspB, OspA is resistant to cleavage by trypsin (Dunn, J. et al., *Prot. Exp. Purif.* 1: 159–168 (1990); Barbour, A. G. et al., *Infect. Immun.* 45: 94–100 (1984)). The relative insensitivity to trypsin is surprising in view of the fact that OspB A has a high (16% for B31) lysine content, and may relate to the relative configuration of OspB A and B in the outer membrane.

Intrinsic Radiolabeling of *Borrelia*

Labeling for lipoproteins was performed as described by Brandt et al. (Brandt et al., *Infect. Immun.* 58: 983–991 (1990)). $^{14}$C-palmitic acid (ICN, Irvine, Calif.) was added to the BSK II media to a final concentration of 0.5 μCi per milliliter (ml). Organisms were cultured at 34° C. in this medium until a density of $10^8$ cells per ml was achieved.

Purification of OspA Protein from *Borrelia* Strain B31

*Borrelia burgdorferi*, either $^{14}$C-palmitic acid-labeled or unlabeled, were harvested and washed as described (Brandt, M. E. et al., *Infect. Immun.* 58: 983–991 (1990)). Whole organisms were trypsinized according to the protocol of Barbour et al. (*Infect. Immun.* 45: 94–100 (1984)) with some modifications. The pellet was suspended in phosphate buffered saline (PBS, 10 mM, pH 7.2), containing 0.8% tosyl-L-phenylalanine chloromethyl ketone (TPCK)-treated trypsin (Sigma, St. Louis, Mo.), the latter at a ratio of 1 μg per $10^8$ cells. Reaction was carried out at 25° C. for 1 hour, following which the cells were centrifuged. The pellet was washed in PBS with 100 μg/ml phenylmethylsulfonyl fluoride (PMSF). Triton X-114 partitioning of the pellet was carried out as described by Brandt et al. (Brandt et al., *Infect. Immun.* 58: 983–991 (1990)). Following trypsin treatment, cells were resuspended in ice-cold 2% (v/v) Triton X-114 in PBS at $10^9$ cells per ml. The suspension was rotated overnight at 4° C., and the insoluble fraction removed as a pellet after centrifugation at 10,000×g for 15 minutes at 4° C. The supernatant (soluble fraction) was incubated at 37° C. for 15 minutes and centrifuged at room temperature at 1000×g for 15 minutes to separate the aqueous and detergent phases. The aqueous phase was decanted, and ice cold PBS added to the lower Triton phase, mixed, warmed to 37° C., and again centrifuged at 1000×g for 15 minutes. Washing was repeated twice more. Finally, detergent was removed from the preparation using a spin column of Bio-beads SM2 (BioRad, Melville, N.Y.) as described (Holloway, P. W., *Anal. Biochem.* 53: 304–308 (1973)).

Ion exchange chromatography was carried out as described by Dunn et al. (Dunn et al., *Prot. Exp. Purif.* 1: 159–168 (1990)) with minor modifications. Crude OspA was dissolved in buffer A (1% Triton X-100, 10 mM phosphate buffer (pH 5.0)) and loaded onto a SP Sepharose resin (Pharmacia, Piscataway, N.J.), pre-equilibrated with buffer A at 25° C. After washing the column with 10 bed-volumes of buffer A, the bound OspA was eluted with buffer B (1% Triton X-100, 10 mM phosphate buffer (pH 8.0)). OspA fractions were detected by protein assay using the BCA method (Pierce, Rockford, Ill.), or as radioactivity when intrinsically labeled material was fractionated. Triton X-100 was removed using a spin column of Bio-beads SM2.

This method purifies OspA from an outer surface membrane preparation. In the absence of trypsin-treatment, OspA and B were the major components of the soluble fraction obtained after Triton partitioning of strain B31. In contrast, when Triton extraction was carried out after trypsin-treatment, the OspB band is not seen. Further purification of OspA-B31 on a SP Sepharose column resulted in a single band by SDS-PAGE. The yield following removal of detergent was approximately 2 mg per liter of culture. This method of purification of OspA, as described herein for strain B31, can be used for other isolates of *Borrelia* as well. For strains such as strain K48, which lack OspB, trypsin treatment can be omitted.

Lipidation Site of OspA-B31

$^{14}$C-palmitic acid labeled OspA from strain B31 was purified as described above and partially digested with endoproteinase Asp-N (data not shown). Following digestion, a new band of lower molecular weight was apparent by SDS-PAGE, found by direct amino-terminal sequencing to begin at $Asp_{25}$. This band had no trace of radioactivity by autoradiography (data not shown). OspA and B contain a signal sequence (L-X-Y-C) similar to the consensus described for lipoproteins of *E. coli*, and it has been predicted that the lipidation site of OspA and B should be the amino-terminal cysteine (Brandt, M. E. et al., *Infect. Immun* 58: 983–991 (1990)). The results presented herein support this prediction.

B. Comparison of OspA Antibody Binding Regions in Nine Strains of *Borrelia Burgdorferi*

The availability of the amino acid sequenced for OspA from a number of different isolates, combined with peptide mapping and Western blot analysis, permitted the identification of the antigenic domains recognized by monoclonal antibodies (MAbs) and allowed inference of the key amino acid residues responsible for specific antibody reactivity.

Strains of *Borrelia Burgdorferi*

Nine strains of *Borrelia*, including seven European strains and two North American strains, were used in this study of antibody binding domains of several proteins. Information concerning the strains is summarized in Table I, below.

TABLE I

Representative *Borrelia* Strains

| Strain | Location and Source | Reference for Strain |
|---|---|---|
| K48 | Czechoslovakia, *Ixodes ricinus* | none |
| PGAU | Germany, human ACA | Wilske, B. et al., J. Clin. Microbiol. 32: 340–350 (1993) |
| DK29 | Denmark, human EM | Wilske, B. et al. |
| PKo | Germany, human EM | Wilske, B. et al. |
| PTrob | Germany, human skin | Wilske, B. et al. |
| Ip3 | Khabarovsk, Russia, *I. persulcatus* | Asbrink, E. et al., Acta Derm. Venereol. 64: 506–512 (1984) |
| Ip90 | Khabarovsk, Russia, *I. persulcatus* | Asbrink, E. et al. |
| 25015 | Millbrook, NY, *I. persulcatus* | Barbour, A. G. et al., Curr. Microbiol. 8: 123–126 (1983) |
| B31 | Shelter Island, NY, *I. scapularis* | Luft, B. J. et al., Infect. Immun. 60: 4309–4321 (1992); ATCC 35210 |
| PKa1 | Germany, human CSF | Wilske, B. et al. |
| ZS7 | Freiburg, Germany, *I. ricinus* | Wallich, R. et al., Nucl. Acids Res. 17: 8864 (1989) |
| N40 | Westchester Co., NY | Fikrig, E. et al., Science 250: 553–556 (1990) |
| PHei | Germany, human CSF | Wilske, B. et al. |
| ACAI | Sweden, human ACA | Luft, B. J. et al., FEMS Microbiol. Lett. 93: 73–68 (1992) |
| PBo | Germany, human CSF | Wilske, B. et al. |

ACA = patient with acrodermatitis chronica atrophicans;
EM = patient with erythema migrans;
CSF = cerebrospinal fluid of patient with Lyme disease Strains K48, PGAU and DK29 were supplied by R. Johnson, University of Minnesota; PKo and PTrob were provided by B. Wilske and V. Preac-Mursic of the Pettenkhofer Institute, Munich, Germany; and Ip3 and Ip90 were supplied by L. Mayer of the Center for Disease Control, Atlanta, Ga. The North American strains included strain 25015, provided by J. Anderson of the Connecticut Department of Agriculture; and strain B31 (ATCC 35210).

Monoclonal Antibodies

Seven monoclonal antibodies (MAbs) were utilized in this study. Five of the MAbs (12, 13, 15, 83 and 336) were produced from hybridomas cloned and subcloned as previously described (Schubach, W. H., et al., *Infect. Immun.* 59(6):1911–1915 (1991)). MAb H5332 (Barbour, A. G. et al., *Infect. Immun.* 41: 795–804 (1983)) was a gift from Drs. Alan Barbour, University of Texas, and MAb CIII.78 (Sears, J. E. et al., *J. Immunol.* 147(6):1995–2000 (1991)) was a gift from Richard A. Flavell, Yale University. MAbs 12 and 15 were raised against whole sonicated B3; MAb 336 was produced against whole PGAU; and MAbs 13 and 83 were raised to a truncated form of OspA cloned from the K48 strain and expressed in *E. coli* using the T7 RNA polymerase system (McGrath, B. C. et al., Vaccines, Cold Spring Harbor Laboratory Press, Plainview, N.Y., pp. 365–370 (1993)). All MAbs were typed as being Immunoglobulin G (IgG).

Methods of Protein Cleavage, Western Blotting and Amino-Terminal Sequencing

Prediction of the various cleavage sites was achieved by knowledge of the primary amino acid sequence derived from the full nucleotide sequences of OspA, many of which are currently available (see Table II, below). Cleavage sites can also be predicted based on the peptide sequence of OspA, which can be determined by standard techniques after isolation and purification of OspA by the method described above. Cleavage of several OspA isolates was conducted to determine the localization of monoclonal antibody binding of the proteins.

Hydroxylamine-HCl (HA), N-chlorosuccinimide (NCS), and cyanogen bromide cleavage of OspA followed the methods described by Bornstein (*Biochem.* 9 (12):2408–2421 (1970)), Shechter et al., (*Biochem.* 15 (23): 5071–5075 (1976)), and Gross (in Hirs, C. H. W. (ed): *Methods in Enzymology*, (N.Y. Acad. Press), 11:238–255 (1967)) respectively. Protease cleavage by endoproteinase, Asp-N (Boehringer Mannheim, Indianapolis, Ind.), was performed as described by Cleveland D. W. et al., (*J. Biol. Chem.* 252: 1102–1106 (1977)). Ten micrograms of OspA were used for each reaction. The ratio of enzyme to OspA was approximately 1 to 10 (w/w).

Proteins and peptides generated by cleavage were separated by SDS-polyacrylamide gel electrophoresis (SDS-PAGE) (Laemmli, U. K., *Nature* (*London*) 227:680–685 (1970)), and electroblotted onto immobilon Polyvinylidine Difluoride (PVDF) membranes (Ploskal, M. G. et al., *Biotechniques* 4: 272–283 (1986)). They were detected by amido black staining or by immunostaining with murine MAbs, followed by alkaline phosphatase-conjugated goat antimouse IgG. Specific binding was detected using a 5-bromo-4-chloro-3-indolylphosphate (BCIP)/nitroblue tetrazolium (NBT) developer system (KPL Inc., Gathersburg, Md.).

In addition, amino-terminal amino acid sequence analysis was carried out on several cleavage products, as described by Luft et al. (*Infect. Immun.* 57: 3637–3645 (1989)). Amido black stained bands were excised from PVDF blots and sequenced by Edman degradation using a Biosystems model 475A sequenator with model 120A PTH analyzer and model 900A control/data analyzer.

Cleavage Products of Outer Surface Protein A Isolates

Purified OspA-B31, labeled with $^{14}$C-palmitic acid, was fragmented with hydroxylamine-HCl (HA) into two peptides, designated HA1 and HA2 (data not shown). The HA1 band migrated at 27 KD and retained its radioactivity, indicating that the peptide included the lipidation site at the N-terminus of the molecule (data not shown). From the predicted cleavage point, HA1 should correspond to residues 1 to 251 of OspA-B31. HA2 had a MW of 21.6 KD by SDS-PAGE, with amino-terminal sequence analysis showing it to begin at Gly72, i.e. residues 72 to 273 of OspA-B31. By contrast, HA cleaved OspA-K48 into three peptides, designated HA1, HA2, and HA3 with apparent MWs of 22 KD, 16 KD and 12 KD, respectively. Amino-terminal sequencing showed HA1 to start at Gly72, and HA3 at Gly142. HA2 was found to have a blocked amino-terminus, as was observed for the full-length OspA protein. HA 1, 2 and 3 of OspA-K48 were predicted to be residues 72–274, 1 to 141 and 142 to 274, respectively.

N-Chlorosuccinimide (NCS) cleaves tryptophan (W), which is at residue 216 of OspA-B31 or residue 217 of OspA-K48 (data not shown). NCS cleaved OspA-B31 into 2 fragments, NCS1, with MW of 23 KD, residues 1–216 of the protein, and NCS2 with a MW of 6.2 KD, residues 217 to 273 (data not shown). Similarly, K48 OspA was divided into 2 pieces, NCS1 residues 1–217, and NCS2 residues 218 to 274 (data not shown).

Cleavage of OspA by cyanogen bromide (CNBr) occurs at the carboxy side of methionine, residue 39. The major fragment, CNBr1, has a MW of 25.7 KD, residues 39–274 by amino-terminal amino acid sequence analysis (data not shown). CNBr2 (about 4 KD) could not be visualized by amido black staining; instead, lightly stained bands of about 20 KD MW were seen. These bands reacted with anti-OspA MAbs, and most likely were degradation products due to cleavage by formic acid.

Determination of Antibody Binding Domains for Anti-OspA Monoclonal Antibodies

The cleavage products of OspA-B31 and OspA-K48 were analyzed by Western blot to assess their ability to bind to the six different MAbs. Preliminary Western blot analysis of the cleavage products demonstrated that strains K48 and DK29 have similar patterns of reactivity, as do Ip3, PGAU and PKo. The OspA of strain PTrob was immunologically distinct from the others, being recognized only by MAb 336. MAb 12 recognized only the two North American strains, B31 and 25015. When the isolates were separated into genogroups, it was remarkable that all the MAbs, except MAb 12, crossed over to react with multiple genogroups.

MAb12, specific for OspA-B31, bound to both HA1 and HA2 of OspA-B31. However, cleavage of OspA-B31 by NCS at residue Trp216 created fragments which did not react with MAb12, suggesting that the relevant domain is near or is structurally dependent upon the integrity of this residue (data not shown). MAb 13 bound only to OspA-K48, and to peptides containing the amino-terminus of that molecule (e.g. HA2; NCS1). It did not bind to CNBr1 residues 39 to 274. Thus the domain recognized by MAb13 is in the amino-terminal end of OspA-K48, near Met38.

MAb15 reacts with the OspA of both the B31 and K48 strains, and to peptides containing the N-terminus of OspA, such as HA 1 of OspA-B31 and NCS 1, but not to peptides HA2 of OspA-B31 and HA 1 of OspA-K48 (data not shown). Both peptides include residue 72 to the C-terminus of the molecules. MAb15 bound to CNBr1 of OspA-K48, indicating the domain for this antibody to be residues 39 to 72, specifically near Gly72 (data not shown).

MAb83 binds to OspA-K48, and to peptides containing the C-terminal portion of the molecule, such as HA1. They do not bind to HA2 of OspA-K48, most likely because the C-terminus of HA2 of OspA-K48 ends at 141. Similar to MAb12 and OspA-B31, binding of MAbs 83 and CIII.78 is eliminated by cleavage of OspA at the tryptophan residue. Thus binding of MAbs 12, 83 and CIII.78 to OspA depends on the structural integrity of the $Trp_{216}$ residue, which appears to be critical for antigenicity. Also apparent is that, although these MAbs bind to a common antigenic domain, the precise epitopes which they recognize are distinct from one another given the varying degrees of cross-reactivity to these MAbs among strains.

Although there is similar loss of binding activity of MAb336 with cleavage at $Trp_{216}$, this MAb does not bind to HA1 of OspA-B31, suggesting the domain for this antibody includes the carboxy-terminal end of the molecule, inclusive of residues 251 to 273. Low MW peptides, such as HA3 (10 KD) and NCS2 (6 KD), of OspA-K48 do not bind this MAb on Western blots. In order to confirm this observation, we tested binding of the 6 MAbs with a recombinant fusion construct p3A/EC that contains a trpE leader protein fused with residues 217 to 273 of OspA-B31 (Schubach, W. H. et al., *Infect. Immun.* 59(6): 1911–1915 (1991)). Only MAb336 reacted with this construct (data not shown). Peptides and antigenic domains localized by fragmentation of OspA are summarized in FIG. 1.

Mapping of Domains to Define the Molecular Basis for the Serotype Analysis

To define the molecular basis for the serotype analysis of OspA, we compared the derived amino acid sequences of OspA for the nine isolates (FIG. 2). At the amino terminus of the protein, these predictions can be more precise given the relatively small number of amino acid substitutions in this region compared to the carboxy terminus. Domain 1, which is recognized by MAb13, includes residues Leu34 to Leu41. MAb13 only binds to the OspA of species K48, DK29 and IP90. Within this region, residue 37 is variable, however Gly37 is conserved amongst the three reactive strains. When Gly37 is changed to Glu37, as it is in OspA of strains B31, PTrob, PGAU, and PKo, MAb13 does not recognize the protein (data not shown). By similar analysis, it can be seen that Asp70 is a crucial residue for Domain 2, which includes residues 65 to 75 and is recognized by MAb15. Domain 3 is reactive with MAbs H5332, 12 and 83, and includes residues 190–220. It is clear that significant heterogeneity exists between MAbs reactive with this domain, and that more than one conformational epitope must be contained within the sequence. Domain 4 binds MAb336, and includes residues 250 to 270. In this region, residue 266 is variable and therefore may be an important determinant. It is apparent, however, that other determinants of the reactivity of this monoclonal antibody reside in the region comprising amino acids 217–250. Furthermore, the structural integrity of Trp216 is essential for antibody reactivity in the intact protein. Finally, it is important to stress that FIG. 2 indicates only the locations of the domains, and does not necessarily encompass the entire domain. Exact epitopes are being analyzed by site-directed mutagenesis of specific residues.

Overall, evidence suggests that the N-terminal portion is not the immunodominant domain of OspA, possibly by virtue of its lipidation, and the putative function of the lipid moiety in anchoring the protein to the outer envelope. The C-terminal end is immunodominant and includes domains that account in part for structural heterogeneity (Wilske, B. et al., *Med. Microbiol. Immunol.* 181: 191–207 (1992)), and may provide epitopes for antibody neutralization (Sears, J. E. et al., *J. Immunol.* 147(6): 1995–2000 (1991)), and relate to other activities, such as the induction of T-cell proliferation (Shanafel, M. M., et al., *J. Immunol.* 148: 218–224 (1992)). There are common epitopes in the carboxy-end of the protein that are shared among genospecies which may have immunoprotective potential (Wilske, B., et al., *Med. Microbiol. Immunol.* 181: 191–207 (1992)).

Prediction of secondary structure on the basis of hydropathy analysis and circular dichroism and fluorescence spectroscopy measurements (McGrath, B. C., et al., Vaccines, Cold Spring Harbor Laboratory Press, Plainview, N.Y.; pp. 365–370 (1993)) suggest domains 3 and 4 to be in a region of the molecule with a propensity to form alpha-helix, whereas domains 1 and 2 occur in regions predicted to be beta-sheets (see FIG. 1). These differences may distinguish domains in accessibility to antibody or to reactive T-cells (Shanafel, M. M. et al., *J. Immunol.* 148: 218–224 (1992)). Site-directed mutagenesis of specific epitopes, as described below in Example 2, aids in identifying exact epitopes.

Example 2

Identification of an Immunologically Important Hypervariable Domain of the Major Outer Surface Protein A of *Borrelia*

This Example describes epitope mapping studies using chemically cleaved OspA and TrpE-OspA fusion proteins. The studies indicate a hypervariable region surrounding the single conserved tryptophan residue of OspA (at residue 216, or in some cases 217), as determined by a moving window population analysis of OspA from fifteen European and North American isolates of *Borrelia*. The hypervariable region is important for immune recognition.

Site-directed mutagenesis was also conducted to examine the hypervariable regions more closely. Fluorescence and circular dichroism spectroscopy have indicated that the conserved tryptophan is part of an alpha-helical region in which the tryptophan is buried in a hydrophobic environment (McGrath, B. C., et al., Vaccines, Cold Spring Harbor Laboratory Press, Plainview, N.Y.; pp. 365–370 (1993)). More polar amino acid side-chains flanking the tryptophan are likely to be exposed to the hydrophilic solvent. The hypervariability of these solvent-exposed residues among the various strains of *Borrelia* suggested that these amino acid residues may contribute to the antigenic variation in OspA. Therefore, site-directed mutagenesis was performed to replace some of the potentially exposed amino acid side chains in the protein from one strain with the analogous residues of a second strain. The altered proteins were then analyzed by Western Blot using monoclonal antibodies which bind OspA on the surface of the intact, non-mutated spirochete. The results indicated that certain specific amino acid changes near the tryptophan can abolish reactivity of OspA to these monoclonal antibodies.

A. Verification of Clustered Polymorphisms in Outer Surface Protein A Sequences Cloning and sequencing of the OspA protein from fifteen European and North American isolates (described above in Table I) demonstrated that amino acid polymorphism is not randomly distributed throughout the protein; rather, polymorphism tended to be clustered in three regions of OspA. The analysis was carried out by plotting the moving, weighted average polymorphism of a window (a fixed length subsection of the total sequence) as it is slid along the sequence. The window size in this analysis was thirteen amino acids, based upon the determination of the largest number of significantly deviating points as established by the method of Tajima (*J. Mol. Evol.* 33: 470–473 (1991)). The average weighted polymorphism was calculated by summing the number of variant alleles for each site. Polymorphism calculations were weighted by the severity of amino acid replacement (Dayhoff, M. O. et al., in: Dayhoff, M. O. (ed.) *Atlas of Protein Sequence and Structure NBRF*, Washington, Vol. 5, Suppl. 3: 345 (1978)). The sum was normalized by the window size and plotted. The amino acid sequence position corresponds to a window that encompasses amino acids 1 through 13. Bootstrap resampling was used to generate 95% confidence intervals on the sliding window analysis. Since *Borrelia* has been shown to be clonal, the bootstrap analysis should give a reliable estimate of the expected variance from polymorphism calculations. The bootstrap was iterated five hundred times at each position, and the mean was calculated from the sum of all positions. The clonal nature of *Borrelia* ensures that the stochastic variance that results from differing genealogical histories of the sequence positions (as would be expected if recombination were prevalent) will be minimized.

Figure 3:
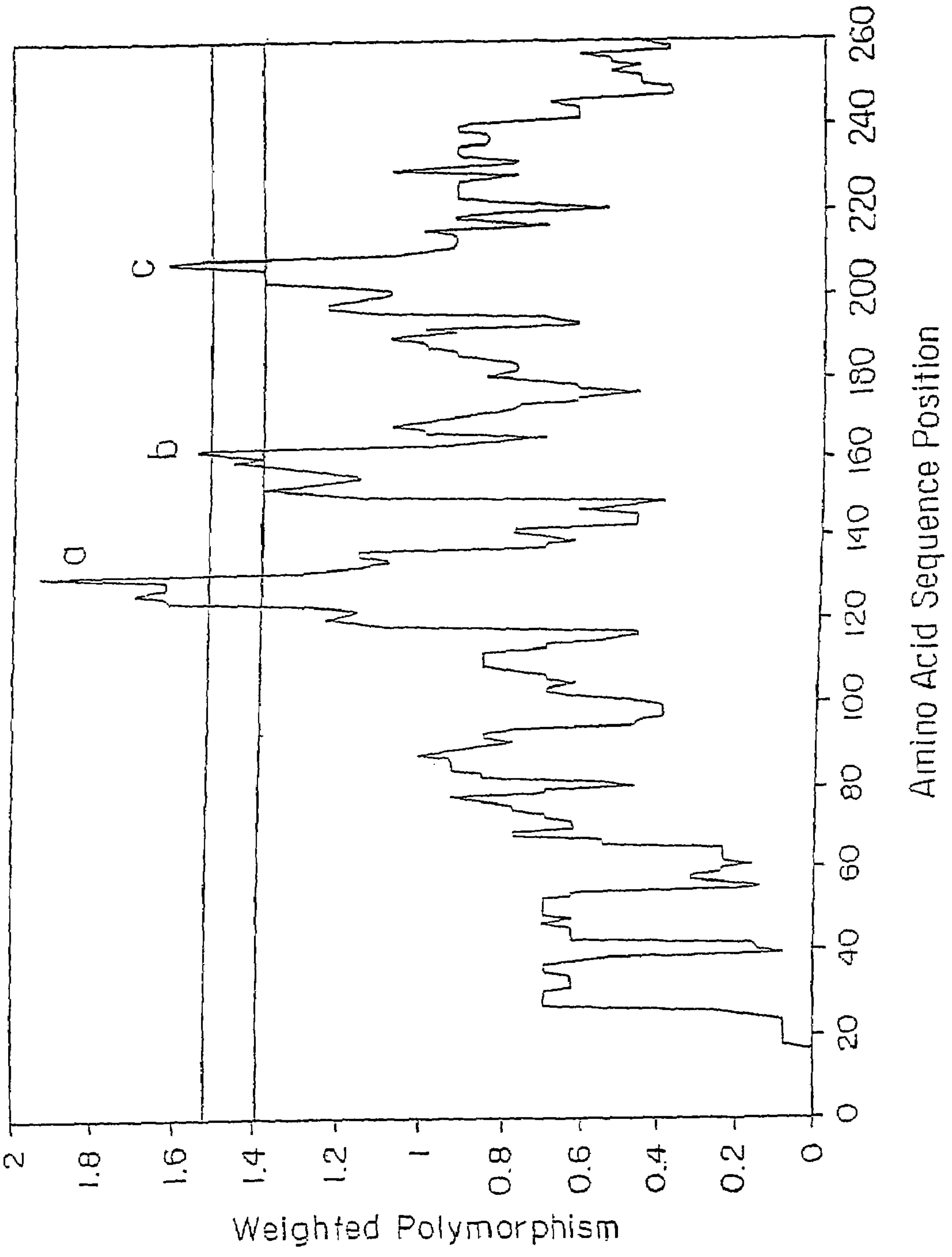
FIG. 3 is a graph depicting a plot of weighted polymorphism versus amino acid position among 14 OspA variants. The marked peaks are: a) amino acids 132–145; b) amino acids 163–177; c) amino acids 208–221. The lower line at polymorphism value 1.395 demarcates statistically significant excesses of polymorphism at p=0.05. The upper line at polymorphism value 1.520 is the same, except that the first 29 amino acids at the monomorphic N-terminus have been removed from the original analysis.
Figure 5:
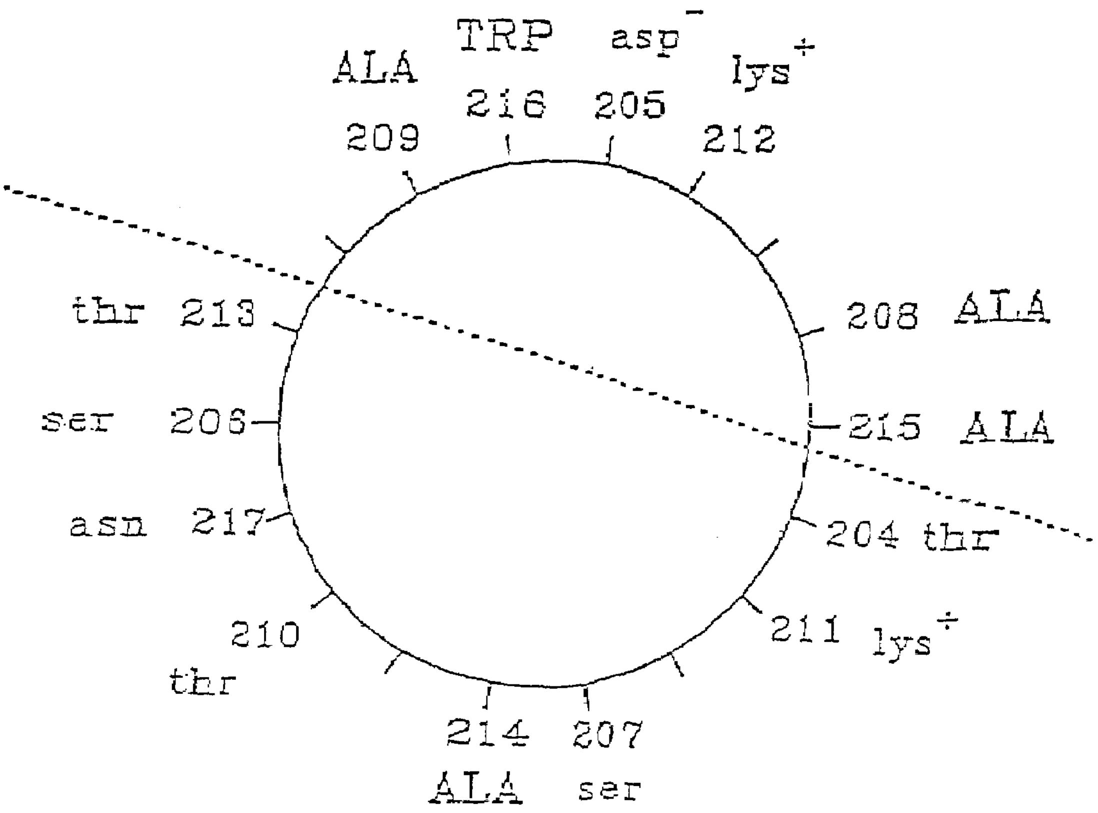
FIG. 5 is a helical wheel projection of residues 204–217 of B31 OspA. Capital letters indicate hydrophobic residues; lower case letters indicate hydrophilic residues; + and – indicate positively and negatively charged residues, respectively. The dashed line indicates division of the alpha-helix into a hydrophobic arc (above the line) and a polar arc (below the line). Adapted from France et al. (*Biochem. Biophys. Acta* 1120: 59 (1992)).
Figure 6:
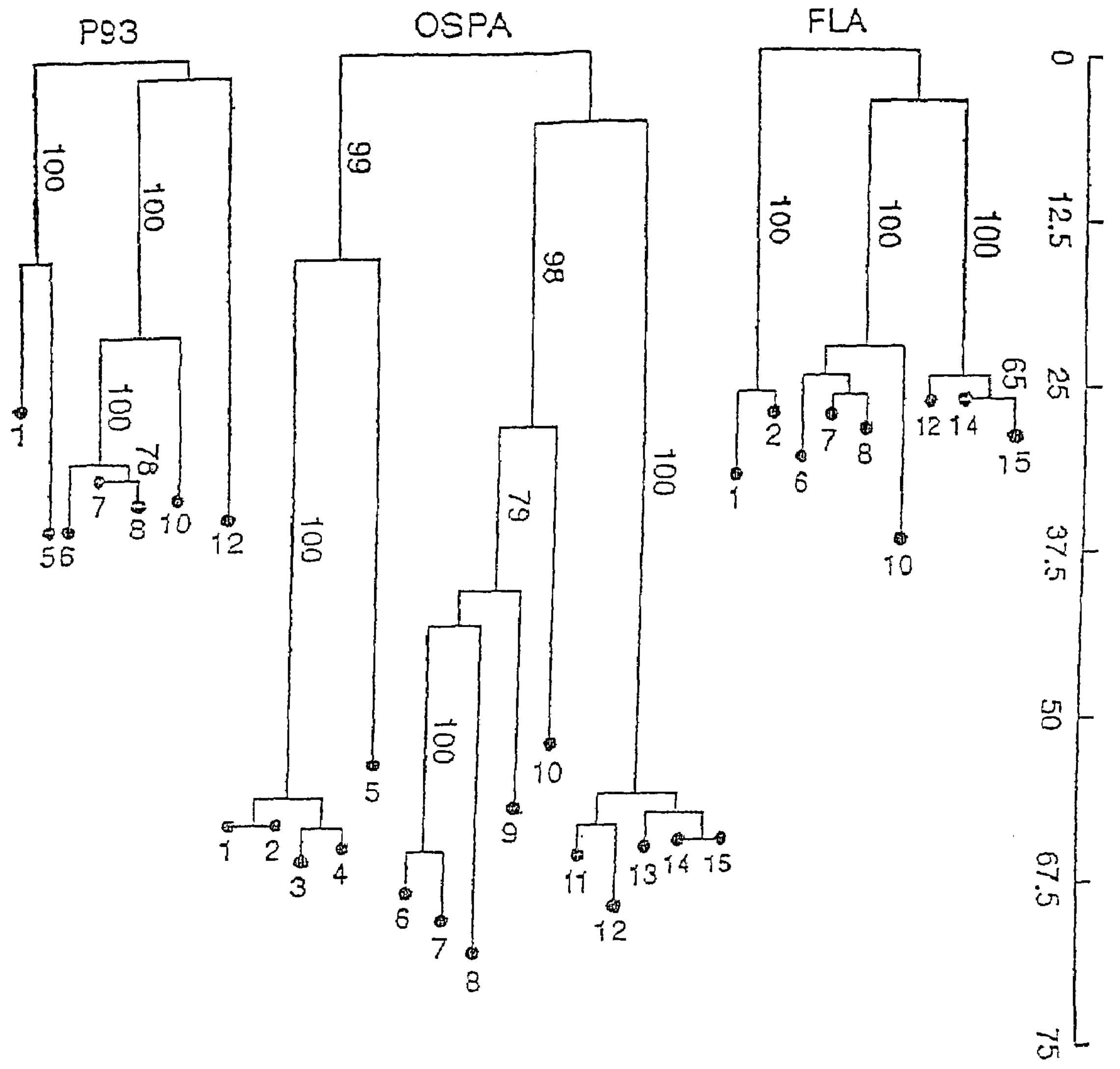
FIG. 6 depicts a phylogenic tree for strains of *Borrelia* described in Table I. The strains are as follows: 1=B31; 2=PKa1; 3=ZS7; 4=N40; 5=25015; 6=K48; 7=DK29; 8=PHei; 9=Ip90; 10=PTrob; 11=ACAI; 12=PGau; 13=Ip3; 14=PBo; 15=PKo.

This test verified that the three regions around the observed peaks all have significant excesses of polymorphism. Excesses of polymorphism were observed in the regions including amino acid residues 132–145, residues 163–177, and residues 208–221 (FIG. 3). An amino acid alignment between residues 200 and 220 for B31, K48 and the four site-directed mutants is shown in FIG. 4. The amino acid 208–221 region includes the region of OspA which has been modeled as an oriented alpha-helix in which the single tryptophan residue at amino acid 216 is buried in a hydrophobic pocket, thereby exposing more polar amino acids to the solvent (FIG. 5) (France, L. L., et al., *Biochem. Biophys. Acta* 1120: 59 (1992)). These potentially solvent-exposed residues showed considerable variability among the OspAs from various strains and may be an important component of OspA antigenic variation. For the purposes of generating chimeric proteins, the hypervariable domains of interest are Domain A, which includes amino acid residues 120–140 of OspA; Domain B, which includes residues 150–180; and Domain C, which includes residues 200–216 or 217.

B. Site-Directed Mutagenesis of the Hypervariable Region

Site-directed mutagenesis was performed to convert residues within the 204–219 domain of the recombinant B31 OspA to the analogous residues of a European OspA variant, K48. In the region of OspA between residues 204 and 219, which includes the helical domain (amino acids 204–217), there are seven amino acid differences between OspA-B31 and OspA-K48. Three oligonucleotides were generated, each containing nucleotide changes which would incorporate K48 amino acids at their analogous positions in the B31 OspA protein. The oligos used to create the site-directed mutants were:

5'-CTTAATGACTCTGACACTAGTGC-3' (#613, which converts serine at position 204 to threonine, and serine at 206 to threonine (Ser204-Thr, Ser206-Thr)) (SEQ ID NO. 1);

5'-GCTACTAAAAAAACCGGGAAATGGAATTCA-3' (#625, which converts alanine at 214 to glycine, and alanine at 215 to lysine (Ala214-Gly, Ala215-Lys)) (SEQ ID NO. 2); and 5'-GCAGCTTGGGATTCAAAAACATCCACTTTAACA-3' (#640, which converts asparagine at 217 to aspartate, and glycine at 219 to lysine (Asn217-Asp, Gly219-Lys)) (SEQ ID NO. 3).

Site-directed mutagenesis was carried out by performing mutagenesis with pairs of the above oligos. Three site-directed mutants were created, each with two changes: OspA 613 (Ser204-Thr, Ser206-Thr), OspA 625 (Ala214-Gly, Ala215-Lys), and 640 (Asn217-Asp, Gly219-Lys). There were also two proteins with four changes: OspA 613/625 (Ser204-Thr, Ser206-Thr, Ala214-Gly, Ala215-Lys) and OspA 613/640 (Ser204-Thr, Ser206-Thr, Asn217-Asp, Gly219-Lys).

Specificity of Antibody Binding to Epitopes of the Non-mutated Hypervariable Region Monoclonal antibodies that agglutinate spirochetes, including several which are neutralizing in vitro, recognize epitopes that map to the hypervariable region around Trp216 (Barbour, A. G. et al., *Infect. and Immun.* 41: 759 (1983); Schubach, W. H. et al., *Infect. and Immun.* 59: 1911 (1991)). Western Blot analysis demonstrated that chemical cleavage of OspA from the B31 strain at Trp 216 abolishes reactivity of the protein with the agglutinating MAb 105, a monoclonal raised against B31 spirochetes (data not shown). The reagent, n-chlorosuccinimide (NCS), cleaves OspA at the Trp 216, forming a 23.2 kd fragment and a 6.2 kd peptide which is not retained on the Imobilon-P membrane after transfer. The uncleaved material binds MAb 105; however, the 23.2 kd fragment is unreactive. Similar Western blots with a TrpE-OspA fusion protein containing the carboxy-terminal portion of the OspA protein demonstrated that the small 6.2 kd piece also fails to bind MAb 105 (Schubach, W. H. et al., *Infect. and Immun.* 59: 1911 (1991)).

Monoclonal antibodies H5332 and H3TS (Barbour, A. G. et al., *Infect. and Immun.* 41: 759 (1983)) have been shown by immunofluorescence to decorate the surface of fixed spirochetes (Wilske, B. et al., *World J Microbiol.* 7: 130 (1991)). These monoclonals also inhibit the growth of the organism in culture. Epitope mapping with fusion proteins has confirmed that the epitopes which bind these MAbs are conformationally determined and reside in the carboxy half of the protein. MAb H5332 is cross-reactive among all of the known phylogenetic groups, whereas MAb H3TS and MAb 105 seem to be specific to the B31 strain to which they were raised. Like MAb 105, the reactivities of H5332 and H3TS to OspA are abrogated by fragmentation of the protein at Trp216 (data not shown). MAb 336 was raised to whole spirochetes of the strain PGau. It cross-reacts to OspA from group 1 (the group to which B31 belongs) but not to group 2 (of which K48 is a member). Previous studies using fusion proteins and chemical cleavage have indicated that this antibody recognizes a domain of OspA in the region between residues 217 and 273 (data not shown). All of these MAbs will agglutinate the B31 spirochete.

Western Blot Analysis of Antibody Binding to Mutated Hypervariable Regions

MAbs were used for Western Blot analysis of the site-directed OspA mutants induced in *E. coli* using the T7 expression system (Dunn, J. J. et al., *Protein Expression and Purification* 1: 159 (1990)). *E. coli* cells carrying pET9c plasmids having a site-directed OspA mutant insert were induced at mid-log phase growth with IPTG for four hours at 37° C. Cell lysates were made by boiling an aliquot of the induced cultures in SDS gel loading dye, and this material was then loaded onto a 12% SDS gel (BioRad mini-Protean II), and electrophoresed. The proteins were then transferred to Imobilon-P membranes (Millipore) 70V, 2 hour at 4° C. using the BioRad mini transfer system. Western analysis was carried out as described by Schubach et al. (*Infect. Immun.* 59: 1911 (1991)).

Western Blot analysis indicated that only the 625 mutant (Ala214-Gly and Ala215-Lys) retained binding to the agglutinating monoclonal H3TS antibody (data not shown). However, the 613/625 mutant which has additional alterations to the amino terminus of Trp216 (Ser204-Thr and Ser206-Thr) did not bind this monoclonal antibody. Both 640 and 613/640 OspAs which have the Asn217-Asp and Gly219-Lys changes on the carboxy-terminal side of Trp216 also failed to bind MAb H3TS. This indicated that the epitope of the B31 OspA which binds MAb H3TS is comprised of amino acid side-chains on both sides of Trp216.

The 613/625 mutant failed to bind MAbs 105 and H5332, while the other mutants retained their ability to bind these MAbs. This is important in light of the data using fusion proteins that indicate that MAb 105 behaves more like MAb H3TS in terms of its serotype specificity and binding to OspA (Wilske, B. et al., *Med. Microbiol. Immunol.* 181: 191 (1992)). The 613/625 protein has, in addition to the differences at residues Ser204 and Ser206, changes immediately amino-terminal to Trp216 (Ala214-Gly and Ala215-Lys). The abrogation of reactivity of MAbs 105 and H5332 to this protein indicated that the epitopes of OspA which bind these monoclonals are comprised of residues on the amino-terminal side of Trp216.

The two proteins carrying the Asn217-Asp and Gly219-Lys replacements on the carboxy-terminal side of Trp216 (OspAs 640 and 613/640) retained binding to MAbs 105 and H5332; however, they failed to react with MAb 336, a monoclonal which has been mapped with TrpE-OspA fusion proteins and by chemical cleavage to a more carboxy-terminal domain. This result may explain why MAb 336 failed to recognize the K48-type of OspA (Group 2).

It is clear that amino acids Ser204 and Ser206 play an important part in the agglutinating epitopes in the region of the B31 OspA flanking Trp216. Replacement of these two residues altered the epitopes of OspA that bind MAbs 105, H3TS and H5332. The ability of the 640 changes alone to abolish reactivity of MAb 336 indicated that Ser204 and Ser206 are not involved in direct interaction with MAb 336.

The results indicated that the epitopes of OspA which are available to MAbs that agglutinate spirochetes are comprised at least in part by amino acids in the immediate vicinity of Trp216. Since recent circular dichroism analysis indicated that the structures of B31 and K48 OspA differ very little within this domain, it is unlikely that the changes made by mutation have radically altered the overall structure of the OspA protein (France, L. L. et al., *Biochem. Biophys. Acta* 1120: 59 (1992); and France et al., *Biochem. Biophys Acta*, submitted (1993)). This hypothesis is supported by the finding that the recombinant, mutant OspAs exhibit the same high solubility and purification properties as the parent B31 protein (data not shown).

In summary, amino acid side-chains at Ser204 and Ser206 are important for many of the agglutinating epitopes. However, a limited set of conservative changes at these sites were not sufficient to abolish binding of all of the agglutinating MAbs. These results suggested that the agglutinating epitopes of OspA are distinct, yet may have some overlap. The results also supported the hypothesis that the surface-exposed epitope around Trp216 which is thought to be important for immune recognition and neutralization is a conformationally-determined and complex domain of OspA.

Example 3

*Borrelia* Strains and Proteins

Proteins and genes from any strain of *Borrelia* can be utilized in the current invention. Representative strains are summarized in Table I, above.

A. Genes Encoding *Borrelia* Proteins

The chimeric peptides of the current invention can comprise peptides derived from any *Borrelia* proteins. Representative proteins include OspA, OspB, OspC, OspD, p12, p39, p41 (fla), p66, and p93. Nucleic acid sequences encoding several *Borrelia* proteins are presently available (see Table II, below); alternatively, nucleic acid sequences encoding *Borrelia* proteins can be isolated and characterized using methods such as those described below.

amino acids than the protein does in nature). Using similar methods as those described below, primers can be generated from known nucleic acid sequences encoding *Borrelia* proteins and used to isolate other genes encoding *Borrelia* proteins. Primers can be designed to amplify all of a gene, as well as to amplify a nucleic acid sequence encoding truncated protein sequences, such as described below for OspC, or nucleic acid sequences encoding a polypeptide derived from a *Borrelia* protein. Primers can also be designed to incorporate unique restriction enzyme cleavage sites into the amplified nucleic acid sequences. Sequence analysis of the amplified nucleic acid sequences can then be performed using standard techniques.

Cloning and Sequencing of OspA Genes and Relevant Nucleic Acid Sequences

*Borrelia* OspA sequences were isolated in the following manner: 100 μl reaction mixtures containing 50 mM KCl , 10 mM TRIS-HCl (pH 8,3), 1.5 mM $MgCl_2$, 200 μM each NTP, 2.5 units of TaqI DNA polymerase (Amplitaq, Perkin-Elmer/Cetus) and 100 pmol each of the 5' and 3' primers (described below) were used. Amplification was performed

TABLE II

References for Nucleic Acid Sequences for Several Proteins of Various *Borrelia* Strains

| Strain | p93 | OspA | p41 (fla) |
|---|---|---|---|
| K48 | X69602 (SID 67) | X62624 (SID 8) | X69610 |
| PGau | SID 73 | X62387 (SID 10) | X69612 (SID 51) |
| DK29 | ND | X63412 (SID 49) | X69608 (SID 53) |
| PKo | X69803 (SID 77) | X65599 (SID 57) | X69613 (SID 131) |
| PTrob | X69604 (SID 71) | X65598 (SID 135) | X69614 |
| Ip3 | ND | X70365 (SID 56) | ND |
| Ip90 | ND | Kryuchechnikov, V. N. et al., J. Microbiol. Epid. Immunobiol. 12: 41–44 (1988) (SID 50) | ND |
| 25015 | X70365 (SID 75) | Fikrig, E. S. et al., J. Immunol. 7: 2256–2260 (1992) (SID 12) | ND |
| B31 | Perng, G. C. et al., Infect. Immun. 59: 2070–74 (1992); Luft, B. J. et al., Infect. Immun. 60: 4309–4321 (1992) (SID 65) | Bergstrom, S. et al., Mol. Microbiol. 3: 479–486 (1989) (SID 6) | Gassmann, G. S. et al., Nucl. Acids Res. 17: 3590 (1989) (SID 127) |
| PKa1 | ND | X69606 (SID 132) | X69611 (SID 129) |
| ZS7 | ND | Jonsson, M. et al., Infect. Immun. 60: 1845–1853 (1992) (SID 134) | ND |
| N40 | ND | Kryuchechnikov, V. N. et al. (SID 133) | ND |
| PHei | ND | X65600 (SID 136) | ND |
| ACAI | ND | Kryuchechnikov, V. N. et al. (SID 58) | ND |
| PBo | X69601 (SID 69) | X65605 (SID 55) | X69610 (SID 130) |

Numbers with an “X” prefix are GenBank data base accession numbers.
SID = SEQ ID NO.

B. Isolation of *Borrelia* Genes

Nucleic acid sequences encoding full length, lipidated proteins from known *Borrelia* strains were isolated using the polymerase chain reaction (PCR) as described below. In addition, nucleic acid sequences were generated which encoded truncated proteins (proteins in which the lipidation signal has been removed, such as by eliminating the nucleic acid sequence encoding the first 18 amino acids, resulting in non-lipidated proteins). Other proteins were generated which encoded polypeptides of a particular gene (i.e., encoding a segment of the protein which has a different number of in a Perkin-Elmer/Cetus thermal cycler as described (Schubach, W. H. et al., *Infect. Immun.* 59: 1811–1915 (1991)). The amplicon was visualized on an agarose gel by ethidium bromide staining. Twenty nanograms of the chloroform-extracted PCR product were cloned directly into the PC-TA vector (Invitrogen) by following the manufacturer's instructions. Recombinant colonies containing the amplified fragment were selected, the plasmids were prepared, and the nucleic acid sequence of each OspA was determined by the dideoxy chain-termination technique using the Sequenase kit (United States Biochemical). Directed sequencing was performed with M13 primers followed by OspA-specific primers derived from sequences, previously obtained with M13 primers.

Because the 5' and 3' ends of the OspA gene are highly conserved (Fikrig, E. S. et al., *J. Immunol.* 7: 2256–2260 (1992); Bergstrom, S. et al., *Mol. Microbiol.* 3: 479–486 (1989); Zumstein, G. et al., *Med. Microbiol. Immunol.* 181: 57–70 (1992)), the 5' and 3' primers for cloning can be based upon any known OspA sequences. For example, the following primers based upon the OspA nucleic acid sequence from strain B31 were used:

5'-GGAGAATATATTATGAAA-3' (−12 to +6) (SEQ ID NO. 4); and

5'-CTCCTTATTTTAAAGCG-3' (+826 to +809) (SEQ ID NO. 5). (Schubach, W. H. et al., *Infect. Immun* 59: 1811–1915 (1991)).

OspA genes isolated in this manner include those for strains B31, K48, PGau, and 25015; the nucleic acid sequences are depicted in the sequence listing as SEQ ID NO. 6 (OspA-B31), SEQ ID NO. 8 (OspA-K48), SEQ ID NO. 10 (OspA-PGau), and SEQ ID NO. 12 (OspA-25015). An alignment of these and other OspA nucleic acid sequences is shown in FIG. 42. The amino acid sequences of the proteins encoded by these nucleic acid sequences are represented as SEQ ID NO. 7 (OspA-B31), SEQ ID NO. 9 (OspA-K48), SEQ ID NO. 11 (OspA-PGau), and SEQ ID NO. 13 (OspA-25015).

The following primers were used to generate specific nucleic acid sequences of the OspA gene, to be used to generate chimeric nucleic acid sequences (as described in Example 4):

5'-GTCTGCAAAAACCATGACAAG-3' (SEQ ID NO. 14)
(plus strand primer #369);

5'-GTCATCAACAGAAGAAAAATTC-3' (SEQ ID NO. 15)
(plus strand primer #357);

5'-CCGGATCCATATGAAAAAATATTTATTGGG-3' (SEQ ID NO. 16)
(plus strand primer #607);

5'-CCGGGATCCATATGGCTAAGCAAAATGTTAGC-3' (SEQ ID NO. 17)
(plus strand primer #584);

5'-GCGTTCAAGTACTCCAGA-3' (SEQ ID NO. 18)
(minus strand primer #200);

5'-GATATCTAGATCTTATTTTAAAGCGTT-3' (SEQ ID NO. 19)
(minus strand primer #586);
and 5'-GGATCCGGTGACCTTTTAAAGCGTTTTTAAT-3' (SEQ ID NO. 20)
(minus strand primer #1169).

Cloning and Sequencing of OspB

Similar methods were also used to isolate OspB genes. One OspB genes isolated is represented as SEQ ID NO. 21 (OspB-B31); its encoded amino acid sequence is SEQ ID NO. 22.

The following primers were used to generate specific nucleic acid sequences of the OspB gene, to be used in generation of chimeric nucleic acid sequences (see Example 4):

5'-GGTACAATTACAGTACAA-3' (SEQ ID NO. 23)
(plus strand primer #721);

5'-CCGAGAATCTCATATGGCACAAAAAGGTGCTGAGTCAATTGG-3' (SEQ ID NO. 24)
(plus strand primer #1105);

5'-CCGATATCGGATCCTATTTTAAAGCGTTTTTAAGC-3' (SEQ ID NO. 25)
(minus strand primer #1106);
and 5'-GGATCCGGTGACCTTTTAAAGCGTTTTTAAG-3' (SEQ ID NO. 26)
(minus strand primer #1170).

Cloning and Sequencing of OspC

Similar methods were also used to isolate OspC genes. The following primers were used to isolate entire OspC genes from *Borrelia* strains B31, K48, PKo, and PTrob:

5'-GTGCGCGACCATATGAAAAAGAATACAT-TAAGTGCG-3' (plus strand primer having Nde1 site combined with start codon) (SEQ ID NO. 27), and 5'-GTCGGCGGATCCTTAAGGTTTTTTTG-GACTTTCTGC-3' (minus strand primer having BamH1 site followed by stop codon) (SEQ ID NO. 28).

The nucleic acid sequences of the OspC genes were then determined by the dideoxy chain-termination technique using the Sequenase kit (United States Biochemical). OspC genes isolated and sequenced in this manner include those for strains B31, K48, PKo, and Tro; the nucleic acid sequences are depicted in the sequence listing as SEQ ID NO. 29 (OspC-B31), SEQ ID NO. 31 (OspC-K48), SEQ ID NO. 33 (OspC-PKo), and SEQ ID NO. 35 (OspC-Tro). An alignment of these sequences is shown in FIG. 38. The amino acid sequences of the proteins encoded by these nucleic acid sequences are represented as SEQ ID NO. 30 (OspC-B31), SEQ ID NO. 32 (OspC-K48), SEQ ID NO. 34 (OspC-PKo), and SEQ ID NO. 36 (OspC-Tro).

Truncated OspC genes were generated using other primers. These primers were designed to amplify nucleic acid sequences, derived from the OspC gene, that lacked the nucleic acids encoding the signal peptidase sequence of the full-length protein. The primers corresponded to bp 58–75 of the natural protein, with codons for Met-Ala attached ahead. For strain B31, the following primer was used: 5'-GTGCGCGACCATATGGCTAATAATTCAGGGAAAGAT-3' (SEQ ID NO. 37).

For strain PKo, 5'-GTGCGCGACCATATGGCTAG-TAATTCAGGGAAAGGT-3' (SEQ ID NO. 38) was used.

For strains PTrob and K48, 5'-GTGCGCGACCATATG-GCTAATAATTCAGGTGGGGAT-3' (SEQ ID NO. 39) was used.

Additional primers were also designed to amplify nucleic acids encoding particular polypeptides, for use in creation of chimeric nucleic acid sequences (see Example 4). These primers included:

5'-CTTGGAAAATTATTTGAA-3' (SEQ ID NO. 40)
(plus strand primer #520);

5'-CACGGTCACCCCATGGGAAATAATTCAGGGAAAGG-3' (SEQ ID NO. 41)
(plus strand primer #58);

-continued (SEQ ID NO. 42)
5'-TATAGATGACAGCAACGC-3'
(minus strand primer #207);
and (SEQ ID NO. 43)
5'-CCGGTGACCCCATGGTACCAGGTTTTTTTGGACTTTCTGC-3'
(minus strand primer #636).

Cloning and Sequencing of OspD

Similar methods can be used to isolate OspD genes. An alignment of four OspD nucleic acid sequences (from strains PBo, PGau, DK29, and K48) is shown in FIG. 39.

Cloning and Sequencing of p12

The p12 gene was similarly identified. Primers used to clone the entire p12 gene included: 5'-CCGGATCCATATG-GTTAAAAAAATAATATTTATTTC-3' (forward primer # 757) (SEQ ID NO. 44); and 5'-GATATCTAGATCTTTAAT-TGCTCTGCTCACTCTCTTC-3' (reverse primer #758) (SEQ ID NO. 45).

To amplify a truncated p12 gene (one in which the transcribed protein is non-lipidated, and begins at amino acid 18 of the native sequence), the following primers were used: 5'-CCGGGATCCATATGGCTAGTGCAATTG-GTCGTGG-3' (forward primer # 759) (SEQ ID NO. 46); and primer #758 (SEQ ID NO. 45).

Cloning and Sequencing of p41 (fla)

A similar approach was used to clone and sequence genes encoding the p41 (fla) protein. The p41 sequences listed in Table II with GenBank accession numbers were isolated using the following primers from strain B31: 5'-ATGAT-TATCAATCATAAT-3' (+1 to +18) (SEQ ID NO. 47); and 5'-TCTGAACAATGACAAAAC-3' (+1008 to +991) (SEQ ID NO. 48). The nucleic acid sequences of p41 isolated in this manner are depicted in the sequence listing as SEQ ID NO. 51 (p41-PGau), and SEQ ID NO. 53 (p41-DK29). An alignment of several p41 nucleic acid sequences, including those for strains B31, PKa1, PGau, PBo, DK29, and PKo, is shown in FIG. 41. The amino acid sequences of the proteins encoded by these nucleic acid sequences are represented as SEQ ID NO. 52 (p41-PGau) and SEQ ID NO. 54 (p41-DK29).

Other primers were designed to amplify nucleic acid sequences encoding polypeptides of p41, to be used in chimeric nucleic acid sequences. These primers included:

(SEQ ID NO. 59)
5'-TTGGATCCGGTCACCCCATGGCTCAATATAACCAATG-3'
(minus strand primer #122);

(SEQ ID NO. 60)
5'-TTGGATCCGGTCACCCCATGGCTTCTCAAAATGTAAG-3'
(plus strand primer #140);

(SEQ ID NO. 61)
5'-TTGGATCCGGTGACCAACTCCGCCTTGAGAAGG-3'
(minus strand primer #234);
and (SEQ ID NO. 62)
5'-TTGGATCCGGTGACCTATTTGAGCATAAGATGC-3'
(minus strand primer #141).

Cloning and Sequencing of p93

The same approach was also used to clone and sequence p93 proteins. Genes encoding p93, as listed in Table II with GenBank accession numbers, were isolated by this method with the following primers from strain B31:

(SEQ ID NO. 63)
5'-GGTGAATTTAGTTGGTAAGG-3' (-54 to -35);
and (SEQ ID NO. 64)
5'-CACCAGTTTCTTTAAGCTGCTCCTGC-3' (+1117 to +1092).

The nucleic acid sequences of p93 isolated in this manner are depicted in the sequence listing as SEQ ID NO. 65 (p93-B31), SEQ ID NO. 67 (p93-K48) SEQ ID NO. 69 (p93-PBo), SEQ ID NO. 71 (p93-PTrob), SEQ ID NO. 73 (p93-PGau), SEQ ID NO. 77 (p93–25015), and SEQ ID NO. 75 (p93-PKo). The amino acid sequences of the proteins encoded by these nucleic acid sequences are represented as SEQ ID NO. 66 (p93-B31), SEQ ID NO. 68 (p93-K48) SEQ ID NO. 70 (p93-PBo), SEQ ID NO. 72 (p93-PTrob), SEQ ID NO. 74 (p93-PGau), SEQ ID NO. 78 (p93–25015), and SEQ ID NO. 76 (p93-PKo).

Other primers were used to amplify nucleic acid sequences encoding polypeptides of p93 to be used in generating chimeric nucleic acid sequences. These primers included:

(SEQ ID NO. 79)
5'-CCGGTCACCCCATGGCTGCTTTAAAGTCTTTA-3'
(plus strand primer #475);

(SEQ ID NO. 80)
5'-CCGGTCACCCCATGAATCTTGATAAAGCTCAG-3'
(plus strand primer #900);

(SEQ ID NO. 81)
5'-CCGGTCACCCCATGGATGAAAAGCTTTTAAAAAGT-3'
(plus strand primer #1168);

(SEQ ID NO. 82)
5'-CCGGTCACCCCCATGGTTGAGAAATTAGATAAG-3'
(plus strand primer #1423);
and (SEQ ID NO. 83)
5'-TTGGATCCGGTGACCCTTAACTTTTTTTAAAG-3'
(minus strand primer #2100).

C. Expression of Proteins from *Borrelia* Genes

The nucleic acid sequences described above can be incorporated into expression plasmids, using standard techniques, and transfected into compatible host cells in order to express the proteins encoded by the nucleic acid sequences. As an example, the expression of the p12 gene and the isolation of p12 protein is set forth.

Amplification of the p12 nucleic acid sequence was conducted with primers that included a NdeI restriction site into the nucleic acid sequence. The PCR product was extracted with phenol/chloroform and precipitated with ethanol. The precipitated product was digested and ligated into an expression plasmid as follows: 15 μl (approximately 1 μg) of PCR DNA was combined with 2 μl 10× restriction buffer for NdeI (Gibco/BRL), 1 μl NdeI (Gibco/BRL), and 2 μl distilled water, and incubated overnight at 37° C. This mixture was subsequently combined with 3 μl 10× buffer (buffer 3, New England BioLabs), 1 μl BamHI (NEB), and 6 μl distilled water, and incubated at 37° for two hours. The resultant material was purified by preparative gel electrophoresis using low melting point agarose, and the band was visualized under long wave ultraviolet light and excised from the gel. The gel slice was treated with Gelase using conditions recommended by the manufacturer (Epicentre Technologies). The resulting DNA pellet was resuspended in 25–50 μl of 10 mM TRIS-CL (pH 8.0) and 1 mM EDTA (TE). An aliquot of this material was ligated into the pET9c expression vector (Dunn, J. J. et al., *Protein Expression and Purification* 1: 159 (1990)).

To ligate the material into the pET9c expression vector, 20–50 ng of p 12 nucleic acid sequences cut and purified as described above was combined with 5 μl 10 One-Phor-All (OPA) buffer (Pharmacia), 30–60 ng pET9c cut with NdeI and BamHI, 2.5 μl 20 mM ATP, 2 μl T4 DNA ligase (Pharmacia) diluted 1:5 in 1×OPA buffer, and sufficient distilled water to bring the final volume to 50 μl. The mixture was incubated at 12° C. overnight.

The resultant ligations were transformed into competent DH5-alpha cells and plated on nutrient agar plates containing 50 μg/ml kanamycin and incubated overnight at 37° C. DH5-alpha is used as a "storage strain" for T7 expression clones, because it is RecA deficient, so that recombination and concatenation are not problematic, and because it lacks the T7 RNA polymerase gene necessary to express the cloned gene. The use of this strain allows for cloning of potentially toxic gene products while minimizing the chance of deletion and/or rearrangement of the desired genes. Other cell lines having similar properties may also be used.

Kanamycin resistant colonies were single-colony purified on nutrient agar plates supplemented with kanamycin at 50 μg/ml. A colony from each isolate was inoculated into 3–5 ml of liquid medium containing 50 μg/ml kanamycin, and incubated at 37° C. without agitation. Plasmid DNA was obtained from 1 ml of each isolate using a hot alkaline lysis procedure (Mantiatis, T. et al., *Molecular Cloning: A Laboratory Manual*, Cold Spring Harbor Laboratory, Cold Spring Harbor, N.Y. (1982)).

Plasmid DNA was digested with EcoRI and BglII in the following manner: 15 μl plasmid DNA was combined with 2 μl 10× buffer 3 (NEB), 1 μl EcoRI (NEB), 1 μl BglII (NEB) and 1 μl distilled water, and incubated for two hours at 37° C. The entire reaction mixture was electrophoresed on an analytical agarose gel. Plasmids carrying the p12 insert were identified by the presence of a band corresponding to 925 base-pairs (full length p12) or 875 base-pairs (nonlipidated p12). One or two plasmid DNAs from the full length and nonlipidated p12 clones in pET9c were used to transform BL21 DE3 pLysS to kanamycin resistance as described by Studier et al. (*Methods in Enzymology*, Goeddel, D. (Ed.), Academic Press, 185: 60–89 (1990)). One or two transformants of the full length and nonlipidated clones were single-colony purified on nutrient plates containing 25 μg/ml chloramphenicol (to maintain pLysS) and 50 μg/ml kanamycin at 37° C. One colony of each isolate was inoculated into liquid medium supplemented with chloramphenicol and kanamycin and incubated overnight at 37° C. The overnight culture was subcultured the following morning into 500 ml of liquid broth with chloramphenicol (25 μg/ml) and kanamycin (50 μg/ml) and grown with aeration at 37° C. in an orbital air-shaker until the absorbance at 600 nm reached 0.4–0.7. Isopropyl-thio-galactoside (IPTG) was added to a final concentration of 0.5 mM, for induction, and the culture was incubated for 3–4 hours at 37° C. as before. The induced cells were pelleted by centrifugation and resuspended in 25 ml of 20 mM $NaPO_4$ (pH 7.7). A small aliquot was removed for analysis by gel electrophoresis. Expressing clones produced proteins which migrated at the 12 kDa position.

A crude cell lysate was prepared from the culture as described for recombinant OspA by Dunn, J. J. et al., (*Protein Expression and Purification* 1: 159 (1990)). The crude lysate was first passed over a Q-sepharose column (Pharmacia) which had been pre-equilibrated in Buffer A: 10 mM $NaPO_4$ (pH 7.7), 10 mM NaCl, 0.5 mM PMSF. The column was washed with 10 mM $NaPO_4$, 50 mM NaCl and 0.5 mM PMSF and then p12 was eluted in 10 mM $NaPO_4$, 0.5 mM PMSF with a NaCl gradient from 50–400 mM. p12 eluted approximately halfway through the gradient between 100 and 200 mM NaCl. The peak fractions were pooled and dialyzed against 10 mM $NaPO_4$ (pH 7.7), 10 mM NaCl, 0.5 mM PMSF. The protein was then concentrated and applied to a Sephadex G50 gel filtration column of approximately 50 ml bed volume (Pharmacia), in 10 mM $NaPO_4$, 200 mM NaCl, 0.5 mM PMSF. p12 would typically elute shortly after the excluded volume marker. Peak fractions were determined by running small aliquots of all fractions on an SDS gel. The p12 peak was pooled and stored in small aliquots at −20° C.

Example 4

Generation of Chimeric Nucleic Acid Sequences and Chimeric Proteins

A. General Protocol for Creation of Chimeric Nucleic Acid Sequences

The megaprimer method of site directed mutagenesis and its modification were used to generate chimeric nucleic acid sequences (Sarkar and Sommer, *Biotechniques* 8(4): 404–407 (1990); Aiyar, A. and J. Leis, *Biotechniques* 14(3): 366–369 (1993) primer for the first genomic template and a 3' fusion oligo are used to amplify the desired region. The fusion primer consists of a 3' end of the first template (DNA that encodes the amino-proximal polypeptide of the fusion protein), coupled to a 5' end of the second template (DNA that encodes the carboxy-proximal polypeptide of the fusion protein).

The PCR amplifications are performed using Taq DNA polymerase, 10×PCR buffer, and $MgCl_2$ (Promega Corp., Madison, Wis.), and Ultrapure dNTPs (Pharmacia, Piscataway, N.J.). One μg of genomic template 1, 5 μl of 10 μM 5' oligo and 5 μl of 10 μM fusion oligo are combined with the following reagents at indicated final concentrations: 10× Buffer-Mg FREE (1×), $MgCl_2$ (2 mM), dNTP mix (200 μM each dNTP), Taq DNA polymerase (2.5 units), water to bring final volume to 100 μl. A Thermal Cycler (Perkin Elmer Cetus, Norwalk, Conn.) is used to amplify under the following conditions: 35 cycles at 95° C. for one minute, 55° C. for two minutes, and 72° for three minutes. This procedure results in a "megaprimer".

The resulting megaprimer is run on a 1×TAE, 4% low-melt agarose gel. The megaprimer band is cut from the gel and purified using the Promega Magic PCR Preps DNA purification system. Purified megaprimer is then used in a second PCR step. One μg of genomic template 2, approximately 0.5 μg of the megaprimer, and 5 μl of 10 μM 3' oligo are added to a cocktail of 10× buffer, $MgCl_2$, dNTPs and Taq at the same final concentrations as noted above, and brought to 100 μl with water. PCR conditions are the same as above. The fusion product resulting from this amplification is also purified using the Promega Magic PCR Preps DNA purification system.

The fusion product is then ligated into TA vector and transformed into *E. coli* using the Invitrogen (San Diego, Calif.) TA Cloning Kit. Approximately 50 ng of PCR fusion product is ligated to 50 ng of pCRII vector with 1× Ligation Buffer, 4 units of T4 ligase, and brought to 10 μl with water.

This ligated product mixture is incubated at 12° C. overnight (approximately 14 hours). Two [I of the ligation product mixture is added to 50 μl competent INC F' cells and 2 μl beta mercaptoethanol. The cells are then incubated for 30 minutes, followed by heat shock treatment at 42° C. for 60 seconds, and an ice quenching for two minutes. 450 μl of warmed SOC media is then added to the cells, resulting in a transformed cell culture which is incubated at 37° C. for one hour with slight shaking. 50 μl of the transformed cell culture is plated on LB+50 μg/μl ampicillin plates and incubated overnight at 37° C. Single white colonies are picked and added to individual overnight cultures containing 3 ml LB with ampicillin (50 μg/μl).

The individual overnight cultures are prepared using Promega's Magic Miniprep DNA purification system. A small amount of the resulting DNA is cut using a restriction digest as a check. DNA sequencing is then performed to check the sequence of the fusion nucleic acid sequence, using the United States Biochemical (Cleveland, Ohio) Sequenase Version 2.0 DNA sequencing kit. Three to five μg of plasmid DNA is used per reaction. 2 μl 2M NaOH/2 mM EDTA are added to the DNA, and the volume is brought to 20 μl with water. The mixture is then incubated at room temperature for five minutes. 7 μl water, 3 μl 3M NaAc, 75 [I EtOH are added. The resultant mixture is mixed by vortex and incubated for ten minutes at −70° C., and then subjected to microcentrifugation. After microcentrifugation for ten minutes, the supernatant is aspirated off, and the pellet is dried in the speed vac for 30 second. 6 μl water, 2 μl annealing buffer, and 2 μl of 10 μM of the appropriate oligo is then added. This mixture is incubated for 10 minutes at 37° C. and then allowed to stand at room temperature for 10 minutes. Subsequently, 5.5 μl of label cocktail (described above) is added to each sample of the mixture, which are incubated at room temperature for an additional five minutes. 3.5 μl labeled DNA is then added to each sample which is then incubated for five minutes at 37° C. 4 μl stop solution is added to each well. The DNA is denatured at 95° for two minutes, and then placed on ice.

Clones with the desired fusion nucleic acid sequences are then reckoned in frame in the pET expression system in the lipidated (full length) and non-lipidated (truncated, i.e., without first 17 amino acids) forms. The product is amplified using restriction sites contained in the PCR primers. The vector and product are cut with the same enzymes and ligated together with T4 ligase. The resultant plasmid is transformed into competent *E. coli* using standard transformation techniques. Colonies are screened as described earlier and positive clones are transformed into expression cells, such as *E. coli* BL21, for protein expression with IPTG for induction. The expressed protein in its bacterial culture lysate form and/or purified form is then injected in mice for antibody production. The mice are bled, and the sera collected for agglutination, in vitro growth inhibition, and complement-dependent and -independent lysis tests.

B. Specific Chimeric Nucleic Acid Sequences

Various chimeric nucleic acid sequences were generated. The nucleic acid sequences are described as encoding polypeptides from *Borrelia* proteins. The chimeric nucleic acid sequences are produced such that the nucleic acid sequence encoding one polypeptide is in the same reading frame as the nucleic acid sequence encoding the next polypeptide in the chimeric protein sequence encoded by the chimeric nucleic acid sequence. The proteins are listed sequentially (in order of presence of the encoding sequence) in the description of the chimeric nucleic acid sequence. For example, if a chimeric nucleic acid sequence consists of bp 1–650 from OspA-1 and bp 651–820 from OspA-2 were sequenced, the sequence of the chimer would include the first 650 base pairs from OspA-1 followed immediately by base pairs 651–820 of OspA-2.

OspA-K48/OspA-PGau

A chimer of OspA from strain K48 (OspA-K48) and OspA from strain PGau (OspA-PGau) was generated using the method described above. This chimeric nucleic acid sequence included bp 1–654 from OspA-K48, followed by bp 655–820 from OspA-PGau. Primers used included: the amino-terminal sequence of OspA primer #607 (SEQ ID NO. 16); the fusion primer, 5'-AAAGTAGAAGTTTTTGAATCCCATTTTCCAGTTTTTTT-3' (minus strand primer #668–654) (SEQ ID NO. 84); the carboxy-terminal sequence of OspA primer #586 (SEQ ID NO. 19); and the sequence primers #369 (SEQ ID NO. 14) and #357 (SEQ ID NO. 15). The chimeric nucleic acid sequence is presented as SEQ ID NO. 85; the chimeric protein encoded by this chimeric nucleic acid sequence is presented as SEQ ID NO. 86.

OspA-B31/OspA-PGau

A chimer of OspA from strain B31 (OspA-B31) and OspA from strain PGau (OspA-PGau) was generated using the method described above. This chimeric nucleic acid sequence included bp 1–651 from OspA-B31, followed by bp 652–820 from OspA-PGau. Primers used included: the fusion primer, 5'-AAAGTAGAAGTTTTTGAATTCCAAGCTGCAGTTTT-3' (minus strand primer #668–651) (SEQ ID NO. 87); and the sequence primer, #369 (SEQ ID NO. 14). The chimeric nucleic acid sequence is presented as SEQ ID NO. 88; the chimeric protein encoded by this chimeric nucleic acid sequence is presented as SEQ ID NO. 89.

OspA-B31/OspA-K48

A chimer of OspA from strain B31 (OspA-B31) and OspA from strain K48 (OspA-K48) was generated using the method described above. This chimeric nucleic acid sequence included bp 1–651 from OspA-B31, followed by bp 652–820 from OspA-K48. Primers used included: the fusion primer, 5'-AAAGTGGAAGTTTTTGAATTCCAAGCTGCAGTTTT-3' (minus strand primer #671–651) (SEQ ID NO. 90); and the sequence primer, #369 (SEQ ID NO. 14). The chimeric nucleic acid sequence is presented as SEQ ID NO. 91; the chimeric protein encoded by this chimeric nucleic acid sequence is presented as SEQ ID NO. 92.

OspA-B31/OspA-25015

A chimer of OspA from strain B31 (OspA-B31) and OspA from strain 25015 (OspA-25015) was generated using the method described above. This chimeric nucleic acid sequence included bp 1–651 from OspA-B31, followed by bp 652–820 from OspA-25015. Primers used included: the fusion primer, 5'-TAAAGTTGAAGTGCCTGCATTCCAAGCTGCAGTTT-3' (SEQ ID NO. 93). The chimeric nucleic acid sequence is presented as SEQ ID NO. 94; the chimeric protein encoded by this chimeric nucleic acid sequence is presented as SEQ ID NO. 95.

OspA-K48/OspA-B31/OspA-K48

A chimer of OspA from strain B31 (OspA-B31) and OspA from strain K48 (OspA-K48) was generated using the method described above. This chimeric nucleic acid sequence included bp 1–570 from OspA-K48, followed by bp 570–651 from OspA-B31, followed by bp 650–820 from OspA-K48. Primers used included: the fusion primer, 5'-CCCCAGATTTTGAAATCTTGCTTAAAACAAC-3' (SEQ ID NO. 96); and the sequence primer, #357 (SEQ ID NO. 15). The chimeric nucleic acid sequence is presented as SEQ ID NO. 97; the chimeric protein encoded by this chimeric nucleic acid sequence is presented as SEQ ID NO. 98.

OspA-B31/OspA-K48/OspA-B31/OspA-K48

A chimer of OspA from strain B31 (OspA-B31) and OspA from strain K48 (OspA-K48) was generated using the method described above. This chimeric nucleic acid sequence included bp 1–420 from OspA-B31, followed by 420–570 from OspA-K48, followed by bp 570–650 from OspA-B31, followed by bp 651–820 from OspA-K48. Primers used included: the fusion primer, 5'CAAGTCTGGTTCCAATTTGCTCTTGTTATTAT-3' (minus strand primer #436–420) (SEQ ID NO. 99); and the sequence primer, #357 (SEQ ID NO. 15). The chimeric nucleic acid sequence is presented as SEQ ID NO. 100; the chimeric protein encoded by this chimeric nucleic acid sequence is presented as SEQ ID NO. 101.

OspA-B31/OspB-B31

A chimer of OspA and OspB from strain B31 (OspA-B31, OspB-B31) was generated using the method described above. The chimeric nucleic acid sequence included bp 1–651 from OspA-B31, followed by bp 652–820 from OspB-B31. Primers used included: the fusion primer, 5'-GTTAAAGTGCTAGTACTGTCATTCCAAGCTGCAGTTTTTTT-3' (minus strand primer #740–651) (SEQ ID NO. 102); the carboxy-terminal sequence of OspB primer #1106 (SEQ ID NO. 25); and the sequence primer #357 (SEQ ID NO. 15). The chimeric nucleic acid sequence is presented as SEQ ID NO. 103; the chimeric protein encoded by this chimeric nucleic acid sequence is presented as SEQ ID NO. 104.

OspA-B31/OspB-B31/OspC-B31

A chimer of OspA, OspB and OspC from strain B31 (OspA-B31, OspB-B31, and OspC-B31) was generated using the method described above. The chimeric nucleic acid sequence included bp 1–650 from OspA-B31, followed by bp 652–820 from OspB-B31, followed by bp 74–630 of OspC-B31. Primers used included: the fusion primer, 5'-TGCAGATGTAATCCCATCCGCCATTTTTAAAGCGTTTTT-3' (SEQ ID NO. 105); and the carboxy-terminal sequence of OspC primer (SEQ ID NO. 28). The chimeric nucleic acid sequence is presented as SEQ ID NO. 106; the chimeric protein encoded by this chimeric nucleic acid sequence is presented as SEQ ID NO. 107.

OspC-B31/OspA-B31/OspB-B31

A chimer of OspA, OspB and OspC from strain B31 (OspA-B31, OspB-B31, and OspC-B31) was generated using the method described above. The chimeric nucleic acid sequence included bp 1–630 from OspC-B31, followed by bp 52–650 from OspA-B31, followed by bp 650–820 of OspB-B31. Primers used included: the amino-terminal sequence of OspC primer having SEQ ID NO. 27; the fusion primer, 5'-GCTGCTAACATTTTGCTTAGGTTTTTTTGGACTTTC-3' (minus strand primer #69-630) (SEQ ID NO. 108); and the sequence primers #520 (SEQ ID NO. 40) and #200 (SEQ ID NO. 18). The chimeric nucleic acid sequence is presented as SEQ ID NO. 109; the chimeric protein encoded by this chimeric nucleic acid sequence is presented as SEQ ID NO. 110.

Additional Chimeric Nucleic Acid Sequences

Using the methods described above, other chimeric nucleic acid sequences were produced. These chimeric nucleic acid sequences, and the proteins encoded, are summarized in Table III.

TABLE III

Chimeric Nucleic acid Sequences and the Encoded Proteins

| Chimers Generated (base pairs) | SEQ ID NO. (nt) | SEQ ID NO. (protein) |
|---|---|---|
| OspA (52–882)/p93 (1168–2100) | 111 | 112 |
| OspB (45–891)/p41 (122–234) | 113 | 114 |
| OspB (45–891)/p41 (122–295) | 115 | 116 |
| OspB (45–891)/p41 (140–234) | 117 | 118 |
| OspB (45–891)/p41 (140–295) | 119 | 120 |
| OspB (45–891)/p41 (122–234)/OspC (58–633) | 121 | 122 |
| OspA-Tro/OspA-Bo | 137 | 138 |
| OspA-PGau/OspA-Bo | 139 | 140 |
| OspA-B31/OspA-PGau/OspA-B31/OspA-K48 | 143 | 144 |
| OspA-PGau/OspA-B31/OspA-K48 | 141 | 142 |

C. Purification of Proteins Generated by Chimeric Nucleic Acid Sequences

The chimeric nucleic acid sequences described above, as well as chimeric nucleic acid sequences produced by the methods described above, are used to produce chimeric proteins encoded by the nucleic acid sequences. Standard methods, such as those described above in Example 3, concerning the expression of proteins from *Borrelia* genes, can be used to express the proteins in a compatible host organism. The chimeric proteins can then be isolated and purified using standard techniques.

If the chimeric protein is soluble, it can be purified on a Sepharose column. Insoluble proteins can be solubilized in guanidine and purified on a $Ni^{2+}$ column; alternatively, they can be solubilized in 10 mM $NaPO_4$ with 0.1–1% TRIXON X 114, and subsequently purified over an S column (Pharmacia). Lipidated proteins were generally purified by the latter method. Solubility was determined by separating both soluble and insoluble fractions of cell lysate on a 12% PAGE gel, and checking for the localization of the protein by Coomasie staining, or by Western blotting with monoclonal antibodies directed to an antigenic polypeptide of the chimeric protein.

Example 5

Generation of OspC/OspA Chimeric Nucleic Acids and Chimeric Proteins

A. General Protocol for Creation of Chimeric Nucleic Acid Sequences

A large number of chimeric nucleic acid sequences encoding proteins comprising at least a first and a second polypeptide from *Borrelia burgdorferi* were generated. These chimeric nucleic acid sequences were produced such that the encoded chimeric protein comprised a *Borrelia burgdorferi* OspC polypeptide upstream of (or N-terminal to) a *Borrelia burgdorferi* OspA polypeptide. The chimeric nucleic acid sequences were also produced such that the nucleic acid encoding one polypeptide was in the same reading frame as the nucleic acid sequence encoding the next polypeptide in the chimeric protein.

The general cloning strategy used to construct the chimeric nucleic acid sequences was as follows. The desired fragment of OspC was amplified using a 5' primer containing a restriction site suitable for cloning the resultant product into a vector of interest and a 3' primer containing a restriction site suitable for ligating the OspC fragment to the OspA fragment. The OspC product is cloned into a suitable vector. For the OspA poriton of the chimeric nucleic acid, the desired OspA fragment was amplified using a 5' primer containing a restriction site for ligating the resultant OspA fragment to the OspC fragment and a 3' primer containing a restriction site suitable for cloning the resultant OspA product into the vector with the OspC product. The use of a restriction site to allow ligation of the OspC and OspA fragment results in the insertion of 0 to about 3 amino acids between the OspC and OspA fragments.

A specific example of such a construction follows. It is understood that other suitable restriction sites could be used with no more than routine experimentation. The resultant OspC/OspA chimers could have, therefore, the addition of 0 to about 3 amino acids between the OspC and OspA fragments, depending on the restriction site used.

For the OspC portions of the chimeric nucleic acids, desired fragments of OspC genes from various strains or genospecies were PCR amplified using a 5' primer containing an NdeI site and a 3' primer containing a NcoI and a BamHI site. The amplified OspC product was then cloned into the NdeI and BamHI sites of the T7 promoter driven expression vector, pET9c. For the OspA portion of the chimeric nucleic acid, desired fragments of OspA genes a strain of interest or genospecies of interest were PCR amplified using a 5' primer containing an NcoI site and a 3' primer containing a BamHI site. This OspA portion could then be directly cloned into the NcoI and BamHI sites of the pET9c vector containing the desired OspC sequence, thereby producing the desired OspC-OspA construct. By including the sequence for the NcoI restriction site in the primers, a nine nucleotide linker sequence encoding the amino acids Ser-Met-Ala was produced at the junction between the N-terminal OspC sequence and the C-terminal OspA sequence. The use of the NcoI restriction enzyme (CCATGG) in this cloning strategy was a suitable choice as *Borrelia* DNA is an AT-rich and therefore possesses only a few NcoI sites in its genome.

As an example, OspC-OspA chimeric nucleic acids which contain unlipidated OspC B31 were generated using the following primers:

(5'OspC-NdeI):

(SEQ ID NO:181)

5'-GT CAT ATG GCT TGT AAT AAT TCA GGG AAA GA-3';

and (3'OspC-Ncol):

(SEQ ID NO:182)

5'-T TTC CAT GGA AGG TTT TTT TGG ACT TTC TG-3'.

For OspC-OspA chimeric nucleic acids which contain unlipidated OspA B31, the following primers were used:

(5'OspA-NcoI:)

(SEQ ID NO: 183)

5'-TT TCC ATG GCC AAG CAA AAT GTT AGC AGC C-3';

and (3'OspA-BamHI):

(SEQ ID NO:184)

5'-TAA GGA TCC TTA TTT TAA AGC GTT TTT-3'.

Lipidated versions of the OspC/A chimeras can be constructed by cloning an expression vector that contains a leader sequence containing a lipidation site, such that the leader sequence is linked upstream of the OspC portion of the chimera and in frame with the chimera. The leader sequence comprising a lipidation signal can be, for example, from a gene encoding the OspA, B or C polypeptides.

Chimeric nucleic acid sequences, and the proteins that they encode, which were produced are summarized in Table IV. Other additional chimeric nucleic acid sequences, and encoded proteins, are also depicted in Table IV. In further embodiments, chimeric OspC/OspA proteins are constructed wherein a first segment of OspA is from B31 and comprises base pairs from about 88 to about 450, and a second segment of OspA comprises base pairs from about 451 to about 537 of PKo. These chimeras can also comprise additional OspA segments such as the last two segments of SEQ ID NOs 167 or 165 or the last segment of SEQ ID NO: 163.

TABLE IV

Chimeric OspC/OspA Nucleic Acid Sequences and Encoded Proteins

| [1]Chimers Generated | SEQ ID NO. (nt) | SEQ ID NO. (protein) | FIG. NO. |
|---|---|---|---|
| OspC-B31(bp55–633)/OspA-B31(bp52–822) | 145 | | 55 |
| OspC-B31(aa19–211)/OspA-B31(aa18–273) | | 146 | 55 |
| OspC-B31(bp55–624)/OspA-B31(bp52–822) | 147 | | 56 |
| OspC-B31(aa19–208)/OspA-B31(aa18–273) | | 148 | 56 |
| OspC-C2(bp55–612)/OspA-B31(bp52–822) | 149 | | 57 |
| OspC-C2(aa19–204)/OspA-B31(aa18–273) | | 150 | 57 |
| OspC-B31(bp55–633)/OspA-B31(bp52–651)/ OspA-K48(bp652–820) | 151 | | 58 |
| OspC-B31(aa19–211)/OspA-B31(aa18–216)/ OspA-K48(aa217–273) | | 152 | 58 |
| OspC-C2(bp55–612)/OspA-B31(bp52–651)/ OspA-K48(bp652–820) | 153 | | 59 |
| OspC-C2(aa19–204)/OspA-B31(aa18–216)/ OspA-K48(aa217–273) | | 154 | 59 |

TABLE IV-continued

Chimeric OspC/OspA Nucleic Acid Sequences and Encoded Proteins

| [1]Chimers Generated | SEQ ID NO. (nt) | SEQ ID NO. (protein) | FIG. NO. |
|---|---|---|---|
| OspC-B31(bp55-633)/OspA-B31(bp52-651)/ OspA-PKo(bp652-820) | 155 | | 60 |
| OspC-B31(aa19-211)/OspA-B31(aa18-216)/ OspA-PKo(aa217-273) | | 156 | 60 |
| OspC-C2(bp55-612)/OspA-B31(52-651)/ OspA-PKo(bp652-820) | 157 | | 61 |
| OspC-C2(aa19-204)/OspA-B31(aa18-216)/ OspA-PKo(aa217-273) | | 158 | 61 |
| OspC-B31(bp55-633)/OspA-K48(bp52-654)/ OspA-Tro(bp655-819) | 159 | | 62 |
| OspC-B31(aa19-211)/OspA-K48(aa18-217)/ OspA-Tro(aa218-273) | | 160 | 62 |
| OspC-C2(bp55-612)/OspA-K48(bp52-654)/ OspA-Tro(bp655-819) | 161 | | 63 |
| OspC-C2(aa19-204)/OspA-K48(aa18-217)/ OspA-Tro(aa218-273) | | 162 | 63 |
| OspC-C12(bp55-612)/OspA-B31(bp88-492)/ OspA-PKo(bp493-537)/OspA-B31(bp538-822) | 163 | | 64 |
| OspC-C12(aa19-204)/OspA-B31(aa30-164)/ OspA-PKo(aa165-179)/OspA-B31(aa180-273) | | 164 | 64 |
| OspC-PKo(bp55-639)/OspA-B31(bp88-492)/ OspA-PKo(bp493-537)/OspA-B31(bp538-651)/ OspA-K48(bp652-825) | 165 | | 65 |
| OspC-PKo(aa19-213)/OspA-B31(aa30-164)/ OspA-PKo(aa165-179)/OspA-B31(aa180-216)/ OspA-K48(aa217-274) | | 166 | 65 |
| OspC-Tro(bp55-624)/OspA-B31(bp88-492)/ OspA-PKo(bp493-537)/OspA-B31(bp538-651)/ OspA-PKo(bp652-822) | 167 | | 66 |
| OspC-Tro(aa19-208)/OspA-B31(aa30-164)/ OspA-PKo(aa165-179)/OspA-B31(aa180-216)/ OspA-PKo(aa217-273) | | 168 | 66 |
| OspC-B31(bp55-633)/OspA-B31(bp394-820) | 169 | | 67 |
| OspC-B31(aa19-211)/OspA-B31(aa132-273) | | 170 | 67 |
| OspC-B31(bp55-631)/OspA-B31(bp394-651)/ OspA-K48(652-820) | 171 | | 68 |
| OspC-B31(aa19-211)/OspA-B31(aa132-216)/ OspA-K48(217-273) | | 172 | 68 |
| OspC-B31(bp55-633)/OspA-B31(bp394-651)/ OspA-PKo(652-820) | 173 | | 69 |
| OspC-B31(aa19-211)/OspA-B31(aa132-216)/ OspA-PKo(217-273) | | 174 | 69 |
| OspC-B31(bp55-633)/OspA-K48(bp394-654)/ OspA-Tro(655-819) | 175 | | 70 |
| OspC-B31(aa19-211)/OspA-K48(aa132-217)/ OspA-Tro(218-273) | | 176 | 70 |
| OspC-B31(bp55-633)/OspA-B31(bp88-492)/ OspA-PKo(bp493-537)/OspA-B31(bp541-651)/ OspA-PKo(bp652-822) | 177 | | 71 |
| OspC-B31(aa19-211)/OspA-B31(aa30-164)/ OspA-PKo(aa165-179, aa164(K > G))/OspA-B31 (aa180-216)(aa190(N-del))/OspA-PKo(aa217-273) | | 178 | 71 |
| OspC-C2(bp55-612)/OspA-B31(bp88-492)/ OspA-PKo(bp493-537)/OspA-B31(bp541-651)/ OspA-PKo(bp652-822) | 179 | | 72 |

TABLE IV-continued

Chimeric OspC/OspA Nucleic Acid Sequences and Encoded Proteins

| ¹Chimers Generated | SEQ ID NO. (nt) | SEQ ID NO. (protein) | FIG. NO. |
|---|---|---|---|
| OspC-C2(aa19–204)/OspA-B31(aa30–164)/ OspA-PKo(aa165–179, aa164(K > G))/OspA-B31 (aa180–216)(aa190(N-del))/OspA-PKo(aa217–273) | | 180 | 72 |

¹Chimers Generated are listed as follows: Nucleotide or polypeptide fragment -strain (sequence in base pairs for the top listing and amino acids for the bottom listing)

Separate nucleotide or polypeptide fragments in the chimer are separated by a /

B. Protein Expression

As described in the previous two examples, it is possible to express and purify *Borrelia* proteins such as OspA, OspC and chimeric OspC/OspA polypeptides. This is accomplished by incorporating the desired nucleic acid sequence, which encodes the protein of choice, into an expression plasmid, using standard techniques. This expression plasmid can then be transfected into a compatible host cell in order to express the desired protein.

The purified OspA, OspC or OspC/OspA chimeric proteins, that were used to immunize mice and in the ELISA tests described below, were generated and purified by cloning either OspA, OspC or OspC/OspA chimeric nucleic acid sequences, in frame, into the pET expression plasmid. The expression plasmid was then transfected into the compatible expression cell line *Escherichia coli* strain BL21 (DE3)/(pLysS) or strain B834 (DE3). The BL21 or B834 cells were then grown in 10 ml LB media (5 g/l NaCl, 10 g/l tryptone, 5 g/l yeast extract, 25 mg/l chloramphenicol and 50 mg/l ampicillin) at 37° C., with shaking. When the optical density at 600% reached 0.3–0.4 units, recombinant protein expression was induced by adding IPTG (isopropyl B-D-thiogalactopyranoside) to a final concentration of 0.5 mM and the cells were grown for an additional three hours. The cultures were harvested by centrifugation at 3800×g for five minutes. The cells were resuspended in 20 mM $NaPO_4$, pH7.7 and stored at −20° C. overnight. Once thawed, the crude extracts were incubated with DNase (2 μg/ml) in the presence of 2.5 mM $MgCl_2$ at room temperature for thirty minutes and then spun at 14,000 rpm (Eppendorf 5417C) for five minutes.

To purify the OspC proteins described below, the crude extracts from the OspC-expressing cells were loaded onto an anion exchange column (Q Sepharose Fast Flow, 2.2×10 cm, Pharmacia) which had been pre-equilibrated with 20 mM Tris-Cl, pH 9.3. The column was washed in the same buffer (20 mM Tris-Cl, pH 9.3) which eluted the OspC protein. The wash fractions that contained OspC were concentrated using Amicon 10K and then were dialyzed with a solution containing 20 mM $NaPO_4$ pH 8.0 and 250 mM NaCl. The partially purified OspC was then passed over a $Ni^{2+}$ metal affinity column (Chelating Sepharose Fast Flow 2.2×10 cm, Pharmacia) equilibrated with 20 mM $NaPO_4$ pH 8.0 and 250 mM NaCl. The column was washed using a decreasing pH gradient of 20 mM sodium acetic acid and 250 mM NaCl and the bound OspC eluted around pH 5.7. The OspC fractions were then concentrated by ultrafiltration and stored at −70° C.

For purification of OspA proteins, the same procedure was followed, except that the dialysis step, after the Amicon 10K cutoff, was done in 20 nM $NaPO_4$, pH 6.0. The partially purified OspA was then applied to a cation exchange column (S Sepharose Fast Flow 2.2×10 cm, Pharmacia) equilibrated with 20 nM $NaPO_4$, pH 6.0. The column was washed using an increasing NaCl gradient from 0 to 100 mM. The OspA-containing fractions were concentrated by ultrafiltration and stored at −70° C.

As previously indicated, both lipidated and non-lipidated (truncated, i.e., without the first 17 amino acids) forms of OspC, OspA and OspC/OspA chimeric proteins were generated.

C. Immunization of Mice and Serologic Characterization Using ELISA (Enzyme-Linked Immunosorbent Assay)

Immunization of Mice

Mice, either C3H-J or ICR, were immunized with 3 ug of lipidated OspC/OspA chimeric protein or 6 ug of non-lipidated OspC/OspA chimers in 100 ul of aluminum hydroxide adjuvant (concentration of 1.8 mg/ml) by (SC) subcutaneous injection. As a negative control, mice were immunized with 100 ul of aluminum hydroxide adjuvant only. All mice received a total of three injections which were given at two week intervals. One week after the final immunization, blood was drawn from each mouse (including negative controls) and the serum was tested for IgG reacivity using the ELISA method described below, for the presence of anti-OspA antibodies to three different purified OspA proteins (*Borrelia burgdorferi* sensu stricto (B31), *Borrelia garinii* (K48) and *Borrelia afzelli* (PGau). The sera was tested at a dilution of 1:1000.

Mice were immunized with the chimeric proteins described in Table V.

TABLE V

Chimeric Proteins Used to Immunize Mice

| Name | Description (amino acid) | SEQ ID NO.: (nucleic acid) | SEQ ID NO.: (poly-peptide) | FIG. No: |
|---|---|---|---|---|
| OspA | OspA-B31(18–273) | 6 | 7 | 47, 48 |
| OspC | OspC-B31(19–211) | 29 | 30 | 47, 48 |
| OspC2-OspA | OspC-C2(19–204)/ OspA-B31(18–273) | 149 | 150 | 47, 48 |
| [1]lip OspAP/Bo | OspA-PGau(1–217)/ OspA-Bo(218–273) | 139 | 140 | 49, 50 |
| [1]lip OspAB/P | OspA-B31(1–216)/ OspA-PKo(217–273) | * | * | 49, 50 |

TABLE V-continued

Chimeric Proteins Used to Immunize Mice

| Name | Description (amino acid) | SEQ ID NO.: (nucleic acid) | SEQ ID NO.: (polypeptide) | FIG. No: |
|---|---|---|---|---|
| OspC-OspAB/P | OspC-B31(19–211)/ OspA-B31(18–216)/ OspA-PKo(217–273) | 155 | 156 | 49, 50, 52, 53, 54 |
| OspCB31-OspAB31 | OspC-B31(19–211)/ OspA-B31(18–273) | 145 | 146 | 51, 52, 53, 54 |
| OspC2-OspAB31 | OspC-C2(19–204)/ OspA-B31(18–273) | 149 | 150 | 51, 52 |
| [1]lip OspA K/T | OspA-K48(1–217)/ OspA-Tro(218–273) | * | * | 52 |
| [1]lip OspC-B31 | OspC-B31(1–211) | 29 | 30 | 51 |
| OspCB31-OspABPBP | OspC-B31(19–211)/ OspA-B31(30–150)/ OspA-PKo(151–179)/ OspA-B31(180–216) (190 N deletion)/ OspA-PKo(217–273) B31/B31/PKo | 177 | 178 | 53, 54 |

[1]"lip" means the chimeric protein contains its native N-terminal lipidation signal Serologic Characterization Using ELISA (Enzyme-Linked Immunosorbent Assay)

Immobilization of antigen onto ELISA Plates

A solution of purified recombinant OspC or OspA protein from each of the *Borrelia burgdorferi* strains B31 (*Borrelia burgdorferi* sensu stricto), K48 (*Borrelia* garinii) and PGau (*Borrelia afzelli*) was added to sodium phosphate buffer, pH 9.0, and was used to coat a commercial microwell plate (MaxiSorp®, Nunc). The coating procedure was as follows: 100 μl of a solution containing the appropriate OspA or OspC protein (made up at a concentration of 250 ng/ml in the following coating buffer: 100 mM Bis-Tris propane, pH 9.7) was added to each well of a microtiter plate which was incubated for one hour at 37° C. The antigen solution was removed from the wells, the plate was washed three times with phosphate buffered saline (PBS) pH 9.0, and 300 μl of blocking buffer solution was added (3% dry milk, 0.1% polyoxyethylenesorbitan (referred to herein as Tween 20™), 0.02% $NaN_3$ in 100 nM Bis-Tris propane, pH 9.7). Following a one hour incubation at 37° C., the plates were washed four times with TBS-Tween 20™ wash buffer (20 mM Tris-Cl, pH 7.5, 136 mM NaCl, 0.1% Tween 20™ and 0.02% $NaN_3$) and then were allowed to dry. The plates were then wrapped in plastic and stored at 4° C. until they were used.

ELISA (Enzyme-Linked Immunosorbent Assay) Tests

The standard procedure for the ELISA tests was as follows: mouse serum was diluted 1:1000 in sample dilution buffer (1% dry milk, 136 mM NaCl, 0.1% Tween 20™, 0.02% $NaN_3$ in 20 mM Tris-Cl, pH7.5) and 100 μl of the diluted serum was added to the ELISA microtiter plate wells that had been coated with antigen as described above. Following incubation for 1 hour at 37° C., the samples were removed and the plates were washed four times in TBS-Tween™ (20 mM Tris-Cl, pH 7.5; 136 mM NaCl; 0.1% Tween 20™ and 0.02% $NaN_3$). For the secondary antibody, goat anti-mouse antisera conjugated to alkaline phosphatase-specific for either IgM (Fc) or IgG (Fab), (Jackson Immuno Research Laboratories) was diluted 1:750 in sample dilution buffer (1% dry milk, 136 mM NaCl, 0.1% Tween 20™, 0.02% $NaN_3$ in 20 mM Tris-Cl, pH7.5) and 100 μl of the diluted secondary antibody was added to each well. Following incubation for thirty minutes at 37° C., the plates were washed three times with TBS-Tween™ (20 mM Tris-Ci, pH 7.5; 136 mM NaCl; 0.1% Tween 20™ and 0.02% $NaN_3$) and 100 μL of Phosphatase Substrate solution (5 mg of p-nitrophenylphosphate tablets dissolved in 1× diethanolamine substrate buffer to yield a 2 mg/ml solution—Kirkegaard Perry Laboratory) was added to each well. The plates were incubated for thirty minutes at 37° C. and 100 μl of stop solution (5% EDTA) was added to each well. The absorbance at 405 nm was read on a microplate reader (Dynatech). A sample was considered positive if it produced an average absorbance greater than the mean of the negative controls plus three standard deviations.

Previous work has demonstrated that it is the carboxy-terminal region of OspA that contains the antigenic sites that provide the immunoprotective response. Thus, in addition to the ELISA test described above, a modified ELISA was performed (herein referred to as the Protective ELISA Test), wherein the purified N-terminal region of B31 OspA (amino acids 18–139) was used to block any antibodies present in the mouse serum that had specificity to this N-terminal OspA region. These protective ELISA tests were performed as above, except that 80 μg/ml of a purified B31 OspA fragment (amino acids 18–139) was added to the diluted mouse serum prior to adding the sera to the antigen-coated ELISA microtiter plate wells.

Results of ELISA Tests

Using the above-described ELISA tests, it was demonstrated that mice immunized with a non-lipidated OspC/OspA chimeric protein (OspC2-OspA-composed of OspC (a.a. 19–204 from strain C2)/OspA (a.a. 18–273 from strain B31) (SEQ ID NO.150) produced an immune response both to OspA and OspC that was comparable to the immune response generated to non-lipidated OspA (OspA—a.a. 18–273 from strain B31) and non-lipidated OspC (OspC—a.a. 19–211 from strain B31) control proteins (FIG. 47). As indicated in FIG. 47 and described above, mice were immunized with OspA, OspC or OspC2-OspA proteins and immune responses of the sera were measured against B31 OspA antigen (stippled bars) and B31 OspC antigen (solid bars).

Using the above-described Protective ELISA Test, it was also shown that mice immunized with the same non-lipidated OspC/OspA chimeric protein (OspC2-OspA-composed of OspC (a.a. 19–204 from strain C2)/OspA (a.a. 18–273 from strain B31) (SEQ ID NO.150) produced an immune response to the C-terminal portion of OspA that was comparable to the immune response generated to the C-terminal portion of a non-lipidated OspA (OspA—a.a. 18–273 from strain B31) control protein (FIG. 48). As indicated in FIG. 48, mice were immunized with OspA, OspC or OspC2-OspA proteins and immune responses of the sera were measured against B31 OspA antigen. The protective antibody response to B31 OspA antigen is indicated in the stippled bars.

Thus, these results clearly demonstrate that non-lipidated chimeric OspC/OspA proteins are able to induce immune responses in mice that are comparable to the immune response generated against non-lipidated OspC and OspA control proteins.

It had been previously thought that the lipidation signals that are present on *Borrelia burgdorferi* outer surface proteins were required for immunogenicity and that OspC and OspA proteins that lacked this lipidation signal would be less or non-immunogenic. To test this idea, mice were immunized with a non-lipidated OspC/OspA chimeric protein (OspC-OspAB/P—composed of OspC (a.a. 19–211 from strain B31)/OspA (a.a. 18–216 from strain B31)/OspA (a.a. 217–273 from strain PKO)(SEQ ID NO: 156) as well as two lipidated OspA proteins, lipOspAP/Bo (composed of OspA (a.a. 1–217 from strain PGau)/OspA (a.a. 218–273 from strain Bo)) and lipOspAB/P (composed of OspA (a.a. 1–216 from strain B31)/OspA (a.a. 217–273 from strain PKo)) and were subjected ELISA tests. Mice immunized with the non-lipidated OspC/OspA chimeric protein (OspC-OspAB/P) produced an immune response to OspA from each of the *Borrelia burgdorferi* strains B31 (*Borrelia burgdorferi* sensu stricto), K48 (*Borrelia* garinii) and PGau (*Borrelia afzelli*), that was equivalent or greater than the immune response generated to the two lipidated OspA control proteins (lipOspAP/Bo and lipOspAb/P) (FIG. 49).

Similar results to these were obtained using the Protective ELISA Test described above. Mice immunized with the non-lipidated OspC/OspA chimeric protein (OspC-OspAB/P) produced an immune response to the C-terminal region of OspA from each of the *Borrelia burgdorferi* strains B31 (*Borrelia burgdorferi* sensu stricto), K48 (*Borrelia* garinii) and PGau (*Borrelia afzelli*), that was equivalent or greater than the immune response generated to the C-terminal region of OspA from the two lipidated OspA control proteins (lipOspAP/Bo and lipOspAb/P) (FIG. 50).

In addition to the comparisons between non-lipidated OspC/OspA chimeric proteins and lipidated OspA control proteins, experiments were also performed to compare non-lipidated OspC/OspA chimeric proteins with a lipidated OspC control protein (FIG. 51). Mice that were immunized with either the non-lipidated OspC/OspA chimeric protein OspCB31-OspAB31 (composed of OspC (a.a. 19–211 from strain B31)/OspA (a.a. 18–273 from strain B31) (SEQ ID NO:146) or the non-lipidated OspC/OspA chimeric protein OspC2-OspAB31 (composed of OspC (a.a. 19–204 from strain C2)/OspA (a.a. 18–273 from strain B31) (SEQ ID NO:150) produced an immune response to OspC derived from the *Borrelia burgdorferi* strain B31 that was comparable to the immune response produced by a lipidated OspC control protein (lip OspC-B31-composed of OspC (a.a. 1–211 from strain B31)) (FIG. 51).

Thus, these results clearly demonstrate that non-lipidated chimeric OspC/OspA proteins are able to induce immune responses against OspA and OspC that are comparable to the immune response generated against OspA and OspC using lipidated OspA or OspC control proteins. The use of unlipidated forms of these proteins as vaccine immunogens or diagnostic antigens is highly desirable because the product yield is much greater and the proteins are much easier to purify. For these reasons, the production of these proteins less expensive.

Figure 52:
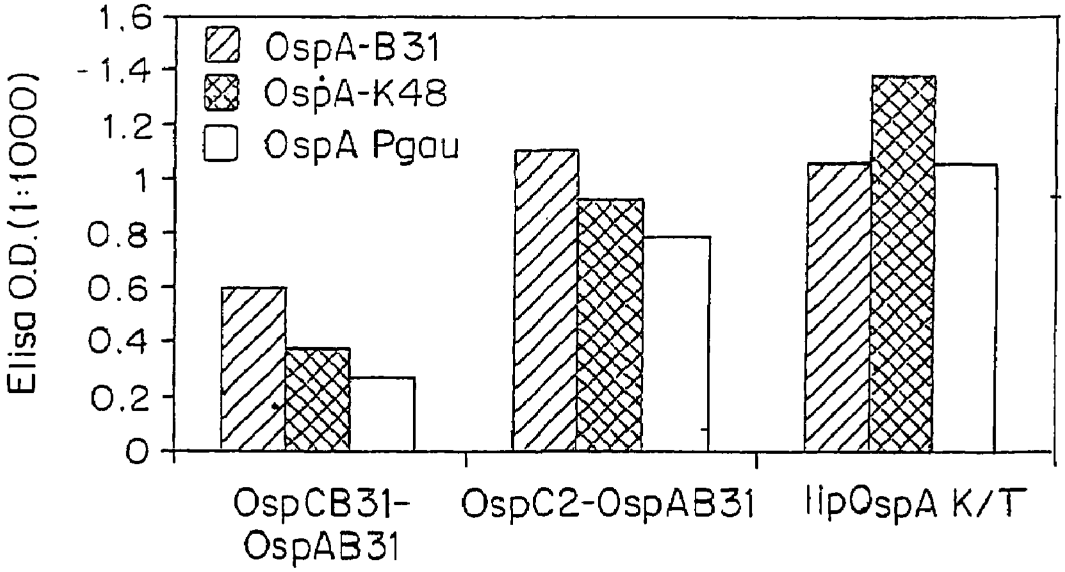
FIG. 52 is a bar graph showing the reactivity of sera from mice immunized with the indicated *Borrelia* chimeric protein (OspCB31-OspAB31, OspC2-OspAB31 or Lip OspA K/T) (X-axis) against the indicated OspA antigens (legend) from strains B31 (*Borrelia burgdorferi* sensu stricto), K48 (*Borrelia garinii*) and PGau (*Borrelia afzelli*).

The OspC/OspA chimeric proteins of the present invention are also able to generate immune responses against OspA proteins that are derived from strains that are not represented in the chimeric protein. Mice immunized with the OspC/OspA chimeric proteins, OspCB3'-OspAB31 (SEQ ID NO:146) and OspC2-OspAB31 (SEQ ID NO: 150), are not only able to generate immune responses that recognize OspA derived from strain B31 (*Borrelia burgdorferi* sensu stricto), but also recognize OspA derived from strain K48 (*Borrelia garinii*) and strain PGau (*Borrelia afzelli*) (FIG. 52). For comparison, mice were also immunized with the lipidated OspA chimeric protein, Lip OspA K/T (composed of OspA (a.a. 1–217 from strain K48)/OspA (a.a. 218–273 from strain Tro)) (FIG. 52).

Figure 53:
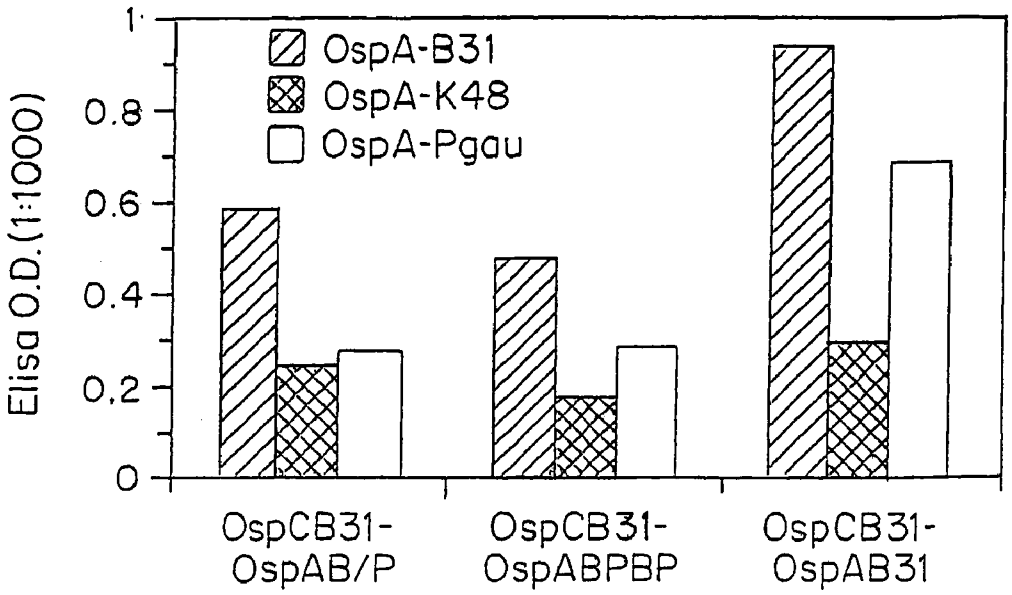
FIG. 53 is a bar graph showing the reactivity of sera from mice immunized with the indicated *Borrelia* chimeric protein (OspCB31-OspAB/P, OspCB31-OspABPBP or OspCB31-OspAB31) (X-axis) against the indicated OspA antigens (legend) from strains B31 (*Borrelia burgdorferi* sensu stricto), K48 (*Borrelia garinii*) and PGau (*Borrelia afzelli*).
Figure 54:
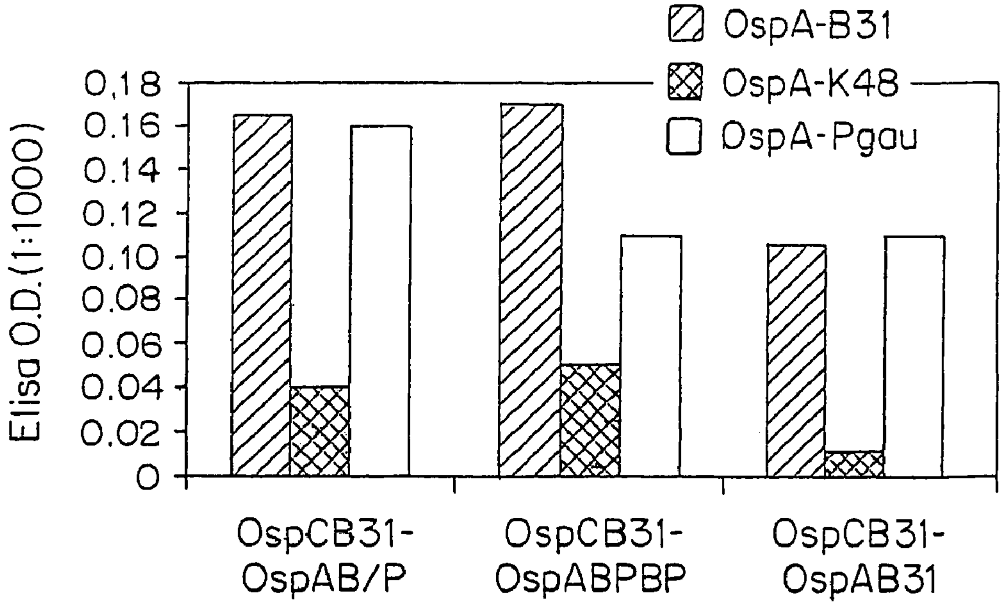
FIG. 54 is a bar graph showing the reactivity of sera from mice immunized with the indicated *Borrelia* chimeric protein (OspCB31-OspAB/P, OspCB31-OspABPBP or OspCB31-OspAB31) (X-axis) against the indicated OspA (legend) from strains B31 (*Borrelia burgdorferi* sensu stricto), K48 (*Borrelia garinii*) and PGau (*Borrelia afzelli*). In all cases, a purified fragment of B31 OspA (amino acids 18–139) was added in excess to the sera so that the detected immune response is specific for the C-terminal region of OspA.

Additional antibody responses to OspA derived from strain B31 (*Borrelia burgdorferi* sensu stricto), strain K48 (*Borrelia garinii*) and strain PGau (*Borrelia* afzelli) are also presented for sera from mice immunized with other OspC/OspA chimeric proteins. Thus, FIG. 53 presents the ELISA results from mice immunized with either OspCB3]-OspAB/P (SEQ ID NO: 156), OspCB3]-OspABPBP (SEQ ID NO: 178) or OspCB31-OspAB31 (SEQ ID NO:146). In each case, sera from the immunized mice was tested against OspA derived from each of strain B31 (*Borrelia burgdorferi* sensu stricto), K48 (*Borrelia garinii*) and PGau (*Borrelia afzelli*). In all cases, a strong immune response was generated (FIG. 53). As with the previously described OspC/OspA chimeric proteins, the three OspC/OspA chimeric proteins used to immunize the mice in FIG. 52 also elicited a strong immune response to the C-terminal region of OspA when examined using the Protective ELISA Test described above (FIG. 54).

Tick Challege of Immunized Mice

Mice, either C3H-J or JCR, that had been immunized as described above, were also challenged with either laboratory-infected nympha or field nympha. The immunized mice were placed in isolation cages and each mouse received 5–10 nymphs. All of the nymphs were collected and counted after 6 days. Four weeks after challenge, the mice were bled and sera was tested using commercially-available Western blot strips to *Borrelia burgdorferi* sensu stricto strain B31 (MarDx strips) and/or *Borrelia garinii* (MRL strips). Eight weeks after challenge, the mice were bled, sera was tested again by Western blot and ear punch and bladder samples were cultured. As a positive control, mice which had been immunized with only aluminum hydroxide adjuvant, as described above, were subjected to the same challenge.

The results of the tick challenge studies (Table VI) demonstrate that while immunization with lipidated OspC protein was unable to protect the mice, as evidenced by a positive Western blot signal (in 4 out of 5 mice), immunization with two different OspC/OspA chimeric proteins (SEQ ID NO.146 and SEQ ID NO.150) did provide protection, as indicated by the absence of Western blot signal (in 0 out of 8 mice and 0 out of 3 mice) (Table VI). The sham positive control showed that the challenge by the ticks was successful in all cases, as evidenced by 100% positive signal in Western blots (Table VI).

TABLE VI

Effect of Vaccination on Transmission of *Borrelia* from Ticks

| Vaccine Candidate | Mouse | Tick-nymph | Seroconversion (Western Blots) Vaccinated | Seroconversion (Western Blots) Sham |
|---|---|---|---|---|
| OspC1-OspAB31 | C3H-J | Long Island | 0+/8 | 8+/8 |
| OspC2-OspAB31 | C3H-J | Long Island | 0+/3 | 4+/4 |
| Lip OspC12 | ICR | Long Island | 4+/5 | 5+/5 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of delivering a chimeric protein comprising at least a first and a second polypeptide, wherein the N-terminus of the chimeric protien comprises the first polypeptide, wherein the first polypeptide comprises *Borrelia burgdorferi* OspC and wherein the second polypeptide comprises *Borrelia burgdorferi* OspA, comprising administering the chimeric protein to an animal.

2. The method of claim 1, wherein the chimeric protein is administered with a physiologically-acceptable vehicle or carrier.

3. The method of claim 1, wherein the chimeric protein is encoded by a nucleic acid selected from the group consisting of: SEQ ID NOs: 145, 147, 149, 151, 153, 155, 157, 159, 161, 163, 165, 167, 169, 171, 173, 175, 177 and 179.

4. The method of claim 1, wherein the chimeric protein comprises an amino acid sequence selected from the group consisting of: SEQ ID NOs: 146, 148, 150, 152, 154, 156, 158, 160, 162, 164, 166, 168, 170, 172, 174, 176, 178 and 180.

5. A method of immunizing an animal or human against Lyme disease, comprising administering a composition comprising a chimeric protein of at least a first and a second polypeptide, wherein the N-terminus of the chimeric protien comprises the first polypeptide, wherein the first polypeptide comprises *Borrelia burgdorferi* OspC and wherein the second polypeptide comprises *Borrelia burgdorferi* OspA.

6. The method of claim 5, wherein the chimeric protein comprises an amino acid sequence selected from the group consisting of: SEQ ID NOs: 146, 148, 150, 152, 154, 156, 158, 160, 162, 164, 166, 168, 170, 172, 174, 176, 178 and 180.

* * * * *

UNITED STATES PATENT AND TRADEMARK OFFICE

CERTIFICATE OF CORRECTION

PATENT NO. : 7,179,448 B2
APPLICATION NO. : 11/196475
DATED : February 20, 2007
INVENTOR(S) : Raymond J. Dattwyler et al.

It is certified that error appears in the above-identified patent and that said Letters Patent is hereby corrected as shown below:

Column 1, line 24, after "Infectious Diseases" add "and with Government support under contract number DE-AC02-98CH10886, awarded by the U.S. Department of Energy"

Signed and Sealed this
Sixteenth Day of August, 2011

David J. Kappos
*Director of the United States Patent and Trademark Office*